US006103905A

United States Patent [19]

[11] Patent Number: 6,103,905

[45] Date of Patent: Aug. 15, 2000

Cuny et al.

[54] QUINOLINE-INDOLE ANTIMICROBIAL AGENTS, USES AND COMPOSITIONS RELATED THERETO

[75] Inventors: Gregory D. Cuny, Hudson; James R. Hauske, Hopkington; Donald L. Heefner, Hudson; Michael Z. Hoemann, Marlborough; Gnanasambandam Kumaravel, North Andover; Anita Melikian-Badalian, Watertown; Richard F. Rossi, Norton; Roger L. Xie, Westborough, all of Mass.

[73] Assignee: Sepracor, Inc., Marlborough, Mass.

[21] Appl. No.: 09/213,385

[22] Filed: Dec. 11, 1998

Related U.S. Application Data

[63] Continuation-in-part of application No. 09/099,640, Jun. 18, 1998, which is a continuation-in-part of application No. 09/045,051, Mar. 19, 1998, which is a continuation-in-part of application No. 08/878,781, Jun. 19, 1997, abandoned.

[51] Int. Cl.[7] ........................ A61K 31/47; C07D 265/30; C07D 295/06

[52] U.S. Cl. ........................ 546/167; 514/314

[58] Field of Search ........................ 546/167; 514/314

[56] References Cited

U.S. PATENT DOCUMENTS

| | | | |
|---|---|---|---|
| 3,799,929 | 3/1974 | Holmes | 260/287 |
| 3,870,712 | 3/1975 | Holmes | 260/240 |
| 3,897,436 | 7/1975 | Goschke | 260/283 |
| 3,905,982 | 9/1975 | Yonan | 260/287 |
| 4,680,299 | 7/1987 | Hesson | 514/311 |
| 4,847,381 | 7/1989 | Sutherland et al. | 546/156 |
| 4,861,783 | 8/1989 | Ackerman et al. | 514/311 |
| 4,968,701 | 11/1990 | Ackerman et al. | 514/312 |
| 4,968,702 | 11/1990 | Poletto et al. | 514/313 |
| 5,204,329 | 4/1993 | Ackerman et al. | 514/15 |
| 5,480,883 | 1/1996 | Spada et al. | 514/249 |
| 5,523,408 | 6/1996 | Batt et al. | 546/167 |
| 5,565,324 | 10/1996 | Still et al. | 436/6 |
| 5,578,609 | 11/1996 | Batt et al. | 514/314 |

FOREIGN PATENT DOCUMENTS

| | | |
|---|---|---|
| 0574618 A1 | 12/1993 | European Pat. Off. . |
| 0 795 547 A1 | 9/1997 | European Pat. Off. . |
| WO 92/20642 | 11/1992 | WIPO . |
| WO 94/08051 | 4/1994 | WIPO . |

OTHER PUBLICATIONS

Giardina et al., "Discovery of a Novel Class of Selective Non–Peptide Antagonists for the Human Neurokinin–3 Receptor. 1. Identificationof the 4–Quinolinecarboxamide Framework", J. Med. Chem.40: 1794–1807 (1997).

Bruni, P. et al., XP–002093218, 6001 Chemical Abstracts, Columbus Ohio, US, vol. 67, No. 25, p. 10998 (Dec. 18, 1967).

Coste, J. eta l., "PyBOP®: A New Piptide Coupling Reagent Devoid of Toxic By–Product", Tet. Lett., vol. 31, No. 2, 205–208 (1990).

Colonna, M. et al., XP–002093220, 6001 Chemical Abstracts, Columbus Ohio, US, vol. 66, No. 21, p. 8874 (May 22, 1967).

Dewitt, S.H. et al., "Diversomers : An approach to nonpeptide, nonoligomeric chemical diversity", Proc,. Natl. Acad. Sci. USA vol. 90, p. 6909–6913, (1993).

Gordon, E. M. et al., "Applications of Combinatorial Technologies to Drug Discovery. 2. Combinatorial Organic Synthesis, Library Screening Strategies, and Future Directions", J. of Medicinal Chemistry, vol. 37, No. 10, p. 1385–1401 (1994).

Humana, M. et al.,XP–002093219, 6001 Chemical Abstracts, Columbus Ohio, US, vol. 67, No. 9, p. 4098 (Aug. 28, 1967).

Hamana, M. et al.,XP–002093216, 6001 Chemical Abstracts, Columbus Ohio, US, vol. 75, No. 23, p. 307 (Dec. 6, 1971).

Hauske, J.R. and Dorff, P., "A Solid Phase CBZ Chloride Equivalent—A New Matrix Specific Linker", Tetrahedron Letters, vol. 36, No. 10, p. 1589–1592, (1995).

Houghten, R. et al., "Generation and Use of Synthetic Peptide Combinatorial Libraries for Basic Research and Drug Discovery", Nature, vol. 354, 84–86 (1991).

Kuprapov, P.B. et al., XP–002093215, 6001 Chemical Abstracts, Columbus Ohio, US, vol. 92, No. 15, p. 614 (Apr. 14, 1980).

Nagayoshi, T. et al.,XP–002093214, 6001 Chemical Abstracts, Columbus Ohio, US, vol. 88, No. 1, p. 563 (Jan. 2, 1978).

Sheinkman, A.K. et al., XP–002093217, 6001 Chemical Abstracts, Columbus Ohio, US, vol. 74, No. 15, p. 432 (Apr. 12, 1971).

Thao, N.M. et al., XP–002078523, 6001 Chemical Abstracts, Columbus Ohio, US, vol. 112, No. 13, p. 426 (Mar. 26, 1990).

Thao, N.M. et al., XP–002093221, 6001 Chemical Abstracts, Columbus Ohio, US, vol. 112, No. 13, p. 426 (Mar. 26, 1990).

Thao, N.M. et al., XP–002093222, 6001 Chemical Abstracts, Columbus Ohio, US, vol. 112, No. 1, p. 719 (Jan. 1, 1990).

Thao, N.M. et al., XP–002093223, 6001 Chemical Abstracts, Columbus Ohio, US, vol. 108, No. 1, p. 553 (Jan. 4, 1988).

Thao, N.M. et al., XP–002093224, 6001 Chemical Abstracts, Columbus Ohio, US, vol. 100, No. 17, p. 632 (Apr. 23, 1984).

Thao, N.M. et al., XP–002078524, 6001 Chemical Abstracts, Columbus Ohio, US, vol. 101, No. 15 (Oct. 8, 1984).

Thao, N.M. et al., XP–002078525, 6001 Chemical Abstracts, Columbus Ohio, US, vol. 101, No. 19, p. 694 (Nov. 5, 1984).

Abgaryan, E.A. et al., XP–002078526, 6001 Chemical Abstracts, Columbus Ohio, US, vol. 103, No. 7, p. 564 (Aug. 19, 1985).

*Primary Examiner*—D. Margaret Seaman

*Attorney, Agent, or Firm*—Matthew P. Vincent; Dana M. Gordon; Foley, Hoag & Eliot LLP

[57] ABSTRACT

The present invention provides methods and pharmaceutical preparations that inhibit the growth of bacteria microorganisms. Additionally, the present invention provides methods and pharmaceutical preparations that kill bacterial microorganisms.

31 Claims, No Drawings

QUINOLINE-INDOLE ANTIMICROBIAL AGENTS, USES AND COMPOSITIONS RELATED THERETO

RELATED APPLICATIONS

This application is a continuation-in-part of U.S. Ser. No. 09/099,640, filed Jun. 18, 1998, which is a continuation-in-part of U.S. Ser. No. 09/045,051, filed Mar. 19, 1998, which is a continuation-in-part of U.S. Ser. No. 08/878,781, filed Jun. 19, 1997, now abandoned.

BACKGROUND OF THE INVENTION

A number of structural classes of compounds with antibacterial properties are known. Historically, the most important classes of antibacterials have been the β-lactams, macrolides, lincosamides, aminoglycosides, tetracyclines, polypeptides, and sulfonamides. The bulk of these antibacterial compounds were isolated originally from molds, fungi or bacteria; synthetic and semi-synthetic compounds, additionally, have proven to be efficacious in the treatment of bacterial infections. In the broadest possible sense, known antibacterials work by influencing at least one of the following cellular processes or characteristics: cell wall synthesis; protein synthesis; nucleic acid synthesis; cellular metabolism; and cytoplasmic membrane permeability. Brief descriptions follow of the mechanisms of action of members of each of the aforementioned classes of antibacterials.

The β-lactam antibiotics inhibit penicillin binding proteins (PBPs). The PBPs are ubiquitous bacterial enzymes that are involved in cell wall biosynthesis (reviewed in Waxman et al., 1983 Annual Review of Biochemistry 58:825–869; Georgopapadkou et al., 1983 Handbook of Experimental Pharmacology 67:1–77; and Ghuysen, 1991 Annual Review of Microbiology 45:37–67); inhibition of these proteins disrupts the biosynthesis of the bacterial cell wall. Specifically, these compounds act as substrate analogs for the PBPs and form an acyl enzyme intermediate. This acyl enzyme intermediate is resistant to subsequent hydrolysis and ties up the enzyme in a relatively long-lived inactive form. Bacteria have responded to the widespread use of β-lactam antibiotics by evolving a class of β-lactam hydrolyzing enzymes known as β-lactamases. These enzymes are one of the sources of drug resistance now being observed in a number of bacterial diseases including tuberculosis, malaria, pneumonia, meningitis, dysentery, bacteremia, and various venereal diseases.

The macrolides are a family of antibiotics whose structures contain large lactone rings linked through glycoside bonds with amino sugars. The most important members of the group are erythromycin and oleandomycin. Erythromycin is active against most Gram-positive bacteria, Neisseria, Legionella and Haemophilus, but not against the Enterobacteriaceae.

Macrolides inhibit bacterial protein synthesis by binding to the 50S ribosomal subunit. Binding inhibits elongation of the protein by peptidyl transferase or prevents translocation of the ribosome or both. Macrolides are bacteriostatic for most bacteria but are bactericidal for a few Gram-positive bacteria.

The lincosamides are sulfur-containing antibiotics isolated from *Streptomyces lincolnensis*. There are two important lincosamides: lincomycin and clindamycin. Clindamycin is preferred over lincomycin due to its greater potency, fewer adverse side effects, and its more favorable pharmacokinetic properties. Bacterial resistance and cross resistance to clindamycin have begun to emerge. The lincosamides are active against Gram-positive bacteria especially cocci, but also non-spore forming anaerobic bacteria, Actinomycetes, Mycoplasm and some Plasmodium. The lincosamides bind to the 50S ribosomal subunit and thereby inhibit protein synthesis. These drugs may be bacteriostatic or bactericidal depending upon several factors, including their local concentration.

Aminoglycosides are important antibacterials used primarily to treat infections caused by susceptible aerobic Gram-negative bacteria. Unfortunately, they have a narrow margin of safety, producing characteristic lesions in kidney, cochlea, and vestibular apparatus within the therapeutic dose range. Because they are polycations, the aminoglycosides cross cellular membranes very poorly.

The tetracyclines consist of eight related antibiotics which are all natural products of Streptotmyces, although some can now be produced semi-synthetically. Tetracycline, chlortetracycline and doxycycline are the best known members of this class. The tetracyclines are broad-spectrum antibiotics with a wide range of activity against both Gram-positive and Gram-negative bacteria. The tetracyclines act by blocking the binding of aminoacyl tRNA to the A site on the ribosome. Tetracyclines inhibit protein synthesis on isolated 70S or 80S (eukaryotic) ribosomes, and in both cases, their effect is on the small ribosomal subunit. Most bacteria possess an active transport system for tetracycline that will allow intracellular accumulation of the antibiotic at concentrations 50 times as great as that in the surrounding medium. This system greatly enhances the antibacterial effectiveness of tetracycline and accounts for its specificity of action, since an effective concentration is not accumulated in host cells. Thus a blood level of tetracycline which is harmless to mammalian tissues can halt protein synthesis in invading bacteria. The tetracyclines have a remarkably low toxicity and minimal side effects in mammals. The combination of their broad spectrum and low toxicity has led to their overuse and misuse by the medical community and the wide-spread development of resistance has reduced their effectiveness. Nonetheless, tetracyclines still have some important uses, such as in the treatment of Lyme disease.

The polypeptide antibacterials have in common their basic structural elements—amino acids. Representatives of this class include vancomycin, and bacitracin. Vancomycin can be used to treat both systemic and gastrointestinal infections, whereas because of serious systemic toxicities bacitracin. is limited to topical applications. Vancomycin inhibits bacterial cell wall synthesis by inhibiting peptidoglycan synthase, apparently by binding to D-alanyl-D-alanine, a component of the cross-link between chains. This action inhibits peptidoglycan chain elongation, and as might be expected, the effect is bactericidal for most organisms if they are dividing rapidly. Because it does not target penicillin-binding enzymes, vancomycin is not cross-resistant with the β-lactams. Bacitracin is a narrow spectrum antibiotic which inhibits cell wall biosynthesis by inhibiting lipid pyrophosphatase; this enzyme is involved in transmembrane transport of peptidoglycan precursors.

The sulphonamides are usually bacteriostatic and arrest cell growth by inhibiting bacterial folic acid synthesis. They are effective against sensitive strains of Gram-negative and Gram-positive bacteria, Actinomyces, Nocardia and Plasmodia. However, extensive clinical use of sulfonamides over many years has resulted in a high level of resistance and their current use is limited.

Additionally, there are miscellaneous antibacterials that do not fit readily into the structural classes outlined above.

A comprehensive discussion of these miscellaneous antibacterials is not warranted; a small number of antibacterials in this group, however, are relevant to the subject compounds. First, U.S. Pat. No. 3,799,929 "Cinchoninic Acid Derivatives", granted to Eli Lilly and Company on Mar. 26, 1974, and 3,870,712 "Cinchoninic Acid Derivatives", granted to Eli Lilly and Company on Mar. 11, 1975, are directed to sets of substituted quinolines represented by structure A. Of particular relevance to the subject compounds, Lilly claims compounds represented by A wherein: 1) R represents 3-indolyl or 1-methyl-3-indolyl; and 2) $R_1$ represents —OH or lower alkoxy of 1 to 3 carbons.

Moreover, a few quinoline-indole compounds have been found to display biological activity other than against bacteria. Published PCT applications WO 95/32948 "Quinoline Derivatives as Tachykinin $NK_3$ Receptor Antagonists", and WO 96/02509 "Quinoline Derivatives as $NK_3$ Antagonists", filed by SmithKline Beecham disclose substituted quinolines represented by structures B and C, respectively. In WO 95/32948, SmithKline Beecham claims compounds represented by B wherein: 1) $R_5$ is branched or linear $C_{1-6}$ alkyl, $C_{3-7}$ cycloalkyl, $C_{4-7}$ cycloalkylalkyl, optionally substituted aryl, or an optionally substituted single or fused ring heterocyclic group, having aromatic character, containing from 5 to 12 ring atoms and comprising up to four hetero-atoms in the or each ring selected from S, O, N; and 2) X is O, S, or N—CN. In WO 96/02509, SmithKline Beecham claims compounds represented by C wherein: 1) Ar is an optionally substituted phenyl or naphthyl group or an optionally substituted single or fused ring heterocyclic group, having aromatic character, containing from 5 to 12 ring atoms and comprising up to four hetero-atoms in the or each ring selected from S, O, N; and 2) X is O, S, $H_2$ or N—CN.

A

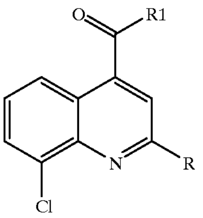

B

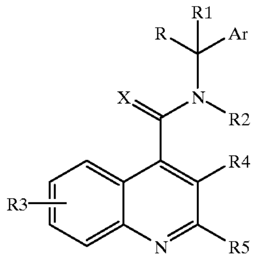

C

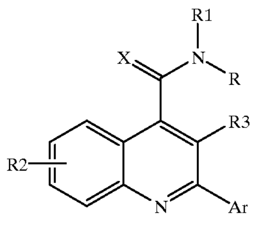

Antibacterial resistance is a global clinical and public health problem that has emerged with alarming rapidity in recent years and undoubtedly will increase in the near future. Resistance is a problem in the community as well as in health care settings, where transmission of bacteria is greatly amplified. Because multiple drug resistance is a growing problem, physicians are now confronted with infections for which there is no effective therapy. The morbidity, mortality, and financial costs of such infections pose an increasing burden for health care systems worldwide, but especially in countries with limited resources. Strategies to address these issues emphasize enhanced surveillance of drug resistance, increased monitoring and improved usage of antimicrobial drugs, professional and public education, development of new drugs, and assessment of alternative therapeutic modalities.

SUMMARY OF THE INVENTION

There exists a need to provide alternative and improved agents for the treatment of bacterial infections particularly for the treatment of infections caused by resistant strains of bacteria, e.g. penicillin-resistant, methicillin-resistant, ciprofloxacin-resistant, and/or vancomycin-resistant strains, as well as for the decontamination of objects bearing such organisms, e.g. non-living matter, hospital equipment, walls of operating rooms, and the like.

In general, the present invention provides a method and pharmaceutical preparations for inhibiting the growth of bacterial microorganisms, such as in the treatment of Gram-positive infections, including Staphylococcus infections, Streptococcus infections, and Enterococcus infections, and in the treatment of Gram-negative infections, including Enterobacteriaceae infections, Mycobacterium infections, Neisseria infections, Pseudomonas infections, Shigella infections, Escherichia infections, Bacillus infections, Micrococcus infections, Arthrobacter infections, and Peptostreptococcus infections. For instance, the compounds of the present invention are particularly useful in the treatment of infections caused by methicillin-resistant strains of bacteria, e.g. methicillin-resistant strains of *Staphylococcus aureus* (MRSA; *Micrococcus pyogenes var. aureus*), ciprofloxacin-resistant strains of bacteria, e.g. ciprofloxacin-resistant strains of *Staphylococcus aureus* (CRSA), and vancomycin-resistant strains of bacteria, e.g. vancomycin-intermediate-resistant *Staphylococcus aureus* (VISA) and vancomycin-resistant *Enterococcus faecalis* (VREF). In preferred embodiments, the present invention can be used to inhibit bacterial infections caused by Gram-positive bacteria, for example, *S. aureus, S. epidermidis, S. pneumonia.*

The invention, as described herein, is directed to the use of small (e.g., $M_r$<1.5 kD) organic molecules, e.g., 2-(3-indolyl)-quinolines and substituted derivatives thereof, and pharmaceutical formulations thereof, in the treatment of bacterial infections. Specifically proposed as antibacterial agents are compounds based on 2-(3-indolyl)-4-quinolinecarboxamide and derivatives thereof, and 2-(3-indolyl)quinoline, and derivatives thereof. As described herein, many of the antibacterials have in vitro minimum inhibitory concentrations (MICs) at or below single-digit micromolar concentrations in assays against cultures of methicillin-resistant *Staphylococcus aureus* (MRSA), ciprofloxacin-resistant *Staphylococcus aureus* (CRSA), vancomycin-resistant Enterococcus spp. (VRE), and/or penicillin-resistant Pseudomonas (PRP). The wide range of antibacterial compounds disclosed herein enables the potential to tailor potency, specificity, solubility, bioavailability, stability, toxicity, and other physical properties to suit specific purposes.

DETAILED DESCRIPTION OF THE INVENTION

In the last decade, the frequency and spectrum of antimicrobial-resistant infections has increased. Certain infections that are essentially untreatable are reaching epidemic proportions in both the developing world and institutional settings in the developed world. Antimicrobial resistance is manifested in increased morbidity, mortality, and health-care costs. *Staphylococcus aureus* is an significant cause of nosocomial infection, especially nosocomial pneumonia, surgical wound infection, and bloodstream infection (Panlilio et al., Infect. Cont. Hosp. Epidemiol. 13: 582–586 (1992)). Other pathogens commonly associated with nosocomial infection include, but are not limited to, *Escherichia coli, Pseudomonas aeruginosa*, Enterococcus spp., Enterobacter spp., coagulase-negative *staphylococci* (CNS). As described above, a considerable amount of effort has been devoted to developing bacteriostatic and bactericidal agents with activity against these and other microorganisms.

The present invention relates to heterocyclic antibacterial agents with antimicrobial activity, and particularly, antibacterial activity against both sensitive and resistant strains. The subject antibacterial compounds comprise two distinct heterocycles that are covalently linked to each other, preferably via a carbon—carbon single bond. In preferred embodiments, the individual heterocyclic moieties are quinoline and indole nuclei interconnected at their respective 2- and 3-positions. Three preferred subclasses of the compounds are disclosed: 1) a subclass in which the substituent at the 4-position of the quinoline nucleus comprises a primary or secondary amine; 2) a subclass in which the substituent at the 4-position of the quinoline nucleus is a hydrogen, halogen, or another group that does not comprise a primary or secondary amine; and 3) a subclass in which a substituent on the B-ring of the quinoline nucleus is a 1-alkynyl group. The remaining positions of the 2-quinolinyl and 3-indolyl nuclei of the subject compounds may independently be unsubstituted or substituted with a variety of groups giving rise to a variety of antimicrobial compounds.

For example, in one embodiment, the compounds of the present invention are represented by the general formula 1, or a pharmnaceutically acceptable salt and/or prodrug thereof:

1

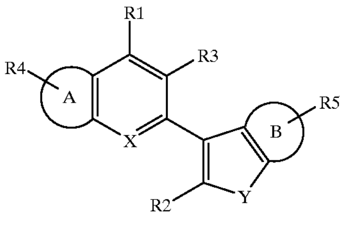

wherein each of A and B independently represent fused rings selected from a group consisting of monocyclic or polycyclic cycloalkyls, cycloalkenyls, aryls, and heterocyclic rings, said rings comprising from 4 to 8 atoms in a ring structure;

X represents CR, N, N(O), P, or As;

Y represents $CR_2$, NR, O, PR, S, AsR, or Se;

R, $R_1$, $R_2$, and $R_3$, for each occurrence, independently represent hydrogen, halogen, alkyl, alkenyl, alkynyl, hydroxyl, alkoxyl, silyloxy, amino, nitro, sulfhydryl. alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $—(CH_2)_m—R_{80}$;

$R_4$ and $R_5$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $—(CH_2)_m—R_{80}$;

A and B independently may be unsubstituted or substituted with $R_4$ and $R_5$, respectively, any number of times up to the limitations imposed by stability and the rules of valence;

$R_1$ and $R_3$ taken together may represent a ring comprising a total of 3–7 atoms in the backbone of said ring; said ring may comprise one or two heteroatoms in its backbone; and said ring may bear additional substituents or be unsubstituted;

$R_{80}$ represents an unsubstituted or substituted aryl, a cycloalkyl, a cycloalkenyl, a heterocycle, or a polycycle; and m is an integer in the range 0 to 8 inclusive.

These compounds are effective against a number of human and veterinary pathogens, including Gram-positive bacteria such as multiply-resistant staphylococci, streptococci and enterococci, and are expected to be active against Gram-negative organisms as well, such as Bacteroides spp. and Clostridia spp. species, and acid-fast organisms such as *Mycobacterium tuberculosis, Mycobacterium avium* and other Mycobacterium spp., and in organisms such as Mycoplasma spp. It is contemplated that the compounds of the invention can be used in combating and/or eliminating an infectious process caused by a microorganism in a host. In a particular aspect of the invention, the high potency and rapid bactericidal activity of these compounds make them attractive candidates for use in preventative therapies, such as sterilization of wounds prior to suture, as well as the sterilization of instruments prior to their use in surgical or other invasive procedures.

The invention is also directed to methods for treating a microbial infection in a host using the compositions of the invention. For instance, the subject method can be used to treat or prevent nosocomial bacteremia and skin/wound infection, or lower respiratory infection, endocarditis, and infections of the urinary tract. According to the present invention, treatment of such bacterial diseases comprises the administration of a pharmaceutical composition of the invention in a therapeutically effective amount to an individual in need of such treatment. The compositions may be administered parenterally by intramuscular, intravenous, intraocular, intraperitoneal, or subcutaneous routes; inhalation; orally, topically and intranasally.

Their antimicrobial activity also renders the compounds of the invention particularly useful in inhibiting unwanted microbial growth in tissue culture, especially those used for production of recombinant proteins or vectors for use in gene therapy.

The invention is also directed to pharmaceutical compositions, comprising one or more of the antimicrobial compounds of the invention as the active ingredient(s), which may be administered to a host animal.

I. Definitions

For convenience, certain terms employed in the specification, examples, and appended claims are collected here.

As used herein, the term "antimicrobial" refers to the ability of the compounds of the invention to prevent, inhibit or destroy the growth of microbes such as bacteria, fungi, protozoa and viruses.

The terms "quinoline" and "indole" are intended to mean compounds having the following general chemical structures, wherein the numbers around their peripheries indicate the art recognized positional designations for the two ring systems, and the capital letters contained within the individual rings are, likewise, their art recognized descriptors:

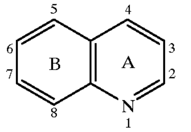
quinoline

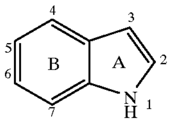
indole

An analog of a quinoline or indole is intended to mean any derivative of a quinoline or indole, in particular derivatives that adhere to the rules of valence in which a nitrogen is replaced by another atom, derivatives in which any of the carbon atoms are replaced with another heavy atom, and derivatives in which additional chemical groups are attached to any of the heavy atoms of the molecule. For example, the present invention contemplates the use of derivatives of 4-quinolinecarboxylic acid, quinazoline and 1H-indazole:

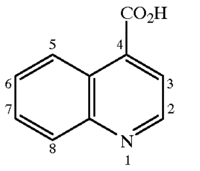
4-quinolinecarboxylic acid

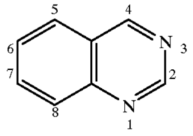
quinazoline

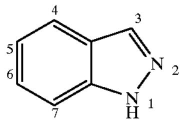
1H-indazole

The term "prodrug" is intended to encompass compounds which, under physiological conditions, are converted into the antibacterial agents of the present invention. A common method for making a prodrug is to select moieties, e.g., for any of the $R_1$–$R_5$ substituents of formula 1, which are hydrolyzed under physiological conditions to provide the desired. In other embodiments, the prodrug is converted by an enzymatic activity of the host animal or the target bacteria.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups (σ[P]=−0.66 for $NH_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine. an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $—CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $—CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $—CF_3$, —CN, or the like.

The term "carbocycle", as used herein, refers to an aromatic or non-aromatic ring in which each atom of the ring is carbon.

As used herein, the term "nitro" means $—NO_2$; the term "halogen" designates —F, —Cl, —Br or —I; the term "sulthydryl" means —SH; the term "hydroxyl" means —OH; and the term "sulfonyl" means $—SO_2—$.

The terms "amine" and "amino" are art-recognized and refer to both unsubstituted and substituted amines, e.g., a moiety that can be represented by the general formula:

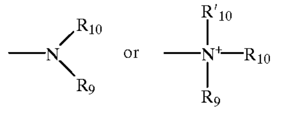

wherein $R_9$, $R_{10}$ and $R'_{10}$ each independently represent a hydrogen, an alkyl, an alkenyl, $—(CH_2)_m—R80$, or $R_9$ and $R_{10}$ taken together with the N atom to which they are attached complete a heterocycle having from 4 to 8 atoms in the ring structure; R80 represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or $—(CH_2)_m—R80$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

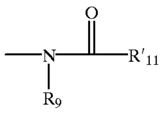

wherein $R_9$ is as defined above, and $R'_{11}$ represents a hydrogen, an alkyl, an alkenyl or $—(CH_2)_m—R80$, where m and R80 are as defined above.

The term "amido" is art recognized as an amino-substituted carbonyl and includes a moiety that can be represented by the general formula:

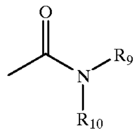

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and $—S—(CH_2)_m—R_{80}$, wherein m and $R_{80}$ are defined above. Representative alkylthio groups include methylthio, ethyl thio, and the like.

The term "carbonyl" is art recognized and includes such moieties as can be represented by the general formula:

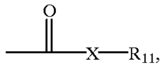 or 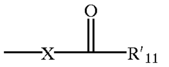

wherein X is a bond or represents an oxygen or a sulfur, and $R_{11}$ represents a hydrogen, an alkyl, an alkenyl, $—(CH_2)_m—R_{80}$ or a pharmaceutically acceptable salt, $R'_{11}$ represents a hydrogen, an alkyl, an alkenyl or $—(CH_2)_m—R_{80}$, where m and $R_{80}$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, $—O—(CH_2)_m—R_{80}$, where m and $R_{80}$ are described above.

The term "sulfonate" is art recognized and includes a moiety that can be represented by the general formula:

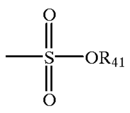

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

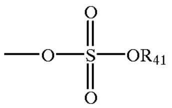

in which $R_{41}$ is as defined above.

The term "sulfonamido" is art recognized and includes a moiety that can be represented by the general formula:

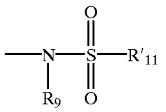

in which $R_9$ and $R'_{11}$ are as defined above.

The term "sulfamoyl" is art-recognized and includes a moiety that can be represented by the general formula:

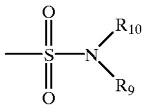

in which $R_9$ and $R_{10}$ are as defined above.

The terms "sulfoxido" or "sulfinyl", as used herein, refers to a moiety that can be represented by the general formula:

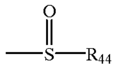

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

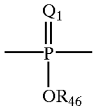

wherein $Q_1$ represented S or O, and $R_{46}$ represents hydrogen a lower alkyl or an aryl. When used to substitute, e.g., an alkyl, the phosphoryl group of the phosphorylalkyl can be represented by the general formula:

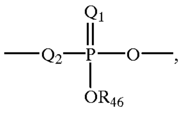, or 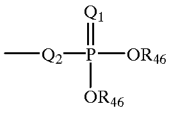

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

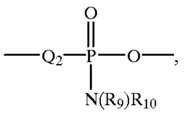, or 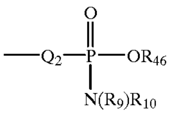

wherein $R_9$ and $R_{10}$ are as defined above, and $Q_2$ represents O, S or N.

A "phosphonamidite" can be represented in the general formula:

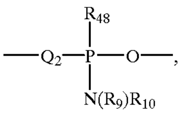, or 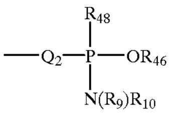

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_{80}$, m and $R_{80}$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to inhibit bacterial cell growth), wherein one or more simple variations of substituents are made which do not adversely affect the efficacy of the compound in inhibiting bacterial cell growth. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, $2^{nd}$ ed.; Wiley: New York, 1991).

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "ligand" refers to a compound that binds at the receptor site.

II. Compounds of the Invention.

As set out above, the present invention makes available a novel class of compounds represented by the general formula 1:

1

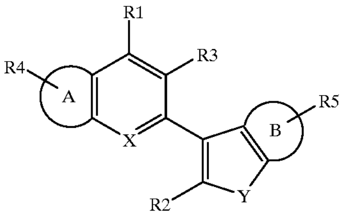

In preferred embodiments, the subject compounds are represented by general formula 1, with the proviso that when X represents N, Y represents NH or $NCH_3$, $R_1$ is —$CO_2H$ or —$CO_2$(lower alkyl), $R_2$ and $R_3$ each represent H, A and B each represent fused benzo rings, and $R_5$ is absent, then $R_4$ does not represent a single chlorine at the 8-position of the quinoline moiety.

In other preferred embodiments, the subject compounds are represented by general formula 1, as generally described above, with the proviso that when X represents N, Y represents NH or $NCH_3$, $R_2$ and $R_3$ each represent H, A and B each represent fused benzo rings, $R_5$ is absent, and $R_1$ comprises an $sp^2$-hybridized carbon at its point of attachment to the aromatic ring containing X, then said $sp^2$-hybridized carbon is itself bonded, via either single or double bonds, to no more than one oxygen atom.

In a further preferred embodiment, the subject compounds are represented by the general formula 1 as defined above, with the proviso that when X represents N, Y represents NH or NMe, $R_2$ and $R_3$ each represent H, and A and B each independently represent fused benzo rings, then the fused benzo ring B is substituted at least once by $R_5$.

In preferred embodiments of the compounds of general formula 1, the above general definitions apply, and B is substituted at least once by an $R_5$.

In preferred embodiments of the compounds of general formula 1, the above general definitions apply, and at least one of $R_2$ or $R_3$ is alkyl or aryl.

In preferred embodiments of the compounds of general formula 1, the above general definitions apply, except that when $R_1$ comprises an $sp^2$-hybridized carbon at its point of attachment to the aromatic ring containing X; said $sp^2$-hybridized carbon is itself bonded, via either single or double bonds, to no more than one oxygen atom.

Certain of the subject compounds can be classified on the basis of whether or not $R_1$ comprises a primary or secondary amine functional group. Merely for ease of reading, the application refers to "Class A" compounds, comprising a primary or secondary amine in $R_1$, and "Class B" compounds, which lack a primary or secondary amine in $R_1$. The presence of the amine, as demonstrated in the examples below, can be correlated with the potency of the instant compounds against Enterococci.

Class A Compounds

In certain embodiments, the subject compounds are represented by the general formula 1, A, B, X, Y, R, $R_2$, $R_3$, $R_4$, $R_5$ being defined above, and $R_1$ representing alkyl(NHR), —C(Z)N(R)(R'—NHR), —C(Z)O(R'—NHR), —$S(Z)_2N$(R)(R'—NHR), or —$P(Z)_2N$(R)(R'—NHR), wherein Z independently for each occurrence represents $(R)_2$, O, S, or NR, and R' represents a covalent linker connecting the two nitrogens explicitly depicted above in the definitions of $R_1$; R' preferably being an alkyl, e.g., preferably a cyclic, branched or straight chain aliphatic group of 2–10 bonds in length, cycloalkyl, alkenyls, cycloalkenyl, alkynyl, aryl, heteroalkyl, or heteroaryl moiety.

In a preferred embodiment, X is N and Y is NR. Where Y represents NR, that occurrence of R is preferably H, alkyl, alkylsulfonyl, arylsulfonyl, or —$(CH_2)_m$—$R_{80}$, wherein $R_{80}$ represents an aryl, a cycloalkyl, a cycloalkenyl, a heterocycle, or a polycycle, and m is an integer in the range 0 to 8 inclusive.

In more preferred embodiments, the subject compounds are represented by the general formula 1, substituents A, B, X, Y, and R being defined above:

wherein

- $R_1$ represents alkyl(NHR), —C(Z)N(R)(R'—NHR), —C(Z)O(R'—NHR), —$S(Z)_2N$(R)(R'—NHR), or —$P(Z)_2N$(R)(R'—NHR), wherein Z independently for each occurrence represents $(R)_2$, O, S, or NR;
- R' represents a covalent linker, preferably an alkyl, e.g., more preferably a cyclic, branched or straight chain aliphatic group of 2–10 bonds in length, cycloalkyl, alkenyls, cycloalkenyl, alkynyl, aryl, heteroalkyl, or heteroaryl moiety;
- $R_2$ and $R_3$, independently for each occurrence, represent H or a hydrophobic aliphatic group, and more preferably $R_2$ and $R_3$ represent H, $C_1$–$C_6$ alkyl, or aryl, and even more preferably H or —$CH_3$;
- $R_4$ independently for each occurrence represents $C_1$–$C_6$ alkyl, 1-alkenyl, 1-alkynyl, aryl, heteroalkyl, heteroaryl, —OR, —$OCF_3$, —$OC(R)_2OR$, —$C(R)_2$ OR, or a small hydrophobic moiety (e.g. a halogen or halogenated alkyl), though preferably $R_4$ is a halogen, trihalogenated methyl, or —$CCR_{60}$ ($R_{60}$ being described below) and more preferably $R_4$ is a halogen, trihalogenated methyl; and
- $R_5$ independently for each occurrence represents a small hydrophobic moiety (e.g. preferably a halogen or a halogenated alkyl, such as a trihalogenated methyl such as —$CF_3$).

In preferred embodiments, when R1 represents —C(Z)O (R'—NHR), X represents N, Y represents NH or $NCH_3$, $R_2$ and $R_3$ each represent H, A and B each represent fused benzo rings, and $R_5$ is absent, then $R_4$ does not represent a single chlorine at the 8-position of the quinoline moiety.

In preferred embodiments of the compounds of class A, the above general definitions apply, and B is substituted at least once by $R_5$.

In preferred embodiments of the compounds of class A, the above general definitions apply, and at least one of $R_2$ or $R_3$ is alkyl or aryl.

In preferred embodiments of the compounds of class A, the above definitions apply, and $R_1$ represents alkyl(NHR), —C(Z)N(R)(R'—NHR), —$S(Z)_2N$(R)(R'—NHR), or —$P(Z)_2N$(R)(R'—NHR).

In more preferred embodiments of this class of compounds, the subject antibacterial compounds are represented by general formula 2:

2

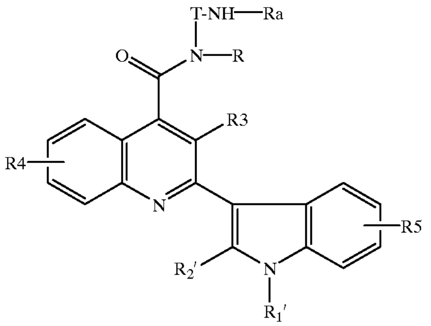

wherein

R, $R_a$, $R_3$, $R_1$', and $R_2$', for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

$R_4$, and $R_5$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

T represents a covalent linker, preferably being an alkyl, e.g., preferably a cyclic, branched or straight chain aliphatic group of 2–10 bonds in length, cycloalkyl, alkenyls, cycloalkenyl, alkynyl, aryl, heteroalkyl, or heteroaryl moiety;

the B-rings of the 2-quinolinyl and 3-indolyl moieties may be unsubstituted or substituted between one and four times inclusive by $R_4$ and $R_5$, respectively;

$R_{80}$ represents an aryl, a cycloalkyl, a cycloalkenyl, a heterocycle, or a polycycle; and m is an integer in the range 0 to 8 inclusive.

In preferred embodiments of the compounds of formula 2:

$R_2$' and $R_3$ independently for each occurrence represent H or a hydrophobic aliphatic group, and more preferably $R_2$' and $R_3$ represent H, $C_1$–$C_6$ alkyl, or aryl, and even more preferably H or —$CH_3$;

$R_4$ independently for each occurrence represents $C_1$–$C_6$ alkyl, 1-alkenyl, 1-alkynyl, aryl, —OR, —$OCF_3$, —OC$(R)_2$OR, —$C(R)_2$OR, or a small hydrophobic moiety (e.g. a halogen or halogenated alkyl), preferably $R_4$ is a halogen, trihalogenated methyl or —$CCR_{60}$ ($R_{60}$ being described below), and more preferably $R_4$ is a halogen or trihalogenated methyl; and $R_5$ independently for each occurrence represents a small hydrophobic moiety (e.g. a halogen or a halogenated alkyl such as a trihalogenated methyl).

In more preferred embodiments of this class of compounds, the subject antibacterial compounds are represented by the general formula below:

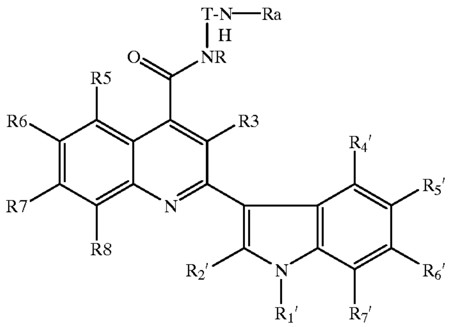

wherein

R, $R_a$, $R_3$, $R_5$, $R_6$, $R_7$, $R_8$, $R_1$', $R_2$', $R_4$', $R_5$', $R_6$', and $R_7$', for each occurrence represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;

T represents a covalent linker, preferably being an alkyl, e.g., preferably a cyclic, branched or straight chain aliphatic group of 2–10 bonds in length, cycloalkyl, alkenyls, cycloalkenyl, alkynyl, aryl, heteroalkyl, or heteroaryl moiety;

$R_{80}$ represents an aryl, a cycloalkyl, a cycloalkenyl, a heterocycle, or a polycycle; and m is an integer in the range 0 to 8 inclusive.

In preferred embodiments of the compounds represented above:

$R_2$' and $R_3$ independently for each occurrence represent H or a hydrophobic aliphatic group, and more preferably $R_2$' and $R_3$ represent H, $C_1$–$C_6$ alkyl, or aryl, and even more preferably H or —$CH_3$;

$R_5$, $R_6$, $R_7$, and $R_8$ independently for each occurrence represent H, $C_1$–$C_6$ alkyl, 1-alkenyl, 1-alkynyl, aryl, —OR, —$OCF_3$, —$OC(R)_2$OR, —$C(R)_2$OR, or a small hydrophobic moiety (e.g. a halogen or halogenated alkyl), and more preferably they are selected from the group comprising halogen, trihalogenated methyl or —$CCR_{60}$ ($R_{60}$ being described below); and $R_4$', $R_5$', $R_6$', and $R_7$' represent, independently for each occurrence, H, a small hydrophobic moiety (e.g. a halogen or a halogenated alkyl such as a trihalogenated methyl).

In more preferred embodiments, the subject antibacterial compounds are represented by the following general formula:

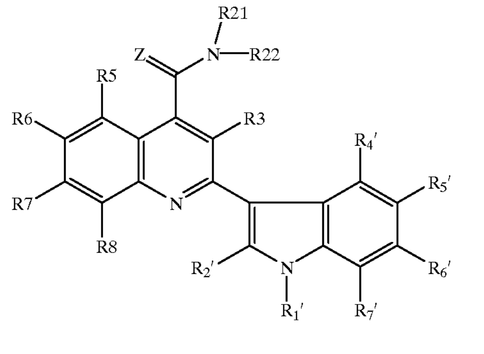

wherein

Z represents O or $(R)_2$;

R, $R_3$, $R_5$, $R_6$, $R_7$, $R_8$, $R_{21}$, $R_{22}$, $R_1'$, $R_2'$, $R_4'$, $R_5'$, $R_6'$, and $R_7'$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silt, thioalkyl, alkylsulfonyl, aryisulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $—(CH_2)_m—R_{80}$;

$R_{80}$ represents an aryl, a cycloalkyl, a cycloalkenyl, a heterocycle, or a polycycle; and m is an integer in the range 0 to 8 inclusive.

In preferred embodiments, Z represents O or $(R)_2$;

R is as defined above;

$R_2'$ and $R_3$, independently for each occurrence, represent H or a hydrophobic aliphatic group, and more preferably $R_2'$ and $R_3$ represent H, $C_1$–$C_6$ alkyl, or aryl, and even more preferably H or $—CH_3$;

$R_5$, $R_6$, $R_7$ and $R_8$ independently for each occurrence represent H, $C_1$–$C_6$ alkyl, 1-alkenyl, 1-alkynyl, aryl, —OR, $—OCF_3$, $—OC(R)_2OR$, $—C(R)_2OR$, or a small hydrophobic moiety (e.g. a halogen or halogenated alkyl), and more preferably $R_5$, $R_6$, $R_7$ and $R_8$ each represent a halogen, trihalogenated methyl or $—CCR_{60}$ ($R_{60}$ being described below);

$R_1'$ represents H, alkyl, p-toluenesulfonyl, $—(CH_2)_nN$(Phth), or $—(CH_2)_nN(R)_2$ wherein n is an integer in the range 1 to 6 inclusive;

$R_4'$, $R_5'$, $R_6'$ and $R_7'$ independently for each occurrence represent H, or a small hydrophobic moiety (e.g. a halogen or a halogenated alkyl, such as a trihalogenated methyl); and $N(R_{21})R_{22}$ taken together represents a heterocycle comprising from 4 to 8 members inclusive; or $R_{21}$ and $R_{22}$ independently for each occurrence represent H, alkyl, heteroalkyl, aryl, heteroaryl, or $—(CH_2)_m—R_{80}$, though more preferably $—(CH_2)_nNH(R_1$40 ), wherein n is an integer in the range 1 to 6 inclusive, or ortho-, meta-, or para-$CH_2C_6H_4CH_2NH(R_1')$, or 2-, 3-, or 4-(($R_1'$)aminomethyl)cyclohexylmethyl, or 2-, 3-, or 4-(($R_1'$)amino)cyclohexyl; with the proviso that $R_{21}$ and $R_{22}$ are selected such that $N(R_{21})R_{22}$ comprises a primary or secondary amine.

The preferred subclass of compounds described above comprises compounds with minimum inhibitory concentrations (MICs) below 25 μg/mL against certain Gram-positive bacteria, especially methicillin-resistant *Staphylococcus aureus*, ciprofloxacin-resistant *Staphylococcus aureus*, vancomycin-resistant Enterococcus spp., and/or *Streptococcus pneumoniae*. Additionally, individual members of the preferred subclass of compounds described above have MICs below 10 μg/mL, and more preferably MIC values less than 7 μg/mL or even less than 1 μg/mL against such bacteria.

Class B Compounds

The absence of a primary or secondary amine in the substituent at the 4-position of the quinoline in general structure 2 was tolerated with respect to maintenance of activity against MRSA and PRP. Other suitable groups could be selected to increase the polarity and/or stability of the resulting compounds. Thus, in yet other embodiments, the subject compounds are represented by the general formula 1, A, B, X, Y, R, $R_2$, $R_3$, $R_4$, $R_5$ being defined in the general formula above, and $R_1$ representing H, Me, lower alkyl, halogen, —C(Z)OR, $—C(Z)N(R)_2$, $—S(Z)_2N(R)_2$, or $—P(Z)_2N(R)_2$, wherein Z independently for each occurrence represents $(R)_2$, O, S, or NR.

In a preferred embodiment, X is N and Y is NR. For those embodiments wherein Y represents NR, that occurrence of R is preferably H, alkyl, alkylsulfonyl, arylsulfonyl, or $—(CH_2)_m—R_{80}$, wherein $R_{80}$ represents an aryl, a cycloalkyl, a cycloalkenyl, a heterocycle, or a polycycle, and m is an integer in the range 0 to 8 inclusive.

In certain preferred embodiments, R1 represents hygrogen or halogen, X represents N, Y represents NH or $NCH_3$, $R_2$ and $R_3$ each independently represent H, lower alkyl, or aryl, A and B each represent fused benzo rings.

In preferred embodiments, when R1 represents —C(Z)OR, X represents N, Y represents NH or $NCH_3$, $R_2$ and $R_3$ each represent H, A and B each represent fused benzo rings, and $R_5$ is absent, then $R_4$ does not represent a single chlorine at the 8-position of the quinoline moiety.

In preferred embodiments of the compounds of class B, the above definitions apply, and B is substituted at least once by an $R_5$.

In preferred embodiments of the compounds of class B, the above definitions apply, and at least one of $R_2$ or $R_3$ is alkyl or aryl.

In more preferred embodiments, the subject compounds are represented by the general formula 1, A, B, X, Y, and R being generally defined above:

wherein $R_1$ represents H, Me, lower alkyl, halogen, —C(Z)OR, $—C(Z)N(R)_2$, $—S(Z)_2N(R)_2$, or $—P(Z)_2N(R)_2$;

Z independently for each occurrence represents $(R)_2$, or O;

$R_2$ and $R_3$ independently for each occurrence represent H or a hydrophobic aliphatic group, and more preferably $R_2$ and $R_3$ represent H, $C_1$–$C_6$ alkyl, or aryl, and even more preferably H or $—CH_3$;

$R_4$ independently for each occurrence represents $C_1$–$C_6$ alkyl, 1-alkenyl, 1-alkynyl, aryl, —OR, $—OCF_3$, $—OC(R)_2OR$, $—C(R)_2OR$, or a small hydrophobic moiety (e.g. a halogen or halogenated alkyl), and more preferably $R_4$ is a halogen, trihalogenated methyl or $—CCR_{60}$ ($R_{60}$ being described below); and $R_5$ independently for each occurrence represents a small hydrophobic moiety (e.g. a halogen or a halogenated alkyl, especially a trihalogenated methyl), $—C(O)N(R)_2$, —CN, $—NO_2$, —OH, —OR, $—O_2C$-aryl, or $—O_2C$-alkyl.

In further preferred embodiments, the above description applies wherein $R_1$ represents H, halogen, Me, lower alkyl, —C(Z)N(R)$_2$, —S(Z)$_2$N(R)$_2$, or —P(Z)$_2$N(R)$_2$.

In another preferred embodiment, the subject compounds are represented by 1, wherein X represents N; Y represents NH or NMe; $R_2$ and $R_3$ each independently represent H; A and B each independently represent a fused benzo ring; and $R_5$ is present at least once.

In certain preferred embodiments, the subject antibacterial compounds are represented by general formula 3:

3

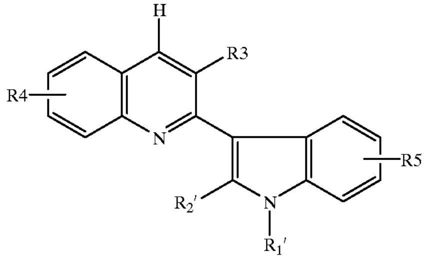

wherein $R_3$, $R_1'$, and $R_2'$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

$R_4$, and $R_5$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

the B-rings of the 2-quinolinyl and 3-indolyl moieties may be unsubstituted or substituted between one and four times inclusive by $R_4$ and $R_5$, respectively;

$R_{80}$ represents an aryl, a cycloalkyl, a cycloalkenyl, a heterocycle , or a polycycle; and m is an integer in the range 0 to 8 inclusive.

In more preferred embodiments of the compounds of formula 3:

$R_1'$ represents H, alkyl, p-toluenesulfonyl, —$(CH_2)_n$N(Phth), or —$(CH_2)_n$N(R)$_2$ wherein n is an integer in the range 1 to 6 inclusive;

$R_2'$ and $R_3$ independently for each occurrence represent H or a hydrophobic aliphatic group, and more preferably $R_2'$ and $R_3$ represent H, $C_1$–$C_6$ alkyl, or aryl, and even more preferably H or —$CH_3$;

$R_4$ independently for each occurrence represents $C_1$–$C_6$ alkyl, 1-alkenyl, 1-alkynyl, aryl, —OR, —$OCF_3$, —OC(R)$_2$OR, —C(R)$_2$OR, or a small hydrophobic moiety (e.g. a halogen or halogenated alkyl), and more preferably $R_4$ represents a halogen, trihalogenated methyl or $CCR_{60}$ ($R_{60}$ being described below); and $R_5$ independently for each occurrence represents a small hydrophobic moiety (e.g. a halogen or a halogenated alkyl, especially a trihalogenated methyl), —C(O)N(R)$_2$, —CN, —$NO_2$, —OH, —OR, —$O_2$Caryl, or —$O_2$Calkyl.

In more preferred embodiments, the subject antibacterial compounds are represented by the following general formula:

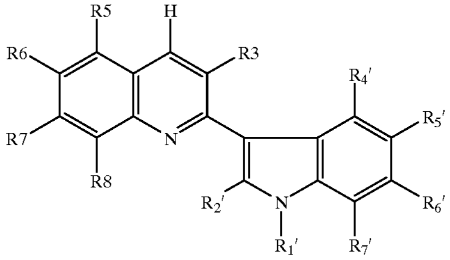

wherein $R_1'$ represents H, alkyl, p-toluenesulfonyl, —$(CH_2)_n$N(Phth), or —$(CH_2)_n$N(R)$_2$ wherein n is an integer in the range 1 to 6 inclusive;

$R_2'$ and $R_3$ independently for each occurrence represent H, $C_1$–$C_6$ alkyl, or aryl;

$R_5$, $R_6$, $R_7$, and $R_8$ independently for each occurrence represent H, $C_1$–$C_6$ alkyl, 1-alkenyl, 1-alkynyl, aryl, —C(O)N(R)$_2$, or a small hydrophobic moiety (e.g. a halogen or halogenated alkyl, preferaby a halogen or trihalogenated methyl); and $R_4'$, $R_5'$, $R_6'$ and $R_7'$ independently for each occurrence represent H, a small hydrophobic moiety (e.g. a halogen or halogenated alkyl, preferably a halogen or trihalogenated methyl), —C(O)$NR_2$, —CN, —$NO_2$, —OH, —OR, —$O_2$Caryl, or —$O_2$Calkyl.

The preferred subclass of compounds described above comprises compounds with minimum inhibitory concentrations (MICs) below 10 $\mu$g/mL against certain Gram-positive bacteria, especially methicillin-resistant *Staphylococcus aureus*, ciprofloxacin-resistant *Staphylococcus aureus*, and/or *Streptococcus pnelumoniae*. In more preferred embodiments, members of this subclass of compounds have MIC values less than 7 $\mu$g/mL or even less than 1 $\mu$g/mL against such bacteria, particularly against methicillin-resistant *Staphylococcus aureus* and/or ciprofloxacin-resistant *Staphylococcus aureus*.

In preferred embodiments, the subject antibacterial compounds are represented by general formula 4:

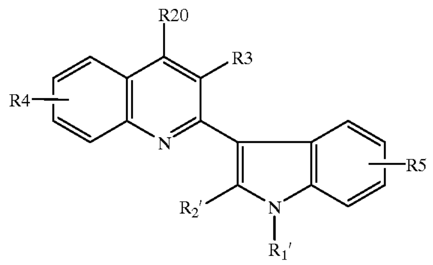

4 wherein $R_{20}$ represents H, Me, lower alkyl, halogen, —C(Z)OR, —C(Z)N(R)$_2$, —S(Z)$_2$N(R)$_2$, or —P(Z)$_2$N(R)$_2$, wherein Z independently for each occurrence represents (R)$_2$, O, S, or NR;

R, $R_3$, $R_1$', and $R_2$', for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

$R_4$, and $R_5$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

the B-rings of the 2-quinolinyl and 3-indolyl moieties may be unsubstituted or substituted between one and four times inclusive by $R_4$ and $R_5$, respectively;

$R_{80}$ represents an aryl, a cycloalkyl, a cycloalkenyl, a heterocycle , or a polycycle; and m is an integer in the range 0 to 8 inclusive.

In preferred embodiments of the compounds 4, when $R_{20}$ represents —C(Z)OR, X represents N, Y represents NH or $NCH_3$, $R_2$ and $R_3$ each represent H, A and B each represent fused benzo rings, and $R_5$ is absent, then $R_4$ does not represent a single chlorine at the 8-position of the quinoline moiety.

In preferred embodiments of the subject compounds 4, the above general definitions apply, and $R_5$ is present at least once.

In preferred embodiments of the subject compounds 4, the above general definitions apply, and at least one of $R_2$ or $R_3$ is alkyl or aryl.

In preferred embodiments of the compounds 4, the above definitions apply, and $R_{20}$ represents —C(Z)N(R)$_2$, —S(Z)$_2$N(R)$_2$, or —P(Z)$_2$N(R)$_2$.

In preferred embodiments of the compounds 4, the above definitions apply, and $R_{20}$ represents halogen.

In certain preferred embodiements, the subject antibacterial compounds are represented by general formula 4, wherein $R_{20}$ represents fluorine, chlorine, bromine, or iodine;

$R_1$' represents H, alkyl, p-toluenesulfonyl, —$(CH_2)_n$N (Phth), or —$(CH_2)_n$N(R)$_2$ wherein n is an integer in the range 1 to 6 inclusive;

$R_2$' and $R_3$ independently for each occurrence represent H, Me, $C_1$–$C_6$ alkyl, or aryl;

the B-rings of the 2-quinolinyl and 3-indolyl moieties may be unsubstituted or substituted between one and four times inclusive by $R_4$ and $R_5$, respectively;

$R_4$ independently for each occurrence represents Me, $C_1$–$C_6$ alkyl, 1-alkenyl, 1-alkynyl, aryl, —OR, —$OCF_3$, —$OCR_2OR$, —$CR_2OR$, or a small hydrophobic moiety (e.g. a halogen or a halogenated alkyl, preferably a trihalogenated methyl); and $R_5$ independently for each occurrence represents a small hydrophobic moiety (e.g. a halogen or a halogenated alkyl, preferably a trihalogenated methyl), —CN, —$NO_2$, —OH, —OR, —$O_2$Caryl, or —$O_2$Calkyl.

In more preferred embodiments, the above definitions apply, and $R_{20}$ is chlorine.

More preferably, the subject antibacterial compounds are represented by general formula 4, wherein $R_{20}$ represents H, Me, lower alkyl, halogen, —C(Z)OR, —C(Z)N(R)$_2$, —S(Z)$_2$N(R)$_2$, or —P(Z)$_2$N(R)$_2$, wherein Z independently for each occurrence represents (R)$_2$, O, S, or NR;

$R_1$' represents H, alkyl, p-toluenesulfonyl, —$(CH_2)_n$N (Phth), or —$(CH_2)_n$N(R)$_2$ wherein n is an integer in the range 1 to 6 inclusive;

$R_2$' and $R_3$ independently for each occurrence represent H, Me, $C_1$–$C_6$ alkyl, or aryl;

the B-rings of the 2-quinolinyl and 3-indolyl moieties may be unsubstituted or substituted between one and four times inclusive by $R_4$ and $R_5$, respectively;

$R_4$ independently for each occurrence represents Me, $C_1$–$C_6$ alkyl, 1-alkenyl, 1-alkynyl, aryl, —OR, —$OCF_3$, —$OCR_2OR$, —$CR_2OR$, or a small hydrophobic moiety (e.g. a halogen or a halogenated alkyl, preferably a trihalogenated methyl); and $R_5$ independently for each occurrence represents a small hydrophobic moiety (e.g. a halogen or a halogenated alkyl, preferably a trihalogenated methyl), —CN, —$NO_2$, —OH, —OR, —$O_2$Caryl, or —$O_2$Calkyl.

In preferred embodiments of the subject compounds, the above general definitions apply, and $R_5$ is present at least once.

In preferred embodiments of the subject compounds, the above general definitions apply, and at least one of $R_2$ or $R_3$ is alkyl or aryl.

In still further preferred embodiments, the subject antibacterial compounds are represented by general formula 4 and the preceding definitions, and $R_{20}$ represents H, Me, lower alkyl, halogen, —C(Z)N(R)$_2$, —S(Z)$_2$N(R)$_2$, or —P(Z)$_2$N(R)$_2$, wherein Z independently for each occurrence represents (R)$_2$, O, S, or NR.

In further preferred embodiments, the above descriptions based on 4 apply wherein $R_{20}$ represents H, Me, lower alkyl, halogen, —C(Z)OR, —C(Z)N(R)$_2$, —S(Z)$_2$N(R)$_2$, or —P(Z)$_2$N(R)$_2$, wherein Z independently for each occurrence represents (R)$_2$, O, S, or NR; and $R_5$ is present at least once.

In additional preferred embodiments, the subject antibacterial compounds are represented by the following general formula:

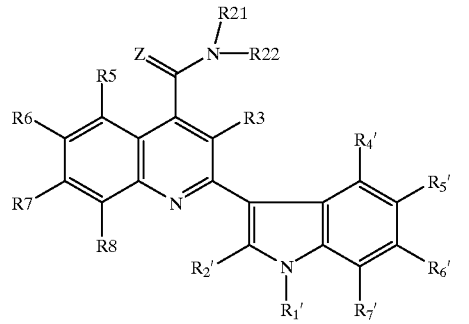

wherein

Z represents O or $(R)_2$;

$R_2'$ and $R_3$ independently for each occurrence represent H or a hydrophobic aliphatic group, and more preferably $R_2'$ and $R_3$ represent H, $C_1$–$C_6$ alkyl, or aryl, and even more preferably H or —$CH_3$;

$R_5$, $R_6$, $R_7$ and $R_8$ independently for each occurrence represent H, $C_1$–$C_6$ alkyl, 1-alkenyl, 1-alkynyl, aryl, —OR, —$OCF_3$, —$OC(R)_2OR$, —$C(R)_2OR$, or a small hydrophobic moiety (e.g. a halogen or halogenated alkyl), and more preferably $R_5$, $R_6$, $R_7$ and $R_8$ represent H, halogen, trihalogenated methyl, or —$CCR_{60}$ ($R_{60}$ being described below);

$R_1'$ represents H, alkyl aryl, p-toluenesulfonyl, —$(CH_2)_n$N(Phth), or —$(CH_2)_nN(R)_2$ wherein n is an integer in the range 1 to 6 inclusive;

$R_4'$, $R_5'$, $R_6'$, and $R_7'$ independently for each occurrence represent H, or a small hydrophobic moiety (e.g. a halogen or a halogenated alkyl, especially a trihalogenated methyl); and $R_{21}$ and $R_{22}$ independently for each occurrence represent H, alkyl, heteroalkyl, aryl, heteroaryl, ortho-, meta-, or para-$CH_2C_6H_4O(R_1')$, ortho-, meta-, or para-$CH_2C_6H_4OMe$, ortho-, meta-, or para-$CH_2C_6H_4OH$, (2-benzimidazolyl)$CH_2$-, 2-, 3-, or 4-methoxyphenyl, 2-, 4-hydroxyphenyl, or 2-, 3-, or 4-($(R_1')_2NCH_2$)cyclohexylmethyl, or 2-, 3-, or 4-($(R_1')_2N$)cyclohexyl; or $N(R_{21})R_{22}$ taken together represents a heterocycle comprising from 4 to 8 members inclusive; with the proviso that, regardless of the specific identity of $N(R_{21})R_{22}$, it does not include a primary or secondary amine.

The preferred subclass of compounds described above comprises compounds with minimum inhibitory concentrations (MICs) below 10 μg/mL against certain Gram-positive bacteria, especially methicillin-resistant *Staphylococcus aureus*, ciprofloxacin-resistant *Staphylococcus aureus*, and/or *Streptococcus pneumoniae*. Additionally, individual members of the preferred subclass of compounds described above have MICs less than 7 μg/mL or even less than 1 μg/mL against such bacteria.

Alkynyl-substituted

In still other embodiments, the subject antibacterial compounds are represented by the following general formula:

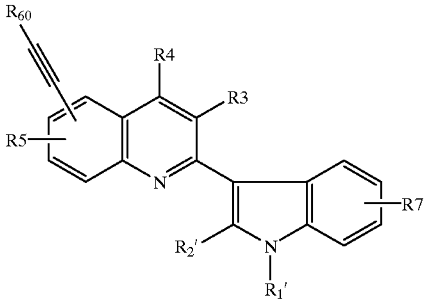

wherein $R_3$, $R_4$, $R_1'$, $R_2'$, and $R_{60}$ for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

$R_5$, and $R_7$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

the B-ring of the 2-quinolinyl moiety may be unsubstituted beyond the alkynyl group or substituted between one and three times inclusive by $R_5$;

the B-ring of the 3-indolyl moiety may be unsubstituted or substituted between one and four times inclusive by $R_7$;

$R_{80}$ represents an aryl, a cycloalkyl, a cycloalkenyl, a heterocycle , or a polycycle; and m is an integer in the range 0 to 8 inclusive.

In preferred embodiments, $R_{60}$ represents alkyl, alkenyl, alkynyl, hydroxyl, alkoxyl, or —C(Z)—$R_6$; where $R_6$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl; Z independently for each occurrence represents $(R)_2$, O, S, or NR; and R is H or a lower alkyl.

In more preferred embodiments, the subject antibacterial compounds are represented by the following general formula:

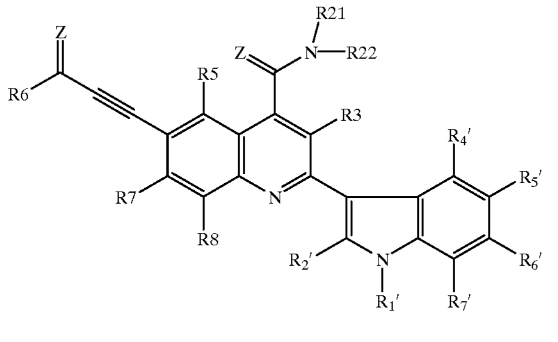

wherein

Z independently for each occurrence represents $(R)_2$, O, S, or NR;

$R_5$, $R_7$, and $R_8$ independently for each occurrence represent H, Me, $C_1$–$C_6$ alkyl, heteroalkyl, 1-alkenyl, 1-alkynyl, aryl, heteroaryl, —OR, —$OCF_3$, —$OCR_2OR$, —$CR_2OR$, —$CO_2R$, or a small hydrophobic moiety (e.g. a halogen or a halogenated alkyl, preferably a trihalogenated methyl);

$R_6$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl;

$R_1$' represents H, alkyl, aryl, p-toluenesulfonyl, —$(CH_2)_n$N(Phth), or —$(CH_2)_nN(R)_2$; wherein n is an integer in the range 1 to 6 inclusive;

$R_2$' and $R_3$ independently for each occurrence represent H, Me, $C_1$–$C_6$ alkyl, or aryl;

$R_4$', $R_5$', $R_6$' and $R_7$' independently for each occurrence represent H, a small hydrophobic moiety (e.g. a halogen or a halogenated alkyl, preferably a trihalogenated methyl), —$C(O)NR_2$, —CN, —$NO_2$, —OH, —OR, —$O_2$Caryl, or —$O_2$Calkyl; and $R_{21}$ and $R_{22}$ independently for each occurrence represent H, alkyl, heteroalkyl, aryl, heteroaryl, —$(C_2)_m$—$R_{80}$, and more preferably —$(CH_2)_nN(R_1')_2$, wherein n is an integer in the range 1 to 6 inclusive, ortho-, meta-, or para-$CH_2C_6H_4CH_2N(R_1')_2$, ortho-, meta-, or para-$C_6H_4CH_2N(R_1')_2$, ortho-, meta-, or para-$CH_2C_6H_4O(R_1')$, ortho-, meta-, or para-$CH_2$ortho-, meta-, or para-$CH_2C_6H_4OH$, (2-benzimidazolyl)$CH_2$-, 2-, 3-, or 4-($R_1$')Ophenyl, 2-, 3-, or 4-methoxyphenyl, 2-, 3-, or 4-hydroxyphenyl, or 2-, 3-, or 4-($(R_1')_2NCH_2$)cyclohexylmethyl, or 2-, 3-, or 4-($(R_1')_2N$)cyclohexylmethyl; or $N(R_{21})R_{22}$ taken together represent a heterocycle comprising from 4 to 8 members inclusive.

In additional preferred embodiments, the subject antibacterial compounds are represented by the following general formula:

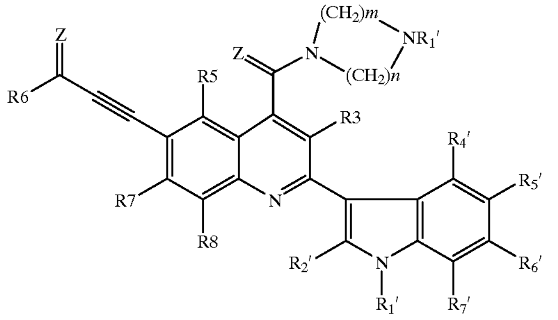

wherein

Z independently for each occurrence represents $(R)_2$, O, S, or NR;

$R_5$, $R_7$, and $R_8$ independently for each occurrence represent H, Me, $C_1$–$C_6$ alkyl, heteroalkyl, 1-alkenyl, 1-alkynyl, aryl, heteroaryl, —OR, —$OCF_3$, —$OCR_2OR$, —$CR_2OR$, —$CO_2R$, or a small hydrophobic moiety (e.g. a halogen or a halogenated alkyl, preferably a trihalogenated methyl);

$R_6$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl;

$R_1$' represents H, alkyl, aryl, p-toluenesulfonyl, —$(CH_2)_n$N(Phth), or —$(CH_2)_nN(R)_2$ wherein n is an integer in the range 1 to 6 inclusive;

$R_2$' and $R_3$ independently for each occurrence represent H, Me, $C_1$–$C_6$ alkyl, or aryl;

$R_4$', $R_5$', $R_6$' and $R_7$' independently for each occurrence represent H, a small hydrophobic moiety (e.g. a halogen or a halogenated alkyl, preferably a trihalogenated methyl), —$C(O)NR_2$, —CN, —$NO_2$, —OH, —OR, —$O_2$Caryl, or —$O_2$Calkyl; and m and n are integers independently selected from the range 1 to 4 inclusive.

The preferred subclasses of compounds described above comprises compounds with minimum inhibitory concentrations (MICs) below 10 μg/mL against certain Gram-positive bacteria, especially methicillin-resistant *Staphylococcus aureus*, ciprofloxacin-resistant *Staphylococcus aureus*, vancomycin-resistant Enterococcus spp., or *Streptococcus pneumoniae*. Additionally, members of this subclass of compounds have MIC values less than 7 μg/mL or even less than 1 μg/mL against such bacteria, particularly against methicillin- and/or ciprofloxacin-resistant *Staphylococcus aureus*.

In more preferred embodiments, the subject antibacterial compounds are represented by the following general formula:

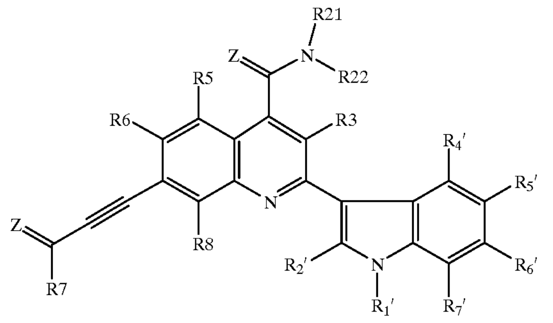

wherein

Z independently for each occurrence represents $(R)_2$, O, S, or NR;

$R_5$, $R_6$, and $R_8$ independently for each occurrence represent H, Me, $C_1$–$C_6$ alkyl, heteroalkyl, 1-alkenyl, 1-alkynyl, aryl, heteroaryl, —OR, —$OCF_3$, —$OCR_2OR$, —$CR_2OR$, —$CO_2R$, or a small hydrophobic moiety (e.g. a halogen or a halogenated alkyl, preferably a trihalogenated methyl);

$R_7$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl;

$R_1'$ represents H, alkyl, aryl, p-toluenesulfonyl, —$(CH_2)_n$N(Phth), or —$(CH_2)_nN(R)_2$; wherein n is an integer in the range 1 to 6 inclusive;

$R_1'$ and $R_3$ independently for each occurrence represent H, Me, $C_1$–$C_6$ alkyl, or aryl;

$R_4'$, $R_5'$, $R_6'$ and $R_7'$ independently for each occurrence represent H, a small hydrophobic moiety (e.g. a halogen or a halogenated alkyl, preferably a trihalogenated methyl), —$C(O)NR_2$, —CN, —$NO_2$, —OH, —OR, —$O_2$Caryl, or —$O_2$Calkyl; and $R_{21}$ and $R_{22}$ independently for each occurrence represent H, alkyl, heteroalkyl, aryl, heteroaryl, —$(CH_2)_m$—$R_{80}$, and more preferably —$(CH_2)_nN(R_1')_2$, wherein n is an integer in the range 1 to 6 inclusive, ortho-, meta-, or para-$CH_2C_6H_4CH_2N(R_1')_2$, ortho-, meta-, or para-$C_6H_4CH_2N(R_1')_2$, ortho-, meta-, or para-$CH_2C_6H_4O(R_1')$, ortho-, meta-, or para-$CH_2C_6H_4OMe$, ortho-, meta-, orpara-$CH_2C_6H_4OH$, (2-benzimidazolyl)$CH_2$—, 2-, 3-, or 4-$(R_1')$Ophenyl, 2-, 3-, or 4-methoxyphenyl, 2-, 3-, or 4-hydroxyphenyl, or 2-, 3-, or 4-$((R_1')_2NCH_2)$cyclohexylmethyl, or 2-, 3-, or 4-$((R_1')_2N)$cyclohexylmethyl; or $N(R_{21},)R_{22}$ taken together represent a heterocycle comprising from 4 to 8 members inclusive.

In additional preferred embodiments, the subject antibacterial compounds are represented by the following general formula:

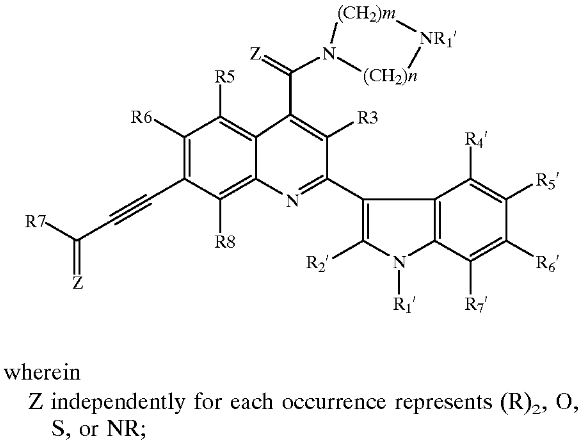

wherein

Z independently for each occurrence represents $(R)_2$, O, S, or NR;

$R_5$, $R_6$, and $R_8$ independently for each occurrence represent H, Me, $C_1$–$C_6$ alkyl, heteroalkyl, 1-alkenyl, 1-alkynyl, aryl, heteroaryl, —OR, —$OCF_3$, —$OCR_2OR$, —$CR_2OR$, —$CO_2R$, or a small hydrophobic moiety (e.g. a halogen or a halogenated alkyl, preferably a trihalogenated methyl);

$R_7$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl;

$R_1'$ represents H, alkyl, aryl, p-toluenesulfonyl, —$(CH_2)_n$N(Phth), or —$(CH_2)_nN(R)_2$ wherein n is an integer in the range 1 to 6 inclusive;

$R_2'$ and $R_3$ independently for each occurrence represent H, Me, $C_1$–$C_6$ alkyl, or aryl;

$R_4'$, $R_5'$, $R_6'$ and $R_7'$ independently for each occurrence represent H, a small hydrophobic moiety (e.g. a halogen or a halogenated alkyl, preferably a trihalogenated methyl), —$C(O)NR_2$, —CN, —$NO_2$, —OH, —OR, —$O_2$Caryl, or —$O_2$Calkyl; and m and n are integers independently selected from the range 1 to 4 inclusive.

In further preferred embodiments, the subject antibacterial compounds are represented by the following general formula:

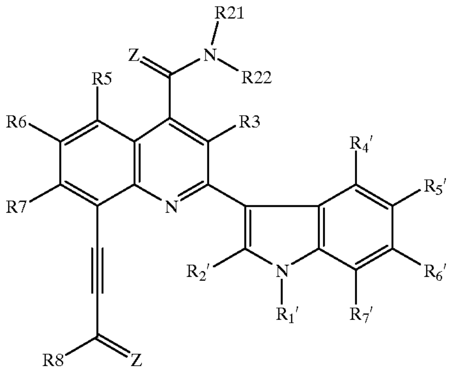

wherein

Z independently for each occurrence represents $(R)_2$, O, S, or NR;

$R_5$, $R_6$, and $R_7$ independently for each occurrence represent H, Me, $C_1$–$C_6$ alkyl, heteroalkyl, 1-alkenyl, 1-alkynyl, aryl, heteroaryl, —OR, —$OCF_3$, —$OCR_2OR$, —$CR_2OR$, —$CO_2R$, or a small hydrophobic moiety (e.g. a halogen or a halogenated alkyl, preferably a trihalogenated methyl);

$R_8$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl;

$R_1'$ represents H, alkyl, aryl, p-toluenesulfonyl, —$(CH_2)_n$(Phth), or —$(CH_2)_nN(R)_2$ wherein n is an integer in the range 1 to 6 inclusive;

$R_2'$ and $R_3$ independently for each occurrence represent H, Me, $C_1$–$C_6$ alkyl, or aryl;

$R_4'$, $R_5'$, $R_6'$ and $R_7'$ independently for each occurrence represent H, a small hydrophobic moiety (e.g. a halogen or a halogenated alkyl, preferably a trihalogenated methyl), —$C(O)NR_2$, —CN, —$NO_2$, —OH, —OR, —$O_2$Caryl, or —$O_2$Calkyl; and $R_{21}$ and $R_{22}$ independently for each occurrence represent H, alkyl, heteroalkyl, aryl, heteroaryl, —$(CH_2)_m$—$R_{80}$, and more preferably —$(CH_2)_nN(R_1')_2$, wherein n is an integer in the range 1 to 6 inclusive, ortho-, meta-, or para-$CH_2C_6H_4CH_2N(R_1')_2$, ortho-, meta-, or para-$C_6H_4CH_2N(R_1')_2$, ortho-, meta-, or para-$CH_2C_6H_4O(R_1')$, ortho-, meta-, or para-$CH_2C_6H_4OMe$, ortho-, meta-, or para-$CH_2C_6H_4OH$, (2-benzimidazolyl)$CH_2$-, 2-, 3-, or 4-$(R_1')$Ophenyl, 2-, 3-, or 4-methoxyphenyl, 2-, 3-, or 4-hydroxyphenyl, or 2-, 3-, or 4-($(R_1')_2NCH_2$) cyclohexylmethyl, or 2-, 3-, or 4-($(R_1')_2N$) cyclohexylmethyl; or $N(R_{21})R_{22}$ taken together represent a heterocycle comprising from 4 to 8 members inclusive.

In additional preferred embodiments, the subject antibacterial compounds are represented by the following general formula:

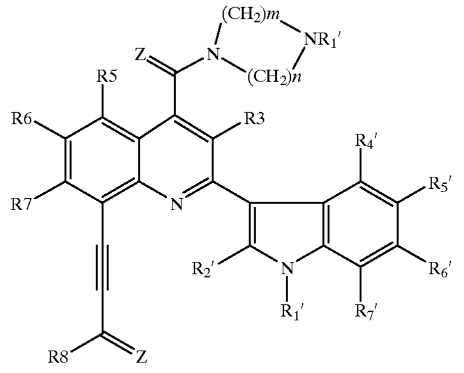

wherein

Z independently for each occurrence represents $(R)_2$, O, S, or NR;

$R_5$, $R_6$, and $R_7$ independently for each occurrence represent H, Me, $C_1$–$C_6$ alkyl, heteroalkyl 1-alkenyl, 1-alkynyl, aryl, heteroaryl, —OR, —$OCF_3$, —$OCR_2OR$, —$CR_2OR$, —$CO_2R$, or a small hydrophobic moiety (e.g. a halogen or a halogenated alkyl, preferably a trihalogenated methyl);

$R_8$ is selected from the group comprising NHR, $N(R)_2$, 1-piperidyl, 1-piperazinyl, 1-pyrrolidinyl, 2-phenylethylamino, 4-morpholinyl, and 4-phenylmethyl-1-piperidyl;

$R_1'$ represents H, alkyl, aryl, p-toluenesulfonyl, —$(CH_2)_n$ N(Phth), or —$(CH_2)_nN(R)_2$ wherein n is an integer in the range 1 to 6 inclusive;

$R_2'$ and $R_3$ independently for each occurrence represent H, Me, $C_1$–$C_6$ alkyl, or aryl;

$R_4'$, $R_5'$, $R_6'$ and $R_7'$ independently for each occurrence represent H, a small hydrophobic moiety (e.g. a halogen or a halogenated alkyl, preferably a trihalogenated methyl), —$C(O)NR_2$, —CN, —$NO_2$, —OH, —OR, —$O_2$Caryl, or —$O_2$Calkyl; and m and n are integers independently selected from the range 1 to 4 inclusive.

In certain embodiments, the subject compounds are represented by the following general structure:

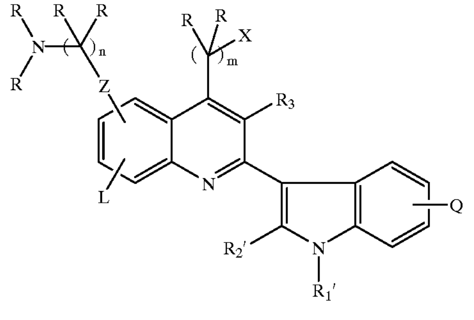

wherein

Q represents a hydrophobic group at any one of positions 4, 5, 6, or 7 of the B-ring of the indole moiety, or is absent;

X represents heterocyclyl, amidinyl, formamidonyl, guanidinyl, —CN, —$C(S)NR_2$, —N(R)C(S)R, —OR, —SR, —$NR_2$, or —$PR_2$;

Z represents —CC—, —(E)—CHCH—, —(Z)—CHCH—, or —$CH_2CH_2$—, and is bonded to any one of positions 5, 6, 7, or 8 of the B-ring of the quinoline moiety;

L represents a hydrophobic group at any one of positions 5, 6, 7, or 8 of the B-ring of the quinoline moiety that is not bonded to Z, or is absent;

R represents, independently for each occurrence, H, lower alkyl, lower heteroalkyl, aryl, heteroaryl, acyl, sulfonyl, or —$(CH_2)_mR_8$;

the two instances of R taken together in an instance of —$NR_2$ may form a ring comprising that nitrogen;

$R_1'$ represents H, alkyl, aryl, p-toluenesulfonyl, —$(CH_2)_d$N(Phth), or —$(CH_2)_dN(R)_2$ wherein d is an integer in the range 1 to 6 inclusive;

$R_2'$ and $R_3$ independently for each occurrence represent H, lower alkyl, or aryl;

$R_8$ represents, independently for each occurrence, aryl, heteroaryl, cycloalkyl, cycloalkenyl, heterocyclyl, or polycyclyl;

m is, independently for each occurrence, an integer selected from the range 1–8 inclusive; and n is an integer selected from the range 1–4 inclusive.

In certain embodiments, the subject compounds are represented by the general structure above and the associated definitions, wherein X is a heteroaryl.

In certain embodiments, the subject compounds are represented by the general structure above and the associated definitions, wherein X is —$NR_2$.

In certain embodiments, the subject compounds are represented by the general structure above and the associated definitions, wherein Z is bonded to the 6-position of the quinoline nucleus.

In certain embodiments, the subject compounds are represented by the general structure above and the associated definitions, wherein Q is bonded to the 5-position of the indole nucleus.

In certain embodiments, the subject compounds are represented by the general structure above and the associated definitions, wherein Q is selected from the group consisting of F, Cl, Br, I, R, —OR, —$NO_2$, and —CN.

In certain embodiments, the subject compounds are represented by the general structure above and the associated definitions, wherein Q is selected from the group consisting of F, Cl, Br, I, R, —OR, —$NO_2$, and —CN; and Q is bonded to the 5-position of the indole nucleus.

In certain embodiments, the subject compounds are represented by the general structure above and the associated definitions, wherein L is selected from the group consisting of F, Cl, Br, I, R, —OR, —$CF_3$, —$OCF_3$, —$CR_2OR$, —$CO_2R$, —$NO_2$, and —CN.

In certain embodiments, the subject compounds are represented by the general structure above and the associated definitions, wherein X represents a heteroaryl; and Q is selected from the group consisting of F, Cl, Br, I, R, —OR, —$NO_2$, and —CN.

In certain embodiments, the subject compounds are represented by the general structure above and the associated definitions, wherein X represents —$NR_2$; and Q is selected from the group consisting of F, Cl, Br, I, R, —OR, —$NO_2$, and —CN.

In certain embodiments, the subject compounds are represented by the general structure above and the associated definitions, wherein X represents a heteroaryl; Q is selected from the group consisting of F, Cl, Br, I, R, —OR, —$NO_2$, and —CN; Z is bonded to the 6-position of the quinoline nucleus; and Q is bonded to the 5-position of the indole nucleus.

In certain embodiments, the subject compounds are represented by the general structure above and the associated definitions, wherein X represents —$NR_2$; Q is selected from the group consisting of F, Cl, Br, I, R, —OR, —$NO_2$, and —CN; Z is bonded to the 6-position of the quinoline nucleus; and Q is bonded to the 5-position of the indole nucleus.

In certain embodiments, the subject compounds are represented by the following general structure:

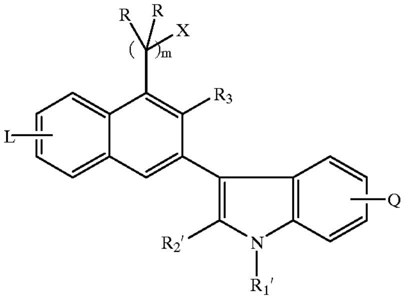

wherein

Q represents a hydrophobic group at any one of positions 4, 5, 6, or 7 of the B-ring of the indole moiety, or is absent;

X represents heterocyclyl, amidinyl, formamidonyl, guanidinyl, —CN, —C(S)$NR_2$, —N(R)C(S)R, —OR, —SR, —$NR_2$, or —$PR_2$;

L represents a hydrophobic group, or groups, at any of positions 5, 6, 7, or 8 of the B-ring of the quinoline moiety, or is absent;

R represents, independently for each occurrence, H, lower alkyl, lower heteroalkyl, aryl, heteroaryl, acyl, sulfonyl, or —$(CH_2)_mR_8$;

the two instances of R taken together in an instance of —$NR_2$ may form a ring comprising that nitrogen;

$R_1$' represents H, alkyl, aryl, p-toluenesulfonyl, —$(CH_2)_d$ N(Phth), or —$(CH_2)_dN(R)_2$ wherein d is an integer in the range 1 to 6 inclusive;

$R_2$' and $R_3$ independently for each occurrence represent H, lower alkyl, or aryl;

$R_8$ represents, independently for each occurrence, aryl, heteroaryl, cycloalkyl, cycloalkenyl, heterocyclyl, or polycyclyl;

m is, independently for each occurrence, an integer selected from the range 1–8 inclusive; and n is an integer selected from the range 1–4 inclusive.

In certain embodiments, the subject compounds are represented by the general structure above and the associated definitions, wherein X is a heteroaryl.

In certain embodiments, the subject compounds are represented by the general structure above and the associated definitions, wherein X is —$NR_2$.

In certain embodiments, the subject compounds are represented by the general structure above and the associated definitions, wherein Q is bonded to the 5-position of the indole nucleus.

In certain embodiments, the subject compounds are represented by the general structure above and the associated definitions, wherein Q is selected from the group consisting of F, Cl, Br, I, R, —OR, —$NO_2$, and —CN.

In certain embodiments, the subject compounds are represented by the general structure above and the associated definitions, wherein Q is selected from the group consisting of F, Cl, Br, I, R, —OR, —$NO_2$, and —CN; and Q is bonded to the 5-position of the indole nucleus.

In certain embodiments, the subject compounds are represented by the general structure above and the associated definitions, wherein L is selected from the group consisting of F, Cl, Br, I, R, —OR, —$CF_3$, —$OCF_3$, —$CR_2OR$, —$CO_2R$, —$NO_2$, and —CN.

In certain embodiments, the subject compounds are represented by the general structure above and the associated definitions, wherein X represents a heteroaryl; and Q is selected from the group consisting of F, Cl, Br, I, R, —OR, —$NO_2$, and —CN.

In certain embodiments, the subject compounds are represented by the general structure above and the associated definitions, wherein X represents —$NR_2$; and Q is selected from the group consisting of F, Cl, Br, I, R, —OR, —$NO_2$, and —CN.

In certain embodiments, the subject compounds are represented by the general structure above and the associated definitions, wherein X represents a heteroaryl; Q is selected from the group consisting of F, Cl, Br, I, R, —OR, —$NO_2$, and —CN; and Q is bonded to the 5-position of the indole nucleus.

In certain embodiments, the subject compounds are represented by the general structure above and the associated definitions, wherein X represents —$NR_2$; Q is selected from the group consisting of F, Cl, Br, I, R, —OR, —$NO_2$, and —CN; and Q is bonded to the 5-position of the indole nucleus.

The antibacterial properties of the compounds of the present invention may be determined from a bacterial lysis assay, as well as by other methods, including, inter alia, growth inhibition assays (e.g., such as described by Blondelie et al. (1992) *Biochemistry* 31:12688), fluorescence-based bacterial viability assays (e.g., Molecular Probes BacLight), flow cytometry analyses (Arroyo et al. (1995) *J. Virol.* 69: 4095–4102), and other standard assays known to those skilled in the art.

The assays for growth inhibition of a microbial target can be used to derive an $ED_{50}$ value for the compound, that is, the concentration of compound required to kill 50% of the microbial sample being tested.

Alternatively, growth inhibition by an antimicrobial compound of the invention may also be characterized in terms of the minimum inhibitory concentration (MIC), which is the concentration of compound required to achieve inhibition of microbial cell growth. Such values are well known to those in the art as representative of the effectiveness of a particular antimicrobial agent (e.g., an antibiotic) against a particular organism or group of organisms. For instance, cytolysis of a bacterial population by an antimicrobial compound can also be characterized, as described above by the minimum inhibitory concentration, which is the concentration required to reduce the viable bacterial population by 99.9%. The value of $MIC_{50}$ can also be used, defined as the concentration of a compound required to reduce the viable bacterial population by 50%. In preferred embodiments, the compounds of the present invention are selected for use based, inter alia, on having MIC values of less than 25 μg/mL, more preferably less than 7 μg/mL, and even more preferably less than 1 μg/mL against a desired bacterial target, e.g., a Gram positive bacteria such as methicillin-resistant *Staphylococcus aureus*, ciprofloxacin-resistant *Staphylococcus aureus*, or *Streptococcus pneumoniae.*

Another parameter useful in identifying and measuring the effectiveness of the antimicrobial compounds of the invention is the determination of the kinetics of the antimicrobial activity of a compound. Such a determination can be made by determining antimicrobial activity as a function of time. In a preferred embodiment, the compounds display kinetics which result in efficient lysis of a microorganism. In a preferred embodiment, the compounds are bacteriocidal.

Furthermore, the preferred antimicrobial compounds of the invention display selective toxicity to target microorganisms and minimal toxicity to mammalian cells. Determination of the toxic dose (or "$LD_{50}$") can be carried using protocols well known in the field of pharmacology. Ascertaining the effect of a compound of the invention on mammalian cells is preferably performed using tissue culture assays, e.g., the present compounds can be evaluated according to standard methods known to those skilled in that art (see for example Gootz, T. D. (1990) *Clin. Microbiol. Rev.* 3:13–31). For mammalian cells, such assay methods include, inter alia, trypan blue exclusion and MTT assays (Moore et al. (1994) *Compound Research* 7:265–269). Where a specific cell type may release a specific metabolite upon changes in membrane permeability, that specific metabolite may be assayed, e.g., the release of hemoglobin upon the lysis of red blood cells (Srinivas et al. (1992) *J. Biol. Chem.* 267:7121–7127). The compounds of the invention are preferably tested against primary cells, e.g., using human skin fibroblasts (HSF) or fetal equine kidney (FEK) cell cultures, or other primary cell cultures routinely used by those skilled in the art. Permanent cell lines may also be used, e.g., Jurkat cells. In preferred embodiments, the subject compounds are selected for use in animals, or animal cell/tissue culture based at least in part on having $LD_{50}$'s at least one order of magnitude greater than the MIC or $ED_{50}$ as the case may be, and even more preferably at least two, three and even four orders of magnitude greater. That is, in preferred embodiments where the subject compounds are to be administered to an animal, a suitable therapeutic index is preferably greater than 10, and more preferably greater than 10, 1000 or even 10,000.

Antibacterial assays for the compounds of the invention can be performed to determine the bacterial activity toward both Gram-positive and Gram-negative microorganisms. Typical Gram-negative pathogens which may be sensitive to the antibacterial agents of the present invention can include, for example, species of genus Escherichia, genus Enterobacter, genus Klebsiella, genus Serratia, genus Proteus and genus Pseudomonas. For example, the subject compositions and methods can be used as part of treatment and prevention regimens for infections by some of the most frequently encountered Gram-negative and Gram-positive organisms, including those involving *Escherichia coli* (*E. Coli*), *Klebsiella peumoniae* (*K. peumoniae*), *Serratia marcescens, Enterobacter aerogenes* and *Enterobacter cloacae* (*E. aerogenes* and *E. cloacae*), *Pseudomonas aeruginosa* (*P. aeruginosa*), *Neisseria meningitidis* (*N. meningitidis*), Group B *Streptococcus aureus* and *Staphylococcus aureus, Streptococcus pneumonia, Streptococcus pyogenes, Corynebacter diphtheriae, Gardnierella vaginalis*, Actinetobacter spp., *Bordella pertussis, Haemophilus aegyptius, Haemophilus influenza, Haemophilus ducreyi*, Shigella spp, Serratia spp., and Propionibacterium acnes.

The above list of pathogens is purely illustrative and is in no way to be interpreted as restrictive.

Examples of conditions which can be treated include illnesses of the respiratory passages and of the pharyngeal cavity; otitis, pharyngitis, pneumonia, peritonitis, pyelonephritis, cystitus, endocarditis, systemic infections, bronchitis, arthritis, local inflammations, skin infections, conjuntivitus, and infections of any surgically created vascular access for the purpose of hemodialysis.

The antibiotics of the present invention can also be used prophylactically in animal breeding and livestock husbandry, and as an agents for promoting and accelerating growth and for improving feedstuff utilization in both healthy and sick animals.

In preferred embodiments, the antibacterial agents of the present invention are selected based on their ability to inhibit growth of Gram-positive bacteria. Such Gram-positive bacteria include bacteria from the following species: Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, and Corynebacterium.

A variety of Gram-positive organisms are capable of causing sepsis. The most common organisms involved in sepsis are *Staphylococcus aureus, Streptoccocus pneumoniae*, coagulase-negative staphylococci, beta-hemolytic streptococci, and enterococci, but any Gram-positive organism may be involved. (see, e.g., Bone, (1993) *J. Critical Care* 8:51–59). Thus, it is specifically contemplated that the subject compositions and methods can be used as part of a therapeutic treatment or prevention program for sepsis involving Gram-positive bacteria.

Accordingly, in one embodiment, *S. aureus* is used as a model of a Gram-positive microorganism in testing/selecting the compounds of the present invention. This bacteria is also a significant clinical target as well because it is refractive to most systemic antibiotic treatments. *Staphylococcus aureus* is the most frequent cause of skin, wound, and blood infections and the second most frequent cause of lower respiratory tract infections, and the microorganism tends to prey on immunocompromised and institutionalized patients. Thus, the subject compounds can be used to treat such infections caused by Staphylococcus, as well as in the treatment of conjunctivitis, outer ear infections and the like.

One of the key contributors to the increase in mortality and morbidity due to bacterial infections is the increasing prevalence of drug-resistant bacteria. Examples of the seriousness of antibiotic resistance are methicillin-resistant *S. aureus* (MRSA), ciprofloxacin-resistant *S. aureus* (CRSA), and the emergence of vancomycin-resistant *S. aureus* which have become resistant to virtually all currently used antibiotics. Thus, methicillin-resistant *S. aureus* may also be used as an antibiotic-resistant model organism for selecting the subject compounds. In a preferred embodiment, the antibacterial agents of the present invention can be used in the treatment and/or prevention of endocarditis, e.g., which may be caused by MRSA or CRSA.

The heavy use of vancomycin to treat MRSA infections has in turn contributed to the emergence of new strains of enterococci, the third most prevalent cause of bacterial infection in the U.S., which are resistant to vancomycin. Enterococcus causes as many as 15 percent of bacterial endocarditis cases; it is also the cause of meningitis, and infections in the urinary tract, stomach and intestines. Infections caused by these vancomycin-resistant enterococci (VRE) frequently do not respond to any current therapies, and in many cases prove fatal. Accordingly, the subject compounds can be selected using an assay based on *E. faecalis* sensitivity, and in particular, the vancomycin-resistant isolates found in clinical settings such as a hospital.

The subject compositions may also be selected for treatment of infection by Streptococcus. Streptococcus species are found associated in a great variety of pathologic conditions among which are gangrene, puerperal infections, subacute bacterial endocarditis, septic sore throat, rheumatic fever, and pneumonia. Agents which are active against Streptococcus species are, therefore, greatly needed.

To further illustrate, *E. coli* and *P. aeruginosa* are examples of Gram-negative organisms which may be sensitive to the subject antibacterial agents. *P. aeruginosa* is a particularly problematic source of disease in such conditions as lung infections in patients with cystic fibrosis, burn infections, eye and urinary tract infections, and infection with *P. aeruginosa* may result in serious septicemia. Moreover, imipenem-resistant *P. aeruginosa* are increasing in the clinical field. Enteropathogenic *E. coli* are responsible for outbreaks of diarrhea in infants and newborns, and diarrhea, including "traveler's diarrhea", in adults. *E. coli* may be invasive and toxin-producing, causing sometimes fatal infections, such as cystitis, pyelitis, pyelonephritis, appendicitis, peritonitis, gallbladder infection, septicemia, meningitis and endocarditis.

In still other cmbodimcnts, the subject compounds can be used in the treatment of infections caused by Serratia spp. For instance, *S. marcescens* is a source of ophthalmic and other topical infections, and can be readily provided in assays intended to identify those compounds of the present invention which are bactercidal at suitable concentrations against that bacteria.

The subject compounds may also be used in the treatment of external ear infections (otitis externa), or in the treatment of sexually transmitted diseases such as *Niesseria gonorrhea* and trichomonas infections.

Certain compounds according to the invention may also be selected on the basis of their activity against typical and atypical Mycobacteria and *Helicobacter pylori*, and also against bacteria-like microorganisms, such as, for example, Mycoplasma and Rickettsia. They are therefore particularly suitable in human and veterinary medicine for the prophylaxis and chemotherapy of local and systemic infections caused by these pathogens. *Mycobacterium boris*, like *M. tuberculosis, M. africanum, M. ulcerans*, and *M. leprae*, is a strict pathogen. *M. bovis* is a significant patbogen throughout much of the world, causing tuberculosis, primarily in cattle.

In other embodiments, the subject compositions can be used in the treatment/prevention of infection by Salmonella. Salmonella spp. cause food poisoning, resulting in nausea, vomiting, diarrhea and sometimes-fatal septicemia. For instance, *S. typhi* is the etiological agent of typhoid fever.

The compositions and methods of the present invention may also be useful in the treatment of infection by Shigella. Shigella spp., including *S. dysenteriae*, are common waterbome pathogenic agents, causing bacillary dysentery as well as bacteremia and pneumonia. In the United States and Canada, *S. sonnei* and *S. flexneri* have become the most common etiological agents in bacillary dysentery.

Bacteria of the genus Yersinia are also pathogens which may be treated by the subject compositions. *Y. Enterocolitica*, for example, is an enteric pathogen. Infection with this microorganism causes severe diarrhea, gastroenteritis and other types of infections such as bacteremia, peritonitis, cholecystis, visceral abscesses, and mesenteric lymphadenitis. Septicemia with 50% mortality has been reported. *Y. pestis* is the etiologic agent of bubonic, pneumonic, and septicemic plague in humans.

The subject compositions can be used for sterilization of surfaces such as countertops, surgical instruments, bandages, and skin; as pharmaceutical compositions, including by way of example creams, lotions, ointments, or solutions for external application to skin and mucosal surfaces, including the cornea, dermal cuts and abrasions, burns, and sites of bacterial or fungal infection; as pharmaceutical compositions, including by way of example creams, lotions, ointments, emulsions, liposome dispersions, tablets, or solutions, for administration to internal mucosal surfaces such as the oral cavity or vagina to inhibit the growth of bacteria (or other microorganisms); and as pharmaceutical compositions such as creams, gels, or ointments for coating indwelling invasive devices such as intravenous lines and catheters and similar implants which are susceptible to harboring bacteria.

The subject compositions are also useful for sterilization of in vitro tissue and cell culture media.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide prodrugs thereof, the route of administration, the time of administration, the rate of excretion of the particular compound being employed, the duration of the treatment, other drugs, compounds and/or materials used in combination with the particular antibacterial employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular, subcutaneous, and topical doses of the compounds of this invention for a patient, when used for the indicated antibacterial effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, and in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered compound has not entirely disappeared when the subsequent compound is administered.

III. Pharmaceutical Compositions

While it is possible for a compound of the present invention to be administered alone, it is preferable to administer the compound as a pharmaceutical formulation (composition). The antibiotic compounds according to the invention may be formulated for administration in any convenient way for use in human or veterinary medicine, by analogy with other antibiotics.

Thus, another aspect of the present invention provides pharmaceutically acceptable compositions comprising a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "therapeutically-effective amount" as used herein means that amount of a compound, material, or composition comprising a compound of the present invention which is effective for producing some desired therapeutic effect by inhibiting bacterial cell growth when administered to an animal, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject antibacterial agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present antibacterials may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, sodium carbonate, and sodium starch glycolate; (5) solution retarding agents, such as paraffin; (6) absorption accelerators, such as quaternary ammonium compounds; (7) wetting agents, such as, for example, cetyl alcohol, glycerol monostearate, and polyethylene oxide-polypropylene oxide copolymer; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g. hydroxypropyl-β-cyclodextrin, may be used to solubilize compounds.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active antibacterial.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the antibacterial in the proper medium. Absorption enhancers can also be used to increase the flux of the antibacterial across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Because solutions are particularly important for intravenous administration, solubilizing agents, e.g. cyclodextrins, can be used.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polypropylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Liposomes are spherical structures composed of bilayers of ampiphiles, a special class of surface active molecules, which are characterized by having a hydrophilic (water-soluble) and a hydrophobic (water-insoluble) group on the same molecule. Liposomes can be large or small, and be composed from one to several of these bilayers. Liposomes can be prepared by a variety of methods well known in the art which include, by way of example, methods using natural ampiphiles, such as phospholipids, as well as methods such as that of Goto et al. set forth in Chem. Pharm. Bull. 37 (5) 1351–1354 (1989) for preparing artificial liposomes. Liposomes may be prepared from an organic solution containing a plurality of ampiphiles. Suitable organic solvents include chloroform, ether, low alkyl alcohols and the like. Liposomes provide an effective means for selectively delivering a variety of agents, such as diagnostic agents and drugs, throughout a body. Liposome-encapsulated agents often have bio-distributions and efficiencies which differ greatly from the free agents. For example, it is often desired to provide drugs through inhalation. The rapid systemic uptake of an agent from the site of administration in the respiratory tract can be eliminated or greatly reduced by administering it in a predominantly liposome-encapsulated form, leading to reduced toxicity and improved therapeutic action over an extended period of time.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

The compounds covered in this invention may be administered alone or in combination with other antibacterial agents or in combination with a pharmaceutically acceptable carrier of dilutent. The compounds of the invention may be administered intravenously, intramuscularly, intraperitoneally, subcutaneously, topically, orally, or by other acceptable means. The compounds may be used to treat bacterial infections in mammals (i.e., humans, livestock, and domestic animals), birds, lizards, and any other organism which can tolerate the compounds, and also to inhibit bacterial growth in cell culture. The compounds can also be used for effects related to their antibacterial activity such as for increasing the weight gain of livestock.

IV. Synthetic Schemes

The subject quinoline-indoles, and congeners thereof, can be prepared readily from individual heterocyclic components by employing the cross-coupling technologies of Suzuki, Stille, and the like. These coupling reactions are carried out under relatively mild conditions and tolerate a wide range of "spectator" functionality. A number of illustrative examples are shown below.

a. Illustrative Suzuki Coupling #1

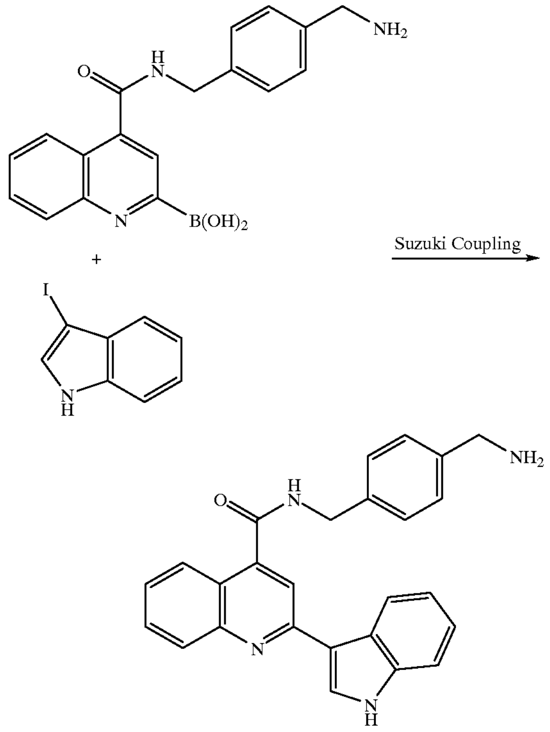

b. Illustrative Szuzki Coupling #2

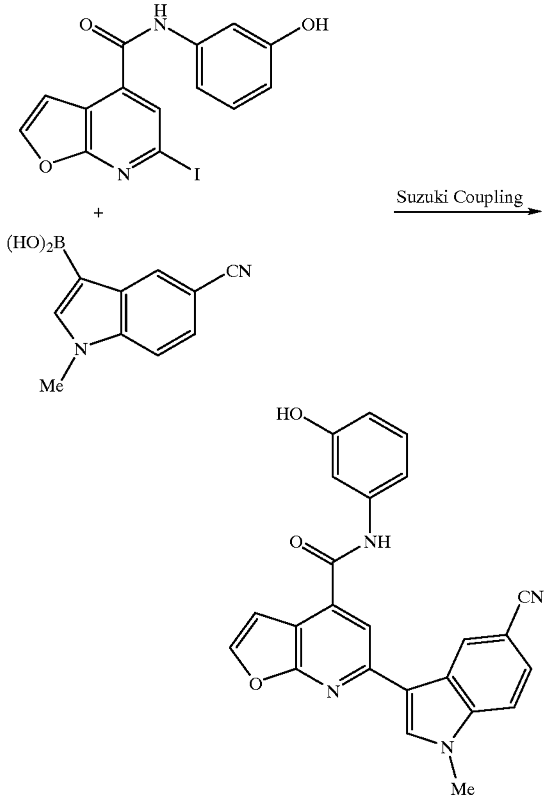

c. Illustrative Stille Coupling #1

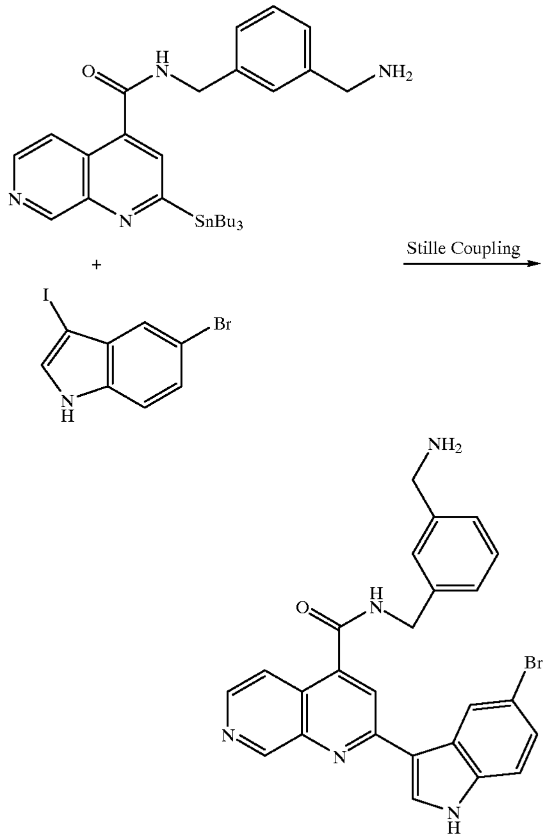

d. Illustrative Stille Coupling #2

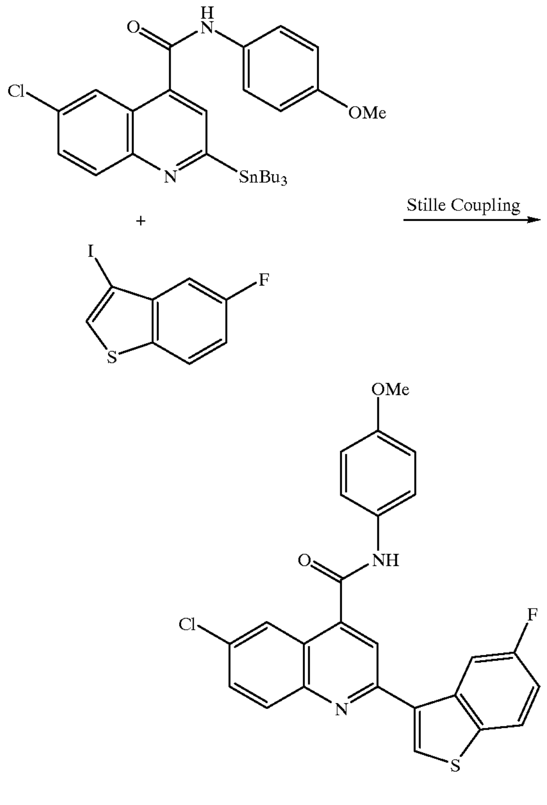

e. Illustrative Stille Coupling #3

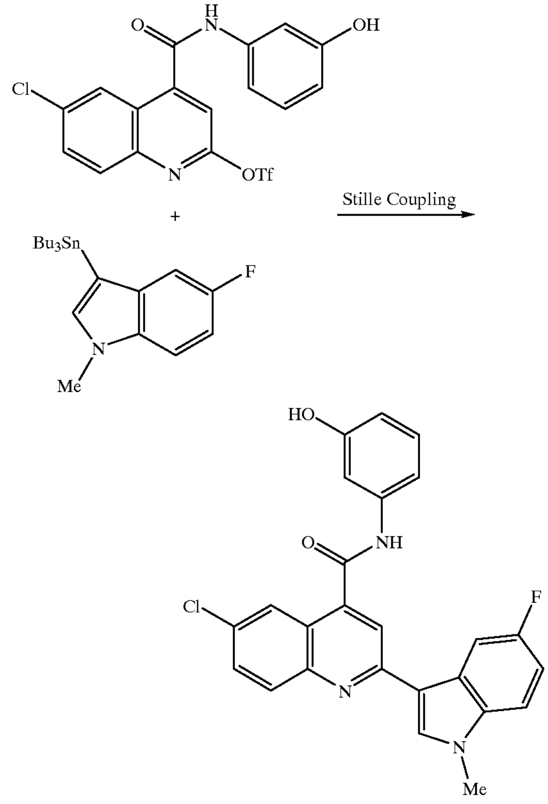

Members of the general classes of coupling substrates outlined above—aryistannanes, arylboronic acids, aryl triflates and aryl halides—are available from the parent heterocycles. In general, the transformations required to prepare a coupling substrate are reliable and amenable to scale-up. Illustrative examples are shown below.

f. Illustrative Preparation of a 3-Iodoindole

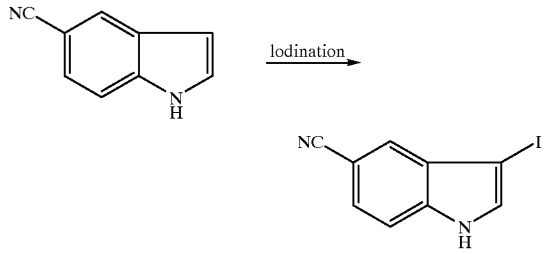

g. Illustrative Preparation of a 2-(Tributylstannyl)quinoline

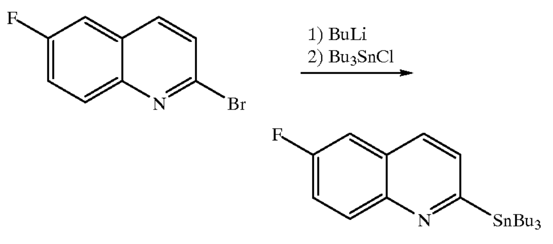

h. Illustrative Preparation of a 2-(Trifluoromethanesulfonyloxy)pyridine

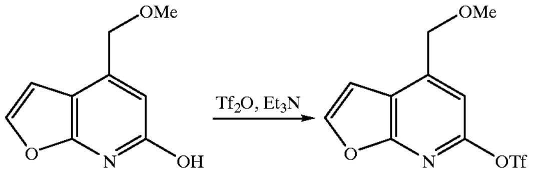

i. Illustrative Preparation of a 3-Indolylboronic Acid

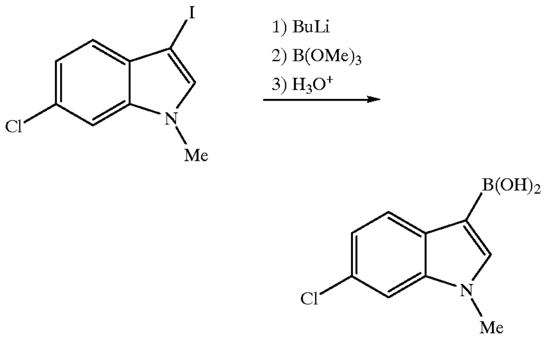

Quinoline, and congeneric, substrates that will ultimately be incorporated into subject antibacterials can be purchased or prepared from readily available starting materials utilizing well-known chemical transformations. The following schemes are illustrative of this fact.

j. Illustrative Quinoline Synthesis #1

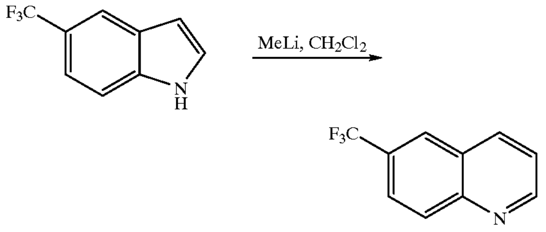

k. Illustrative Quinoline Synthesis #2

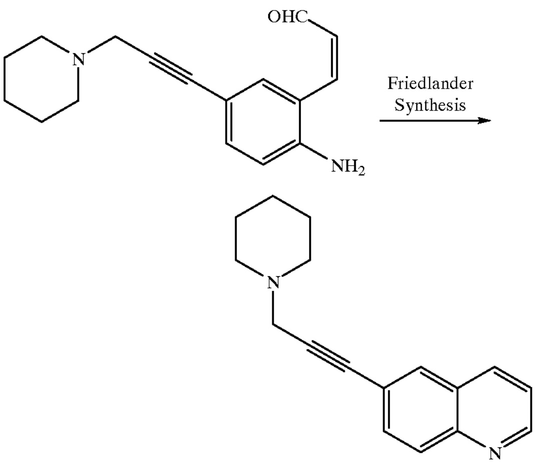

l. Illustrative Quinoline Synthesis #3

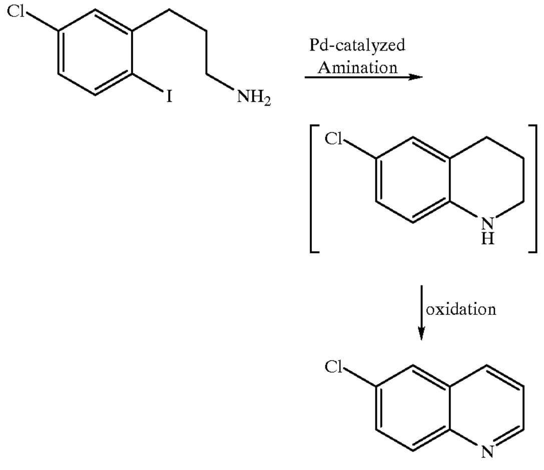

m. Illustrative Indole Synthesis

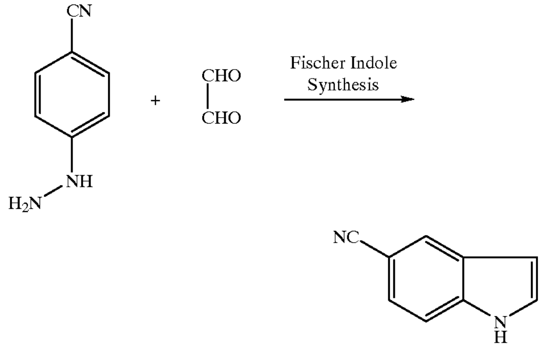

n. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g. a variegated library of compounds represented by formula 1 above, can be screened rapidly in high throughput assays in order to identify potential antibacterial lead compounds, as well as to refine the specificity, toxicity, and/or cytotoxic-kinetic profile of a lead compound. For instance, simple turbidimetric assays (e.g. measuring the $A_{600}$ of a culture), or spotting compounds on bacterial lawns, can be used to screen a library of the subject compounds for those having inhibitory activity toward a particular bacterial strain.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject antibacterials. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCI publication WO 94/08051; Chen et al. (1994) *JACS* 116:2661: Kerr et al. (1993) *JACS* 115:252; PCT publications W092/10092, WO93/09668 and WO91/07087; and the Lerner et al. PCT publication WO93/20242). Accordingly, a variety of libraries on the order of about 100 to 1,000,000 or more diversomers of the subject antibacterials can be synthesized and screened for particular activity or property.

In an exemplary embodiment, a library of candidate antibacterial diversomers can be synthesized utilizing a scheme adapted to the techniques described in the Still et al. PCT publication WO 94/08051, e.g., being linked to a polymer bead by a hydrolyzable or photolyzable group e.g., located at one of the positions of the candidate antibacterials or a substituent of a synthetic intermediate. According to the Still et al. technique, the library is synthesized on a set of beads, each bead including a set of tags identifying the particular diversomer on that bead. The bead library can then be "plated" on a lawn of bacteria for which an inhibitor is sought. The diversomers can be released from the bead, e.g. by hydrolysis. Beads surrounded by areas of no, or diminished, bacterial growth, e.g. a "halo", can be selected, and their tags can be "read" to establish the identity of the particular diversomer.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments. as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., lioughten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S. P. A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529–2531), orthogonality in synthesis is achieved by employing acid-labile protection for the coding strand and base-labile protection for the compound strand.

In an alternative approach (Nikolaiev et al. (1993) Pept Res 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

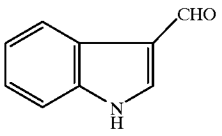

Indole-3-carboxaldehyde

To a 500 mL round bottom flask containing 250 mL of DMF at 0° C. was added 105 mL (1.12 mol) of phosphorous oxychloride dropwise via an addition funnel. The reaction mixture was stirred for 30 min at 0° C. and then indole (0.51 mol) was added as a solid. The reaction mixture was heated to 80° C. for 6 h and then cooled in an ice bath. The cold solidified reaction was quenched with water (~2 L) until all the solid had dissolved. The solution was kept cool and the pH was adjusted to ~11 by the addition of 50% NaOH. The precipitate was filtered and washed with water. The filter cake was dried in vacuo in the presence of $P_2O_5$ to yield crude indole-3-carboxaldehyde (90–95% yield).

Example 2

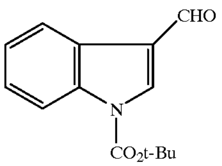

N-Boc-Indole-3-carboxaldehyde

To a 500 mL round bottom flask containing a solution of crude indole-3-carboxaldehyde (0.5 mol) in 300 mL of DCM was added 6.1 g (0.05 mol) of 4-dimethylaminopyridine. The reaction mixture was cooled to 0° C. and 600 mL of a solution of di-tert-butyldicarbonate (1.0 M in THF) was added slowly dropwise via an addition funnel. The reaction mixture was allowed to warm to room temperature for 6 h. The reaction mixture was quenched with 1.0 L of water and the organic layer separated. The organic layer was washed with 5% HCl (2×1.0 L) and sat. NaCl (1.0 L), dried ($MgSO_4$), filtered, and concentrated in vacuo. The crude solid was purified by dissolving it in DCM (~1.0 L) and precipitating it by the addition of hexanes (~1.0 L) and filtering with a fritted funnel. The filter cake was washed with hexanes and dried in vacuo to give N-Boc-indole-3-carboxaldehyde (80–85% yield).

Example 3

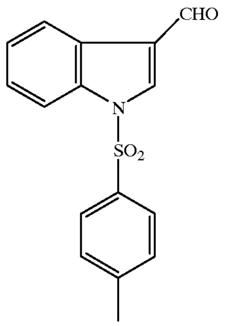

N-Tosyl-Indole-3-carboxaldehyde

To a 25 mL round bottom flask containing a solution of crude indole-3-carboxaldehyde (4.5 mmol) in 10 mL of triethylamine was added 1.3 g (6.7 mmol) of tosyl chloride. The reaction mixture was heated to 95° C. for 4 h. The reaction mixture was quenched by pouring into 10 mL of ice water and filtered. The solid was washed with water (3×10 mL), triterated with ether (25 mL), and dried in vacuio to give N-tosyl-indole-3-carboxaldehyde (85–90% yield).

Example 4

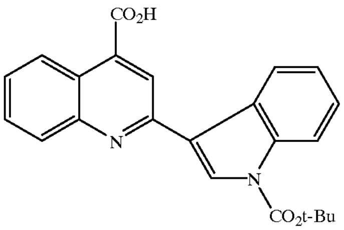

2-(N-Boc-3-Indolyl)-4-quinolinecarboxylic Acid

To a 500 mL round bottom flask was added 27.2 g (0.31 mol) of pyruvic acid (Lancaster), N-Boc-indole-3-carboxaldehyde (0.16 mol) and 200 mL of acetic acid. The reaction mixture was heated at 85° C. until all the solid material had dissolved (~30 min). Then aniline (0.31 mol) was added and the reaction mixture was stirred for 90 minutes at 85° C. The precipitate was filtered hot in a fritted funnel and washed with acetic acid (2×50 mL) and then with ether (2×50 mL). The solid filter cake was dried in vacuo to yield 2-(N-Boc-3-indolyl)-4-quinolinecarboxylic Acid (3–50% yield) of pure (>95%) material.

Example 5

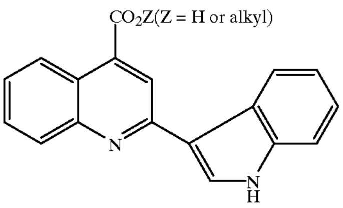

2-(3-Indolyl)-4-quinolinecarboxylic Acid or Ester

To a 10 mL pear-shaped flask was added 2-(N-Boc-3-indolyl)-4-quinolinecarboxylic acid or ester (1 mmol) and 3 mL of a 50% mixture of TFA and DCM. The reaction mixture was stirred for 30 min at 20° C. The solvent was removed under reduced pressure and the residual solid lyophilized to give 2-(3-indolyl)-4-quinolinecarboxylic acid or ester (95–100% yield).

Example 6

Resin-Bound Diamine

To a 200 mL glass frit flask was added 10 g (8.0 mmol) of Wang resin, 13.0 g (80 mmol) of CDI, and 100 mL of THF. The reaction mixture was agitated on an orbital shaker for 24 h. The reaction mixture was filtered and the resin washed with THF (3×100 mL). To the glass frit flask containing the activated resin was added diamine (80 mmol) dissolved in 100 mL, of THF. The reaction mixture was agitated on an orbital shaker for 24 h. The reaction mixture was filtered and the resin washed with THF (3×100 mL), DMF (3×100 mL), MeOH (3×100 mL), and DCM (3×100 mL) and dried under vacuum to give 11.3 g (0.70 mmol/g) of resin.

Example 7

Resin-Bound 2-(3-Indolyl)quinoline-4-carboxylate or -carboxamide

To a 10 mL pear-shaped flask was added 2-(3-indolyl)-4-quinolinecarboxylic acid (0.2 mmol), 104 mg of PyBOP® (0.2 mmol), 1 mL of DMF and 44 μL of N-methylmorpholine (0.4 mmol). The reaction mixture was stirred for 10 min and then added to a 3 mL plastic tube fitted with a frit containing 100 mg of Wang or Rink resin (0.08 mmol) and ~1 mg of DMAP (0.001 mmol). The reaction mixture was agitated overnight on an orbital shaker at ambient temperature. The solvent was removed by filtration and the resin washed successively with DMF (3×3 mL), MeOH (3×3 mL), and DCM (3×3 mL) and dried under vacuum to give resin-bound 2-(3-indolyl)quinoline-4-carboxylate or -carboxamide.

Example 8

Resin-Bound 2-(3-Indolyl)quinoline-4-aminoalkylcarboxamide

To a 10 mL pear-shaped flask was added of 2-(3-indolyl)-4-quinolinecarboxylic acid (0.088 mmol), 46 mg of PyBOP® (0.088 mmol), 1 mL of DMF and 19 μL of N-methylmorpholine (0.176 mmol). The reaction mixture was stirred for 10 min and then added to a 3 mL plastic tube fitted with a frit containing 50 mg of diamine-capped resin (0.035 mmol) and ~1 mg of DMAP (0.001 mmol). The reaction mixture was agitated overnight on an orbital shaker at ambient temperature. The solvent was removed by filtration and the resin washed successively with DMF (3×3 mL), MeOH (3×3 mL), and DCM (3×3 mL) and dried under vacuum to give resin-bound 2-(3-indolyl)quinoline-4-aminoalkylcarboxamide.

Example 9

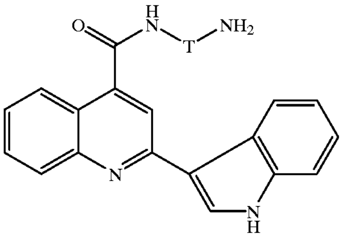

2-(3-Indolyl)quinoline-4-aminoalkylcarboxamide

To a 3 mL plastic tube fitted with a frit containing 50 mg of resin-bound 2-(3-indolyl)quinoline-4-carboxamide (0.035 mmol) was added 1 mL of a 50% mixture of TFA and DCM. The reaction mixture was agitated on an orbital shaker for 30 min. The mixture was filtered and the resin washed with DCM (3×3 mL). The organic solutions were combined and evaporated by a stream of $N_2$. The residual solid was lyophilized to give 2-(3-indolyl)quinoline-4-aminoalkylcarboxamide (80–100% yield).

Example 10

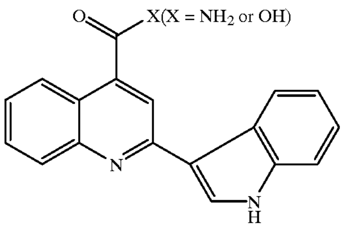

2-(3-Indolyl)quinoline-4-carboxylic Acid or Amide

To a 3 mL plastic tube fitted with a frit containing 50 mg of resin-bound 2-(3-indolyl)quinoline-4-carboxylate (0.035 mmol) was added 1 mL of a 50% mixture of TFA and DCM. The reaction mixture was agitated on an orbital shaker for 30 min. The mixture was filtered and the resin washed with DCM (3×3 mL). The organic solutions were combined and evaporated by a stream of nitrogen. The residual solid was lyophilized to give 2-(3-indolyl)quinoline-4-carboxylic acid or amide (80–100% yield).

Example 11

Resin-Bound Propargylaminoalkynyl-Substituted 2-(3-Indolyl)quinoline-4-aminoalkylcarboxamide To a 3 ml plastic tube fitted with a frit containing 50 mg (0.035 mmol) of resin-bound 2-(3-indolyl)-(5,6,7, or 8)-iodoquinoline-4-aminoalkylcarboxamide was added 6.5 mg of palladium(II) acetate (0.028 mmol), 0.3 mg of copper (I) iodide (1.8 umol), 11 mg of triphenylphosphine (0.042 mmol), 1 mL of THF, 25 μL of propargyl bromide (0.28 mmol) and amine (0.7 mmol). The reaction mixture was agitated on an orbital shaker for 12 h. The reaction mixture was filtered and the resin washed with THF (3×3 mL), DMF (3×3 mL), MeOH (3×3 mL), DCM (3×3 mL), and dried under vacuum to give resin-bound propargylaminoalkynyl-substituted 2-(3-indolyl)quinoline-4-aminoalkylcarboxamide.

Example 12

Resin-Bound Aryl-Substituted 2-(3-Indolyl)quinoline-4-aminoalkylcarboxamide

To a 3 mL plastic tube fitted with a frit containing 50 mg (0.035 mmol) of resin-bound 2-(3-indolyl)-(5,6,7, or 8)-bromoquinoline-4-aminoalkylcarboxamide was added arylboronic acid (0.35 mmol), 4.3 mg of palladium tetrakistriphenylphosphine (3.5 umol) 1 mL of DMF, and 104 μL of triethylamine (0.75 mmol). The reaction mixture was agitated on an orbital shaker for 12 h in a Fischer heating block at 60° C. The reaction mixture was filtered and the resin washed with DMF (3×3 mL,), MeOH (3×3 mL), DCM (3×3 mL), and dried under vacuum to give resin-bound aryl-substituted 2-(3-indolyl)quinoline-4-aminoalkylcarboxamide.

Example 13

Resin-Bound 2-(3-N-Methylindolyl)quinoline-4-carboxylate

To a 3 mL plastic tube fitted with a frit containing 500 mg (0.35 mmol) of resin-bound 2-(3-indolyl)quinoline-4- carboxylate was added 342 mg of cesium carbonate (1.1 mmol), 3 mL of DMF, and 440 $\mu$L (7.0 mmol) of methyl iodide. The reaction mixture was agitated on an orbital shaker for 4 h. The resin was filtered and washed with DMF (3x3 mL), $H_2O$ (3x3 mL), MeOH (3x3 mL), and DCM (3x3 mL) and dried under vacuum. This process was repeated once to give resin-bound 2-(3-N-methylindolyl)quinoline-4-carboxylate.

Example 14

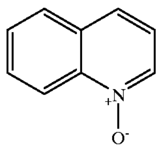

Quinoline-N-oxide

To a 100 mL round bottom flask containing a solution of quinoline (12.2 mmol) in 50 mL DCM was added 5.3 g of m-CPBA (30.6 mmol). The reaction mixture was stirred for 24 h. The reaction mixture was then diluted DCM (100 mL), washed with 5% NaOH (2x100 mL), dried ($MgSO_4$), filtered, and concentrated in vacuo to give solid quinoline-N-oxide (90–95% yield).

Example 15

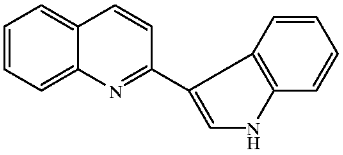

2-(3-Indolyl)quinoline

To a solution of quinoline-N-oxide (0.5 mmol) in 2 mL DCM at 0° C. in a 3 mL plastic tube fitted with a frit was added 58 uL of benzoyl chloride (0.5 mmol). The reaction mixture was stirred for 15 min at 0° C. and then indole (0.5 mmol) was added. The reaction was warmed to 20° C. and stirred for 4 h. The solid precipitate was filtered and washed with DCM (3x2 mL) to give solid 2-(3-indolyl)quinoline (6–100% yield).

Example 16

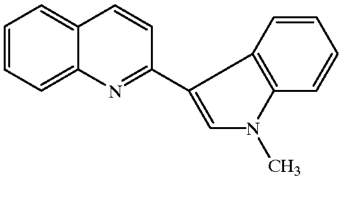

2-(3-N-Methylindolyl )quinoline

To a 10x130 mm test tube containing 2-(3-indolyl) quinoline (0.1 mmol) in 1 mL of DMF was added 130 mg of cesium carbonate (0.4 mmol and 12 $\mu$L (0.2 mmol) of methyl iodide. The reaction mixture was agitated on an orbital shaker in a Fischer heating block at 40° C. for 12 h. The reaction mixture was filtered and the organic layer diluted with DCM (4 mL) and washed with water (1x5 mL). The organic solvent was evaporated under a stream of nitrogen and the residual solid lyophilized to give solid 2-(3-N-methylindolyl)quinoline (95–100% yield).

Example 17

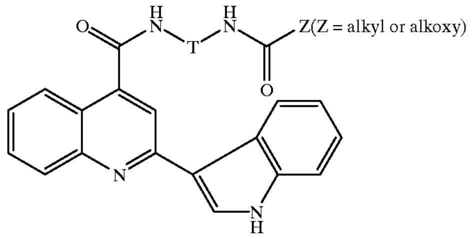

N-Acyl-Substituted 2-(3-Indolyl)quinoline-4-aminoalkylcarboxamide

To a 9 mL test tube containing 2-(3-indolyl)quinoline-4-aminoalkylcarboxamide (0.1 mmol) in 2 mL of EtOAc and 2 mL of sat. $NaHCO_3$ was added 300 $\mu$L of a solution of acid chloride or chloroformate (0.3 mmoL) in 0.3 mL of DCM. The reaction mixture was agitated for 4 h on an orbital shaker. The layers were allowed to separate and the top organic layer was pipeted off and the solvent removed under reduced pressure to give N-acyl-substituted 2-(3-indolyl) quinoline-4-aminoalkylcarboxamide (60–80% yield).

Example 18

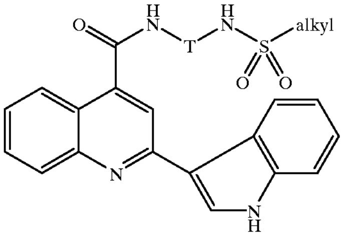

N-Alkylsulfonyl-Substituted 2-(3-Indolyl)quinoline-4-aminoalkylcarboxamide

To a 9 mL test tube containing 2-(3-indolyl)quinoline-4-aminoalkylcarboxamide (0.1 mmol) in 2 mL of EtOAc and 2 mL of sat. $NaHCO_3$ was added 300 $\mu$L of a solution of an alkylsulfonyl chloride (0.3 mmol) in 0.3 mL of DCM. The reaction mixture was agitated for 4 h on an orbital shaker. The layers were allowed to separate and the top organic layer was pipeted off. To the organic solution was added ~50 mg of aminomethyl resin and the mixture agitated on an orbital shaker for 1 h. The mixture was filtered and the solvent removed under reduced pressure to give N-alkylsulfonyl-substituted 2-(3-indolyl)quinoline-4-aminoalkylcarboxamide (60–80% yield).

Example 19

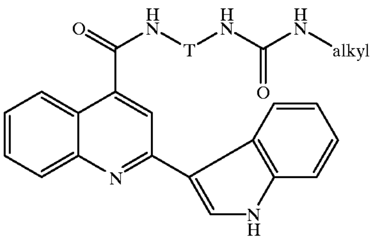

N-Alkylurea-Substituted 2-(3-Indolyl)quinoline-4-aminoalkylcarboxamide

To a 9 mL test tube containing 2-(3-indolyl)quinoline-4-aminoalkylcarboxamide (0.1 mmol) in 2 mL of THF was added 300 $\mu$L of a solution of alkylisocyanate (0.3 mmoL) in 0.3 mL of THF. The reaction mixture was agitated for 4 h on an orbital shaker. To the reaction mixture was added ~50 mg of aminomethyl resin and the mixture agitated on an orbital shaker for 1 h. The mixture was filtered and the solvent removed under reduced pressure to give N-alkylurea-substituted 2-(3-indolyl)quinoline-4-aminoalkylcarboxamide (60–80% yield).

Example 20

N-Terminal Resin-Bound Amino Acid

To a 10 mL pear-shaped flask was added Fmoc protected amino acid (0.4 mmol), 250 mg of PyBOP (0.4 mmol), 2 mL of DMF and 81 uL of N-methylmorpholine (0.8 mmol). The reaction mixture was stirred for 10 min and then added to a 3 mL plastic tube fitted with a frit containing 50 mg of Rink or Wang resin (0.08 mmol) and ~1 mg of DMAP (0.001 mmol). The reaction mixture was agitated overnight on an orbital shaker at ambient temperature. The solvent was removed by filtration and the resin washed successively with DMF (3x3 mL), MeOH (3x3 mL), and DCM (3x3 mL) and dried under vacuum to give resin-bound Fmoc protected amino acid. The resin was then suspended in 2 mL of a 30% solution of piperidine in DCM. The resin was then filtered and washed with DCM (3x3 mL) to give N-terminal resin bound amino acid.

Example 21

Resin-Bound 2-(3-Indolyl)quinoline-4-amino Acid

To a 10 mL pear-shaped flask was added of 2-(3-indolyl)-4-quinolinecarboxylic acid (0.088 mmol), 46 mg of PyBOP (0.088 mmol), 1 ml of DMF and 19 uL of N-methylmorpholine (0.176 mmol). The reaction mixture was stirred for 10 min and then added to a 3 mL plastic tube fitted with a frit containing 50 mg of N-terminal resin-bound amino acid (0.035 mmol) and ~1 mg of DMAP (0.001 mmol). The reaction mixture was agitated overnight on an orbital shaker at ambient temperature. The solvent was removed by filtration and the resin washed successively with DMF (3x3 mL), MeOH (3x3 mL), and DCM (3x3 mL) and dried under vacuum to give resin-bound 2-(3-indolyl) quinoline-4-amino acid.

Example 22

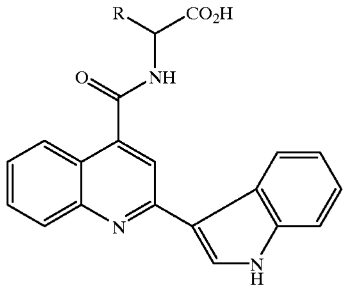

2-(3-Indolyl)quinoline-4-amino Acid

To a 3 mL plastic tube fitted with a frit containing 50 mg of resin-bound 2-(3-indolyl)quinoline-4-amino acid (0.035 mmol) was added 1 mL of a 50% mixture of TFA and DCM. The reaction mixture was agitated on an orbital shaker for 30 min. The mixture was filtered and the resin washed with DCM (3x3 mL). The organic solutions were combined and evaporated by a stream of $N_2$. The residual solid was lyophilized to give 2-(3-indolyl)quinoline-4-amino acid (80–100% yield).

Example 23

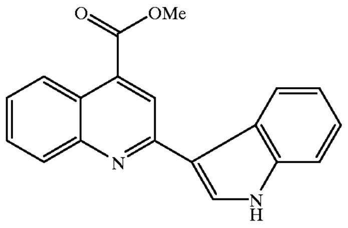

Methyl 2-(3-indolyl)-4-quinolinecarboxylate

To a 10 mL pear-shaped flask was added 2-(3-indolyl)-4-quinolinecarboxylic acid (1 mmol) and 2 mL of acetonitrile followed by a solution of diazomethane (5 mmol) in 2 mL of ether. The reaction mixture was stirred for 1 h and the solvent removed in vacuo to give methyl-2-(3-indolyl)-4-quinolinecarboxylate (95–100% yield).

Example 24

Resin-Bound 4-(Aminoalkyl)-2-(3-indolyl)quinoline

To a 3 mL plastic tube fitted with a frit containing 50 mg of N-terminal resin-bound 4-aminoalkylcarboxamide (0.035 mmol) was added 1.0 mL a 1.0 M solution of borane in THF (1.0 mmol). The reaction mixture was agitated for 1 h at 50° C. on an orbital shaker. The reaction mixture was cooled and then quenched by slow addition of methanol. The mixture was filtered and the resin washed with MeOH (3x3 mL) and DCM (3x3 mL). To the resin was added 2 mL of a 0.6 M solution of DBU in a 9:1 mixture of DMF and MeOH. The reaction mixture was agitated for 2 h at 20° C. on an orbital shaker. The mixture was filtered and the resin washed with DMF, (3x3 mL), MeOH (3x3 ml), and DCM (3x3 mL) and dried under vacuum to give resin-bound 4-(aminoalkyl)-2-(3-indolyl)quinoline.

Example 25

Synthesis of Compound 154

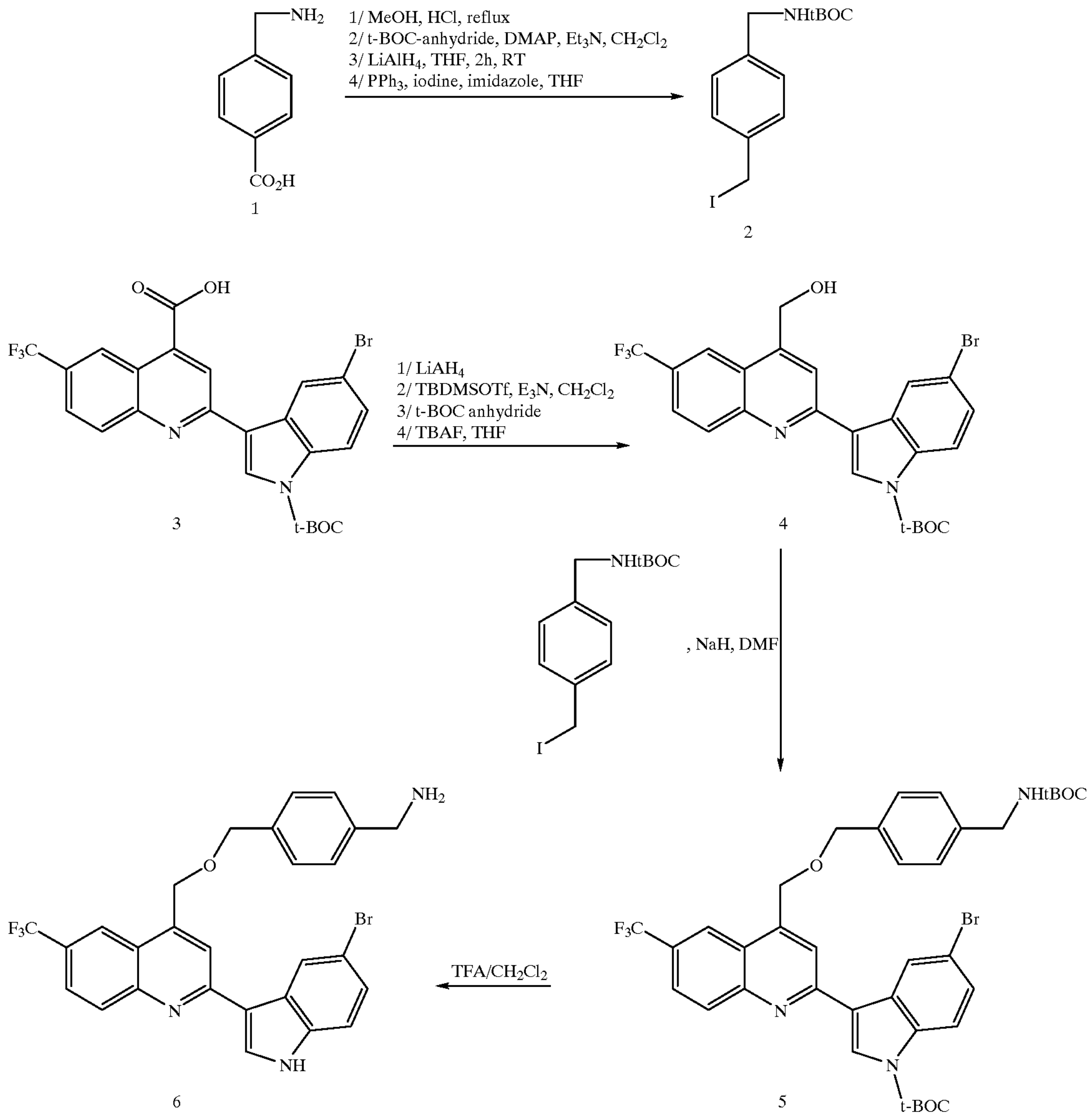

Scheme for Example 25

2: A solution of 4-(aminomethyl)benzoic acid (1 g, 6.6 mmol) in methanol (20 mL) saturated with HCl was heated at reflux overnight. The solution was concentrated, diluted with 15 ml of saturated aqueous sodium bicarbonate, and subsequently extracted with dichloromethane (3x50 mL). The combined organic layers were dried over magnesium sulfate, filtered, and concentrated under vacuum to give 622 mg of a yellow oil. This oil was dissolved in dichloromethane (10 mL); triethylamine (532.6 mg) and di-t-butyl dicarbonate (4.88 ml, 1M solution in THF) were added to this solution. The reaction mixture was stirred under $N_2$ for 1 h. Saturated sodium bicarbonate (10 mL) was added to the mixture, and it was extracted with dichloromethane (3x50 mL). The combined organic layers were dried over magnesium sulfate, filtered and concentrated under vacuum to give 1 g of a white powder. The white powder (750 mg, 4.54 mmol) was dissolved in THF (20 mL) and the solution cooled to 0° C. under $N_2$. Lithium aluminum hydride (258 mg) was added and, after 2 h, saturated aqueous sodium bicarbonate (15 mL) was added, followed by 1 N sodium hydroxide (2 mL). The mixture was extracted with ethyl acetate (3x15 mL), and the combined organic layers were dried over magnesium sulfate, filtered and concentrated under vacuum to yield 600 mg white solid. The alcohol (400 mg, 1.64 mmol) was dissolved in THF (20 mL), and the solution was cooled to 0° C. under $N_2$. Triphenylphosphine (856 mg, 2.26 mmol) was added slowly, followed by imidazole(220 mg, 2.26 mmol) and iodine (827.4 mg, 2.26 mmol); the resulting mixture was stirred for 1 h. The reaction mixture was filtered, and the filtrate was concentrated. The residue was purified via silica gel flash chromatography (EtOAc-hexane, 1:4) to afford a white solid (300 mg).

4: Carboxylic acid 3 (400 mg, 0.749 mmol) was dissolved in THF (10 mL) and lithiumaluminum hydride(85.27 mg, 2.247 mmol) was added. The resulting suspension was heated at reflux overnight under nitrogen. Saturated aqueous sodium bicarbonate (20 mL) was added, and the resulting mixture was extracted with dichloromethane (3x50 mL). The combined organic layers were dried over magnesium sulfate, filtered, and concentrated under vacuum. The crude residue (240 mg, 0.57 mmol) was dissolved in dichloromethane (5 mL), and the solution was cooled to 0° C. under $N_2$. 2,6-Lutidine (183.24 mg, 1.71 mmol) and tert-butyldimethylsilyl trifluoromethanesulfonate(452.02 mg) were added, and the mixture was stirred for 2 h. Saturated aqueous sodium bicarbonate (20 mL) was added, and the mixture was stirred for 30 minutes at room temperature. The reaction mixture was extracted with dichloromethane (3×50 mL), and the combined organic layers were dried over magnesium sulfate, filtered and concentrated under vacuum. The crude material was dissolved in dichloromethane (3 mL), and cooled to 0° C. under $N_2$. DMAP (7 mg, 0.057 mmol) and di-tert-butyl dicarbonate (0.74 ml, 0.741 mmol, 1 M in THF) were added to the solution. After being stirred for 30 minutes, saturated aqueous sodium bicarbonate (10 mL) was added, and the resulting mixture was extracted with dichloromethane (3×30 mL). The combined the organic layers were dried over magnesium sulfate, filtered and concentrated under vacuum. The crude material was dissolved in THF (5 mL), and tetrabutylammonium fluoride (0.684 mL, 1 M in tetrahydrofuran) was added. After 1 h at room temperature, the reaction mixture was concentrated under vacuum. Saturated aqueous sodium bicarbonate (10 mL) was added, and the mixture was extracted with dichloromethane (3×30 mL). The combined organic layers were dried over magnesium sulfate, filtered, and concentrated in vacuo. The crude material was purified via silica gel flash chromatography (EtOAc-MeOH, 19:1) to give the desired compound (130 mg).

Y: 44%. MS: 520.90, 420.90, 404.

5: Compound 4 (120 mg, 0.23 mmol) was dissolved in anhydrous dimethylformamide (1 mL), and sodium hydride (12 mg, 0.299 mmol, 60% dispersion) was added. The reaction mixture was heated at 80° C. for 1 h. Saturated aqueous sodium bicarbonate (10 mL) was added, and the mixture was extracted with dichloromethane (3×30 mL). The combined organic layers were dried over magnesium sulfate, filtered, and concentrated in vacuo to give 5 (140 mg).

Y: 82% MS: 741.74

6: Compound 5 (140 mg, 0.19 mmol) was dissolved in dichloromethane (5 mL) and 30% trifluoroacetic acid was added; the resulting solution was stirred at room temperature for 45 minutes. The reaction mixture was concentrated in vacuo, and the residue was combined with saturated aqueous sodium bicarbonate (5 mL), and this mixture was extracted with dichloromethane (3×30 mL). The combined organic layers were dried over magnesium sulfate, filtered, and concentrated in vacuo to give 6 (80 mg).

Y: 78% MS: 541.83

Example 26

Synthesis of Compound 48

48

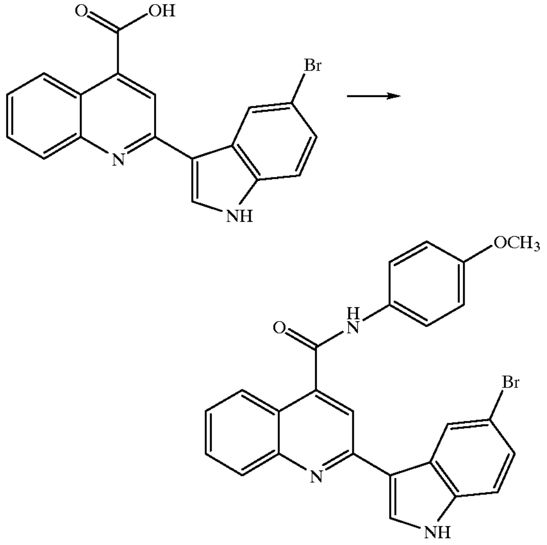

The carboxylic acid (500 mg, 1.366 mmol) was dissolved in dimethylformamide (3 mL), and Py-Bop (852 mg, 1.63 mmol), and N-methyl morpholine (164 mg, 1.63 mmol) were added, followed by stirring for 30 minutes. p-Anisidine (200 mg, 1.63 mmol) was added, and the mixture was stirred overnight. Water (30 mL) was added dropwise to the reaction mixture and a precipitate formed. The reaction mixture was filtered and the collected solid was dried in vaczio to give 48 (350 mg).

Y: 54% MS: 470

Example 27

Synthesis of Compound 87

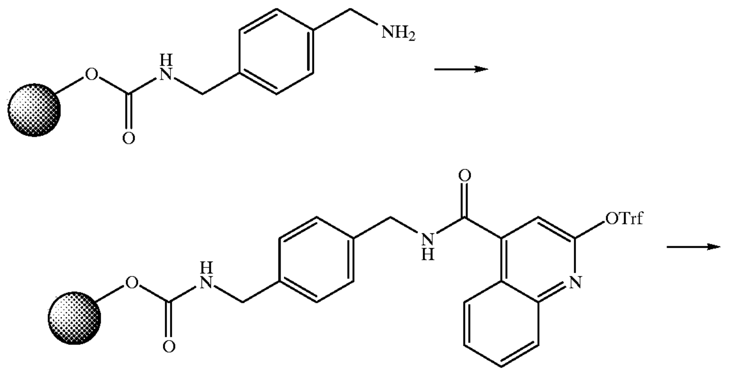

-continued

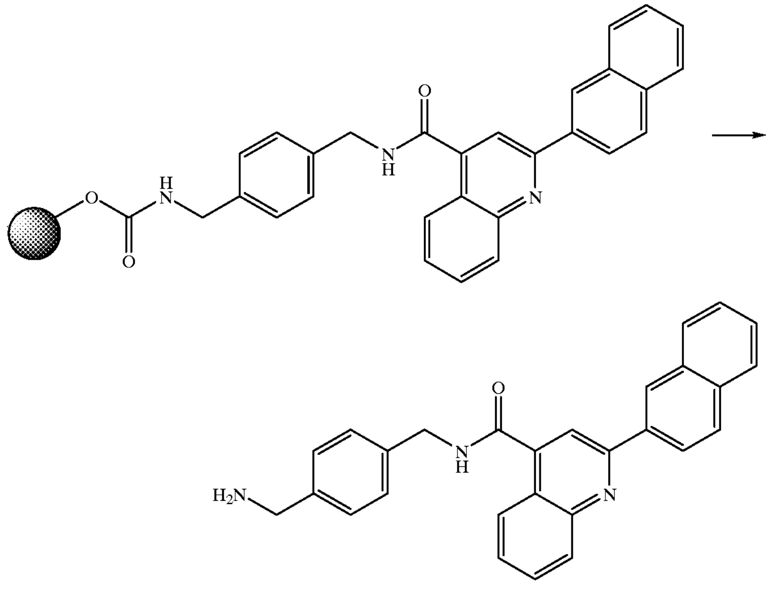

Resin-bound 2-hydroxyquinoline-4-carboxylic acid (5 mmol) was suspended in dichloromethane (150 mL), pyridine (8.4 g, 100 mmol) was added, and the solution was cooled to 0° C. Trifluoromethanesulfonic anhydride (14.1 g, 50 mmol) was added dropwise and the suspension was shaken for 1 h. The mixture was filtered, and the resin was washed with dichloromethane, THF and methanol. The resin (0.059 mmol) was suspended in THF (10 mL), and 2-naphtaleneboronic acid (30.44 mg, 0.177 mmol), 2 M aqueous sodium carbonate (18.76 μL, 0.177 mmol), and tetrakis(triphenylphosphine)palladium(0) (10 mg, 0.008 mmol) were added in series; the mixture was shaken overnight at 60° C. The suspension was filtered, washed with THF, dichloromethane, and methanol. The resin was suspended in dichloromethane (5 mL), 30% TFA was added, and the suspension was shaken for 30 minutes. The suspension was filtered, the resin was rinsed with dichloromethane and the combined organics were concentrated in vacuo to give an orange solid (20 mg).

Y: 83% MS: 418.3

Example 28

Synthesis of Compound 92

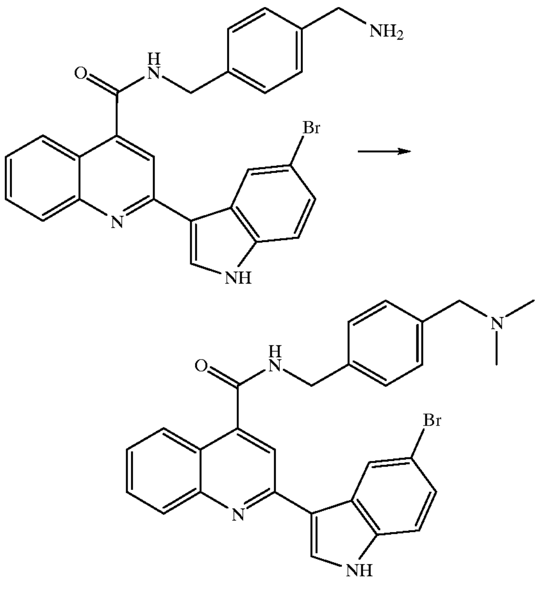

The amine (25 mg, 0.058 mmol) was dissolved in chloroform (5 mL), followed by addition of 37% formaldehyde (18.46 μL, 0.24 mmol) and formic acid (8.44 μL, 0.24 mmol). The mixture was heated at reflux for 6 h, and allowed to cool to rom temperature. Saturated aqueous sodium bicarbonate (5 mL) was added, and the mixture was extracted with dichloromethane (3×15 mL). The combined organic layers were dried over magnesium sulfate, filtered and concentrated in vacuo. Methanol (4 mL) was added to the residue to give a beige powder (15 mg).

Y: 50% MS: 514

Example 29

Synthesis of Compound 91

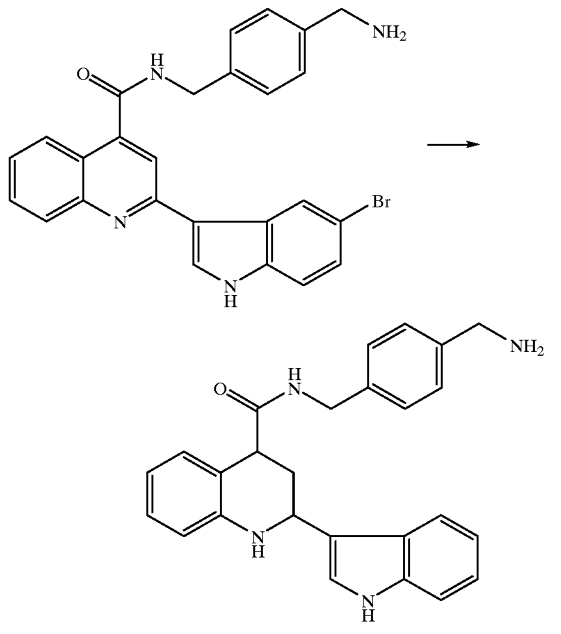

The amine (30 mg, 0.06 mmol) was suspended in methanol (5 mL), and 1 drop of concentrated HCl (1 drop) was added to give a soluble ammonium ion. Adam's catalyst (5 mg, $PtO_2$) was added, and the mixture was shaken overnight under an atmosphere of hydrogen (30 psi). The reaction mixture was filtered, and the filtrate was concentrated in vacuo to give the 2-(5-bromo-3-indolyl)tetrahydroquinoline (20 mg).

Y: 81% MS: 411.17

Example 30

Synthesis of Compound 267

A mixture of 6-chloro-2-[6-fluoro-3-indolyl]quinoline (29.6 mg), prepared utilizing a procedure previous described, and sodium hydride (4 mg) in dimethylacetamide (2 mL) was heated at 60° C. under an inert (Ar) atmosphere for 30 min. Next, N-(4-bromobutyl)phthalimide (29.6 mg) was added and heating at 60° C. was continued for 24 h. The reaction mixture was allowed to cool to room temperature before being quenched with water. The mixture was extracted several times with dichloromethane. The organic extracted were combined, washed with brine, dried over anhydrous magnesium sulfate, filtered, and concentrated to give a yellow oil. The oil was purified by spin plate chromatography on silica gel eluting with hexane/ethyl acetate (70:30) to give 10 mg of 267 as a tan solid. $^1H$ NMR (300 MHz, $CDCl_3$): δ1.75–1.81 (m, 2H), 1.90–1.98 (m, 2H); 3.74 (t, 2H, J=6.6 Hz); 4.21 (t, 2H, J=6.6 Hz); 7.06 (d, 2H, J=9.3 Hz); 7.61 (dd, 1H, $J_1$=8.9 Hz, $J_2$=2.7 Hz); 7.69–8.06 (m, 9H); 8.73 (dd, 1H, $J_1$=8.7 Hz, $J_2$=5.7 Hz).

Example 31

Determination of MIC Values

Stock solutions of compounds are prepared with a concentration of 10 mg/mL. These solutions are then diluted 1:4 to give a concentration of 2.5 mg/mL. The compounds are then serially diluted 1:2 for 6 iterations. The concentrations made for each compound are 2.5, 1.25, 0.625, 0.3125, 0.156, 0.078, and 0.039 mg/mL. A control sample (no compound) is run along with each compound tested. All dilutions are made in DMSO.

All wells of a 96 well microtiter plate are filled with 100 μL of BHI (Brain-Heart Infusion) broth. Columns on the plate are labeled 1–12, and rows are labeled A–H. Each column of wells is used to test one series of diluted compounds. Into each well of 100 μL of BHI broth, 1 μL of diluted compound is placed for a 1:100 dilution. This makes the final concentration of each drug series 25, 12.5, 6.25, 3.125, 1.56, 0.78, 0.39, and 0 μg/mL.

Test Organism: A sterile 15 mL screw cap tube is filled with 3 mL of BHI broth. Next, 2–3 colonies of test organism are inoculated into the tube. The tube is then incubated at 37° C. in a $CO_2$ (approx. 7%) atmosphere jar. The organisms are allowed to grow to the density of a 0.5 McFarland standard ($10^8$ cells/mL). The organism is then inoculated into each well of the microtiter plate containing the diluted compounds to be tested for MIC. The inoculum is 1 μL in volume and represents $10^5$ to $10^6$ cells/mL.

After inoculation the plates are covered and incubated at 37° C. and approx. 7–10% $CO_2$ atmosphere overnight (about 16 hours). The plates are then observed for growth, the well with the lowest concentration of drug and no observable growth represents the well determining the MIC.

Example 32

Table of MIC Values (μg/mL) for Subject Compounds

| Cmpd. # | STRUCTURE | | MRSA | | VREF | *S. pneu* |
|---|---|---|---|---|---|---|
| 1 | 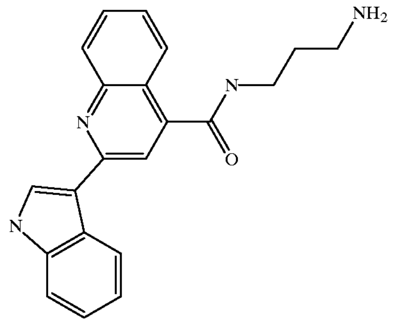 | > | 25 | > | 25 | |
| 2 | 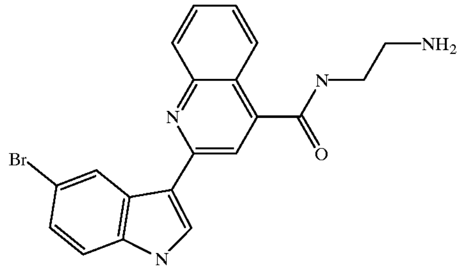 | < | 25 | < | 25 | |
| 3 | 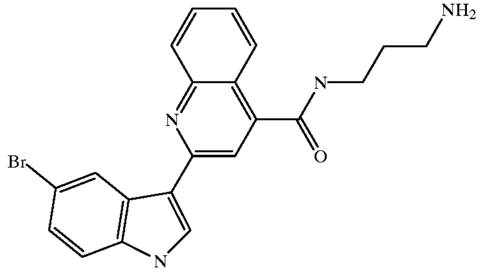 | < | 25 | < | 25 | |

-continued
| Cmpd. # | STRUCTURE | | MRSA | | VREF | S. pneu |
|---|---|---|---|---|---|---|
| 4 | 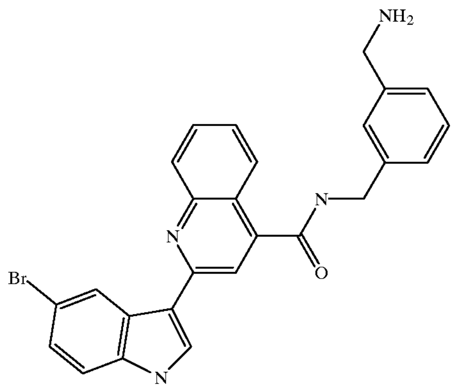 | < | 25 | < | 7 | |
| 5 | 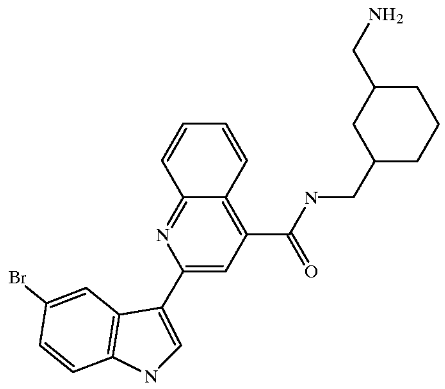 | < | 7 | < | 7 | |

-continued
| Cmpd. # | STRUCTURE | | MRSA | | VREF | S. pneu |
|---|---|---|---|---|---|---|
| 6 | 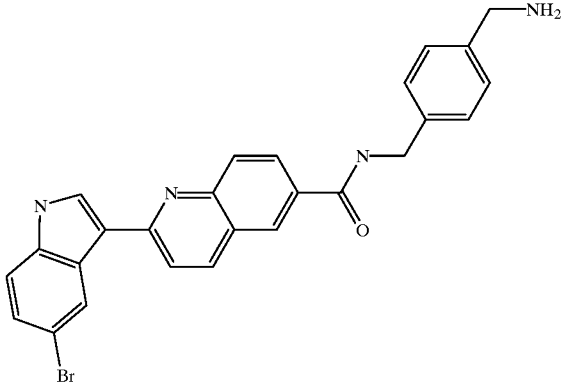 | > | 25 | > | 25 | |
| 7 | 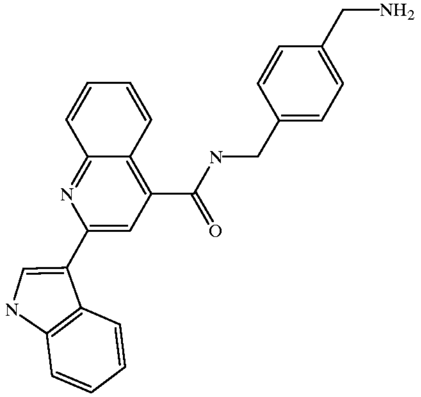 | > | 25 | > | 25 | |

-continued
| Cmpd. # | STRUCTURE | MRSA | VREF | S. pneu |
|---|---|---|---|---|
| 8 | 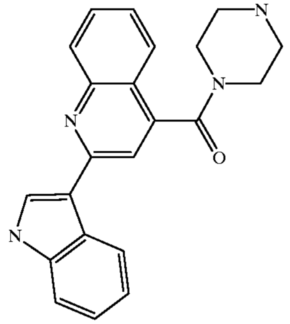 | > 25 | > 25 | |
| 9 | 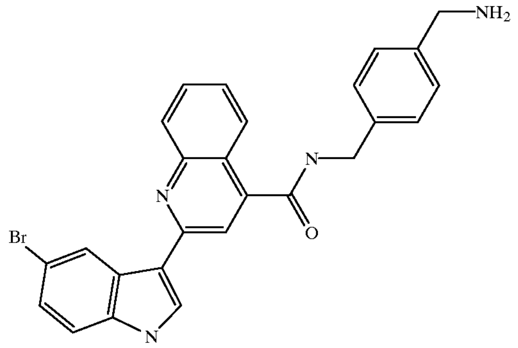 | < 7 | < 7 | < 7 |
| 10 | 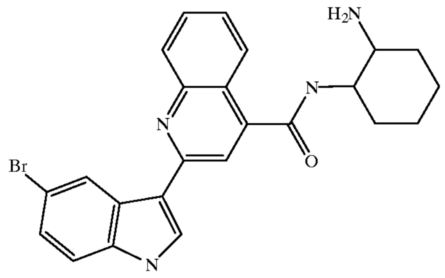 | < 25 | < 25 | |

-continued
| Cmpd. # | STRUCTURE | | MRSA | | VREF | S. pneu |
|---|---|---|---|---|---|---|
| 11 | 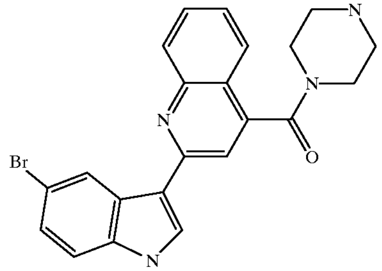 | < | 25 | < | 25 | |
| 12 | 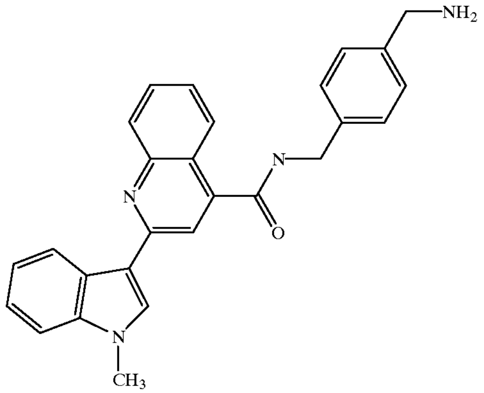 | > | 25 | > | 25 | |
| 13 | 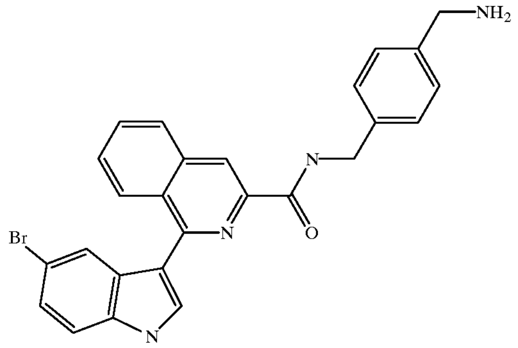 | < | 7 | < | 25 | |

-continued
| Cmpd. # | STRUCTURE | MRSA | VREF | *S. pneu* |
|---|---|---|---|---|
| 14 | 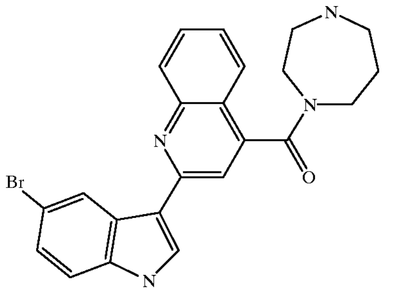 | < 25 | < 25 | |
| 15 | 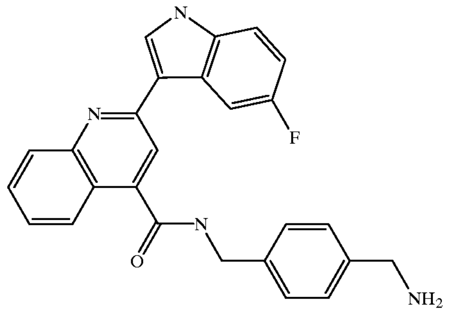 | < 25 | > 25 | |
| 16 | 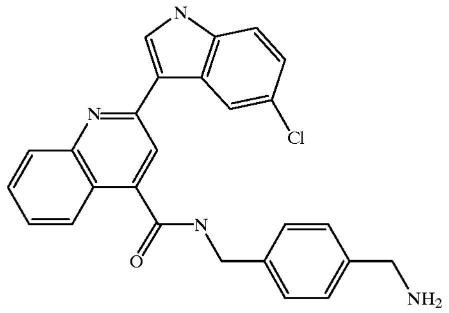 | < 7 | < 25 | |

-continued
| Cmpd. # | STRUCTURE | | MRSA | | VREF | *S. pneu* |
|---|---|---|---|---|---|---|
| 17 | 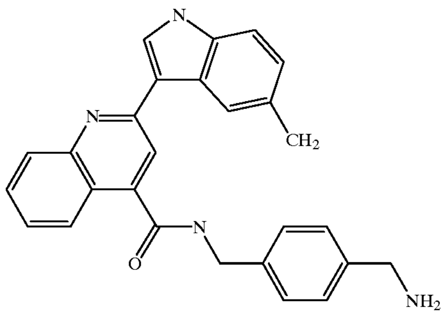 | < | 25 | > | 25 | |
| 18 | 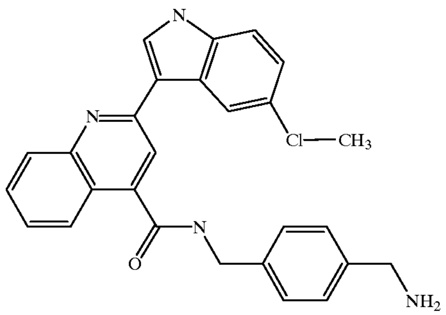 | > | 25 | > | 25 | |

-continued
| Cmpd. # | STRUCTURE | | MRSA | | VREF | S. pneu |
|---|---|---|---|---|---|---|
| 19 | 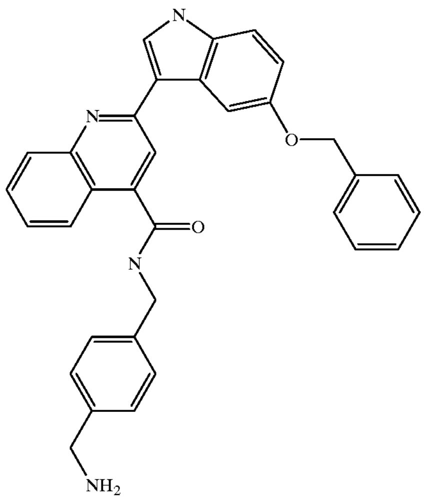 | < | 25 | < | 25 | |
| 20 | 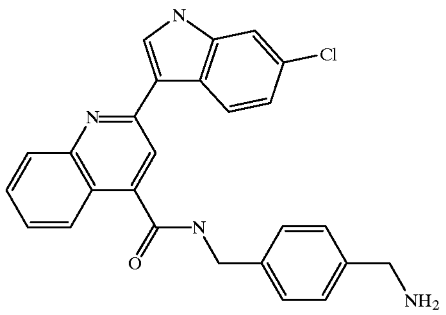 | < | 25 | < | 25 | |

-continued
| Cmpd. # | STRUCTURE | MRSA | VREF | *S. pneu* |
|---|---|---|---|---|
| 21 | 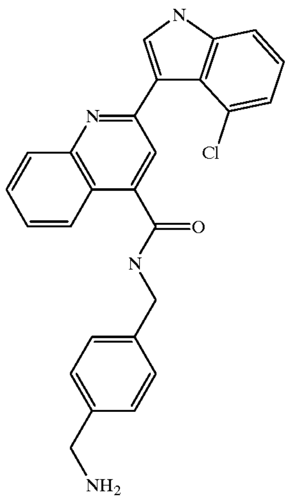 | > 25 | > 25 | |
| 22 | 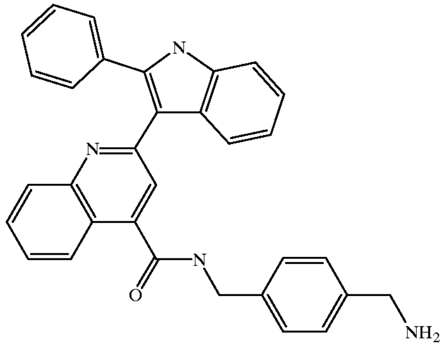 | > 25 | > 25 | |

-continued
| Cmpd. # | STRUCTURE | | MRSA | | VREF | *S. pneu* |
|---|---|---|---|---|---|---|
| 23 | 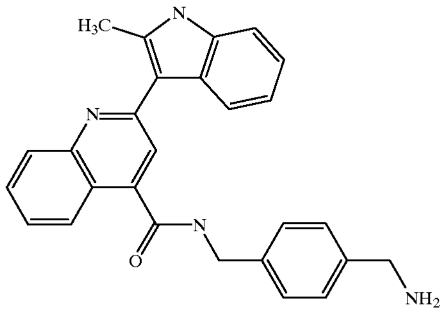 | > | 25 | > | 25 | |
| 24 | 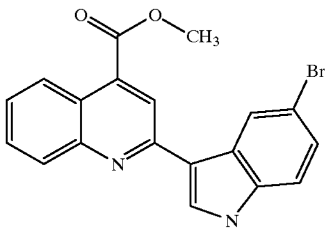 | > | 25 | > | 25 | |
| 25 | 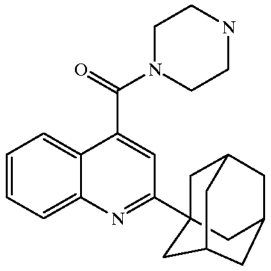 | > | 25 | > | 25 | |

-continued
| Cmpd. # | STRUCTURE | MRSA | VREF | *S. pneu* |
|---|---|---|---|---|
| 26 | 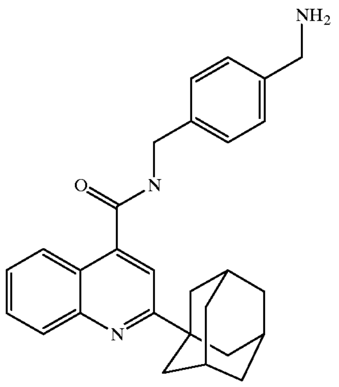 | < 25 | < 25 | |
| 27 | 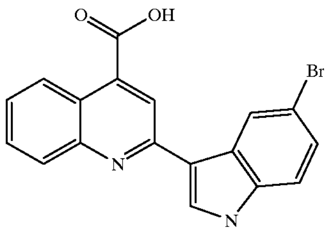 | > 25 | > 25 | |
| 28 | 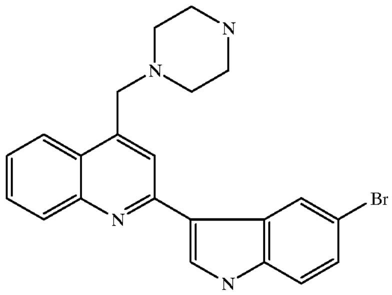 | < 25 | < 25 | |

-continued
| Cmpd. # | STRUCTURE | | MRSA | | VREF | *S. pneu* |
|---|---|---|---|---|---|---|
| 29 | 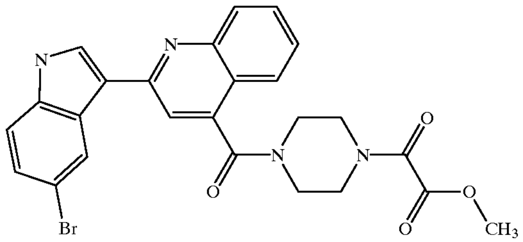 | < | 25 | < | 25 | |
| 30 | 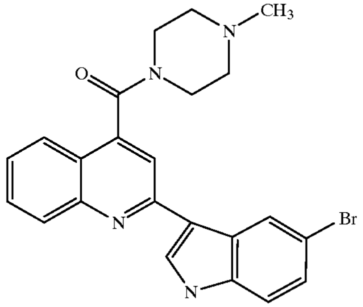 | < | 25 | > | 25 | |
| 31 | 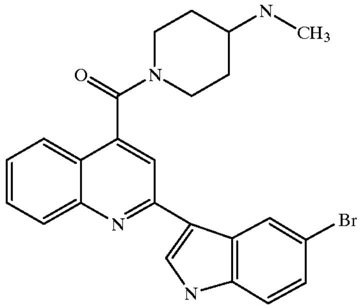 | < | 25 | < | 25 | |

-continued
| Cmpd. # | STRUCTURE | | MRSA | | VREF | S. pneu |
|---|---|---|---|---|---|---|
| 32 | 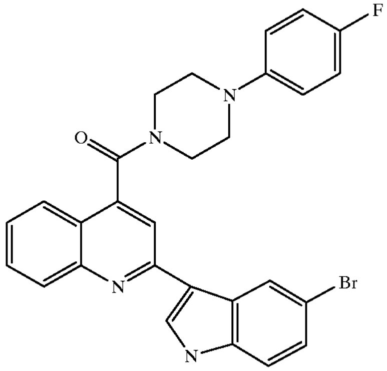 | < | 25 | < | 25 | |
| 33 | 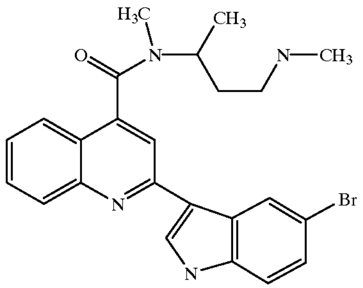 | < | 7 | < | 7 | |
| 34 | 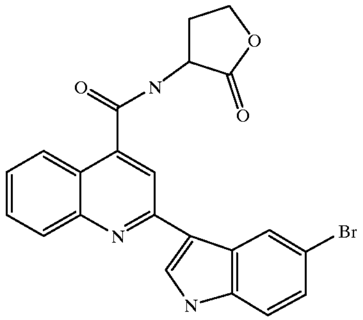 | < | 25 | < | 25 | |

-continued
| Cmpd. # | STRUCTURE | | MRSA | | VREF | *S. pneu* |
|---|---|---|---|---|---|---|
| 35 | 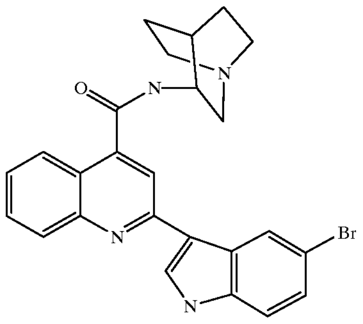 | < | 25 | > | 25 | |
| 36 | 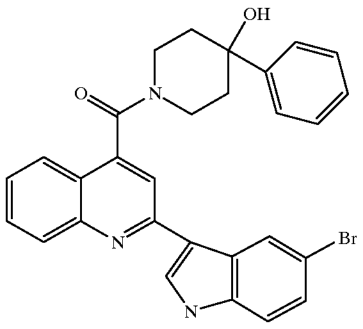 | < | 25 | < | 25 | |
| 37 | 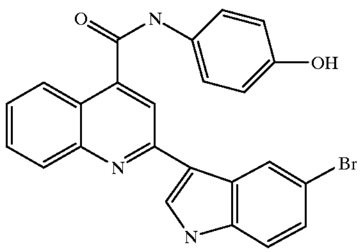 | < | 7 | > | 25 | |

-continued
| Cmpd. # | STRUCTURE | MRSA | VREF | S. pneu |
|---|---|---|---|---|
| 38 | 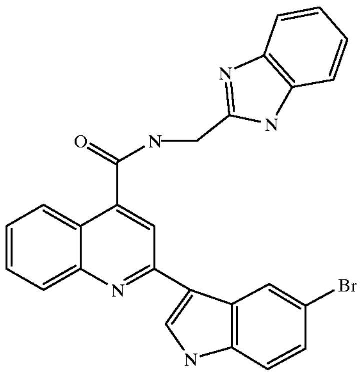 | < 7 | > 25 | |
| 39 | 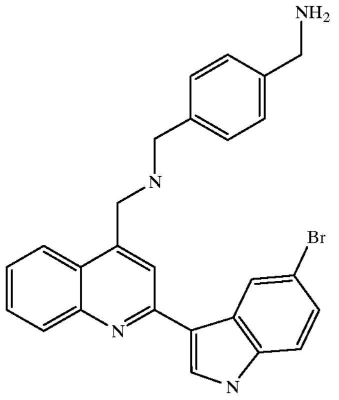 | < 7 | < 7 | |

-continued
| Cmpd. # | STRUCTURE | MRSA | VREF | S. pneu |
|---|---|---|---|---|
| 40 | 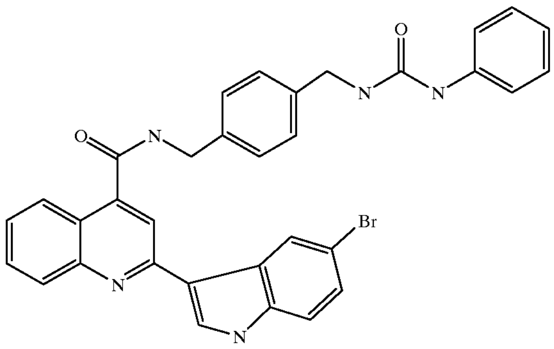 | > 25 | > 25 | |
| 41 | 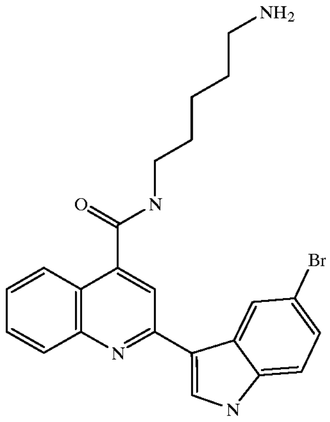 | < 25 | < 25 | |

-continued
| Cmpd. # | STRUCTURE | | MRSA | | VREF | S. pneu |
|---|---|---|---|---|---|---|
| 42 | 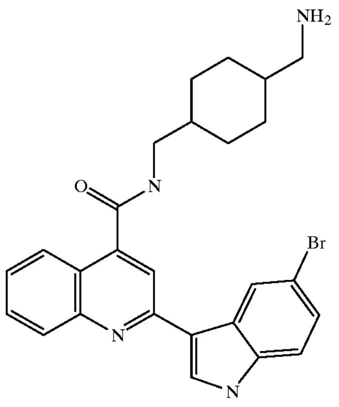 | > | 25 | < | 25 | |
| 43 | 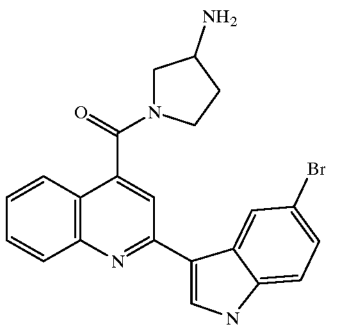 | < | 25 | < | 25 | |
| 44 | 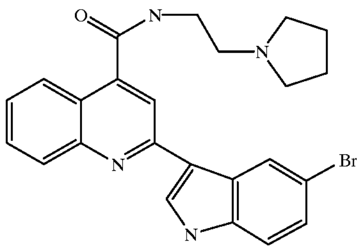 | < | 25 | < | 25 | |

-continued
| Cmpd. # | STRUCTURE | MRSA | VREF | *S. pneu* |
|---|---|---|---|---|
| 45 | 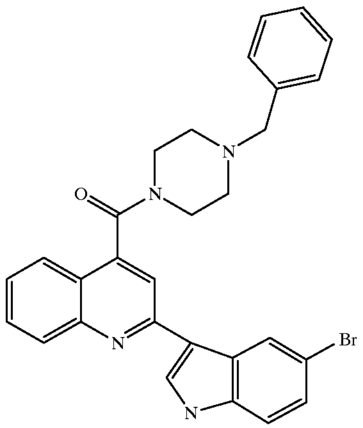 | > 25 | > 25 | |
| 46 | 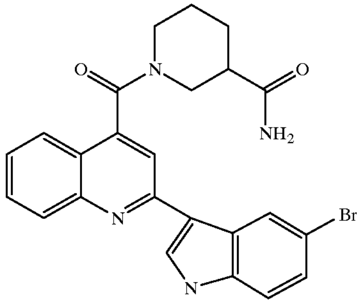 | < 25 | < 25 | |

-continued
| Cmpd. # | STRUCTURE | | MRSA | | VREF | | *S. pneu* |
|---|---|---|---|---|---|---|---|
| 47 | 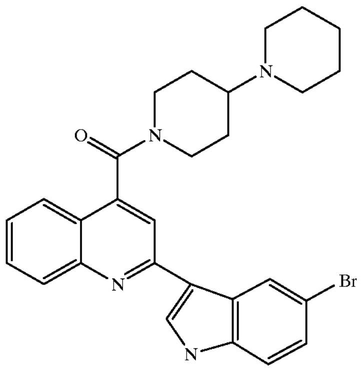 | < | 25 | < | 25 | | |
| 48 | 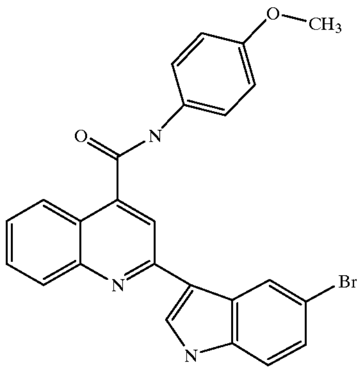 | < | 7 | > | 25 | < | 7 |

-continued
| Cmpd. # | STRUCTURE | MRSA | VREF | *S. pneu* |
|---|---|---|---|---|
| 49 | 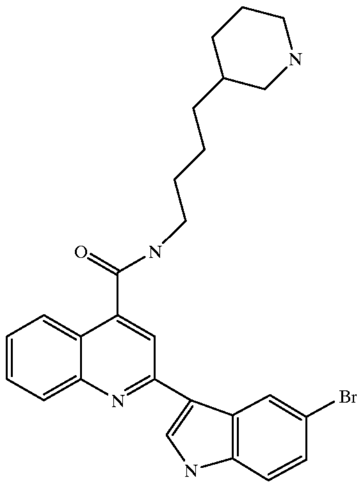 | < 7 | < 7 | |
| 50 | 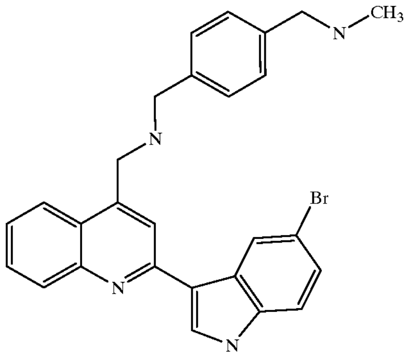 | < 7 | < 25 | |

-continued
| Cmpd. # | STRUCTURE | MRSA | VREF | S. pneu |
|---|---|---|---|---|
| 51 | 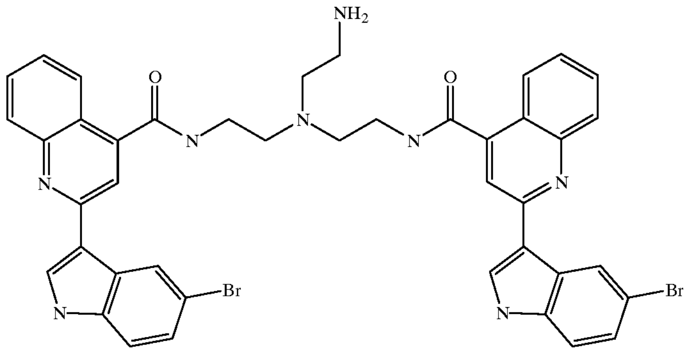 | < 7 | < 7 | |
| 52 | 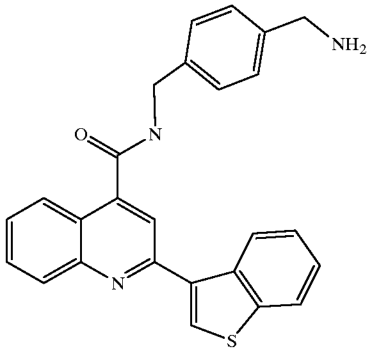 | < 25 | < 25 | |

-continued
| Cmpd. # | STRUCTURE | | MRSA | | VREF | | *S. pneu* |
|---|---|---|---|---|---|---|---|
| 53 | 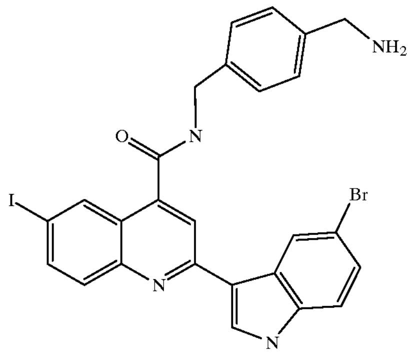 | < | 7 | < | 7 | < | 7 |
| 54 | 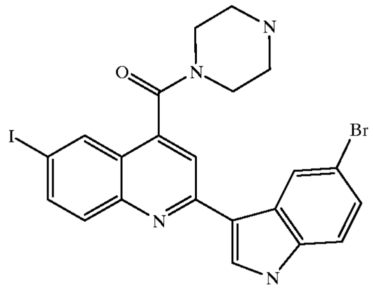 | < | 7 | < | 7 | | |
| 55 | 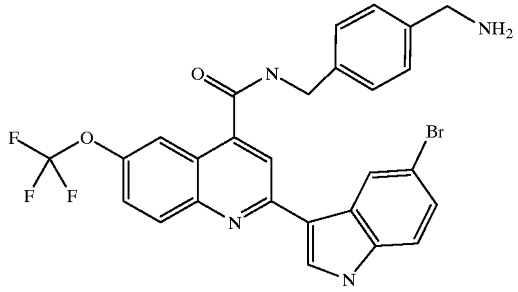 | < | 7 | < | 7 | | |

-continued
| Cmpd. # | STRUCTURE | MRSA | VREF | *S. pneu* |
|---|---|---|---|---|
| 56 | 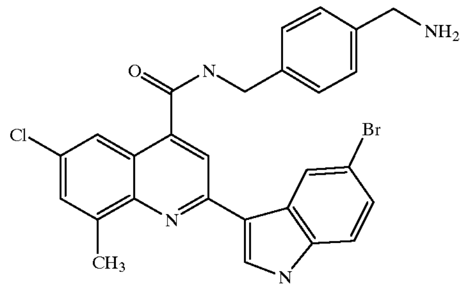 | < 25 | < 25 | |
| 57 | 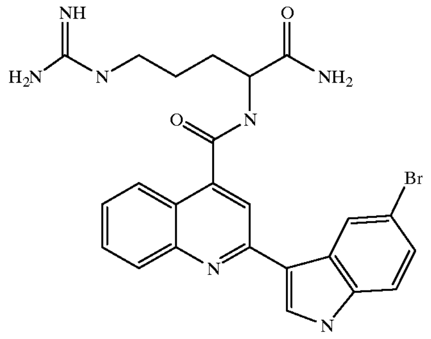 | < 25 | < 25 | |

-continued
| Cmpd. # | STRUCTURE | | MRSA | | VREF | *S. pneu* |
|---|---|---|---|---|---|---|
| 58 | 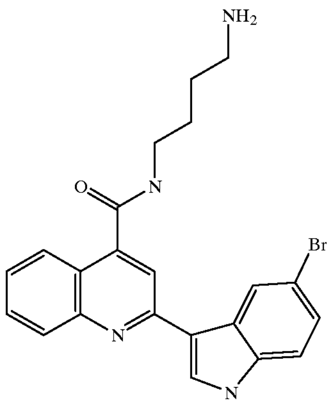 | < | 25 | < | 25 | |
| 59 | 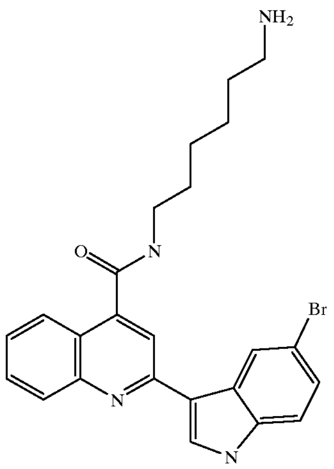 | < | 7 | < | 7 | |

-continued
| Cmpd. # | STRUCTURE | MRSA | VREF | S. pneu |
|---|---|---|---|---|
| 60 | 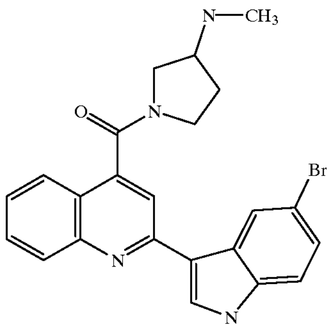 | < 25 | < 25 | |
| 61 | 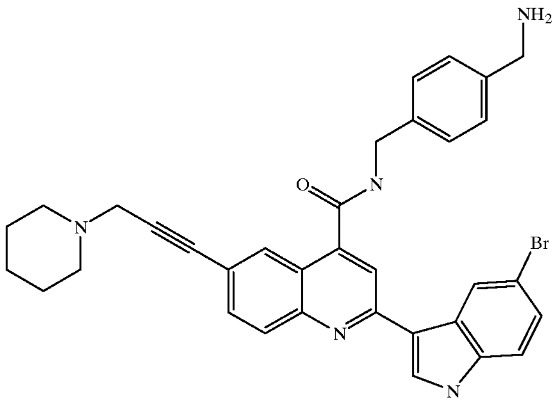 | < 7 | < 7 | < 7 |

-continued
| Cmpd. # | STRUCTURE | MRSA | VREF | S. pneu |
|---|---|---|---|---|
| 62 | 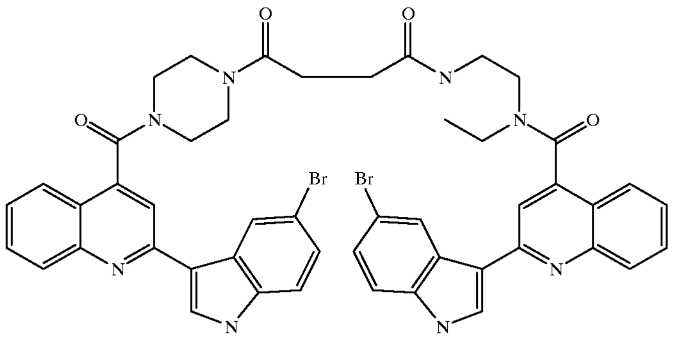 | > 25 | > 25 | |
| 63 | 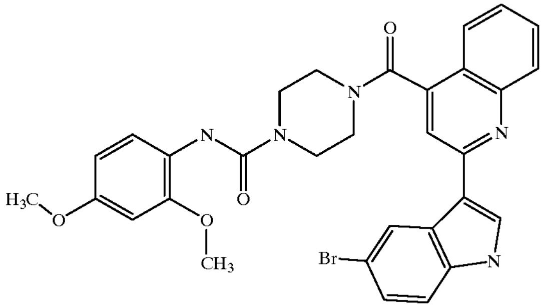 | > 25 | > 25 | |
| 64 | 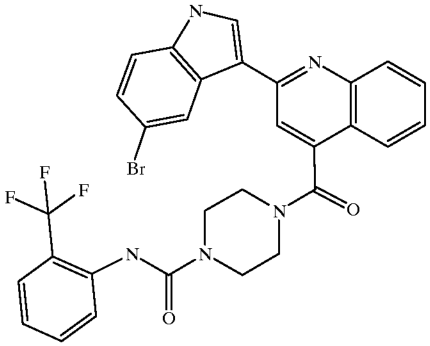 | > 25 | > 25 | |

-continued
| Cmpd. # | STRUCTURE | | MRSA | | VREF | *S. pneu* |
|---|---|---|---|---|---|---|
| 65 | 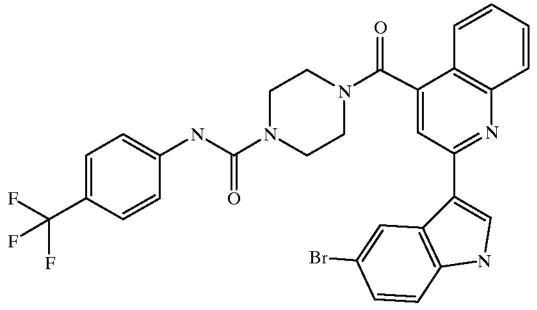 | < | 25 | < | 7 | |
| 66 | 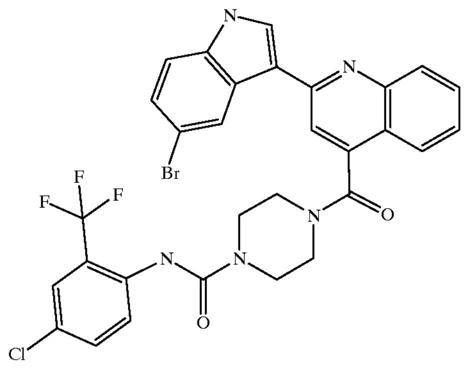 | > | 25 | > | 25 | |

-continued
| Cmpd. # | STRUCTURE | MRSA | | VREF | | *S. pneu* |
|---|---|---|---|---|---|---|
| 67 | 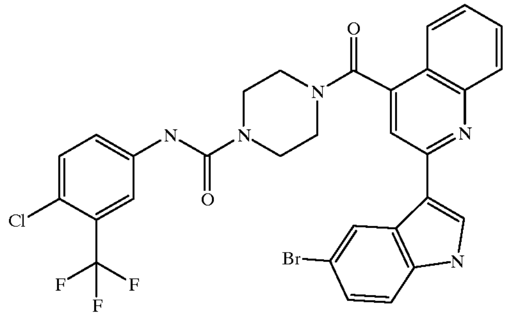 | < | 7 | < | 7 | |
| 68 | 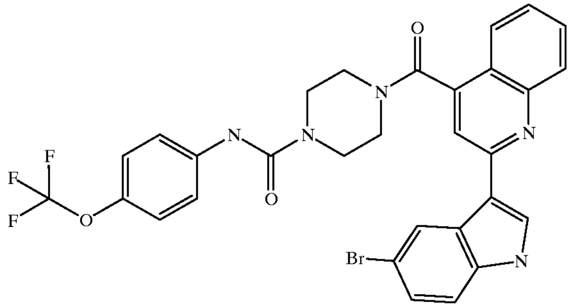 | < | 7 | < | 7 | |
| 69 | 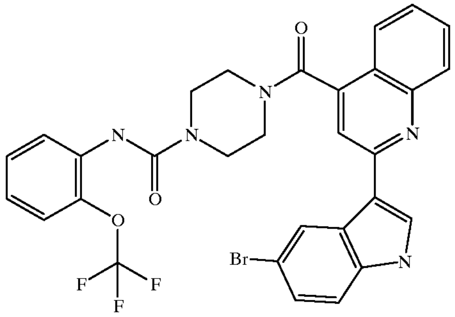 | > | 25 | > | 25 | |

-continued
| Cmpd. # | STRUCTURE | | MRSA | | VREF | *S. pneu* |
|---|---|---|---|---|---|---|
| 70 | 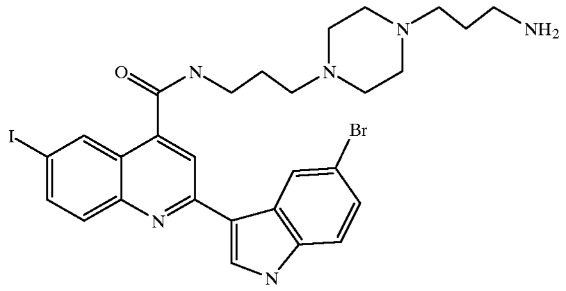 | < | 7 | < | 25 | |
| 71 | 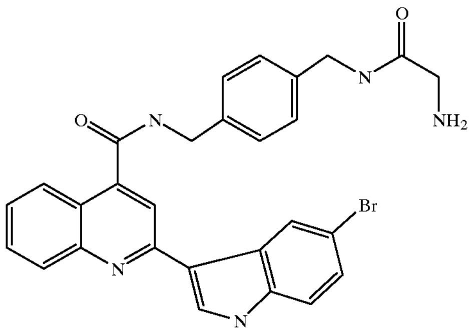 | < | 25 | > | 25 | |
| 72 | 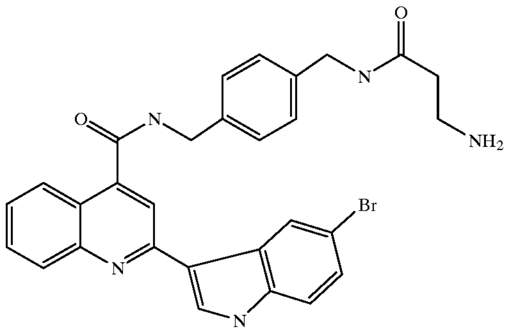 | > | 25 | > | 25 | |

-continued
| Cmpd. # | STRUCTURE | | MRSA | | VREF | S. pneu |
|---|---|---|---|---|---|---|
| 73 | 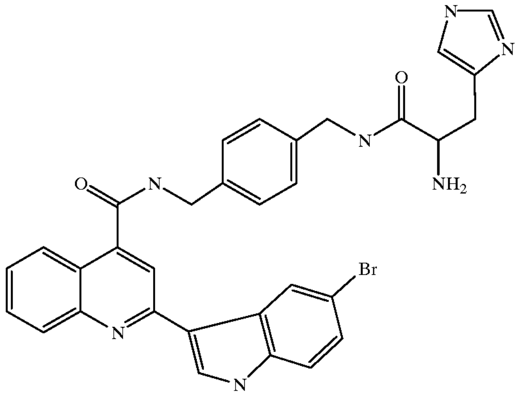 | < | 25 | < | 25 | |
| 74 | 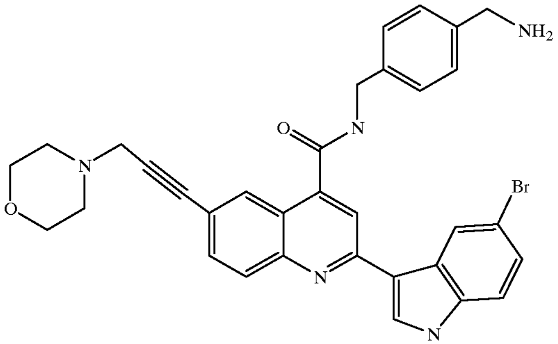 | < | 7 | < | 25 | |

-continued
| Cmpd. # | STRUCTURE | | MRSA | | VREF | | *S. pneu* |
|---|---|---|---|---|---|---|---|
| 75 | 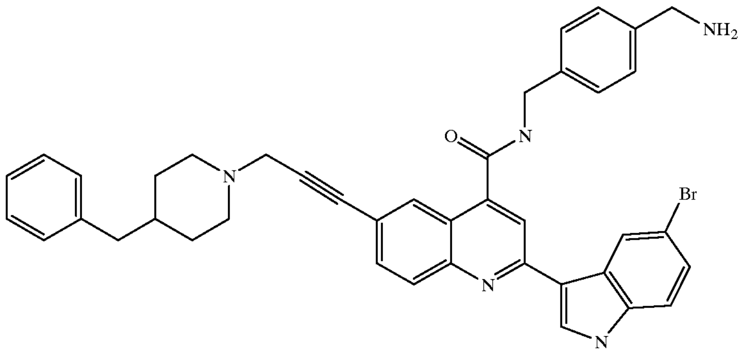 | > | 25 | > | 25 | | |
| 76 | 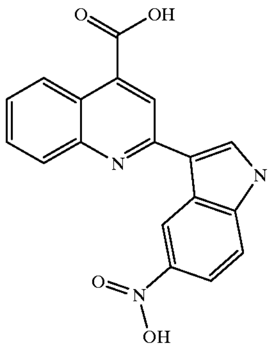 | > | 25 | > | 25 | > | 25 |
| 77 | 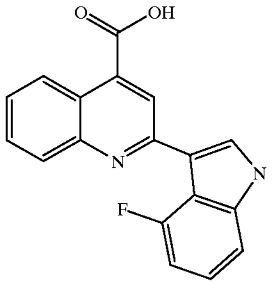 | > | 25 | > | 25 | | |

-continued
| Cmpd. # | STRUCTURE | MRSA | | VREF | | *S. pneu* |
|---|---|---|---|---|---|---|
| 78 | 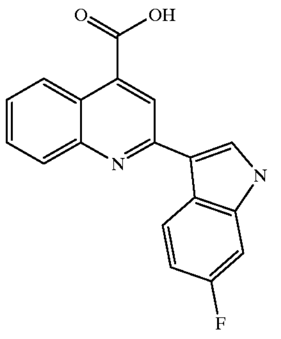 | > | 25 | > | 25 | |
| 79 | 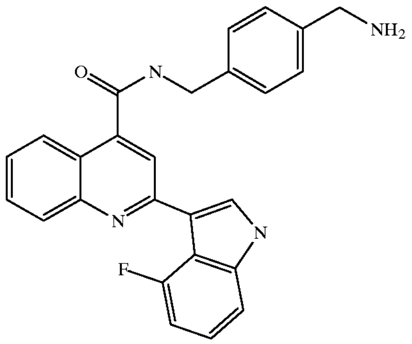 | > | 25 | > | 25 | |

-continued
| Cmpd. # | STRUCTURE | | MRSA | | VREF | *S. pneu* |
|---|---|---|---|---|---|---|
| 80 | 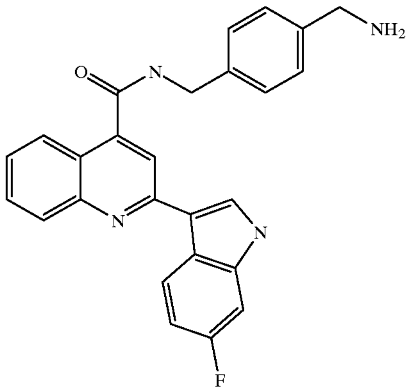 | < | 25 | < | 25 | |
| 81 | 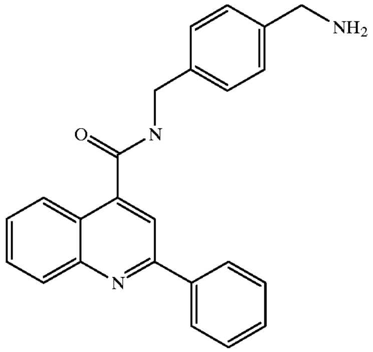 | > | 25 | > | 25 | |

-continued
| Cmpd. # | STRUCTURE | | MRSA | | VREF | *S. pneu* |
|---|---|---|---|---|---|---|
| 82 | 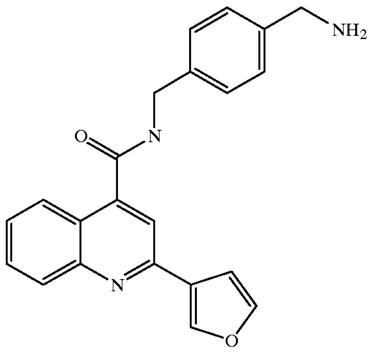 | > | 25 | > | 25 | |
| 83 | 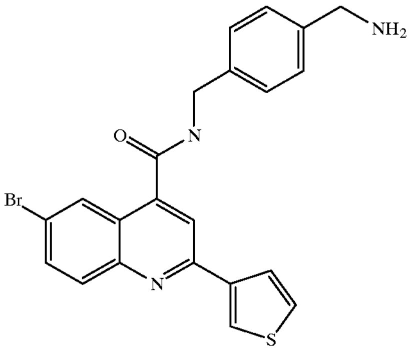 | > | 25 | > | 25 | |
| 84 | 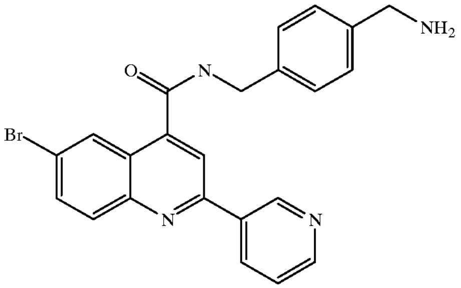 | < | 7 | < | 25 | |

-continued
| Cmpd. # | STRUCTURE | MRSA | VREF | *S. pneu* |
|---|---|---|---|---|
| 85 | 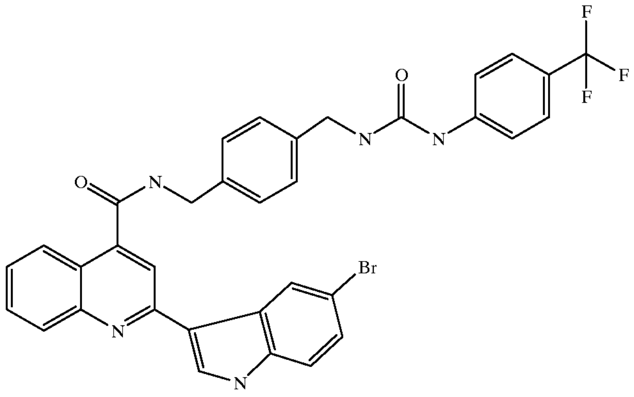 | < 7 | < 25 | |
| 86 | 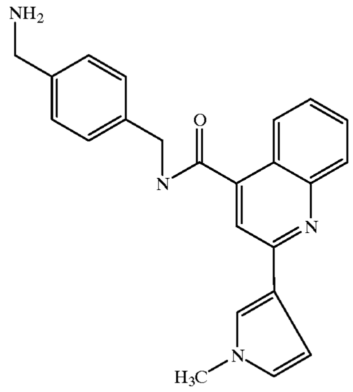 | > 25 | > 25 | |

-continued
| Cmpd. # | STRUCTURE | | MRSA | | VREF | *S. pneu* |
|---|---|---|---|---|---|---|
| 87 | 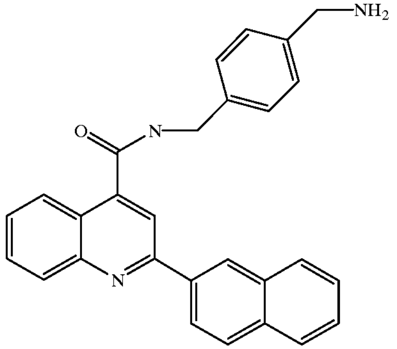 | < | 25 | < | 25 | |
| 88 | 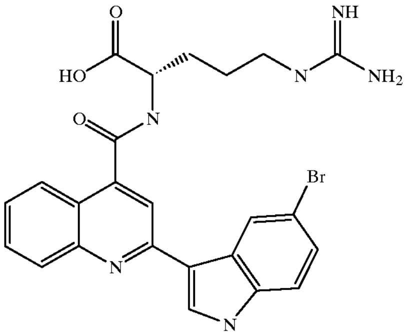 | > | 25 | > | 25 | |

-continued
| Cmpd. # | STRUCTURE | | MRSA | | VREF | *S. pneu* |
|---|---|---|---|---|---|---|
| 89 | 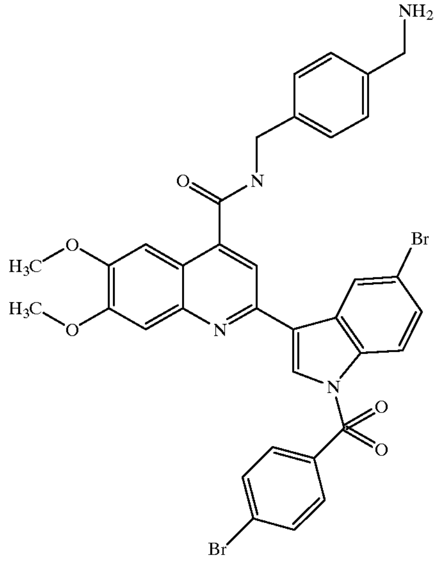 | < | 25 | > | 25 | |
| 90 | 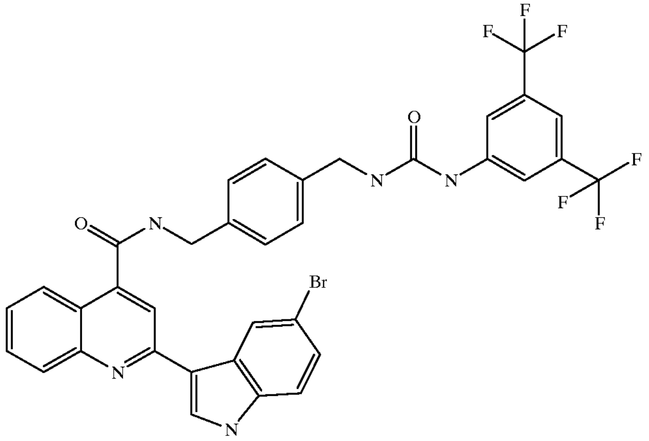 | < | 25 | < | 7 | |

-continued
| Cmpd. # | STRUCTURE | | MRSA | | VREF | *S. pneu* |
|---|---|---|---|---|---|---|
| 91 | 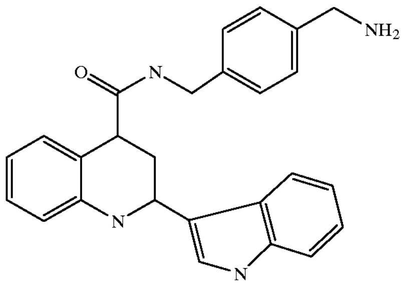 | > | 25 | > | 25 | |
| 92 | 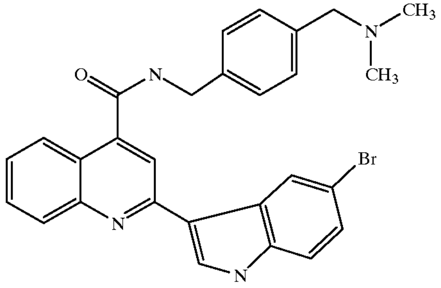 | < | 25 | < | 25 | |
| 93 | 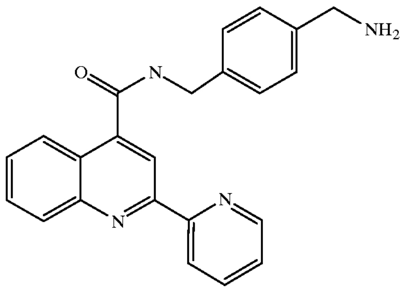 | > | 25 | > | 25 | |

-continued
| Cmpd. # | STRUCTURE | | MRSA | | VREF | | *S. pneu* |
|---|---|---|---|---|---|---|---|
| 94 | 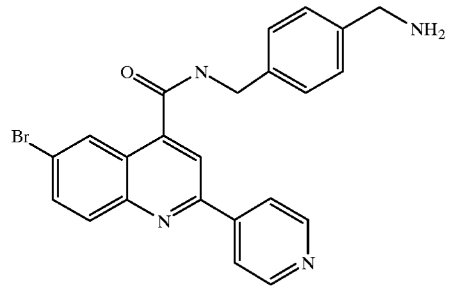 | > | 25 | > | 25 | | |
| 95 | 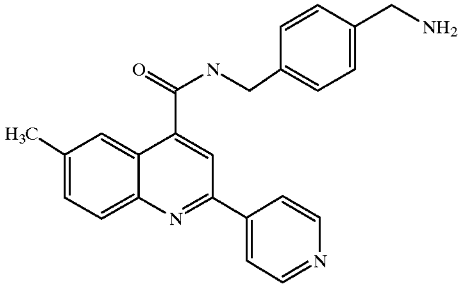 | > | 25 | > | 25 | | |
| 96 | 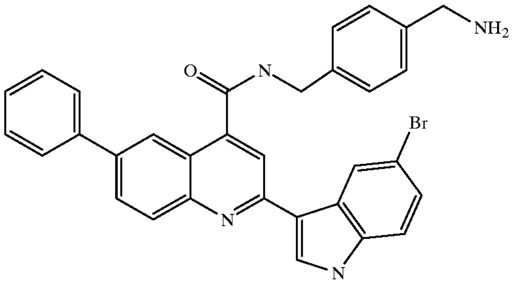 | < | 7 | < | 7 | < | 7 |

-continued
| Cmpd. # | STRUCTURE | | MRSA | | VREF | *S. pneu* |
|---|---|---|---|---|---|---|
| 97 | 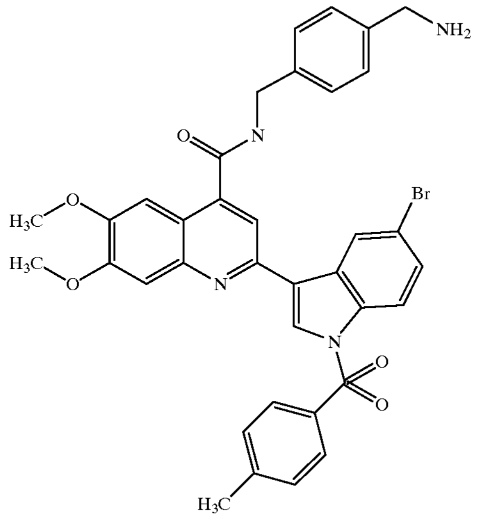 | > | 25 | > | 25 | |
| 98 | 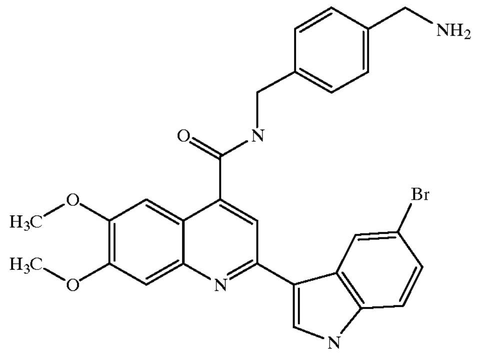 | < | 25 | < | 25 | |

-continued
| Cmpd. # | STRUCTURE | | MRSA | | VREF | *S. pneu* |
|---|---|---|---|---|---|---|
| 99 | 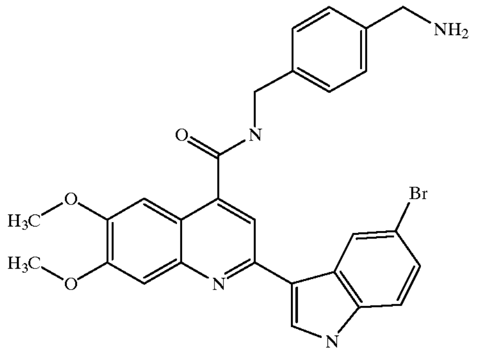 | < | 25 | < | 25 | |
| 100 | 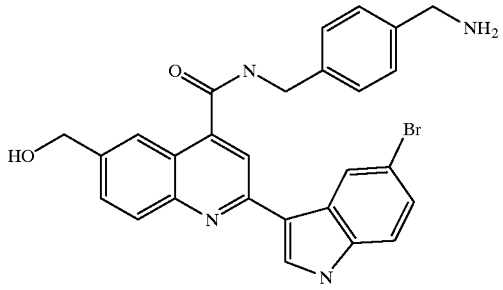 | > | 25 | > | 25 | |

-continued
| Cmpd. # | STRUCTURE | MRSA | | VREF | | *S. pneu* | |
|---|---|---|---|---|---|---|---|
| 101 | 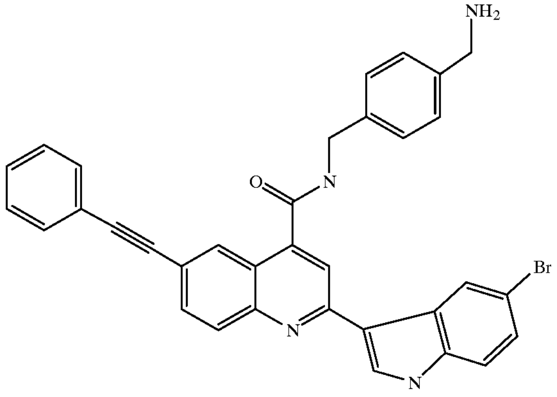 | < | 7 | < | 7 | | |
| 102 | 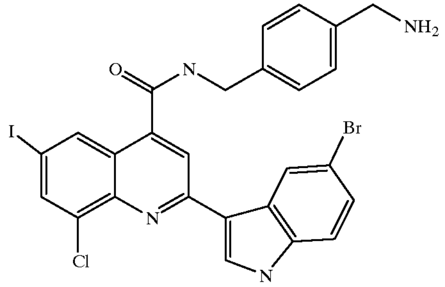 | < | 7 | < | 7 | < | 7 |

-continued
| Cmpd. # | STRUCTURE | MRSA | | VREF | | *S. pneu* | |
|---|---|---|---|---|---|---|---|
| 103 | 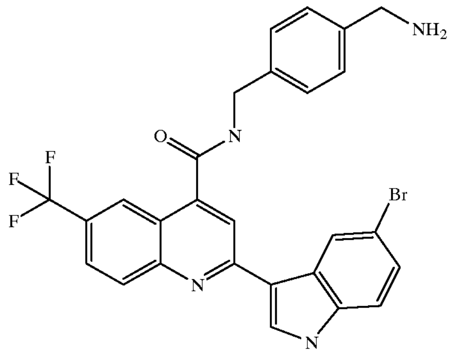 | < | 7 | < | 7 | < | 7 |
| 104 | 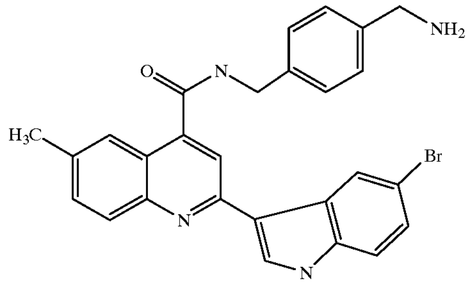 | < | 7 | < | 7 | < | 7 |
| 105 | 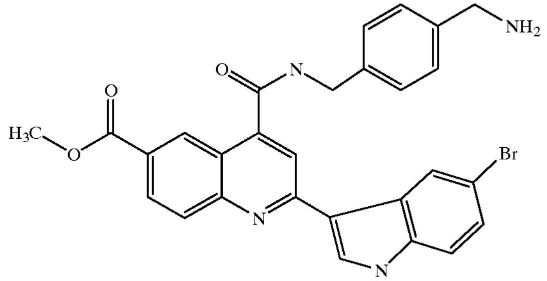 | > | 25 | < | 25 | | |

-continued
| Cmpd. # | STRUCTURE | MRSA | VREF | S. pneu |
|---|---|---|---|---|
| 106 | 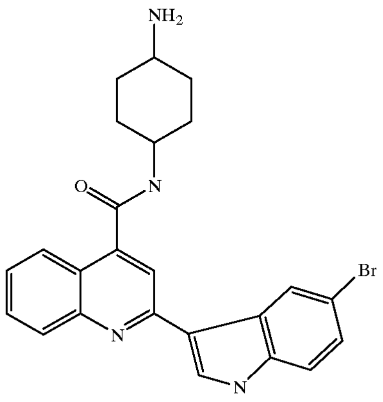 | < 25 | < 25 | |
| 107 | 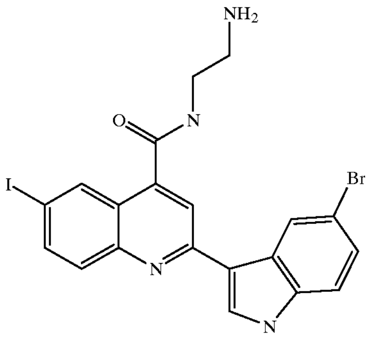 | < 7 | < 7 | < 7 |

-continued
| Cmpd. # | STRUCTURE | MRSA | VREF | S. pneu |
| --- | --- | --- | --- | --- |
| 108 | 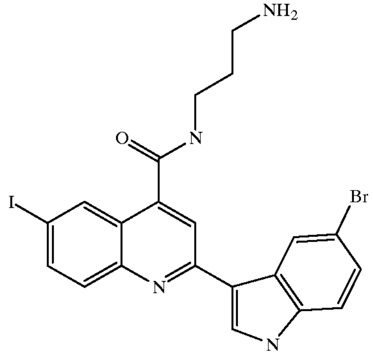 | < 7 | < 7 | < 7 |
| 109 | 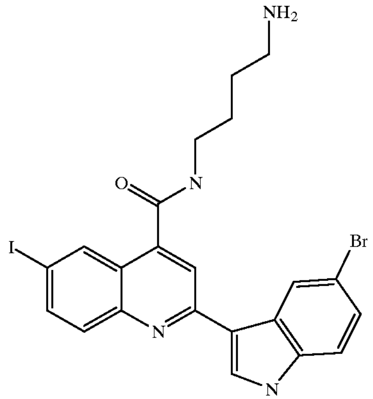 | < 7 | < 7 | < 7 |

-continued
| Cmpd. # | STRUCTURE | | MRSA | | VREF | | *S. pneu* |
|---|---|---|---|---|---|---|---|
| 110 | 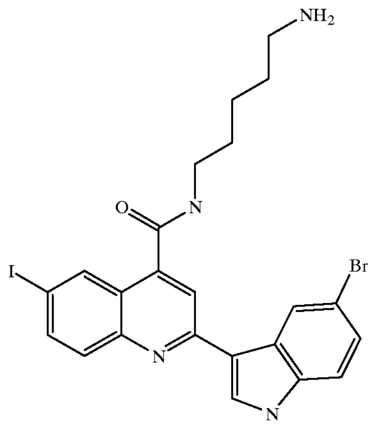 | < | 7 | < | 7 | < | 7 |
| 111 | 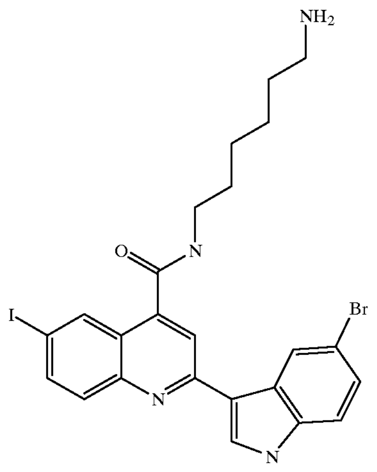 | < | 7 | < | 7 | < | 7 |

-continued
| Cmpd. # | STRUCTURE | | MRSA | | VREF | | *S. pneu* |
|---|---|---|---|---|---|---|---|
| 112 | 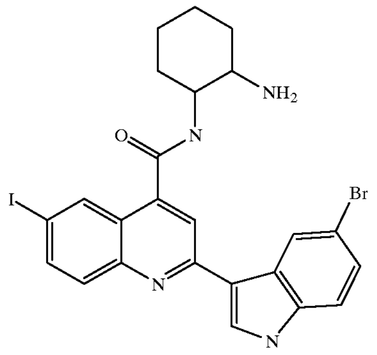 | < | 7 | < | 7 | < | 7 |
| 113 | 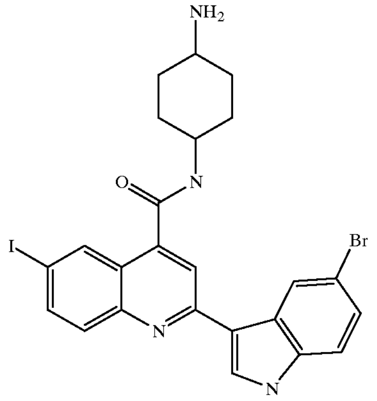 | < | 7 | < | 7 | < | 7 |

-continued
| Cmpd. # | STRUCTURE | | MRSA | | VREF | | *S. pneu* |
|---|---|---|---|---|---|---|---|
| 114 | 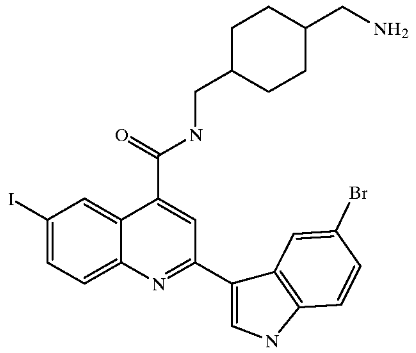 | < | 7 | < | 7 | < | 7 |
| 115 | 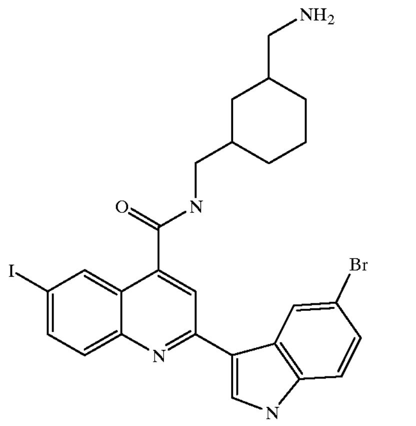 | < | 7 | < | 7 | < | 7 |

-continued
| Cmpd. # | STRUCTURE | | MRSA | | VREF | | *S. pneu* |
|---|---|---|---|---|---|---|---|
| 116 | 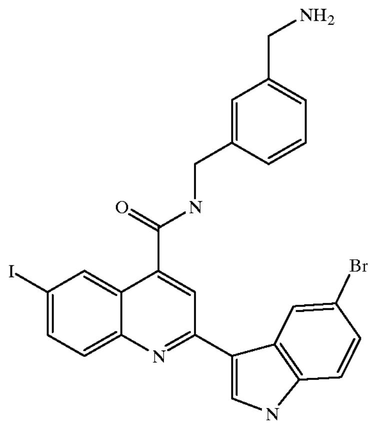 | < | 7 | < | 7 | < | 7 |
| 117 | 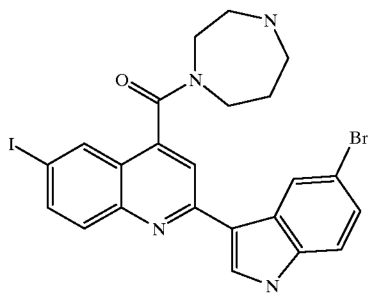 | < | 7 | < | 7 | < | 7 |

-continued
| Cmpd. # | STRUCTURE | | MRSA | | VREF | | *S. pneu* |
|---|---|---|---|---|---|---|---|
| 118 | 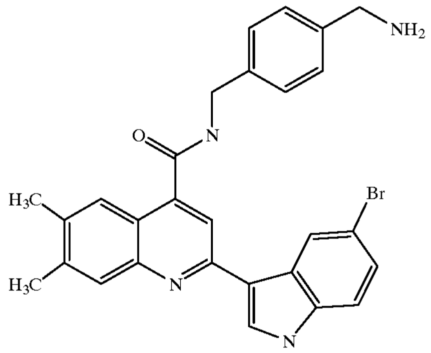 | < | 7 | < | 7 | < | 7 |
| 119 | 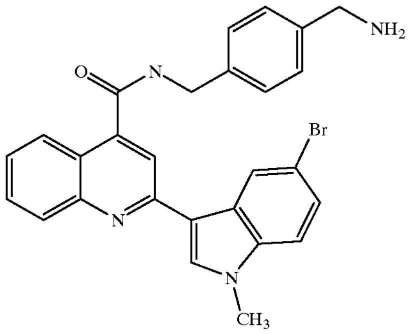 | < | 7 | < | 25 | < | 7 |
| 120 | 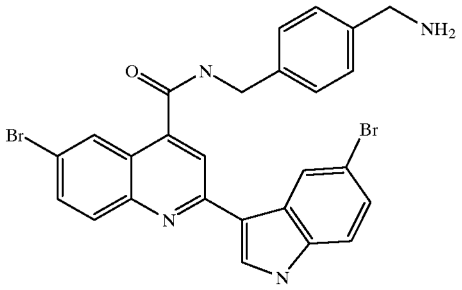 | < | 7 | < | 7 | | |

-continued
| Cmpd. # | STRUCTURE | MRSA | VREF | *S. pneu* |
| --- | --- | --- | --- | --- |
| 121 | 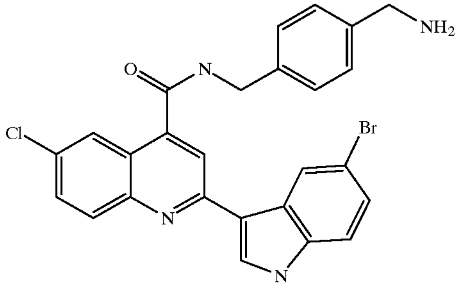 | < 7 | < 7 | |
| 122 | 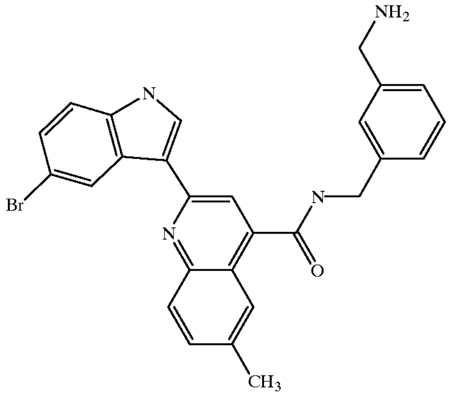 | < 7 | < 7 | < 7 |

-continued
| Cmpd. # | STRUCTURE | | MRSA | | VREF | | *S. pneu* |
|---|---|---|---|---|---|---|---|
| 123 | 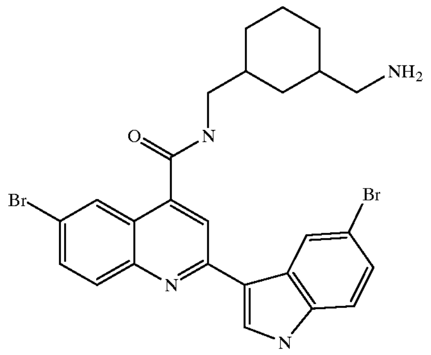 | < | 7 | < | 7 | < | 7 |
| 124 | 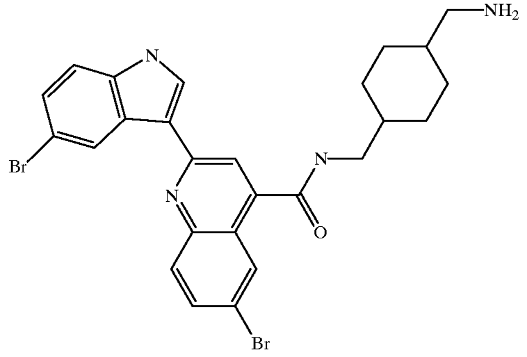 | < | 7 | < | 7 | < | 7 |

-continued
| Cmpd. # | STRUCTURE | MRSA | VREF | *S. pneu* |
| --- | --- | --- | --- | --- |
| 125 | 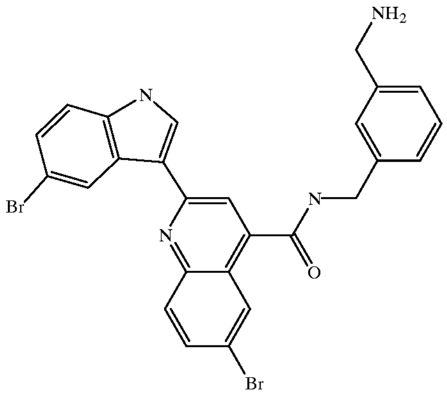 | < 7 | < 7 | |
| 126 | 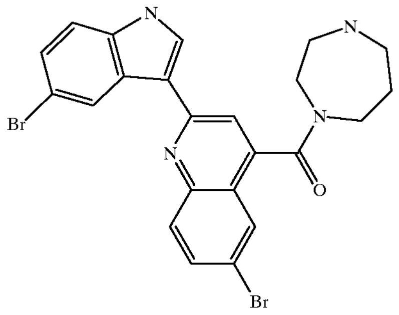 | < 7 | < 7 | |

-continued
| Cmpd. # | STRUCTURE | | MRSA | | VREF | | *S. pneu* |
|---|---|---|---|---|---|---|---|
| 127 | 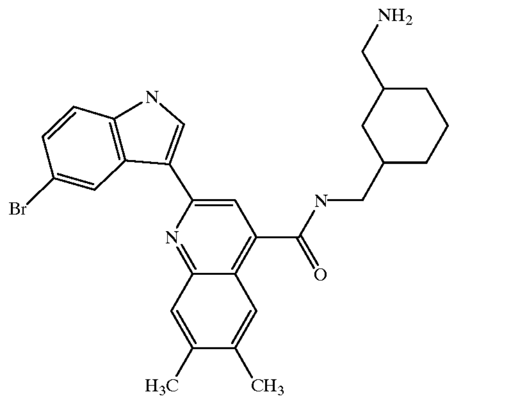 | < | 7 | < | 7 | < | 7 |
| 128 | 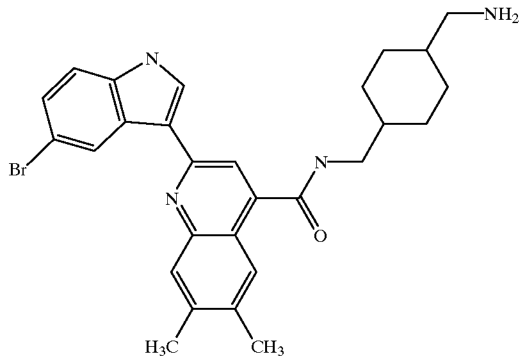 | < | 7 | < | 7 | < | 7 |

-continued
| Cmpd. # | STRUCTURE | MRSA | VREF | *S. pneu* |
|---|---|---|---|---|
| 129 | 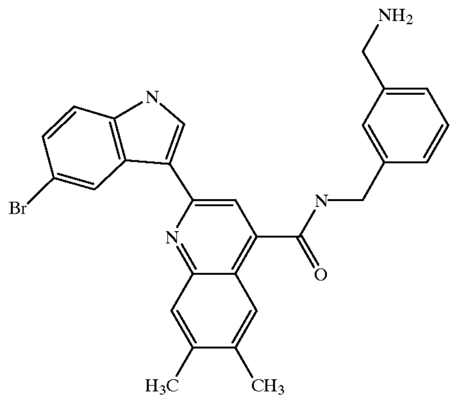 | < 7 | < 7 | |
| 130 | 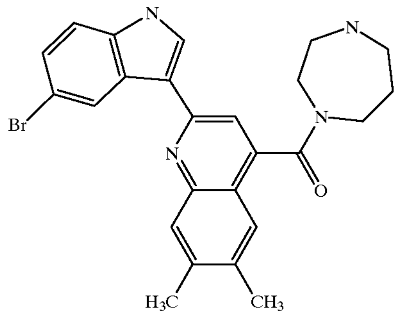 | < 7 | < 7 | |

-continued
| Cmpd. # | STRUCTURE | | MRSA | | VREF | | *S. pneu* |
|---|---|---|---|---|---|---|---|
| 131 | 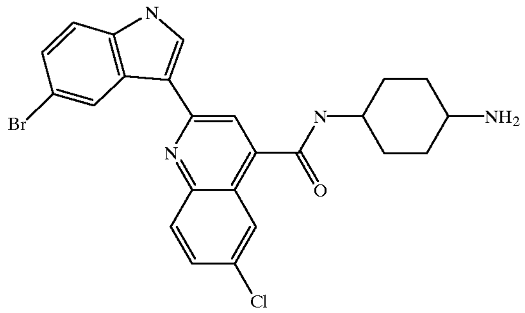 | < | 7 | < | 25 | < | 7 |
| 132 | 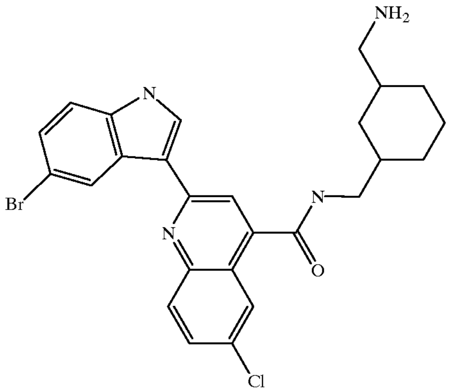 | < | 7 | < | 7 | < | 7 |

-continued
| Cmpd. # | STRUCTURE | | MRSA | | VREF | | *S. pneu* |
|---|---|---|---|---|---|---|---|
| 133 | 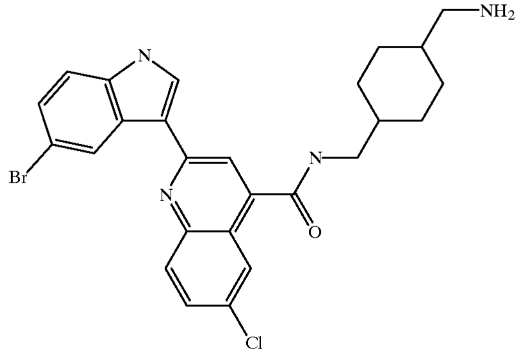 | < | 7 | < | 7 | < | 7 |
| 134 | 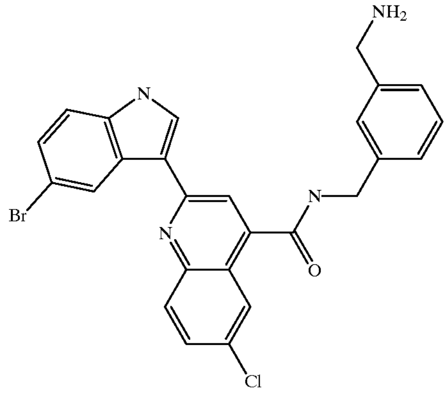 | < | 7 | < | 7 | < | 7 |

-continued
| Cmpd. # | STRUCTURE | MRSA | VREF | *S. pneu* |
|---|---|---|---|---|
| 135 | 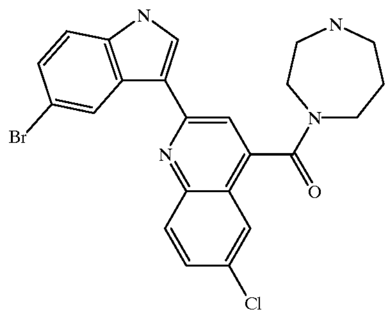 | < 7 | < 7 | |
| 136 | 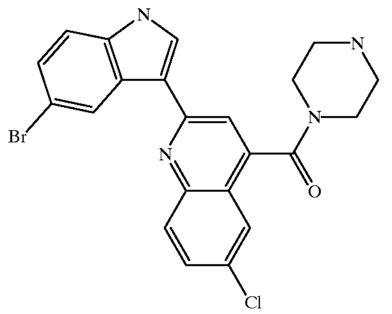 | < 7 | < 7 | < 7 |

-continued
| Cmpd. # | STRUCTURE | | MRSA | | VREF | | *S. pneu* |
|---|---|---|---|---|---|---|---|
| 137 | 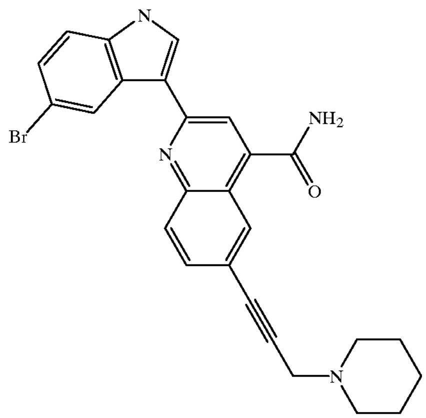 | < | 25 | < | 25 | | |
| 138 | 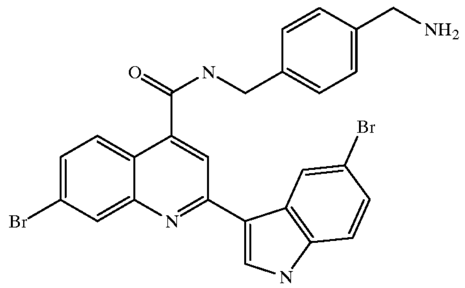 | < | 7 | < | 7 | < | 7 |
| 139 | 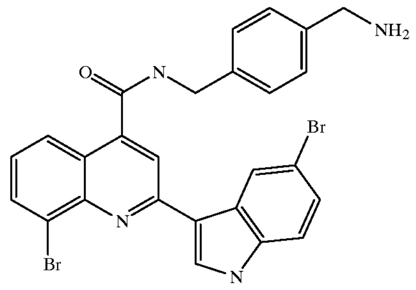 | < | 7 | < | 7 | < | 7 |

-continued
| Cmpd. # | STRUCTURE | | MRSA | | VREF | | *S. pneu* |
|---|---|---|---|---|---|---|---|
| 140 | 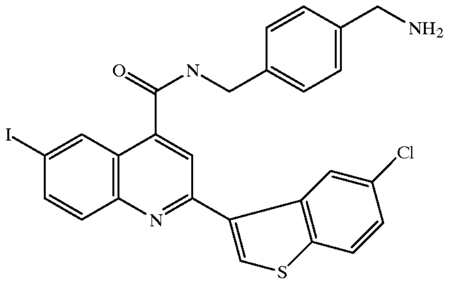 | > | 25 | < | 25 | | |
| 141 | 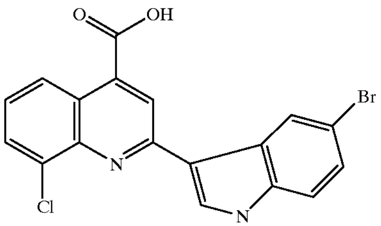 | > | 25 | > | 25 | | |
| 142 | 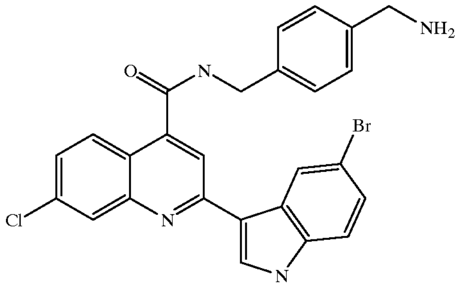 | < | 7 | < | 7 | < | 7 |

-continued
| Cmpd. # | STRUCTURE | | MRSA | | VREF | | *S. pneu* |
|---|---|---|---|---|---|---|---|
| 143 | 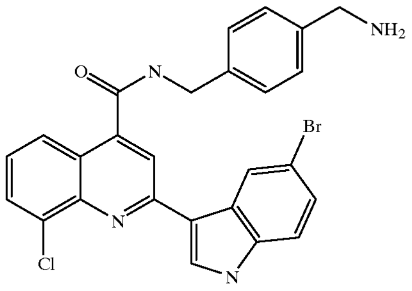 | < | 7 | < | 7 | < | 7 |
| 144 | 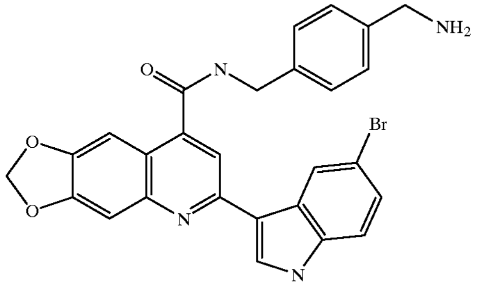 | < | 7 | < | 25 | < | 25 |

-continued
| Cmpd. # | STRUCTURE | | MRSA | | VREF | *S. pneu* |
|---|---|---|---|---|---|---|
| 145 | 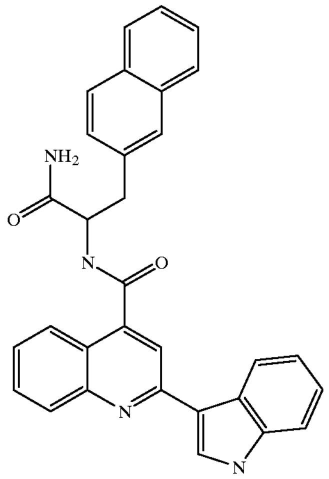 | < | 7 | < | 25 | |
| 146 | 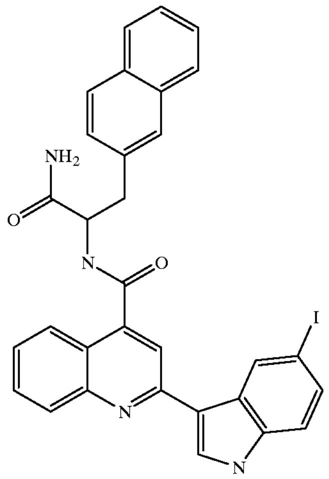 | < | 7 | < | 25 | |

-continued
| Cmpd. # | STRUCTURE | MRSA | | VREF | | S. pneu |
|---|---|---|---|---|---|---|
| 147 | 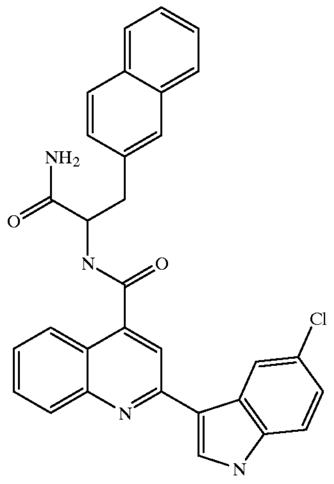 | < | 7 | < | 7 | |
| 148 | 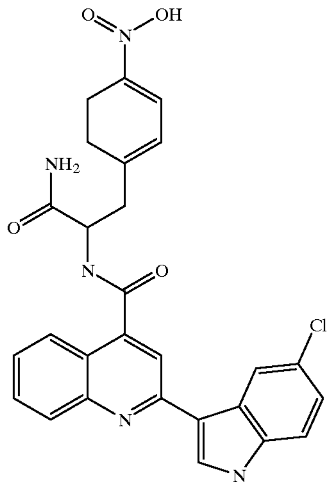 | < | 7 | < | 25 | |

-continued
| Cmpd. # | STRUCTURE | | MRSA | | VREF | *S. pneu* |
|---|---|---|---|---|---|---|
| 149 | 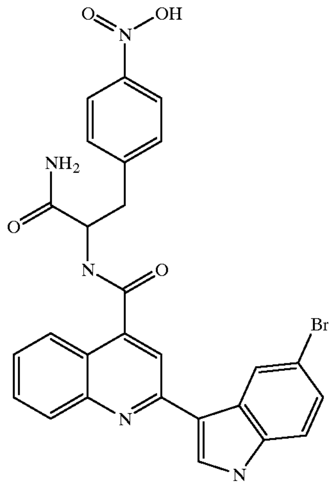 | < | 7 | > | 25 | |
| 150 | 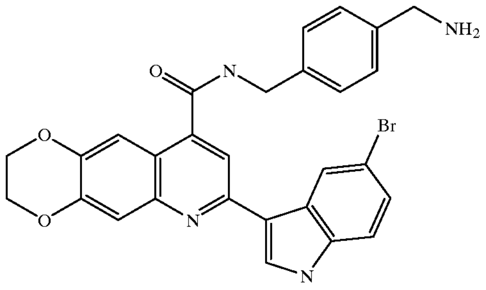 | > | 25 | > | 25 | |

-continued
| Cmpd. # | STRUCTURE | | MRSA | | VREF | | *S. pneu* |
|---|---|---|---|---|---|---|---|
| 151 | 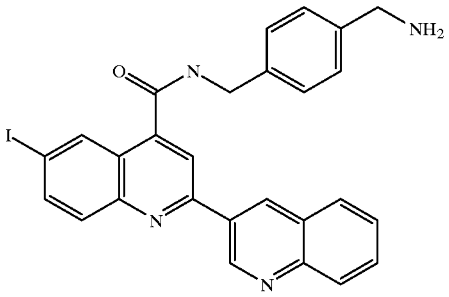 | > | 25 | > | 25 | > | 25 |
| 152 | 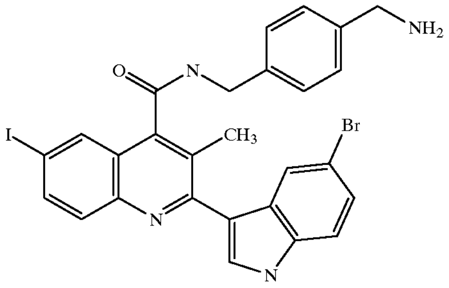 | < | 7 | < | 25 | | |
| 153 | 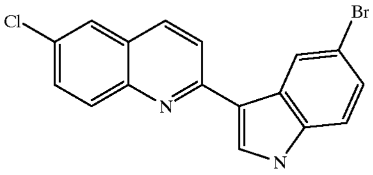 | < | 7 | > | 25 | < | 7 |

-continued
| Cmpd. # | STRUCTURE | | MRSA | | VREF | | *S. pneu* |
|---|---|---|---|---|---|---|---|
| 154 | 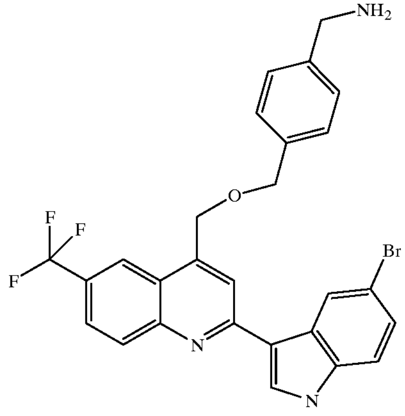 | < | 7 | < | 7 | < | 7 |
| 155 | 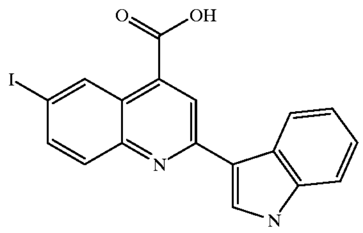 | > | 25 | > | 25 | | |
| 156 | 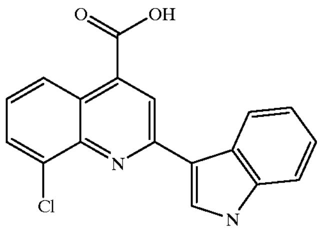 | > | 25 | > | 25 | | |

-continued
| Cmpd. # | STRUCTURE | MRSA | VREF | S. pneu |
|---|---|---|---|---|
| 157 | 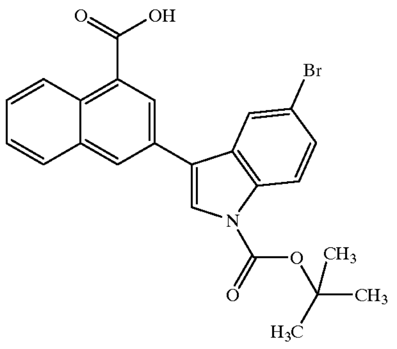 | > 25 | > 25 | |
| 158 | 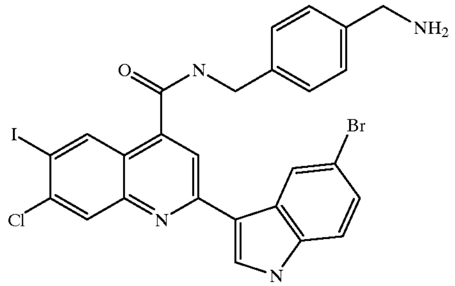 | < 7 | < 7 | < 7 |
| 159 | 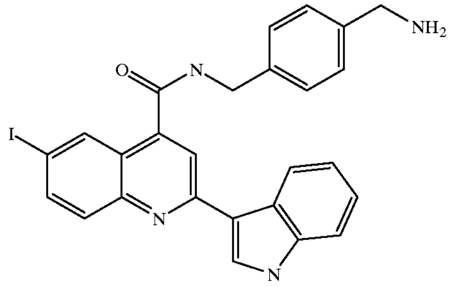 | < 7 | < 25 | < 25 |

-continued
| Cmpd. # | STRUCTURE | | MRSA | | VREF | | *S. pneu* |
|---|---|---|---|---|---|---|---|
| 160 | 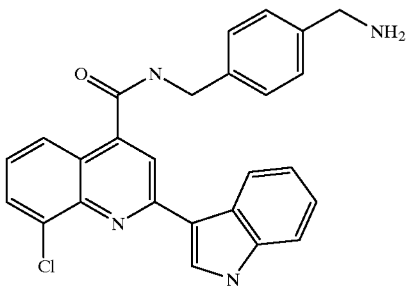 | < | 25 | < | 25 | | |
| 161 | 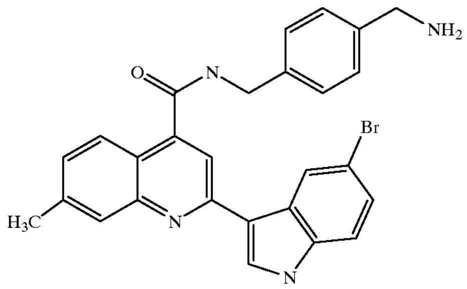 | < | 7 | < | 7 | < | 7 |
| 162 | 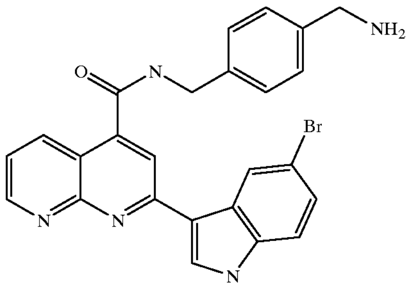 | > | 25 | > | 25 | | |

-continued
| Cmpd. # | STRUCTURE | | MRSA | | VREF | | S. pneu |
|---|---|---|---|---|---|---|---|
| 163 | 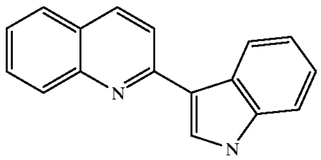 | < | 25 | > | 25 | > | 25 |
| 164 | 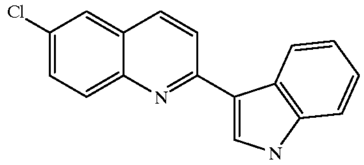 | < | 7 | < | 5 | < | 7 |
| 165 | 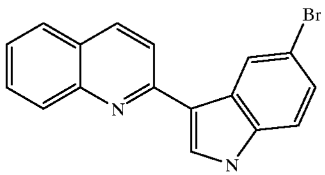 | < | 7 | < | 7 | < | 7 |
| 166 | 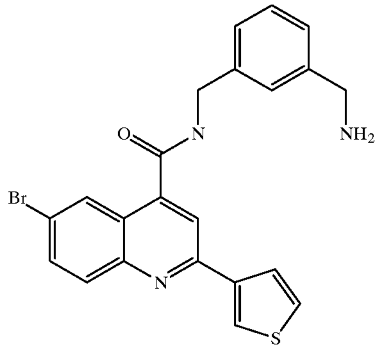 | > | 25 | > | 25 | | |

-continued
| Cmpd. # | STRUCTURE | | MRSA | | VREF | | *S. pneu* |
|---|---|---|---|---|---|---|---|
| 167 | 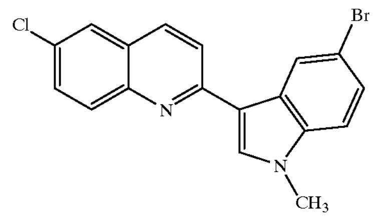 | > | 25 | > | 25 | | |
| 168 | 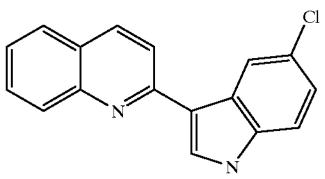 | < | 7 | > | 25 | < | 7 |
| 169 | 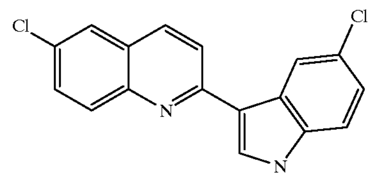 | < | 7 | > | 25 | < | 7 |
| 170 | 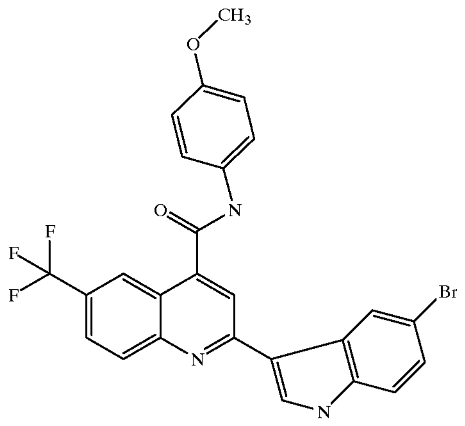 | < | 7 | > | 25 | < | 7 |

-continued
| Cmpd. # | STRUCTURE | | MRSA | | VREF | | *S. pneu* |
|---|---|---|---|---|---|---|---|
| 171 | 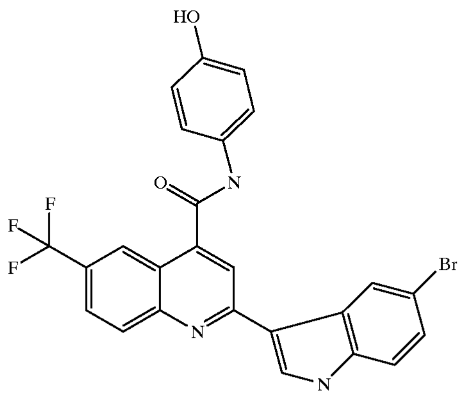 | < | 7 | < | 7 | < | 7 |
| 172 | 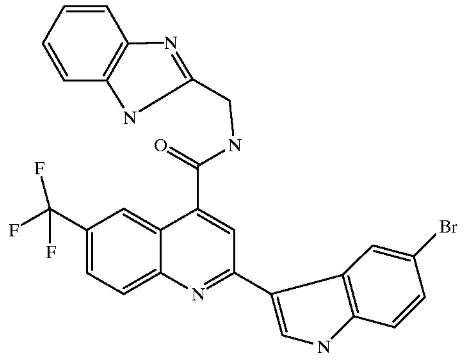 | < | 7 | > | 25 | < | 7 |

-continued
| Cmpd. # | STRUCTURE | | MRSA | | VREF | | *S. pneu* |
|---|---|---|---|---|---|---|---|
| 173 | 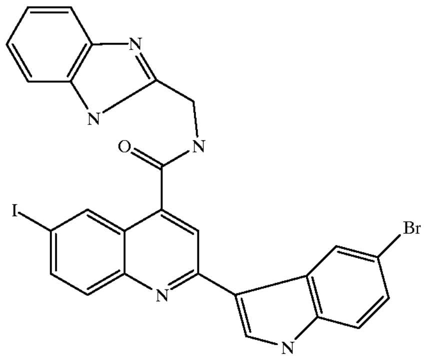 | < | 7 | > | 25 | < | 7 |
| 174 | 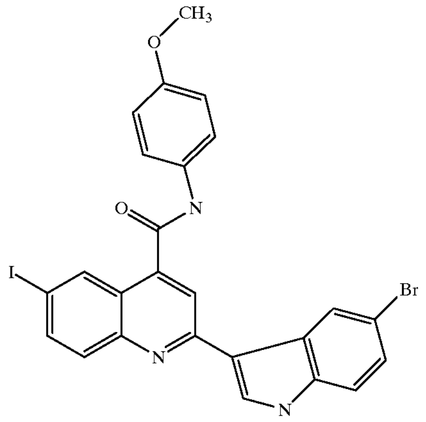 | < | 7 | > | 25 | < | 25 |

-continued
| Cmpd. # | STRUCTURE | | MRSA | | VREF | | *S. pneu* |
|---|---|---|---|---|---|---|---|
| 175 | 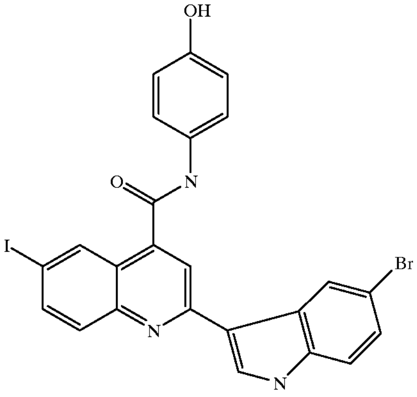 | < | 7 | < | 25 | < | 7 |
| 176 | 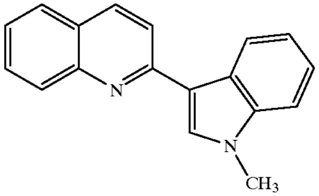 | > | 25 | > | 25 | | |
| 177 | 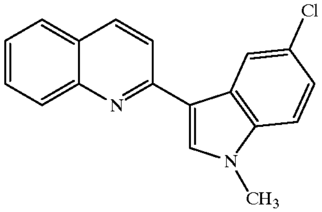 | > | 25 | > | 25 | | |

-continued
| Cmpd. # | STRUCTURE | | MRSA | | VREF | | *S. pneu* |
|---|---|---|---|---|---|---|---|
| 178 | 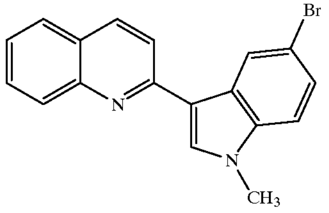 | > | 25 | > | 25 | | |
| 179 | 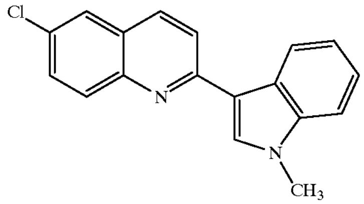 | > | 25 | > | 25 | | |
| 180 | 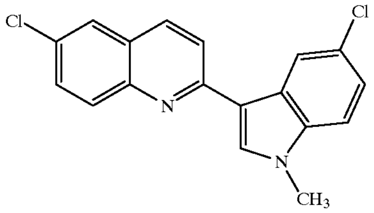 | > | 25 | > | 25 | | |
| 181 | 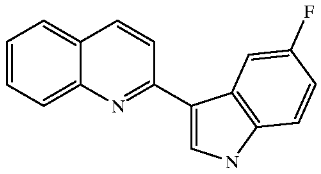 | < | 7 | < | 25 | < | 7 |

-continued
| Cmpd. # | STRUCTURE | | MRSA | | VREF | | *S. pneu* |
|---|---|---|---|---|---|---|---|
| 182 | 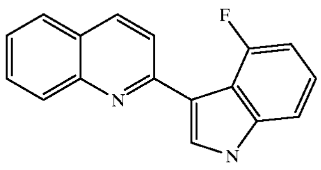 | > | 25 | > | 25 | | |
| 183 | 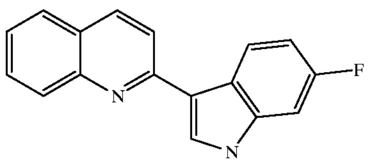 | < | 25 | > | 25 | > | 25 |
| 184 | 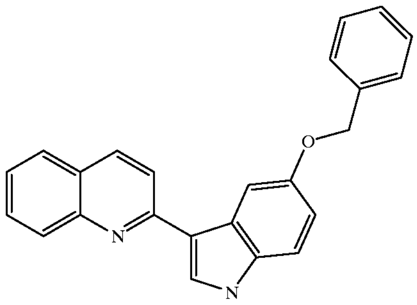 | > | 25 | > | 25 | < | 7 |
| 185 | 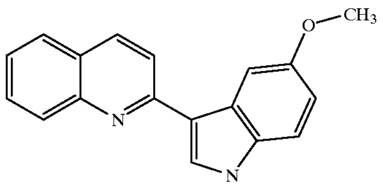 | < | 25 | > | 25 | | |

-continued
| Cmpd. # | STRUCTURE | | MRSA | | VREF | *S. pneu* |
|---|---|---|---|---|---|---|
| 186 | 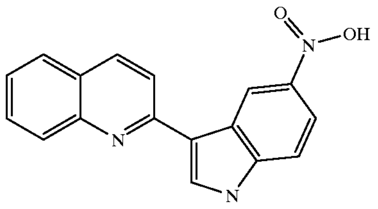 | > | 25 | > | 25 | |
| 187 | 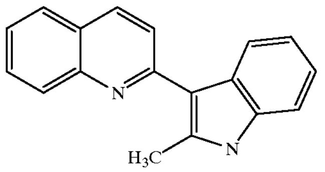 | > | 25 | > | 25 | |
| 188 | 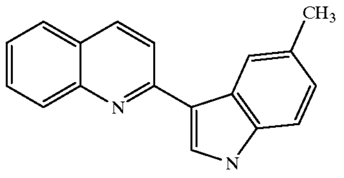 | > | 25 | > | 25 | |
| 189 | 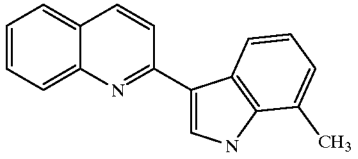 | < | 25 | < | 25 | |
| 190 | 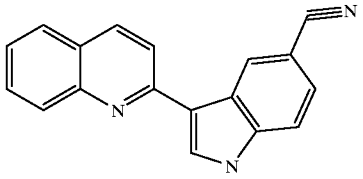 | > | 25 | > | 25 | |

-continued
| Cmpd. # | STRUCTURE | | MRSA | | VREF | | *S. pneu* |
|---|---|---|---|---|---|---|---|
| 191 | 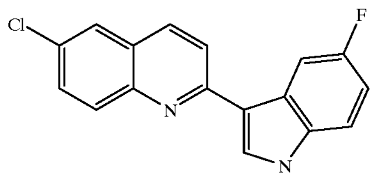 | < | 7 | < | 25 | < | 7 |
| 192 | 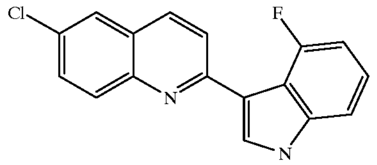 | > | 25 | > | 25 | | |
| 193 | 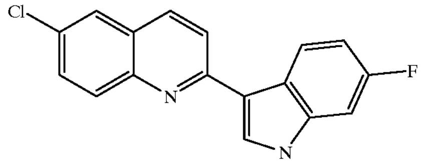 | < | 7 | < | 7 | < | 7 |
| 194 | 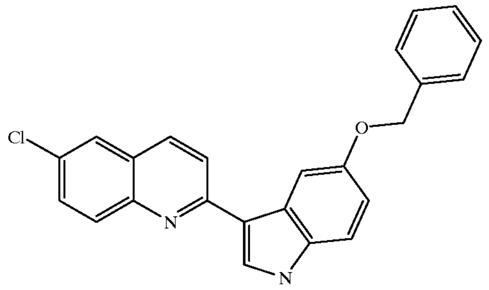 | < | 7 | > | 25 | < | 7 |

-continued
| Cmpd. # | STRUCTURE | | MRSA | | VREF | | *S. pneu* |
|---|---|---|---|---|---|---|---|
| 195 | 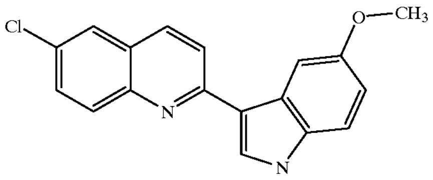 | > | 25 | > | 25 | > | 25 |
| 196 | 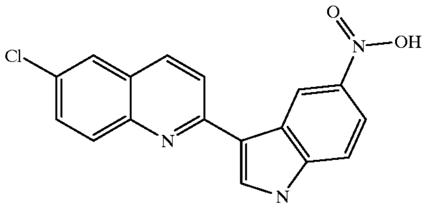 | < | 7 | > | 25 | < | 25 |
| 197 | 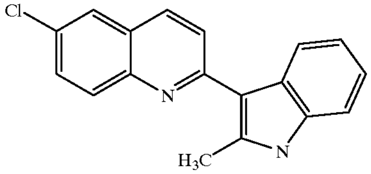 | < | 7 | > | 25 | | |
| 198 | 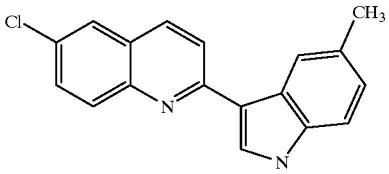 | > | 25 | > | 25 | | |
| 199 | 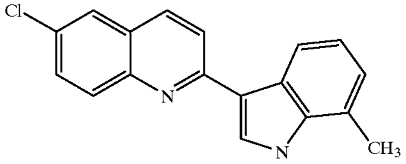 | > | 25 | > | 25 | > | 25 |

-continued
| Cmpd. # | STRUCTURE | | MRSA | | VREF | | *S. pneu* |
|---|---|---|---|---|---|---|---|
| 200 | 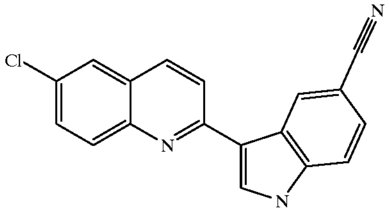 | < | 7 | > | 25 | > | 25 |
| 201 | 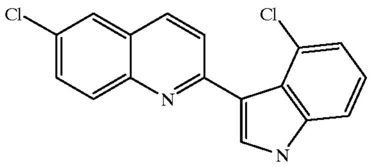 | < | 7 | < | 25 | < | 7 |
| 202 | 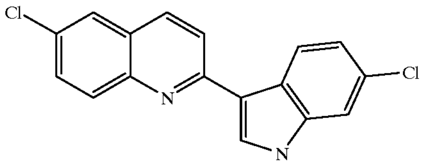 | < | 7 | > | 25 | < | 7 |
| 203 | 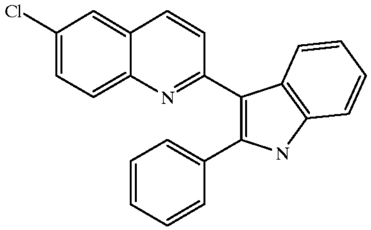 | > | 25 | > | 25 | | |

-continued
| Cmpd. # | STRUCTURE | | MRSA | | VREF | | *S. pneu* |
|---|---|---|---|---|---|---|---|
| 204 | 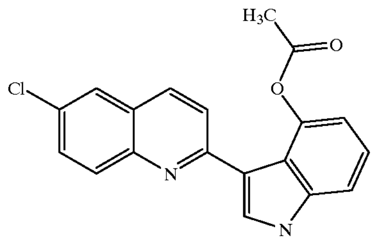 | < | 7 | < | 25 | < | 7 |
| 205 | 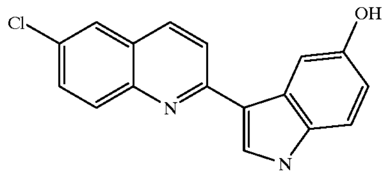 | < | 25 | < | 25 | | |
| 206 | 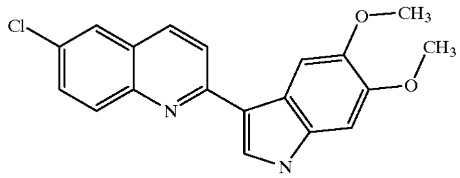 | > | 25 | > | 25 | | |
| 207 | 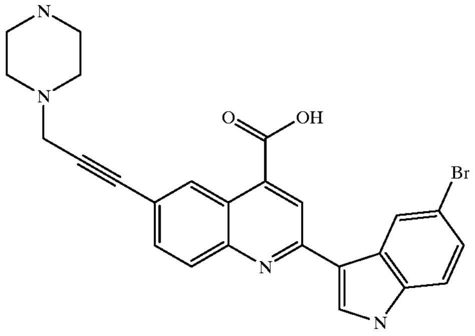 | > | 25 | < | 25 | | |

-continued
| Cmpd. # | STRUCTURE | | MRSA | | VREF | | *S. pneu* |
|---|---|---|---|---|---|---|---|
| 208 | 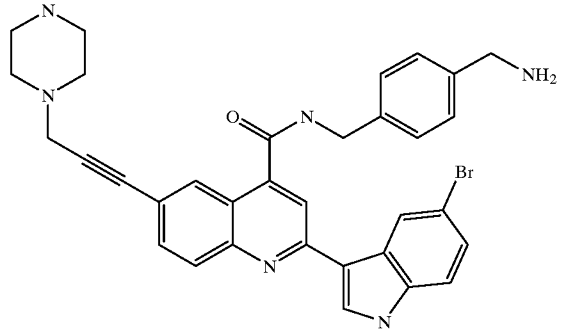 | < | 7 | < | 25 | < | 25 |
| 209 | 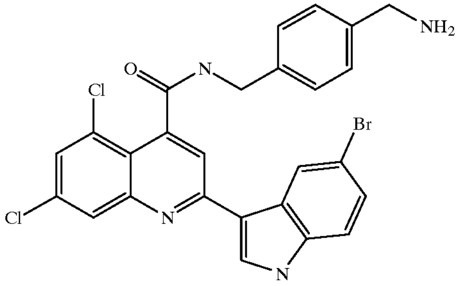 | < | 7 | < | 7 | < | 7 |
| 210 | 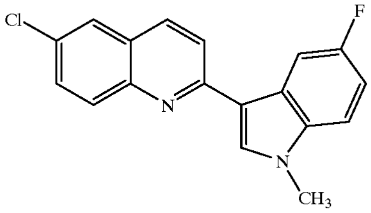 | < | 7 | > | 25 | | |

-continued
| Cmpd. # | STRUCTURE | MRSA | VREF | *S. pneu* |
|---|---|---|---|---|
| 211 | 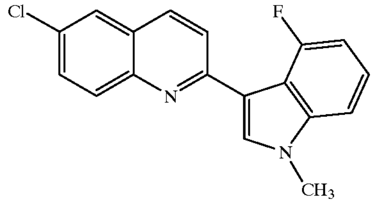 | < 25 | > 25 | > 25 |
| 212 | 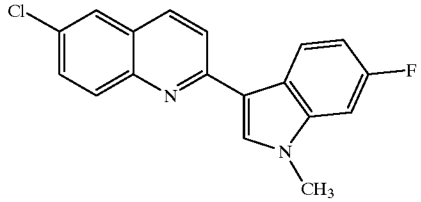 | > 25 | > 25 | |
| 213 | 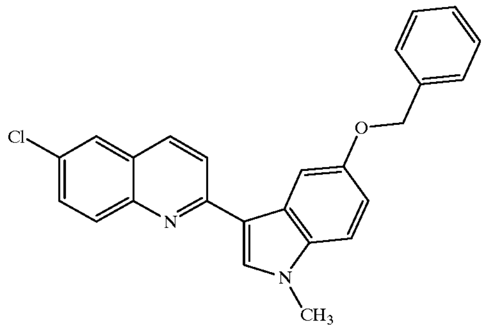 | < 25 | < 25 | |
| 214 | 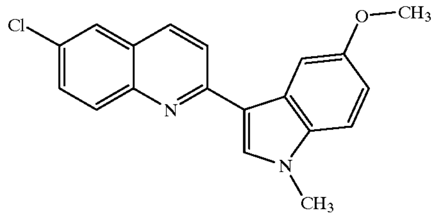 | < 25 | > 25 | |

-continued
| Cmpd. # | STRUCTURE | | MRSA | | VREF | | *S. pneu* |
|---|---|---|---|---|---|---|---|
| 215 | 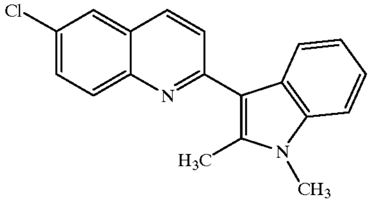 | < | 7 | < | 25 | | |
| 216 | 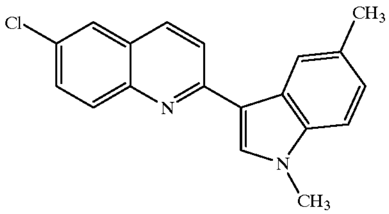 | < | 25 | > | 25 | | |
| 217 | 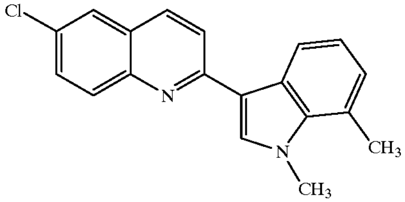 | < | 25 | < | 25 | < | 7 |
| 218 | 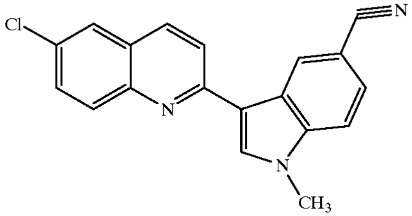 | < | 7 | > | 25 | > | 25 |

-continued
| Cmpd. # | STRUCTURE | | MRSA | | VREF | | *S. pneu* |
|---|---|---|---|---|---|---|---|
| 219 | 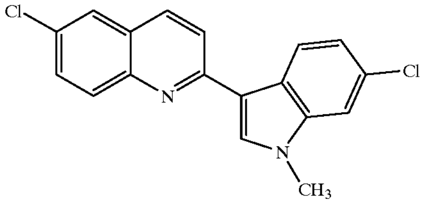 | > | 25 | > | 25 | < | 25 |
| 220 | 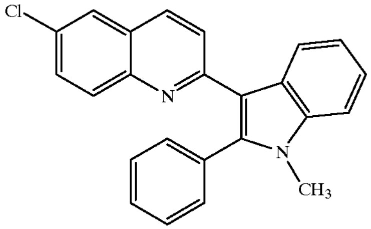 | < | 25 | > | 25 | | |
| 221 | 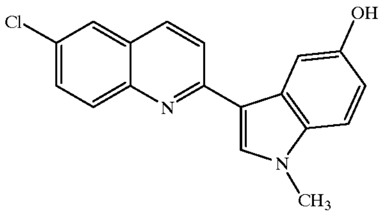 | < | 7 | < | 7 | < | 7 |
| 222 | 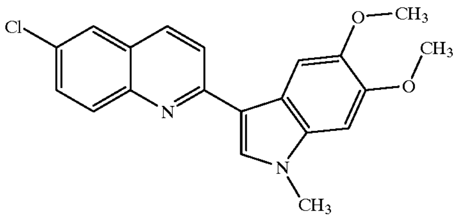 | > | 25 | > | 25 | | |

-continued
| Cmpd. # | STRUCTURE | MRSA | | VREF | | *S. pneu* | |
|---|---|---|---|---|---|---|---|
| 223 | 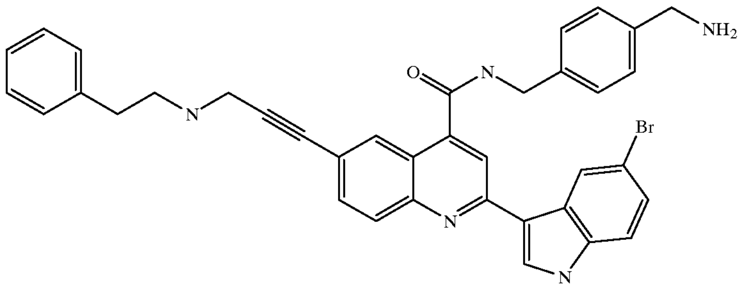 | < | 7 | < | 7 | < | 7 |
| 224 | 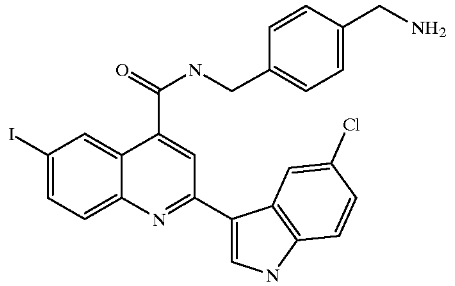 | < | 7 | < | 7 | < | 7 |
| 225 | 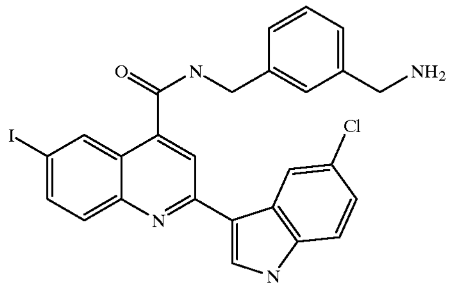 | < | 7 | < | 7 | < | 7 |

-continued
| Cmpd. # | STRUCTURE | MRSA | | VREF | | *S. pneu* | |
|---|---|---|---|---|---|---|---|
| 226 | 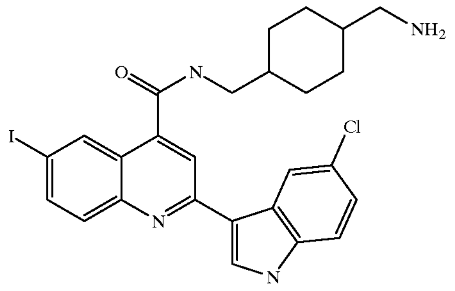 | < | 25 | < | 25 | < | 7 |
| 227 | 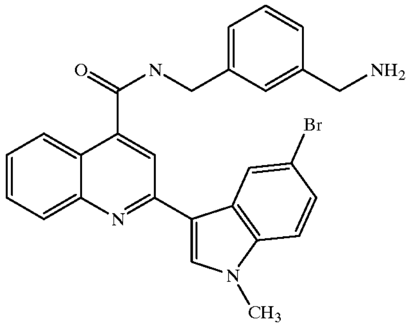 | < | 7 | < | 7 | < | 7 |
| 228 | 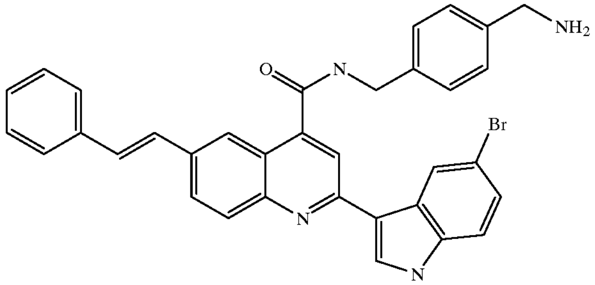 | > | 25 | > | 25 | > | 25 |

-continued
| Cmpd. # | STRUCTURE | | MRSA | | VREF | | *S. pneu* |
|---|---|---|---|---|---|---|---|
| 229 | 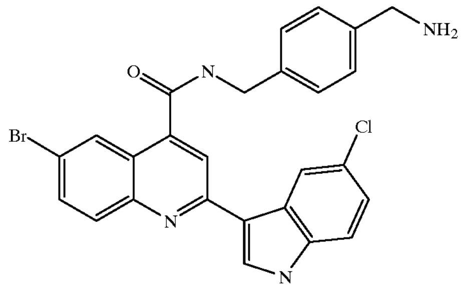 | < | 7 | < | 7 | < | 7 |
| 230 | 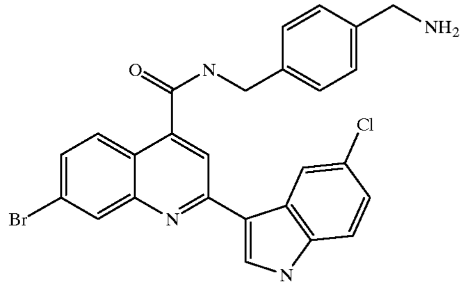 | < | 7 | < | 7 | < | 7 |
| 231 | 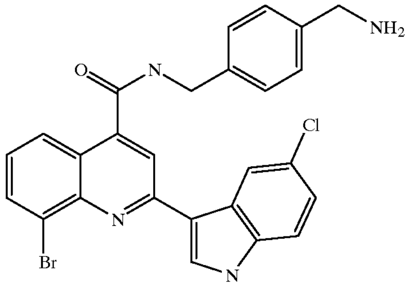 | < | 7 | < | 7 | < | 7 |

-continued
| Cmpd. # | STRUCTURE | | MRSA | | VREF | | *S. pneu* |
|---|---|---|---|---|---|---|---|
| 232 | 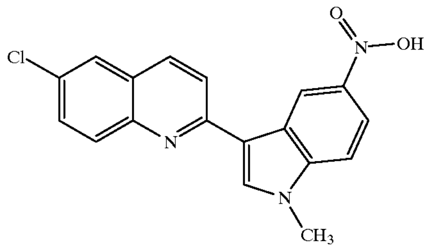 | < | 7 | < | 7 | < | 7 |
| 233 | 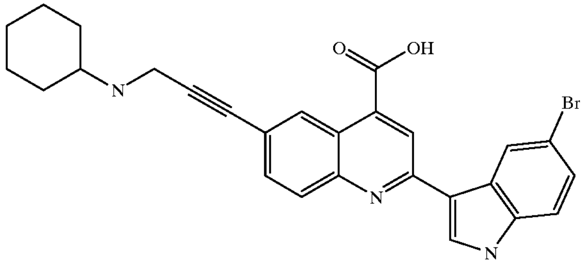 | > | 25 | < | 25 | < | 25 |
| 234 | 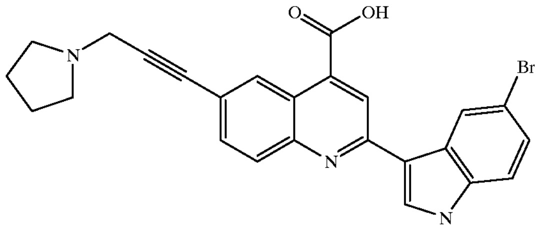 | > | 25 | > | 25 | > | 25 |

-continued
| Cmpd. # | STRUCTURE | MRSA | VREF | *S. pneu* |
|---|---|---|---|---|
| 235 | 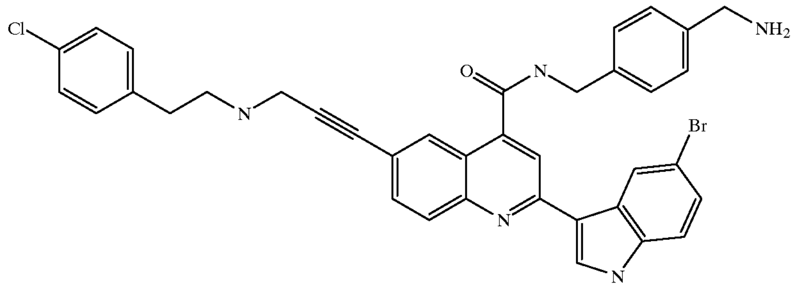 | < 7 | < 7 | < 7 |
| 236 | 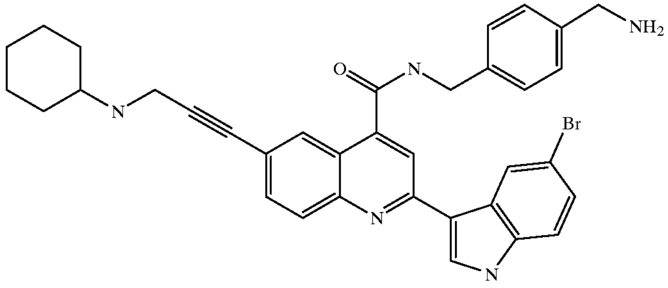 | < 7 | < 7 | < 7 |
| 237 | 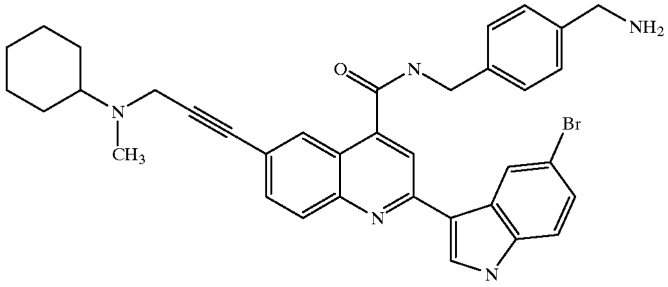 | < 7 | < 7 | |

-continued
| Cmpd. # | STRUCTURE | | MRSA | | VREF | | *S. pneu* |
|---|---|---|---|---|---|---|---|
| 238 | 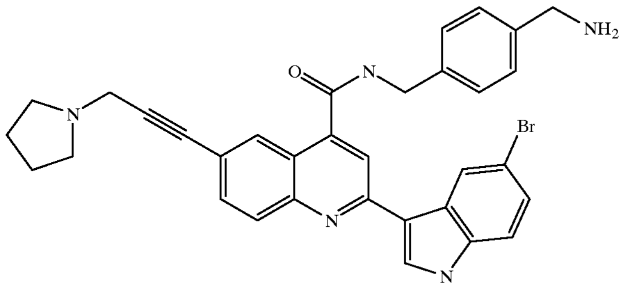 | < | 7 | < | 25 | < | 7 |
| 239 | 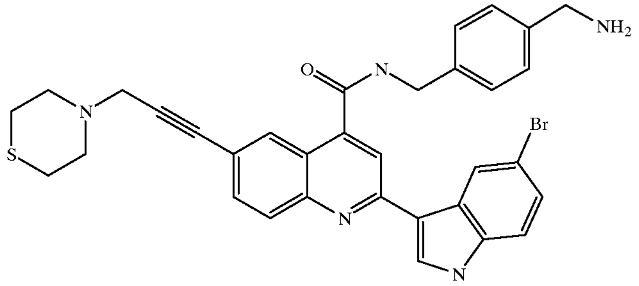 | < | 7 | < | 7 | > | 25 |
| 240 | 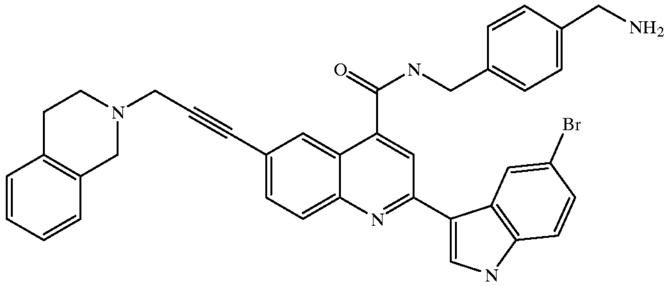 | < | 7 | < | 25 | > | 25 |

-continued
| Cmpd. # | STRUCTURE | | MRSA | | VREF | | *S. pneu* |
|---|---|---|---|---|---|---|---|
| 241 | 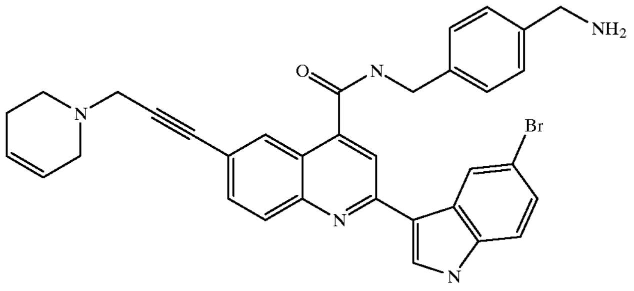 | < | 7 | < | 7 | < | 7 |
| 242 | 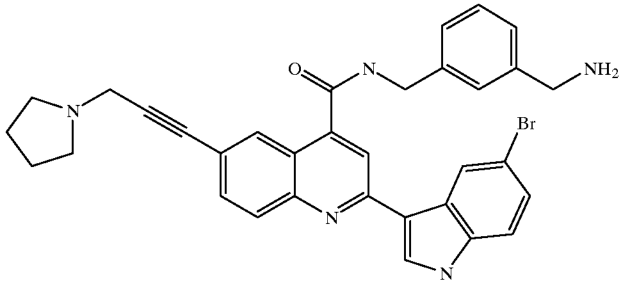 | < | 7 | < | 25 | < | 7 |
| 243 | 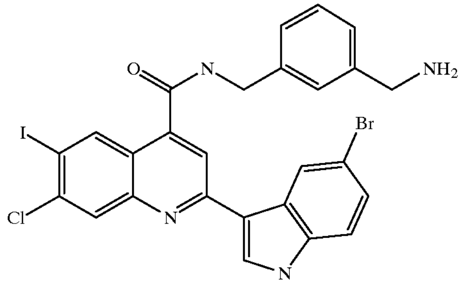 | < | 7 | < | 7 | < | 7 |

-continued
| Cmpd. # | STRUCTURE | | MRSA | | VREF | | S. pneu |
|---|---|---|---|---|---|---|---|
| 244 | 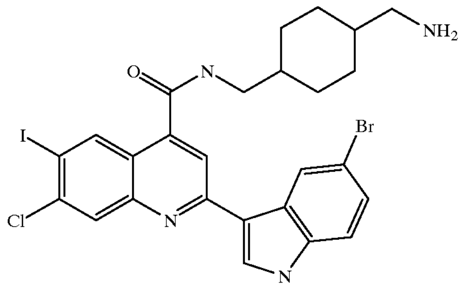 | < | 7 | < | 7 | < | 7 |
| 245 | 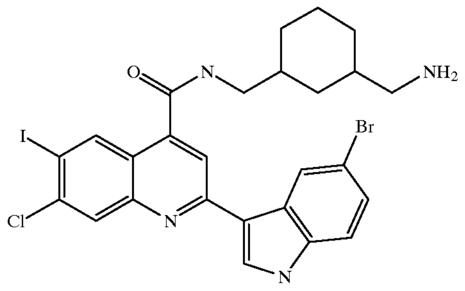 | < | 7 | < | 7 | < | 7 |
| 246 | 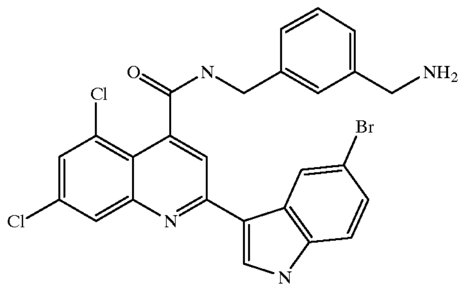 | < | 7 | < | 7 | < | 7 |

-continued
| Cmpd. # | STRUCTURE | MRSA | | VREF | | *S. pneu* | |
|---|---|---|---|---|---|---|---|
| 247 | 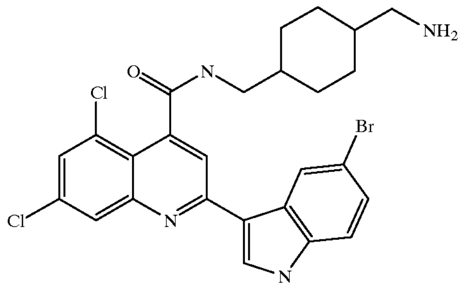 | < | 7 | < | 7 | < | 7 |
| 248 | 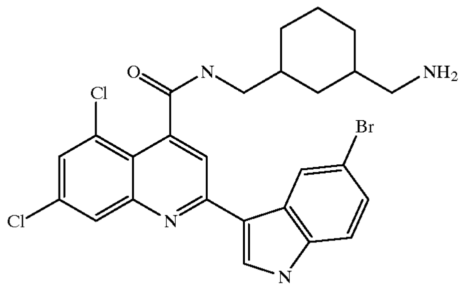 | < | 7 | < | 7 | < | 7 |
| 249 | 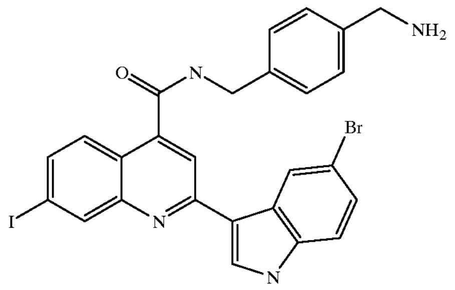 | < | 7 | < | 7 | < | 7 |

-continued
| Cmpd. # | STRUCTURE | MRSA | VREF | *S. pneu* |
|---|---|---|---|---|
| 250 | 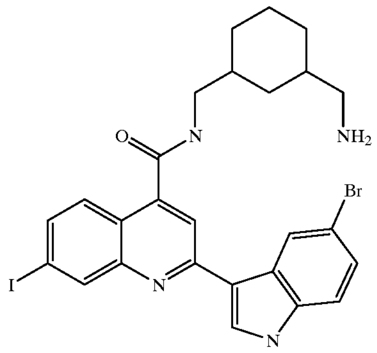 | < 7 | < 7 | < 7 |
| 251 | 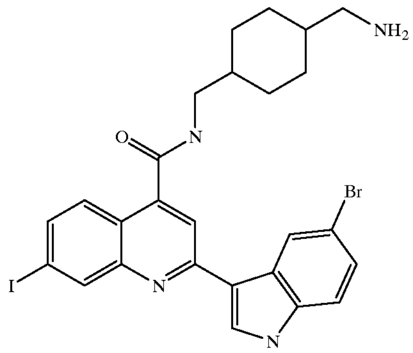 | < 7 | < 7 | < 7 |

-continued
| Cmpd. # | STRUCTURE | | MRSA | | VREF | | *S. pneu* |
|---|---|---|---|---|---|---|---|
| 252 | 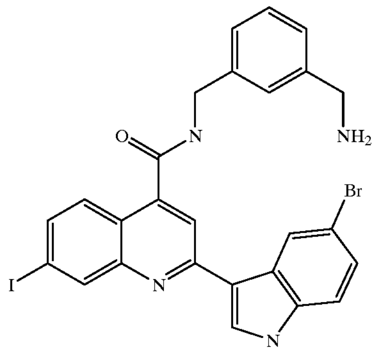 | < | 7 | < | 7 | < | 7 |
| 253 | 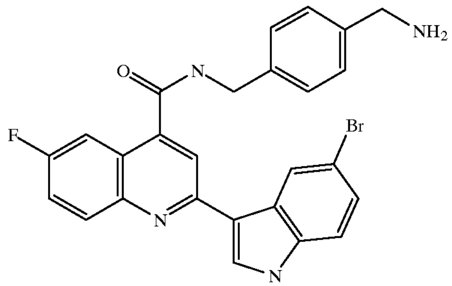 | < | 7 | < | 25 | < | 7 |
| 254 | 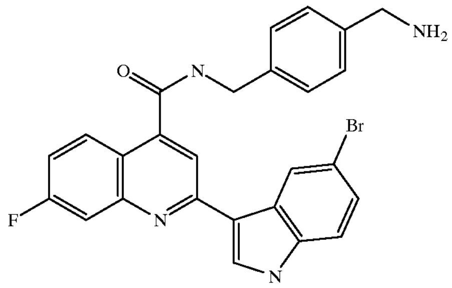 | < | 7 | < | 7 | < | 7 |

-continued
| Cmpd. # | STRUCTURE | MRSA | | VREF | | *S. pneu* | |
|---|---|---|---|---|---|---|---|
| 255 | 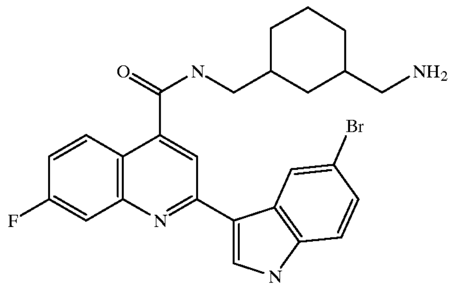 | < | 7 | < | 7 | | |
| 256 | 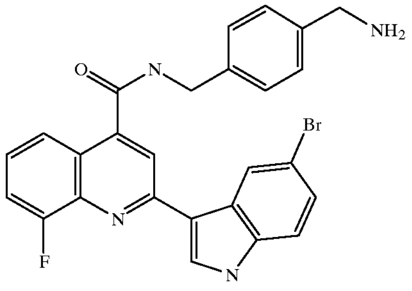 | < | 7 | < | 7 | < | 7 |
| 257 | 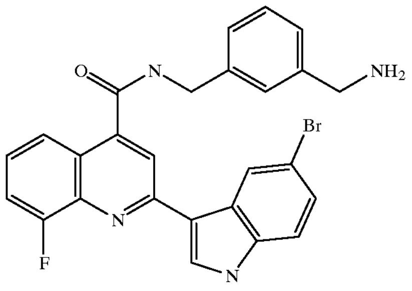 | < | 7 | < | 7 | < | 7 |

-continued
| Cmpd. # | STRUCTURE | | MRSA | | VREF | | *S. pneu* |
|---|---|---|---|---|---|---|---|
| 258 | 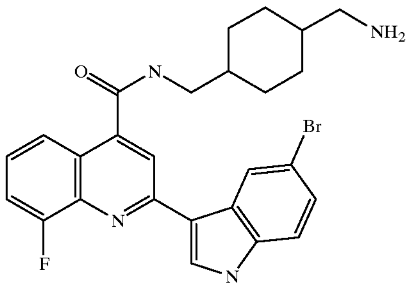 | < | 7 | < | 7 | < | 7 |
| 259 | 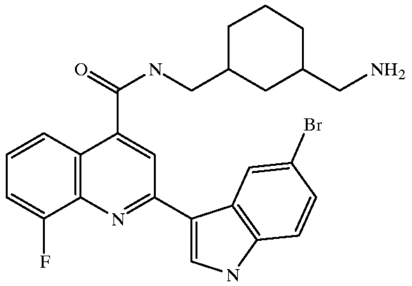 | < | 7 | < | 7 | < | 7 |
| 260 | 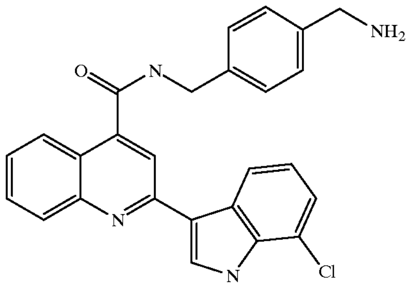 | < | 25 | < | 25 | < | 25 |

-continued
| Cmpd. # | STRUCTURE | | MRSA | | VREF | | *S. pneu* |
|---|---|---|---|---|---|---|---|
| 261 | 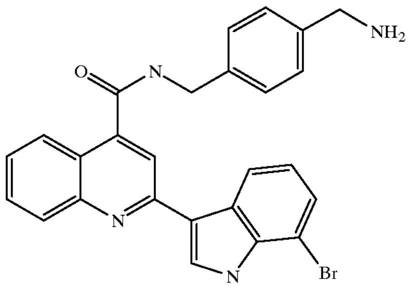 | < | 25 | < | 25 | < | 25 |
| 262 | 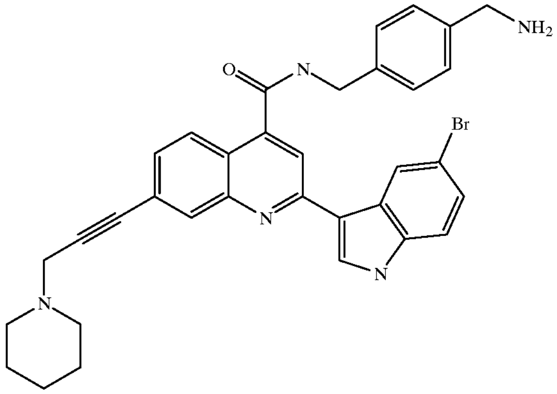 | < | 7 | < | 7 | < | 7 |

-continued
| Cmpd. # | STRUCTURE | | MRSA | | VREF | | *S. pneu* |
|---|---|---|---|---|---|---|---|
| 263 | 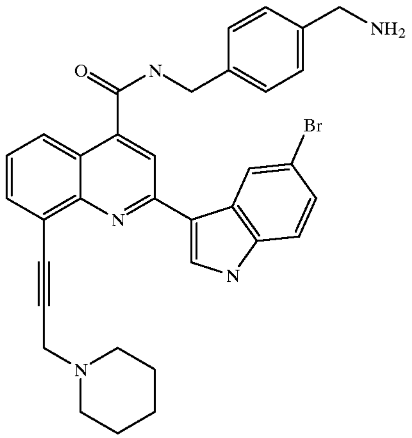 | < | 25 | < | 25 | < | 7 |
| 264 | 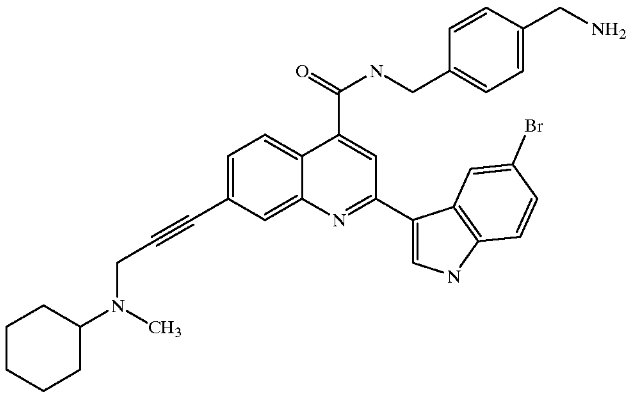 | < | 7 | < | 25 | | |

-continued
| Cmpd. # | STRUCTURE | MRSA | | VREF | | *S. pneu* | |
|---|---|---|---|---|---|---|---|
| 265 | 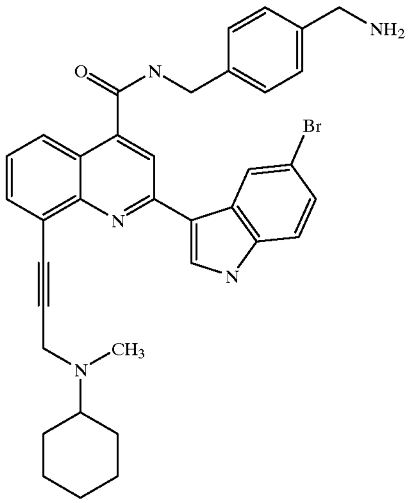 | < | 7 | < | 7 | | |
| 266 | 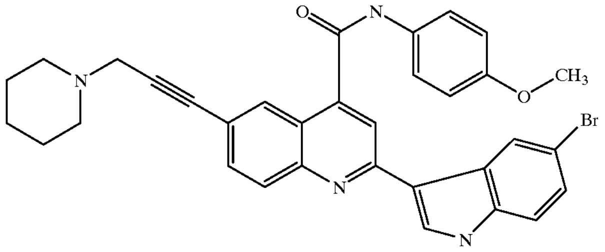 | < | 7 | > | 25 | < | 7 |

-continued
| Cmpd. # | STRUCTURE | | MRSA | | VREF | *S. pneu* |
| --- | --- | --- | --- | --- | --- | --- |
| 267 | 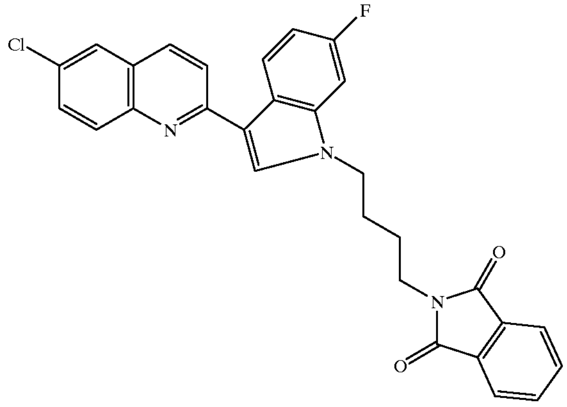 | > | 25 | > | 25 | |
| 268 | 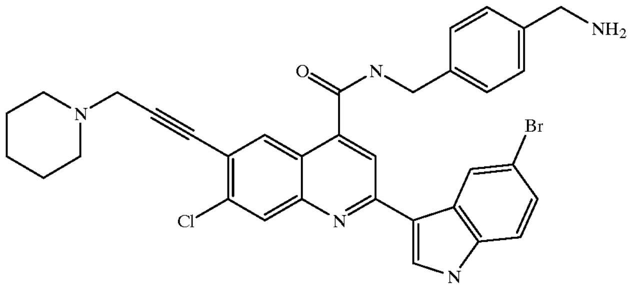 | < | 7 | < | 7 | |

-continued
| Cmpd. # | STRUCTURE | | MRSA | | VREF | | *S. pneu* |
|---|---|---|---|---|---|---|---|
| 269 | 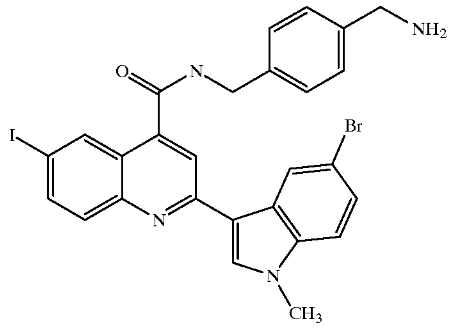 | < | 7 | < | 7 | | |
| 270 | 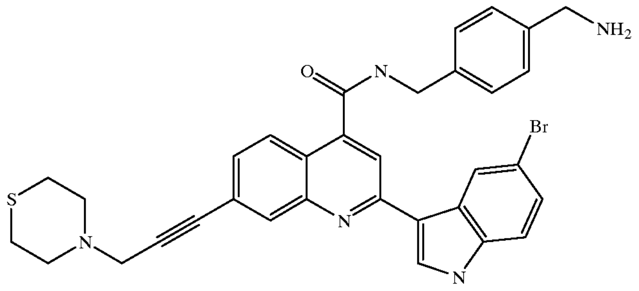 | < | 25 | < | 25 | > | 25 |

-continued
| Cmpd. # | STRUCTURE | | MRSA | | VREF | | *S. pneu* |
|---|---|---|---|---|---|---|---|
| 271 | 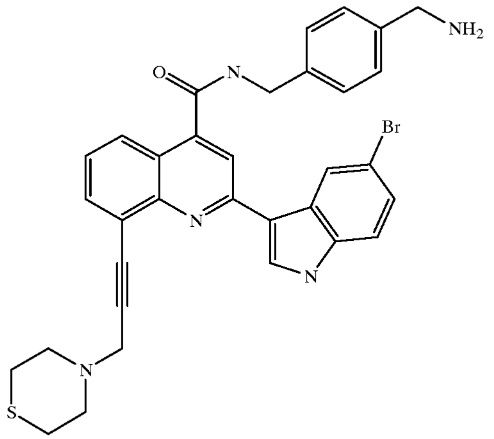 | < | 7 | < | 25 | < | 7 |
| 272 | 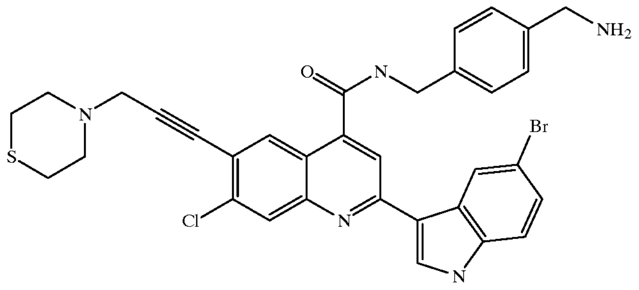 | < | 7 | < | 7 | < | 7 |

-continued
| Cmpd. # | STRUCTURE | | MRSA | | VREF | | *S. pneu* |
|---|---|---|---|---|---|---|---|
| 273 | 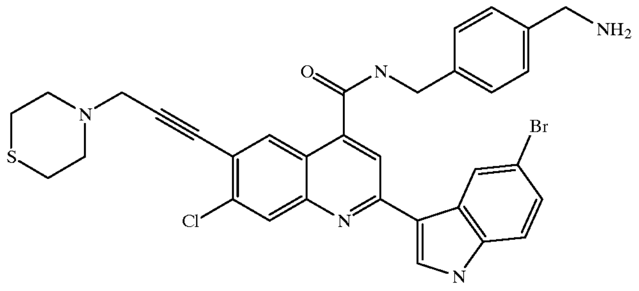 | < | 7 | < | 7 | < | 7 |
| 274 | 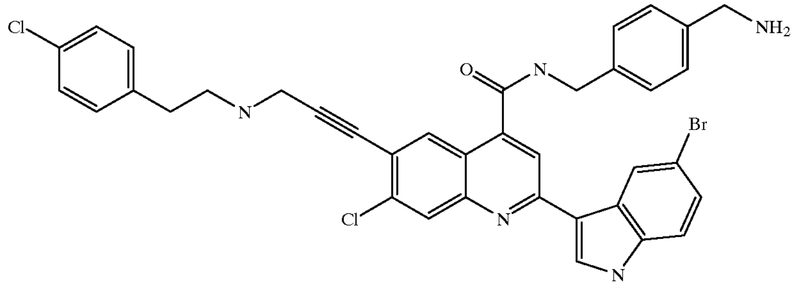 | < | 25 | > | 25 | < | 7 |
| 275 | 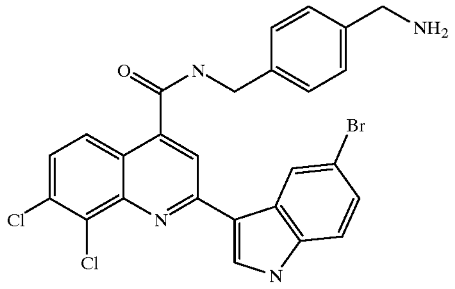 | < | 7 | < | 7 | < | 25 |

-continued
| Cmpd. # | STRUCTURE | | MRSA | | VREF | | S. pneu |
|---|---|---|---|---|---|---|---|
| 276 | 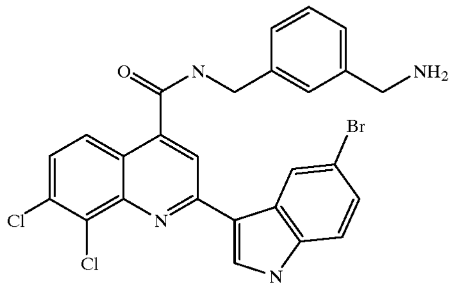 | < | 7 | < | 7 | > | 25 |
| 277 | 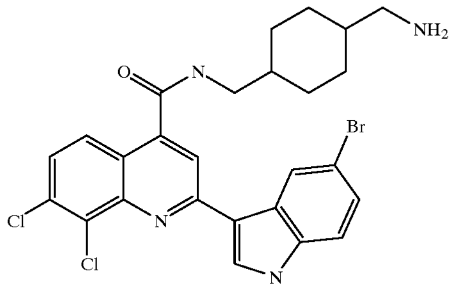 | < | 7 | < | 7 | < | 7 |
| 278 | 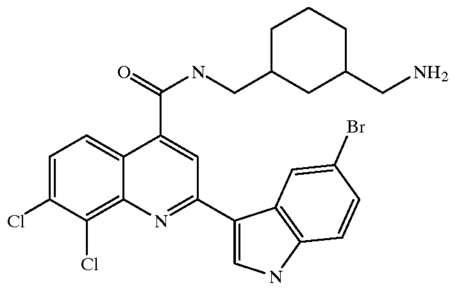 | < | 7 | < | 7 | < | 7 |

-continued
| Cmpd. # | STRUCTURE | | MRSA | | VREF | | *S. pneu* |
|---|---|---|---|---|---|---|---|
| 279 | 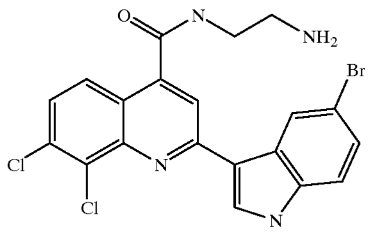 | < | 7 | < | 7 | < | 7 |
| 280 | 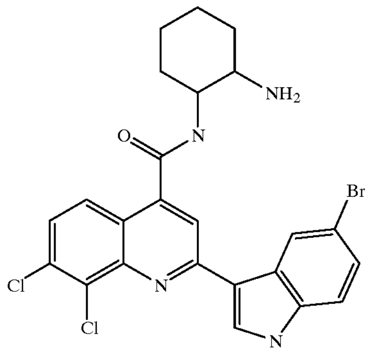 | < | 7 | < | 7 | < | 7 |
| 281 | 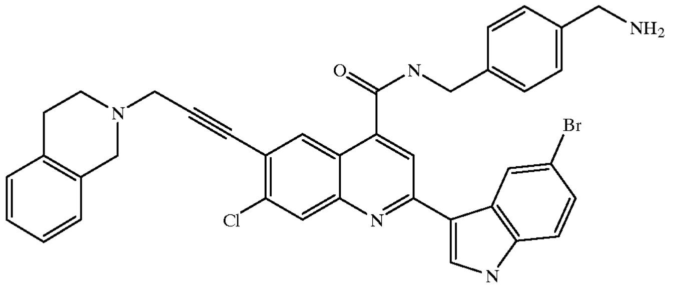 | < | 25 | > | 25 | > | 25 |

-continued
| Cmpd. # | STRUCTURE | | MRSA | | VREF | | *S. pneu* |
|---|---|---|---|---|---|---|---|
| 282 | 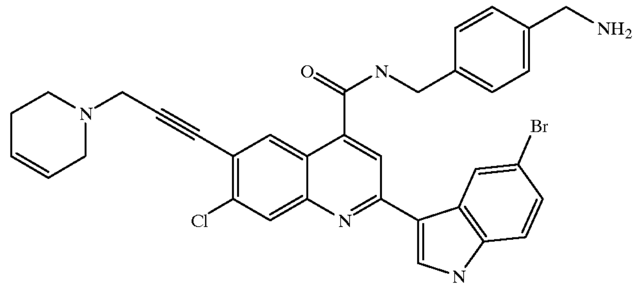 | < | 7 | < | 7 | < | 7 |
| 283 | 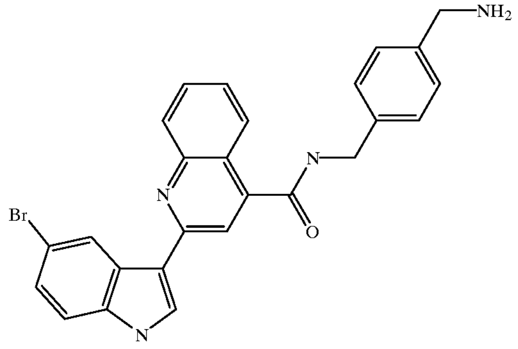 | < | 7 | < | 7 | < | 7 |
| 284 | 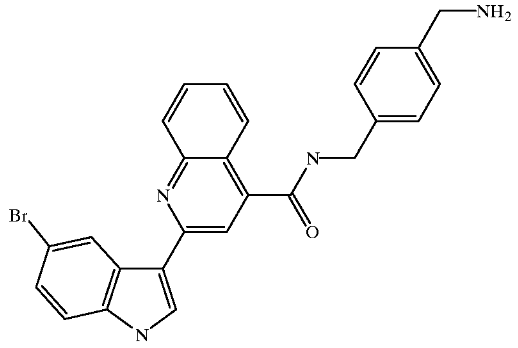 | < | 7 [CRSA] | < | 7 | < | 7 |

-continued
| Cmpd. # | STRUCTURE | | MRSA | | VREF | | *S. pneu* |
|---|---|---|---|---|---|---|---|
| 285 | 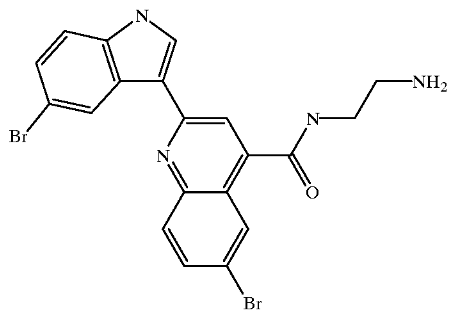 | < | 7 | < | 7 | < | 7 |
| 286 | 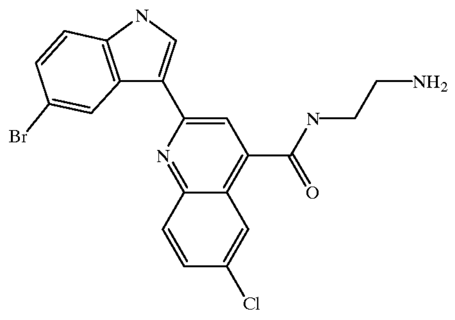 | < | 7 [CRSA] | < | 7 | < | 7 |
| 287 | 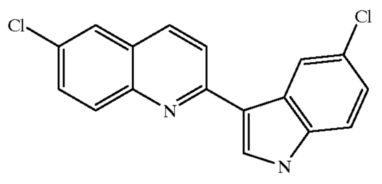 | < | 7 | > | 25 | < | 7 |
| 288 | 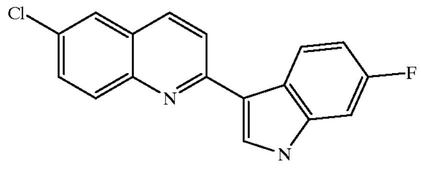 | < | 7 | < | 7 | < | 7 |

-continued
| Cmpd. # | STRUCTURE | | MRSA | | VREF | | *S. pneu* |
|---|---|---|---|---|---|---|---|
| 289 | 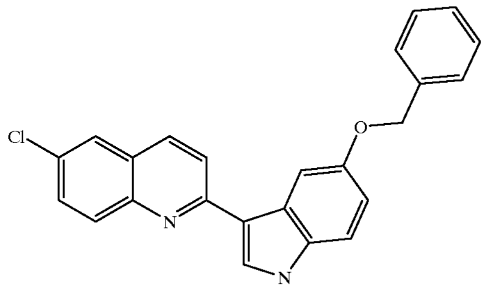 | < | 7 | > | 25 | < | 7 |
| 290 | 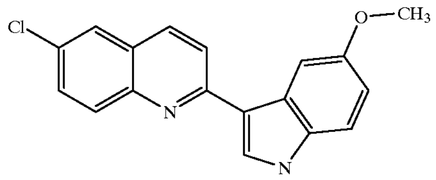 | > | 25 | > | 25 | > | 25 |
| 291 | 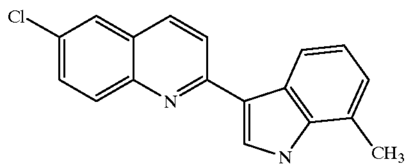 | > | 25 | > | 25 | > | 25 |
| 292 | 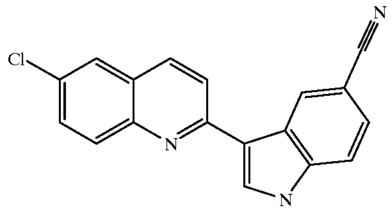 | > | 25 | > | 25 | > | 25 |

-continued
| Cmpd. # | STRUCTURE | | MRSA | | VREF | | *S. pneu* |
|---|---|---|---|---|---|---|---|
| 293 | 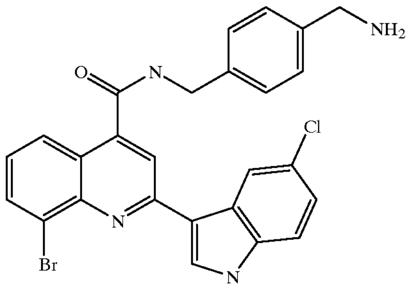 | < | 7 | < | 7 | < | 7 |
| 294 | 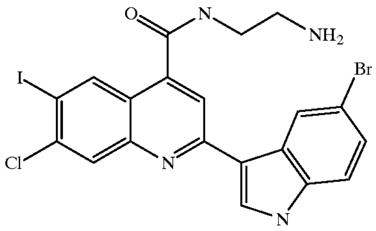 | < | 7 | < | 7 | < | 7 |
| 295 | 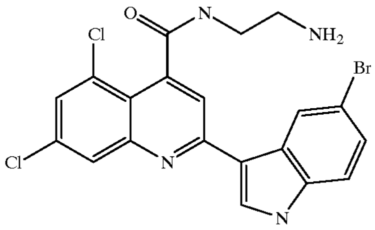 | < | 7 | < | 7 | < | 7 |
| 296 | 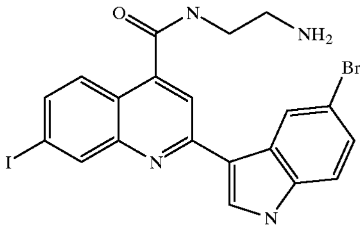 | < | 7 [CRSA] | < | 7 | < | 7 |

-continued
| Cmpd. # | STRUCTURE | | MRSA | | VREF | | *S. pneu* |
|---|---|---|---|---|---|---|---|
| 297 | 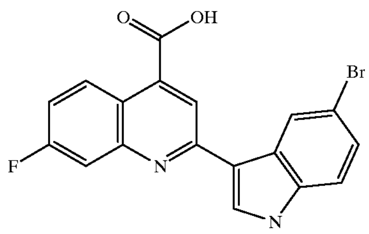 | < | 25 | < | 25 | < | 25 |
| 298 | 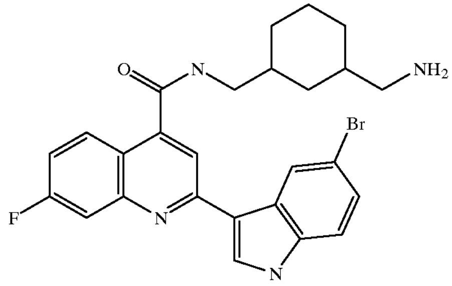 | < | 7 | < | 7 | < | 7 |
| 299 | 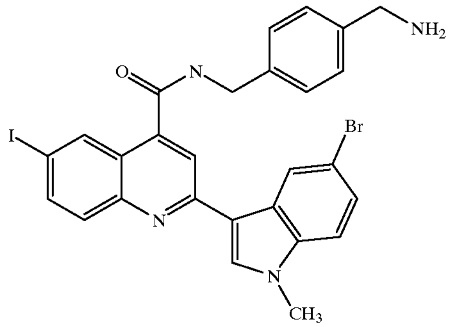 | < | 7 | < | 7 | < | 7 |

-continued
| Cmpd. # | STRUCTURE | | MRSA | | VREF | | *S. pneu* |
|---|---|---|---|---|---|---|---|
| 300 | 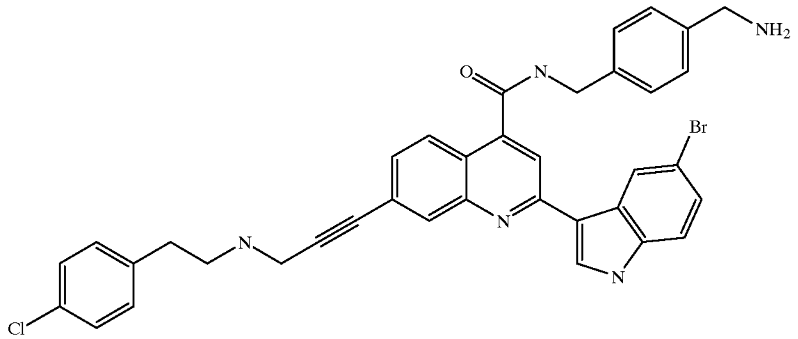 | < | 7 | < | 7 | < | 25 |
| 301 | 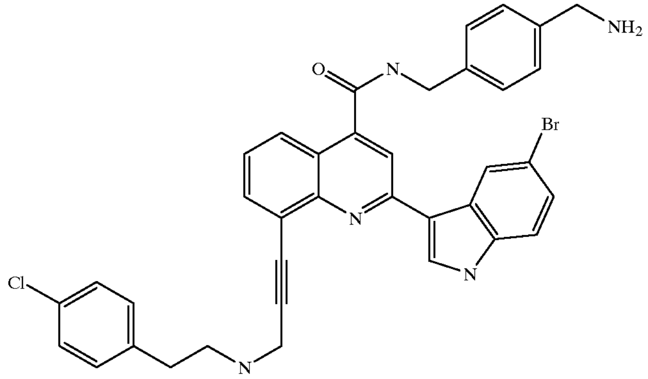 | < | 7 | < | 25 | < | 25 |
| 302 | 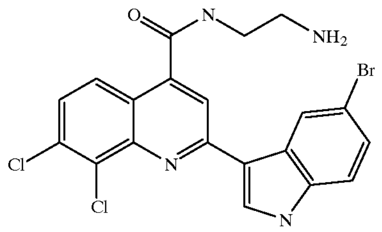 | < | 7 | < | 7 | < | 7 |

-continued
| Cmpd. # | STRUCTURE | | MRSA | | VREF | | *S. pneu* |
|---|---|---|---|---|---|---|---|
| 303 | 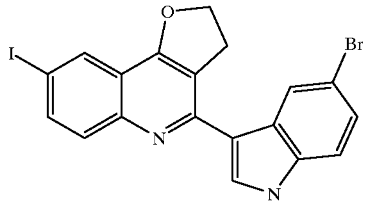 | < | 7 | > | 25 | < | 7 |
| 304 | 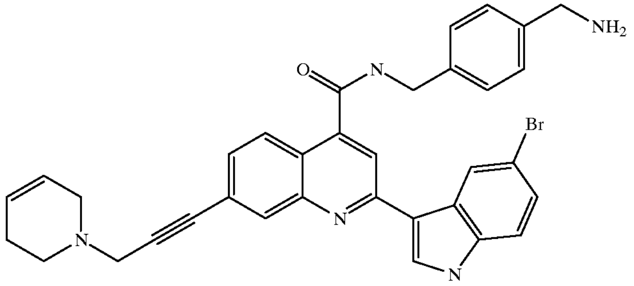 | < | 7 | < | 7 | < | 7 |
| 305 | 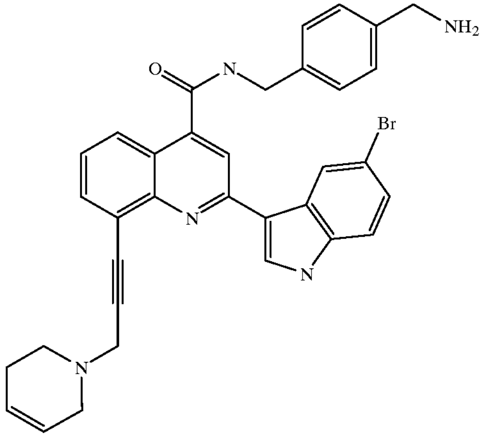 | < | 7 | < | 7 | < | 7 |

-continued
| Cmpd. # | STRUCTURE | | MRSA | | VREF | | *S. pneu* |
|---|---|---|---|---|---|---|---|
| 306 | 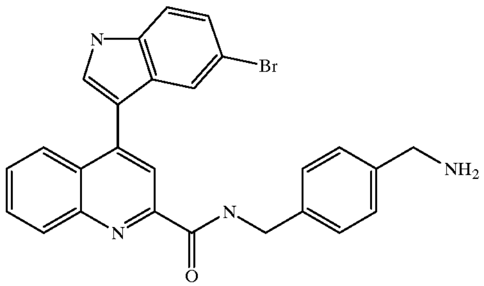 | < | 7 | < | 7 | < | 7 |
| 307 | 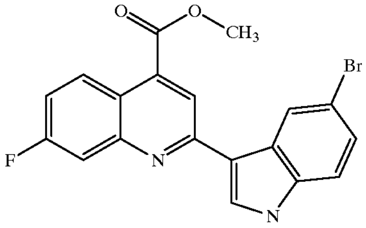 | < | 7 | < | 7 | < | 7 |
| 308 | 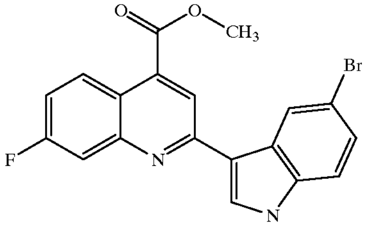 | < | 7 | < | 7 | < | 7 |

-continued
| Cmpd. # | STRUCTURE | | MRSA | | VREF | | *S. pneu* |
|---|---|---|---|---|---|---|---|
| 309 | 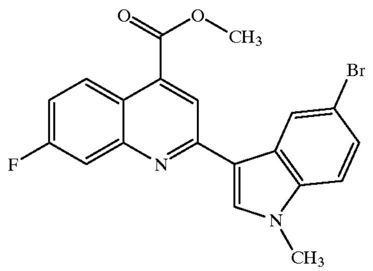 | > | 25 | > | 25 | > | 25 |
| 310 | 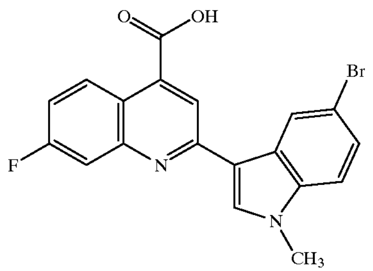 | < | 25 | > | 25 | < | 25 |
| 311 | 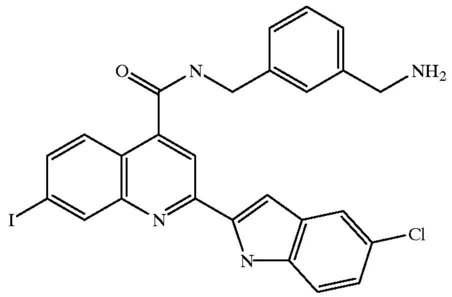 | > | 25 | > | 25 | > | 25 |

-continued
| Cmpd. # | STRUCTURE | MRSA | VREF | *S. pneu* |
|---|---|---|---|---|
| 312 | 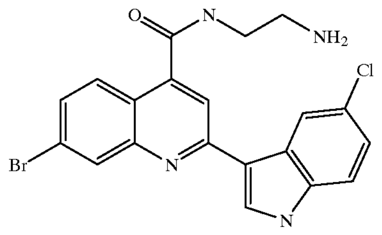 | < 7 | < 7 | < 7 |
| 313 | 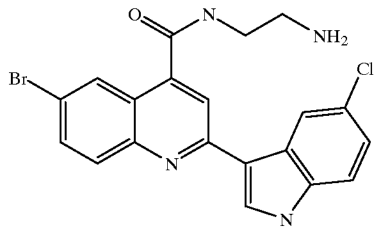 | < 7 | < 7 | < 7 |
| 314 | 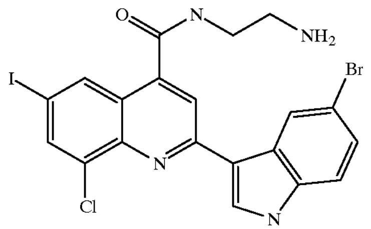 | < 7 | < 7 | < 7 |
| 315 | 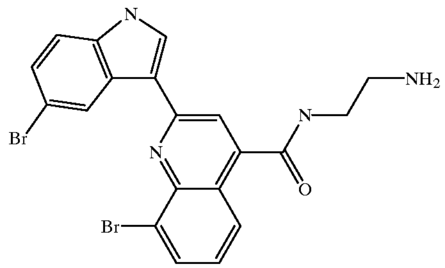 | < 7 | < 7 | < 7 |

-continued
| Cmpd. # | STRUCTURE | MRSA | | VREF | | *S. pneu* | |
|---|---|---|---|---|---|---|---|
| 316 | 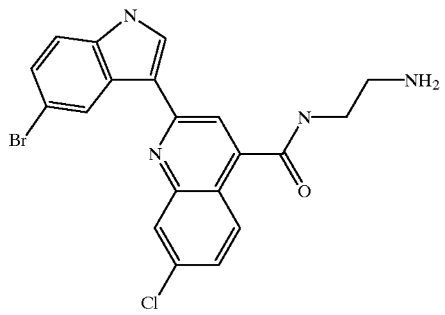 | < | 7 | < | 7 | < | 7 |
| 317 | 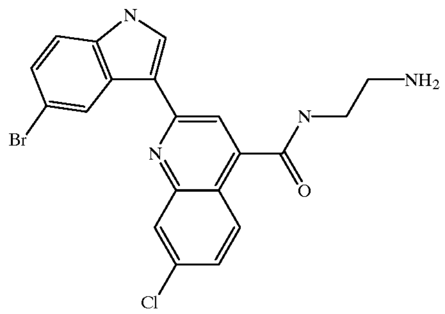 | < | 7 | < | 7 | < | 7 |
| 318 | 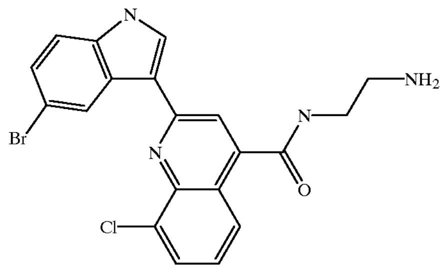 | < | 7 | < | 7 | < | 7 |

-continued
| Cmpd. # | STRUCTURE | | MRSA | | VREF | | *S. pneu* |
|---|---|---|---|---|---|---|---|
| 319 | 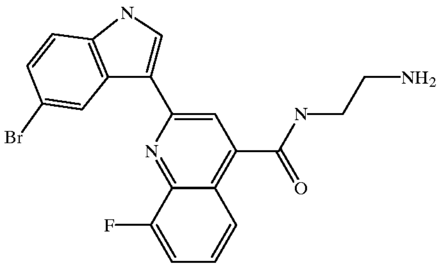 | < | 7 | < | 25 | < | 7 |
| 320 | 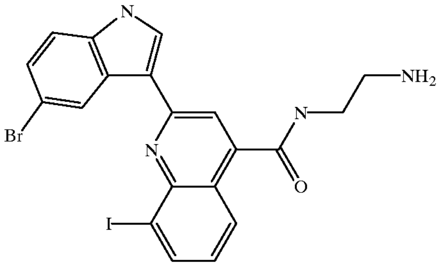 | < | 7 [CRSA] | < | 7 | < | 7 |
| 321 | 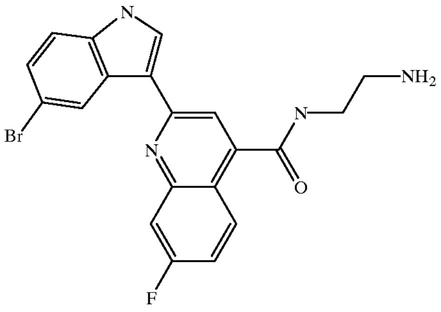 | < | 7 | < | 7 | < | 7 |

-continued
| Cmpd. # | STRUCTURE | | MRSA | | VREF | | *S. pneu* |
|---|---|---|---|---|---|---|---|
| 322 | 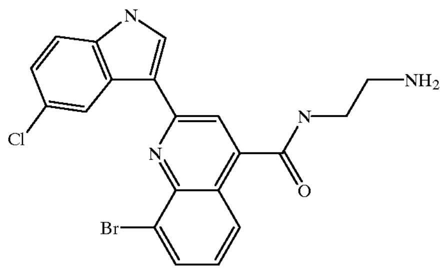 | < | 7 | < | 7 | < | 7 |
| 323 | 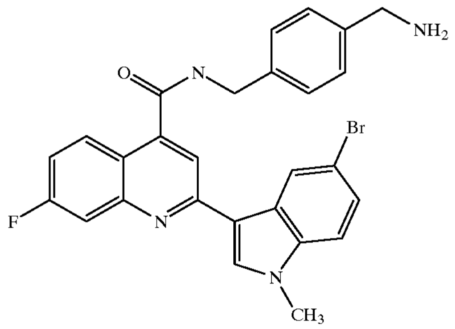 | < | 7 [CRSA] | < | 25 | < | 7 |

-continued
| Cmpd. # | STRUCTURE | | MRSA | | VREF | | *S. pneu* |
|---|---|---|---|---|---|---|---|
| 324 | 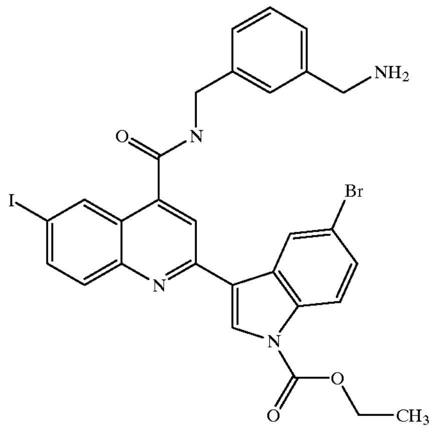 | > | 25 [CRSA] | > | 25 | > | 25 |
| 325 | 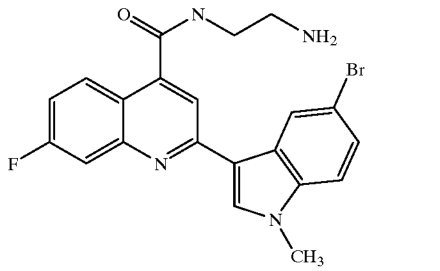 | < | 7 | < | 7 | < | 7 |

-continued
| Cmpd. # | STRUCTURE | | MRSA | | VREF | | *S. pneu* |
|---|---|---|---|---|---|---|---|
| 326 | 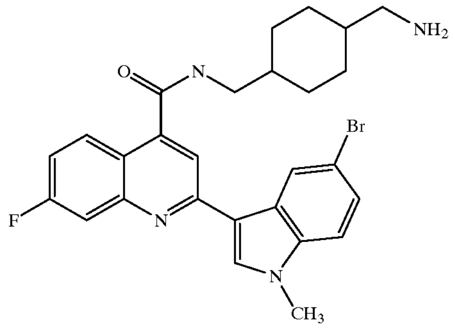 | < | 7 | < | 7 | < | 7 |
| 327 | 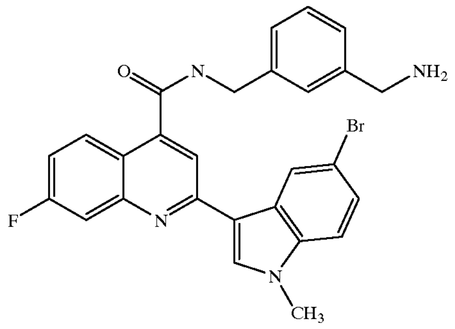 | < | 25 | > | 25 | < | 7 |
| 328 | 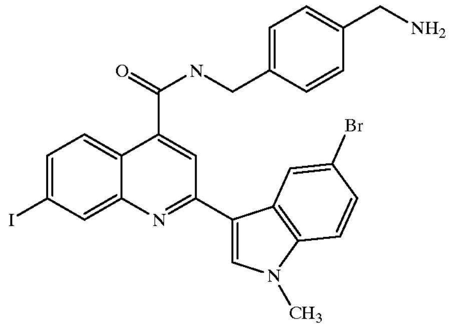 | > | 25 | > | 25 | < | 7 |

-continued
| Cmpd. # | STRUCTURE | | MRSA | | VREF | | *S. pneu* |
|---|---|---|---|---|---|---|---|
| 329 | 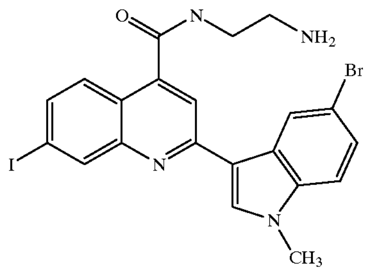 | < | 7 [CRSA] | < | 7 | < | 7 |
| 330 | 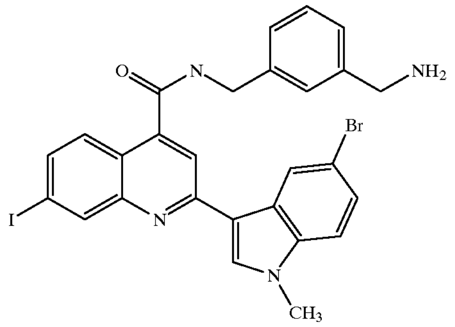 | < | 7 | < | 7 | < | 7 |
| 331 | 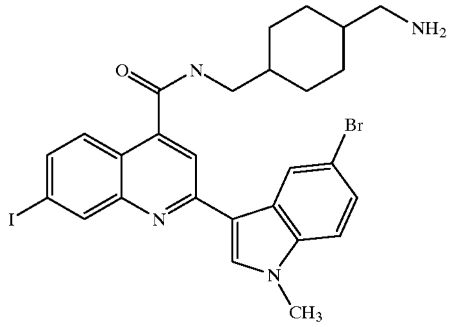 | < | 7 | < | 7 | < | 7 |

-continued
| Cmpd. # | STRUCTURE | | MRSA | | VREF | | *S. pneu* |
|---|---|---|---|---|---|---|---|
| 332 | 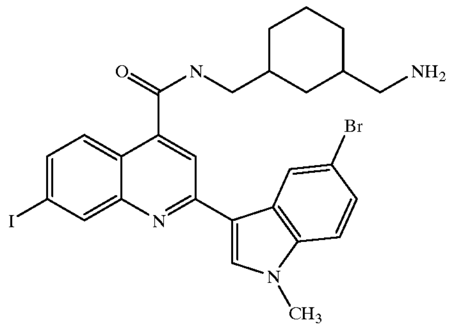 | < | 7 | < | 7 | < | 7 |
| 333 | 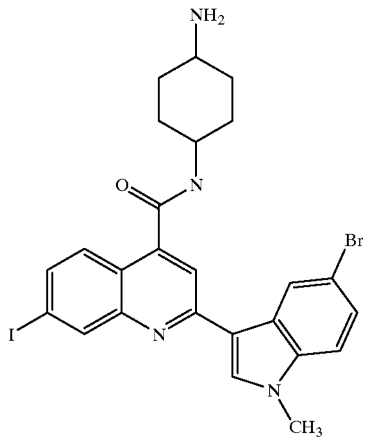 | < | 7 | < | 7 | < | 7 |

-continued
| Cmpd. # | STRUCTURE | | MRSA | | VREF | | S. pneu |
|---|---|---|---|---|---|---|---|
| 334 | 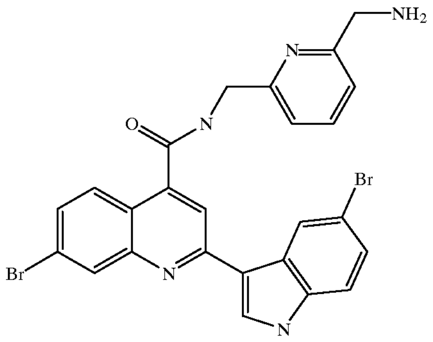 | < | 7 | < | 7 | < | 7 |
| 335 | 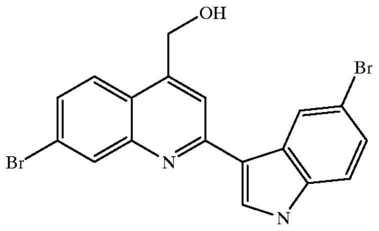 | < | 7 | < | 7 | < | 7 |
| 336 | 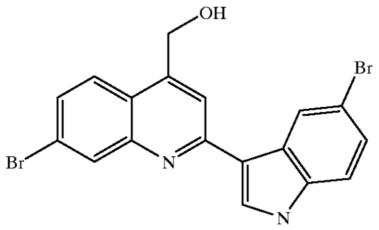 | < | 7 | < | 7 | < | 7 |

-continued
| Cmpd. # | STRUCTURE | | MRSA | | VREF | | *S. pneu* |
|---|---|---|---|---|---|---|---|
| 337 | 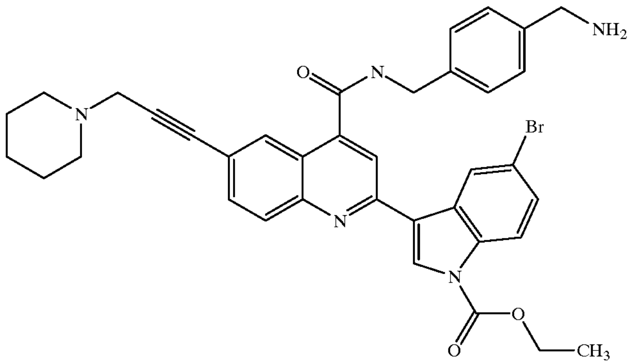 | > | 25 | > | 25 | > | 25 |
| 338 | 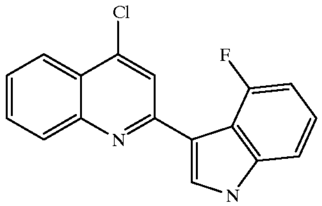 | < | 25 | > | 25 | < | 7 |
| 339 | 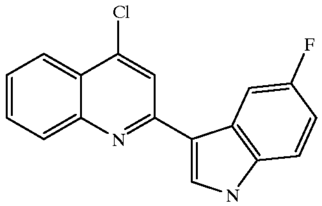 | < | 7 | < | 7 | < | 7 |

-continued
| Cmpd. # | STRUCTURE | | MRSA | | VREF | | *S. pneu* |
|---|---|---|---|---|---|---|---|
| 340 | 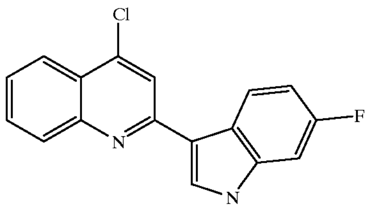 | < | 7 | < | 7 | < | 7 |
| 341 | 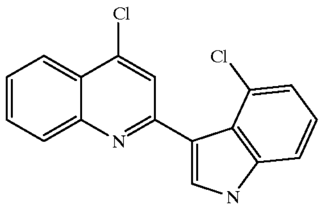 | < | 7 | < | 7 | < | 7 |
| 342 | 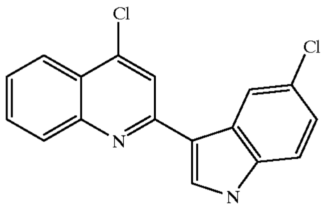 | < | 7 | > | 25 | < | 7 |
| 343 | 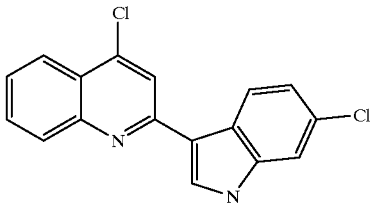 | < | 7 | > | 25 | < | 7 |

-continued
| Cmpd. # | STRUCTURE | | MRSA | | VREF | | *S. pneu* |
|---|---|---|---|---|---|---|---|
| 344 | 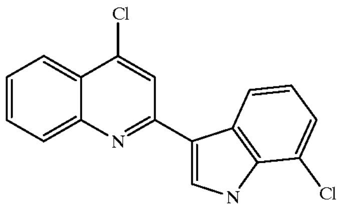 | < | 7 | > | 25 | < | 7 |
| 345 | 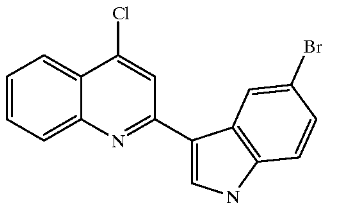 | < | 7 | > | 25 | < | 7 |
| 346 | 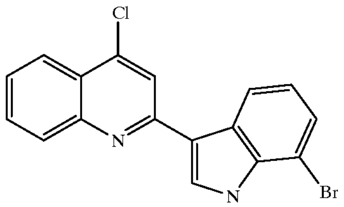 | < | 25 | > | 25 | < | 25 |
| 347 | 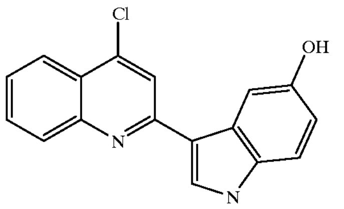 | < | 25 | > | 25 | < | 25 |

-continued
| Cmpd. # | STRUCTURE | | MRSA | | VREF | | *S. pneu* |
|---|---|---|---|---|---|---|---|
| 348 | 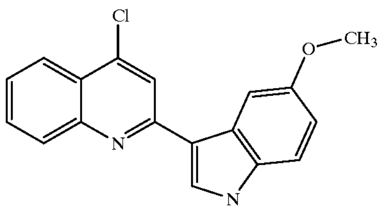 | < | 7 | > | 25 | < | 7 |
| 349 | 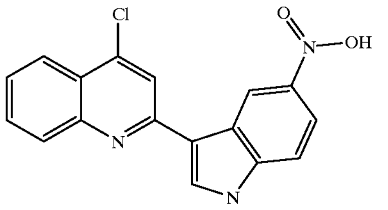 | > | 25 | > | 25 | > | 25 |
| 350 | 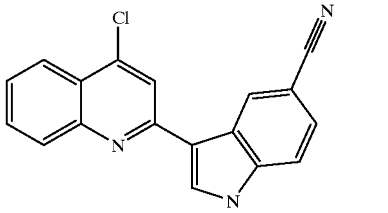 | > | 25 | > | 25 | > | 25 |
| 351 | 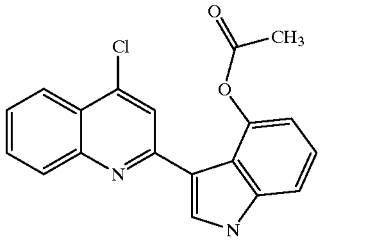 | < | 7 | > | 25 | < | 7 |

-continued
| Cmpd. # | STRUCTURE | | MRSA | | VREF | | *S. pneu* |
|---|---|---|---|---|---|---|---|
| 352 | 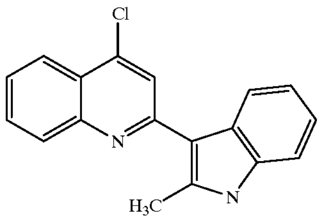 | < | 7 | > | 25 | < | 7 |
| 353 | 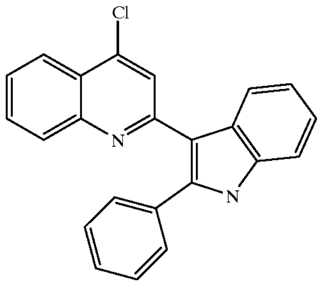 | > | 25 | > | 25 | > | 25 |
| 354 | 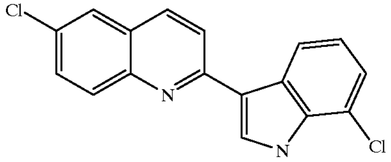 | > | 25 | > | 25 | > | 25 |
| 355 | 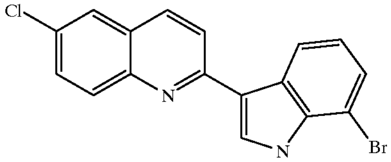 | > | 25 | > | 25 | > | 25 |

-continued
| Cmpd. # | STRUCTURE | MRSA | | VREF | | *S. pneu* | |
|---|---|---|---|---|---|---|---|
| 356 | 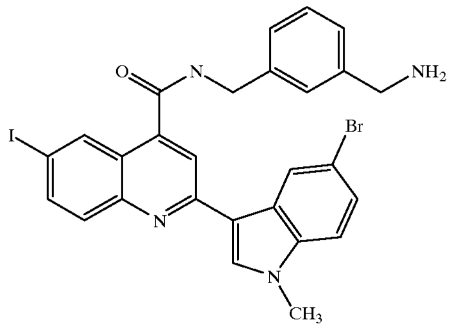 | < | 7 | < | 7 | < | 7 |
| 357 | 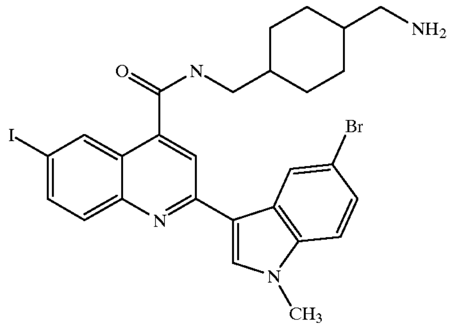 | < | 7 | < | 7 | < | 7 |
| 358 | 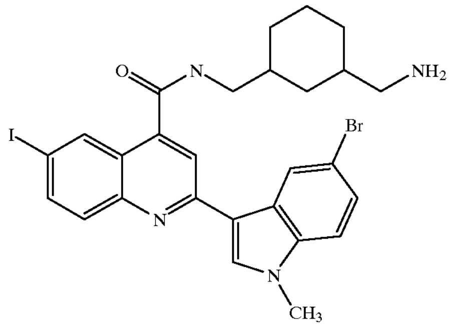 | < | 7 | < | 7 | < | 7 |

-continued
| Cmpd. # | STRUCTURE | MRSA | VREF | S. pneu |
|---|---|---|---|---|
| 359 | 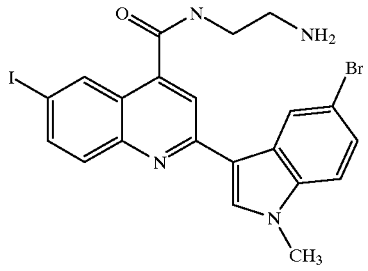 | < 7 | < 7 | < 7 |
| 360 | 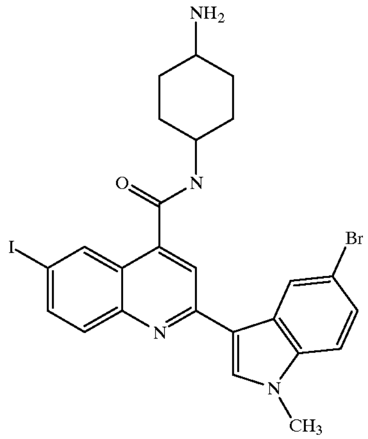 | < 7 | < 7 | < 7 |

-continued
| Cmpd. # | STRUCTURE | | MRSA | | VREF | | *S. pneu* |
|---|---|---|---|---|---|---|---|
| 361 | 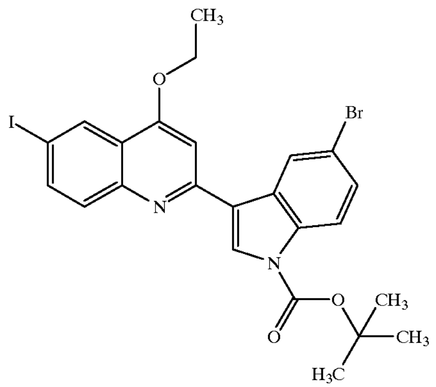 | > | 25 | > | 25 | > | 25 |
| 362 | 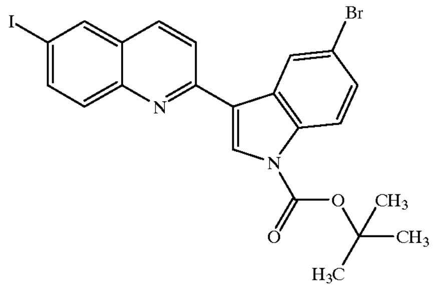 | > | 25 | > | 25 | > | 25 |
| 363 | 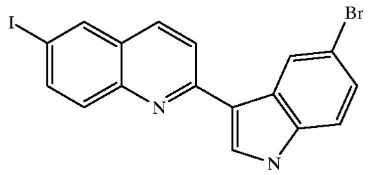 | < | 7 | < | 7 | < | 7 |

-continued
| Cmpd. # | STRUCTURE | | MRSA | | VREF | | *S. pneu* |
|---|---|---|---|---|---|---|---|
| 364 | 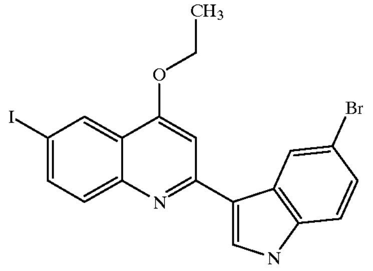 | < | 7 | < | 25 | < | 7 |
| 365 | 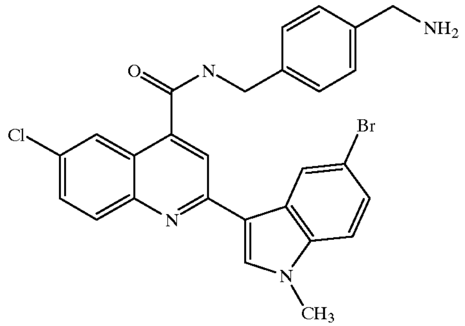 | < | 7 | < | 7 | < | 7 |
| 366 | 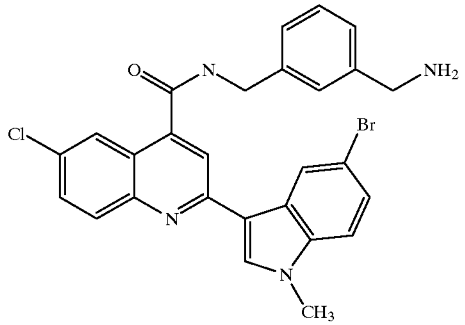 | > | 25 | > | 25 | > | 25 |

-continued
| Cmpd. # | STRUCTURE | | MRSA | | VREF | | *S. pneu* |
|---|---|---|---|---|---|---|---|
| 367 | 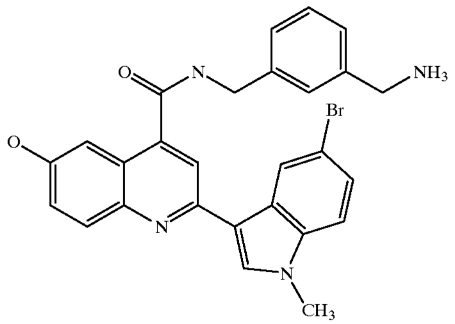 | > | 25 | > | 25 | > | 25 |
| 368 | 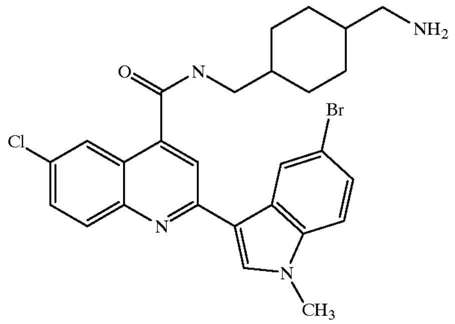 | < | 7 | < | 7 | < | 7 |
| 369 | 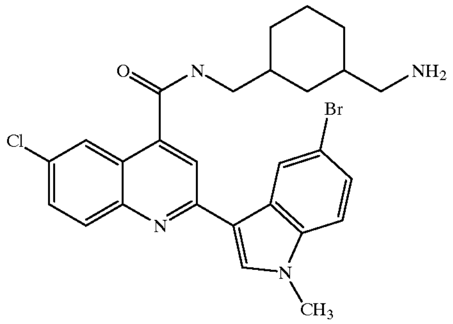 | < | 7 | < | 7 | < | 7 |

-continued
| Cmpd. # | STRUCTURE | | MRSA | | VREF | | *S. pneu* |
|---|---|---|---|---|---|---|---|
| 370 | 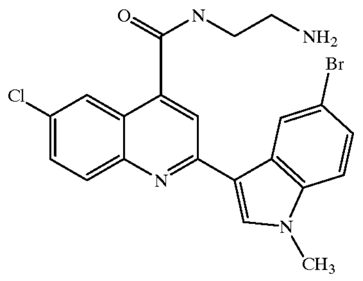 | < | 7 | < | 7 | < | 7 |
| 371 | 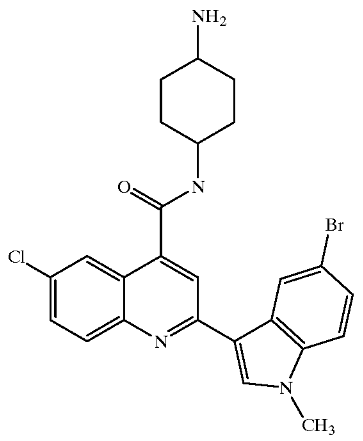 | < | 7 | < | 7 | < | 7 |
| 372 | 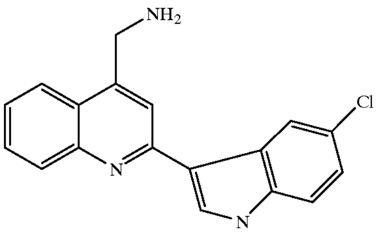 | < | 7 | < | 25 | < | 7 |

-continued
| Cmpd. # | STRUCTURE | | MRSA | | VREF | | *S. pneu* |
|---|---|---|---|---|---|---|---|
| 373 | 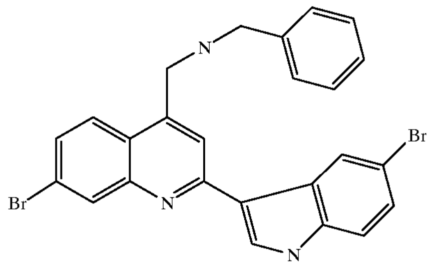 | < | 7 | < | 7 | < | 7 |
| 374 | 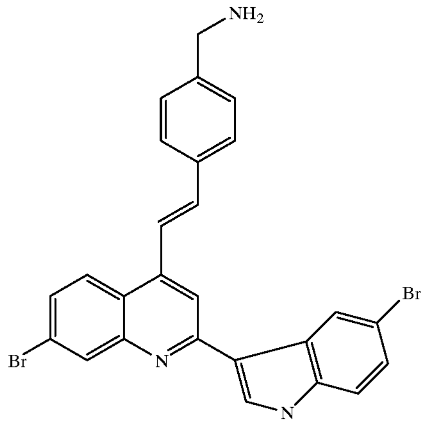 | < | 7 | < | 7 | < | 7 |
| 375 | 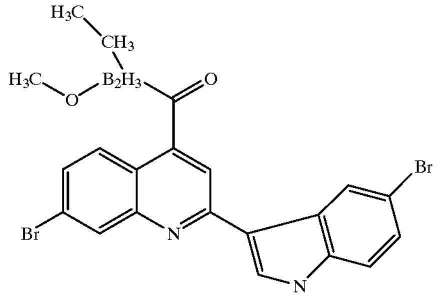 | > | 25 | > | 25 | > | 25 |

-continued
| Cmpd. # | STRUCTURE | | MRSA | | VREF | | *S. pneu* |
|---|---|---|---|---|---|---|---|
| 376 | 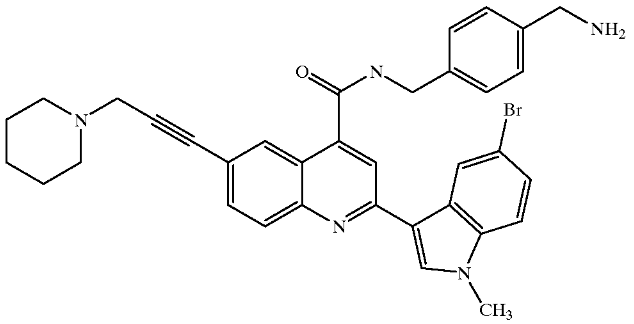 | < | 25 | < | 25 | < | 7 |
| 377 | 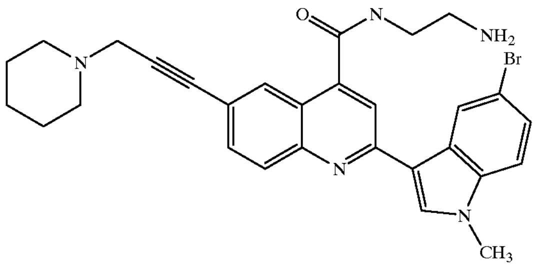 | < | 7 | < | 7 | < | 7 |
| 378 | 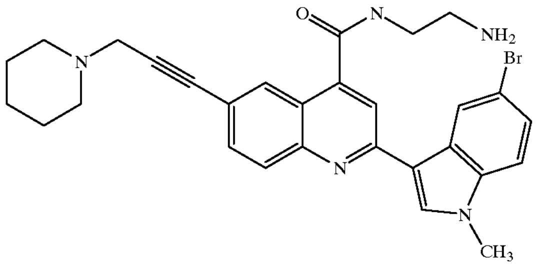 | < | 7 | < | 7 | < | 7 |

-continued
| Cmpd. # | STRUCTURE | | MRSA | | VREF | | *S. pneu* |
|---|---|---|---|---|---|---|---|
| 379 | 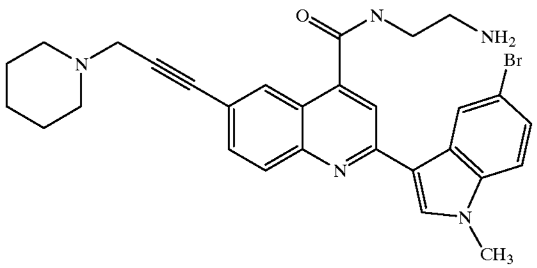 | < | 7 | < | 7 | < | 7 |
| 380 | 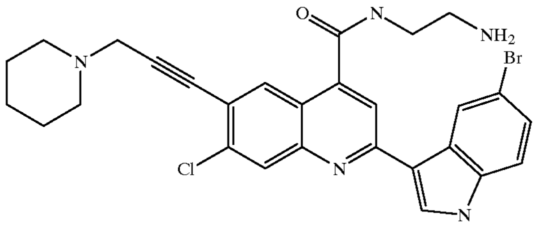 | < | 7 | < | 7 | < | 7 |
| 381 | 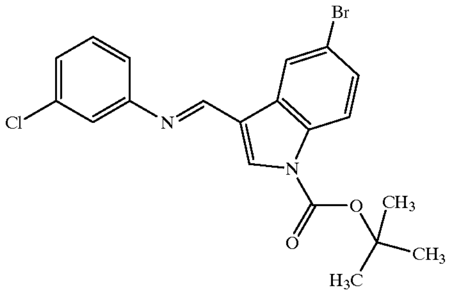 | > | 25 | > | 25 | > | 25 |

-continued
| Cmpd. # | STRUCTURE | | MRSA | | VREF | | *S. pneu* |
|---|---|---|---|---|---|---|---|
| 382 | 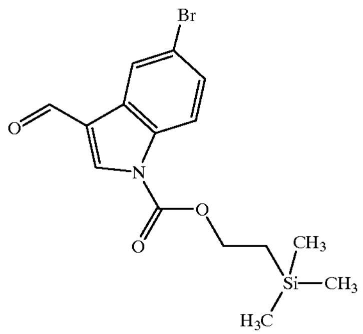 | > | 25 | > | 25 | > | 25 |
| 383 | 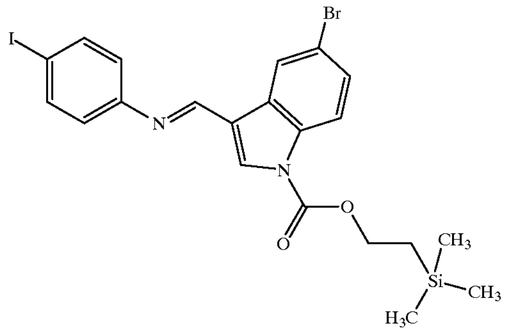 | > | 25 | > | 25 | > | 25 |
| 384 | 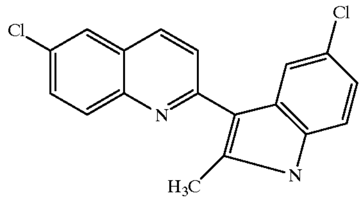 | < | 7 | > | 25 | < | 7 |

-continued
| Cmpd. # | STRUCTURE | MRSA | VREF | *S. pneu* |
|---|---|---|---|---|
| 385 | 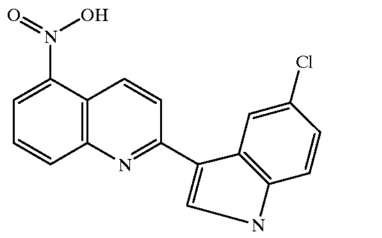 | > 25 | > 25 | > 25 |
| 386 | 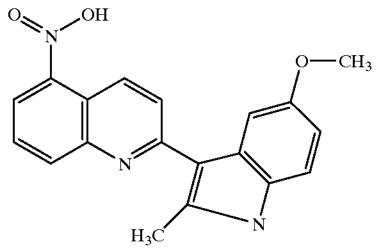 | > 25 | > 25 | > 25 |
| 387 | 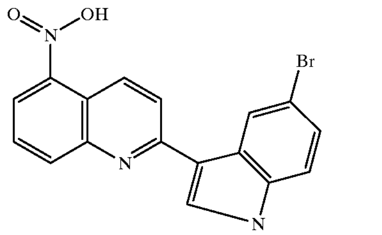 | > 25 | > 25 | > 25 |
| 388 | 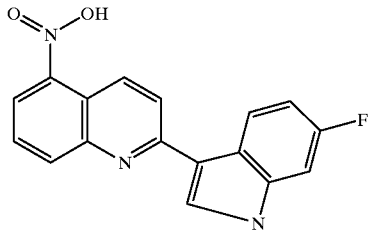 | > 25 | > 25 | > 25 |

-continued
| Cmpd. # | STRUCTURE | | MRSA | | VREF | | *S. pneu* |
|---|---|---|---|---|---|---|---|
| 389 | 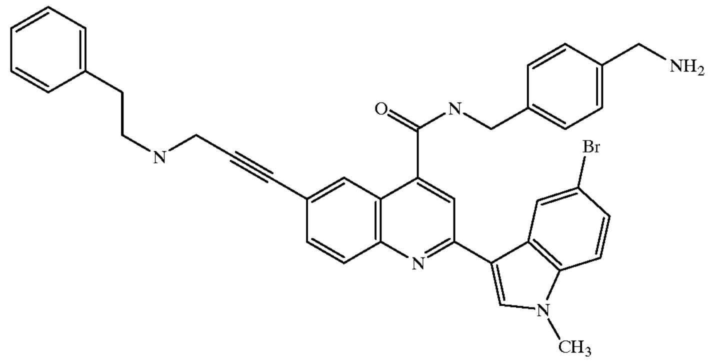 | < | 7 | < | 7 | < | 25 |
| 390 | 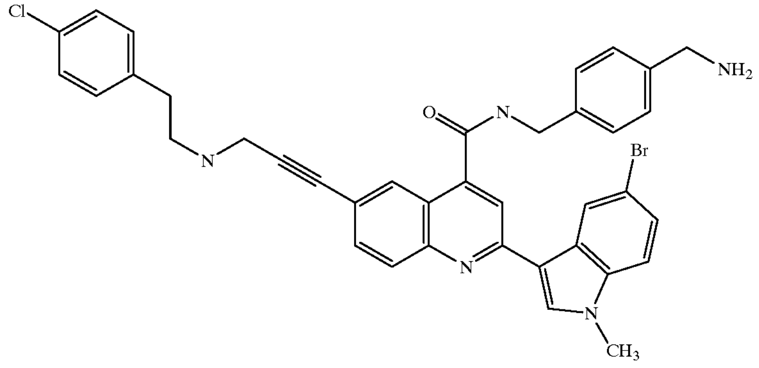 | < | 25 | < | 7 | < | 7 |

-continued
| Cmpd. # | STRUCTURE | | MRSA | | VREF | | *S. pneu* |
|---|---|---|---|---|---|---|---|
| 391 | 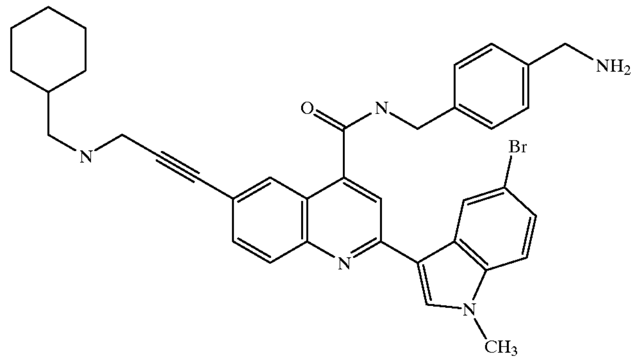 | < | 7 | < | 7 | < | 7 |
| 392 | 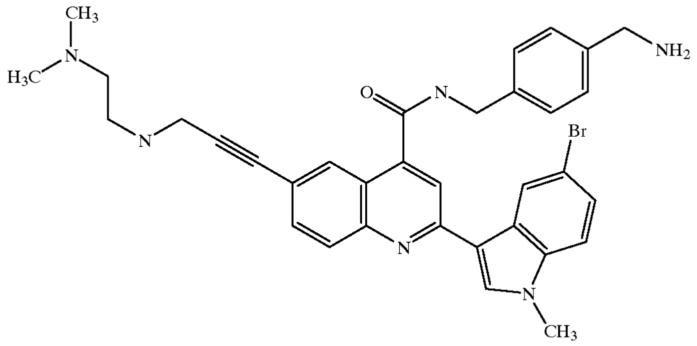 | < | 7 | < | 7 | < | 7 |

-continued
| Cmpd. # | STRUCTURE | | MRSA | | VREF | | *S. pneu* |
|---|---|---|---|---|---|---|---|
| 393 | 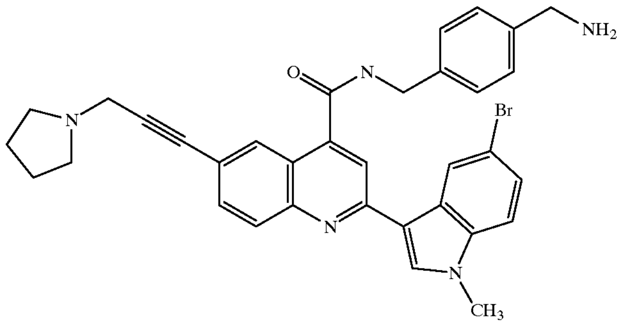 | < | 7 | < | 25 | < | 25 |
| 394 | 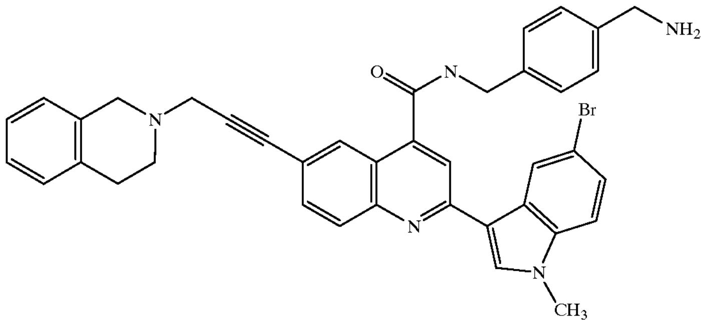 | > | 25 | > | 25 | > | 25 |
| 395 | 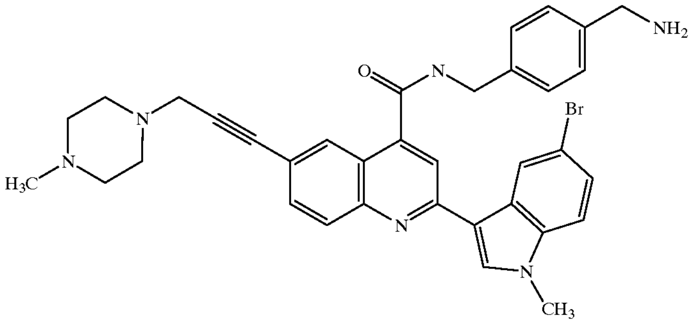 | < | 7 | < | 25 | < | 25 |

-continued
| Cmpd. # | STRUCTURE | | MRSA | | VREF | | *S. pneu* |
|---|---|---|---|---|---|---|---|
| 396 | 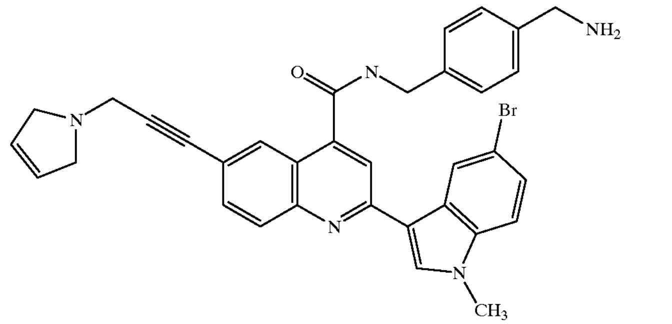 | > | 25 | > | 25 | > | 25 |
| 397 | 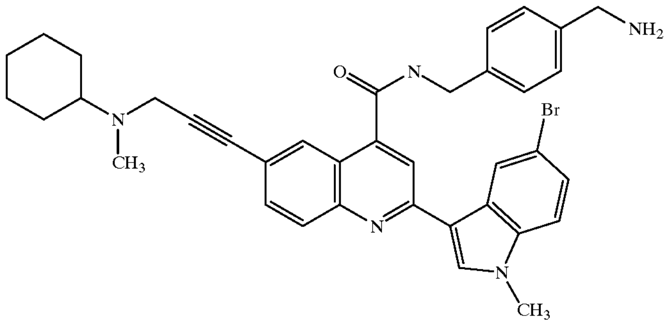 | < | 7 | < | 7 | < | 7 |
| 398 | 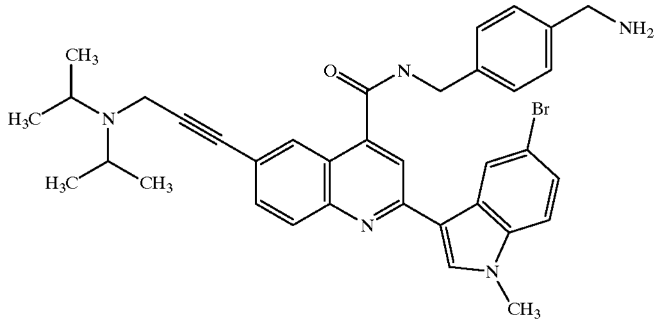 | < | 7 | < | 7 | < | 7 |

-continued
| Cmpd. # | STRUCTURE | MRSA | | VREF | | *S. pneu* | |
|---|---|---|---|---|---|---|---|
| 399 | 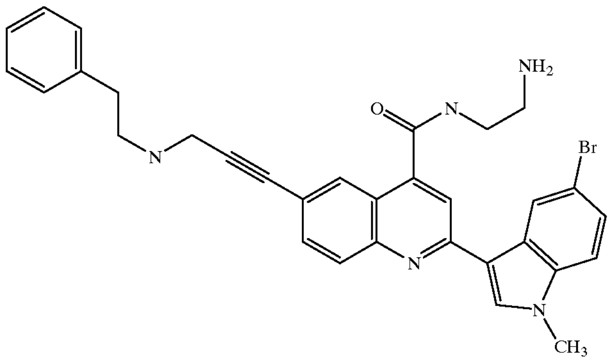 | < | 7 | < | 7 | < | 7 |
| 400 | 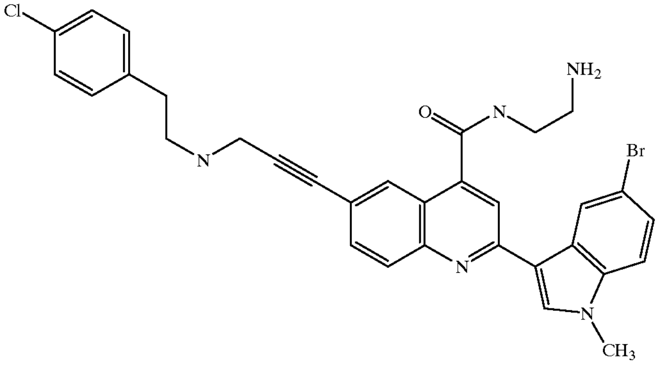 | < | 7 | < | 7 | < | 7 |

-continued
| Cmpd. # | STRUCTURE | | MRSA | | VREF | | *S. pneu* |
|---|---|---|---|---|---|---|---|
| 401 | 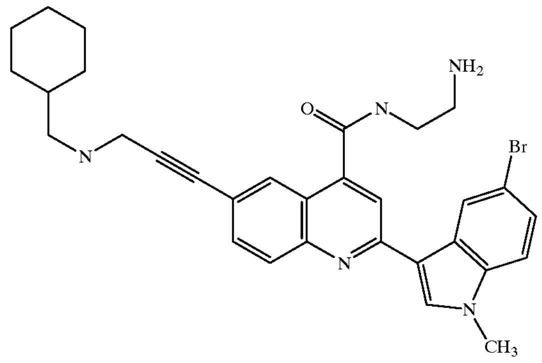 | < | 7 | < | 7 | < | 7 |
| 402 | 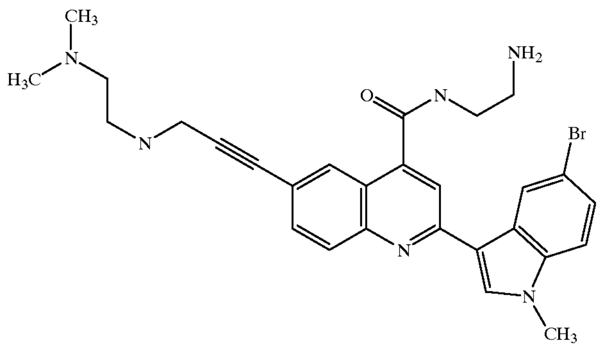 | < | 7 | < | 7 | < | 7 |

-continued
| Cmpd. # | STRUCTURE | | MRSA | | VREF | | *S. pneu* |
|---|---|---|---|---|---|---|---|
| 403 | 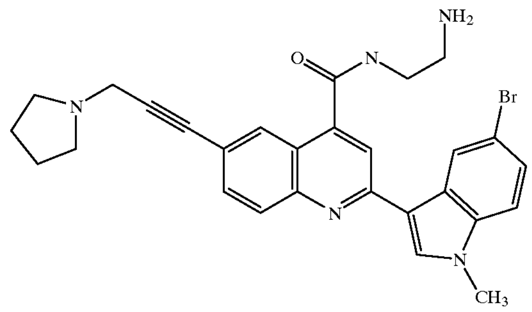 | < | 7 | < | 7 | < | 7 |
| 404 | 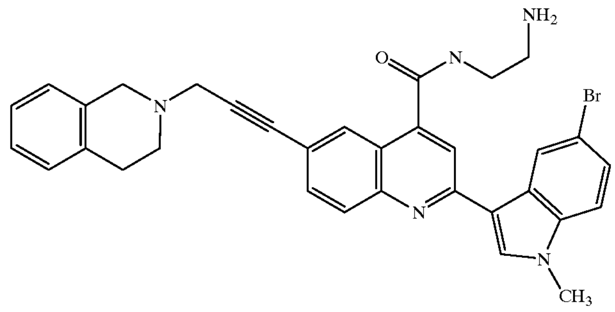 | < | 7 | < | 7 | < | 7 |
| 405 | 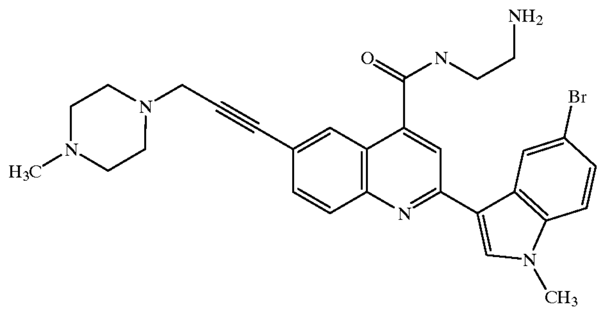 | < | 25 | < | 25 | < | 25 |

-continued
| Cmpd. # | STRUCTURE | | MRSA | | VREF | | *S. pneu* |
|---|---|---|---|---|---|---|---|
| 406 | 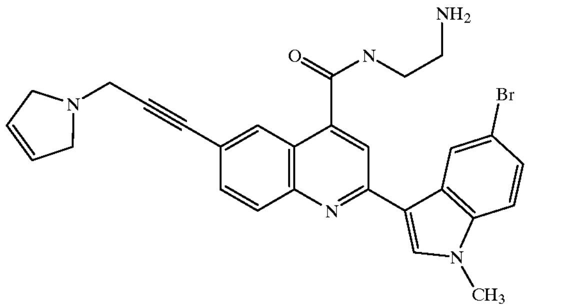 | < | 7 | < | 7 | < | 7 |
| 407 | 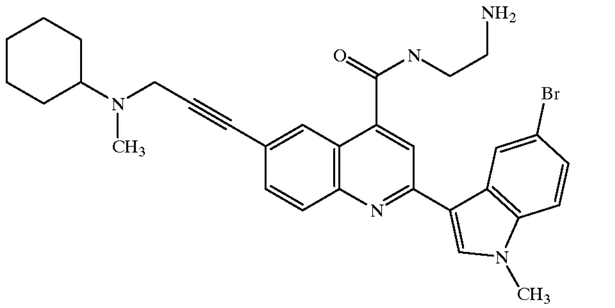 | < | 7 | < | 7 | < | 7 |
| 408 | 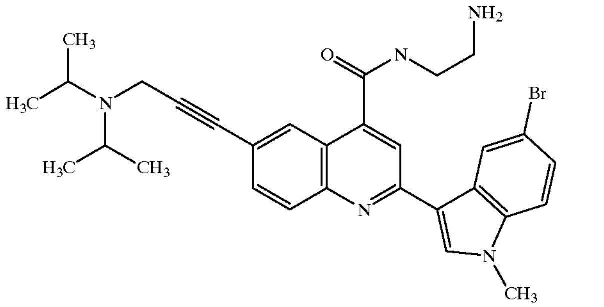 | < | 7 | < | 7 | < | 7 |

-continued
| Cmpd. # | STRUCTURE | | MRSA | | VREF | | *S. pneu* |
|---|---|---|---|---|---|---|---|
| 409 | 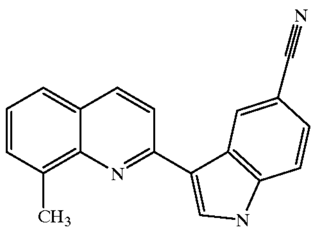 | > | 25 | > | 25 | > | 25 |
| 410 | 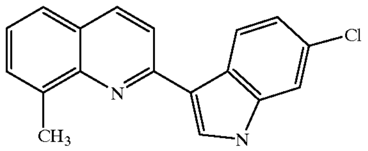 | < | 25 | > | 25 | < | 25 |
| 411 | 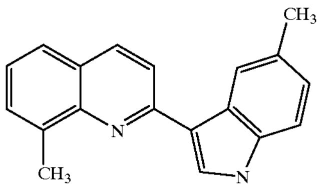 | > | 25 | > | 25 | > | 25 |
| 412 | 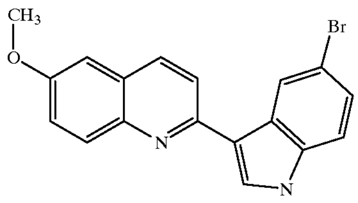 | < | 7 | > | 25 | > | 25 |
| 413 | 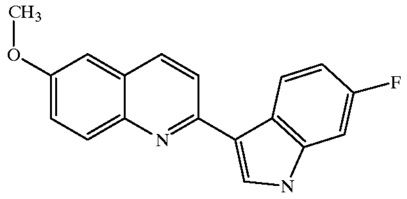 | > | 25 | > | 25 | > | 25 |

-continued
| Cmpd. # | STRUCTURE | | MRSA | | VREF | | *S. pneu* |
|---|---|---|---|---|---|---|---|
| 414 | 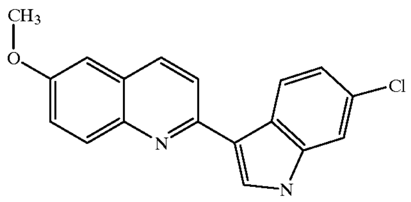 | > | 25 | > | 25 | > | 25 |
| 415 | 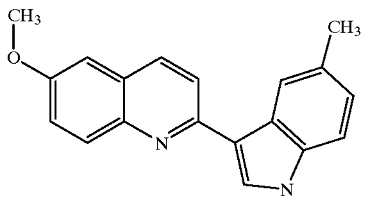 | < | 7 | > | 25 | > | 25 |
| 416 | 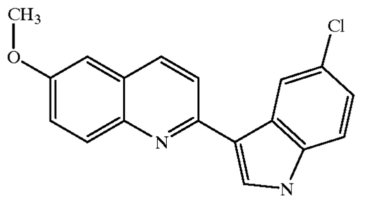 | < | 7 | > | 25 | < | 7 |
| 417 | 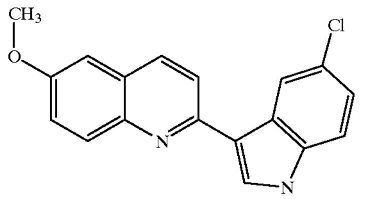 | < | 7 | > | 25 | < | 7 |

-continued
| Cmpd. # | STRUCTURE | MRSA | | VREF | | *S. pneu* | |
|---|---|---|---|---|---|---|---|
| 418 | 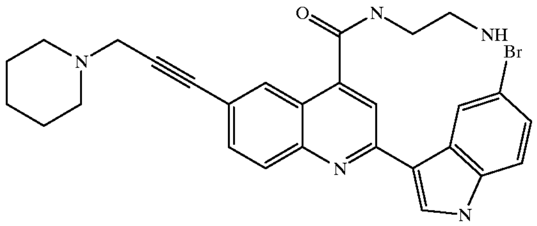 | < | 7 | < | 7 | < | 7 |
| 419 | 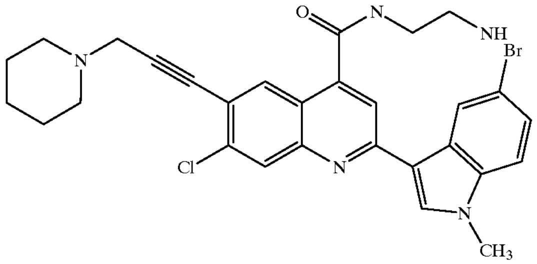 | < | 7 | < | 7 | < | 7 |
| 420 | 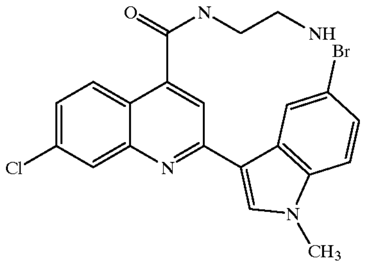 | < | 7 | < | 7 | < | 7 |

-continued
| Cmpd. # | STRUCTURE | | MRSA | | VREF | | *S. pneu* |
|---|---|---|---|---|---|---|---|
| 421 | 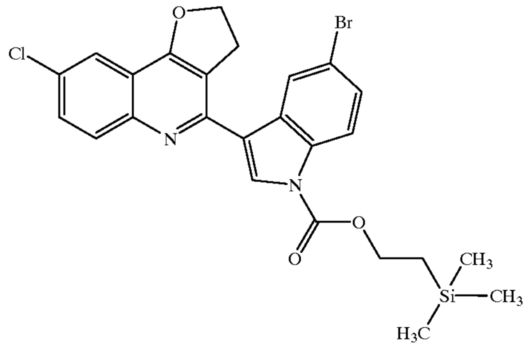 | > | 25 | > | 25 | > | 25 |
| 422 | 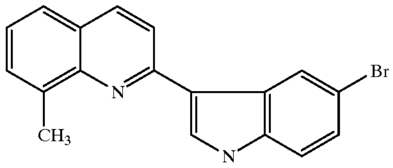 | > | 25 | > | 25 | > | 25 |
| 423 | 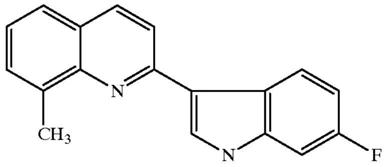 | > | 25 | > | 25 | > | 25 |
| 424 | 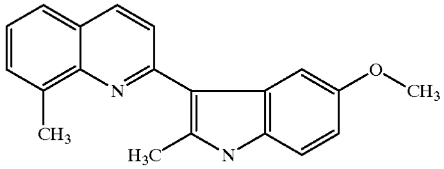 | < | 25 | > | 25 | < | 25 |

-continued
| Cmpd. # | STRUCTURE | | MRSA | | VREF | | *S. pneu* |
|---|---|---|---|---|---|---|---|
| 425 | 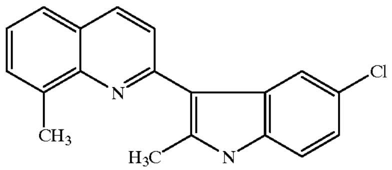 | < | 7 | < | 7 | < | 7 |
| 426 | 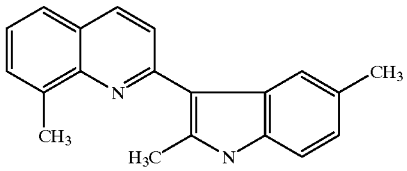 | < | 25 | > | 25 | < | 25 |
| 427 | 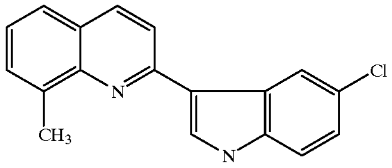 | > | 25 | > | 25 | > | 25 |
| 428 | 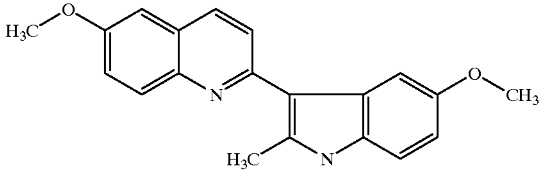 | > | 25 | > | 25 | > | 25 |
| 429 | 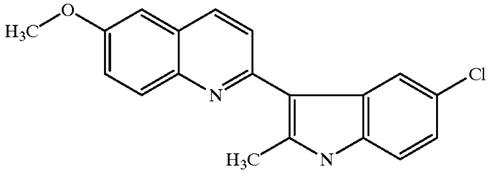 | < | 7 | > | 25 | < | 7 |

-continued
| Cmpd. # | STRUCTURE | | MRSA | | VREF | | *S. pneu* |
|---|---|---|---|---|---|---|---|
| 430 | 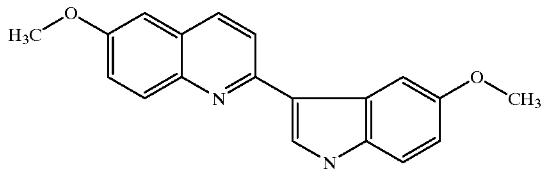 | < | 25 | > | 25 | < | 25 |
| 431 | 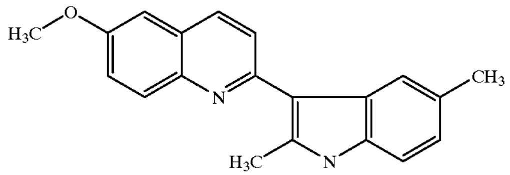 | > | 25 | > | 25 | > | 25 |
| 432 | 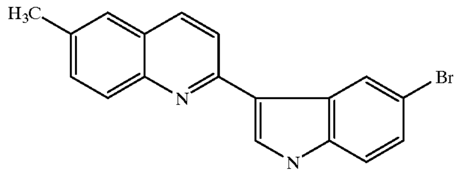 | < | 7 | > | 25 | < | 7 |
| 433 | 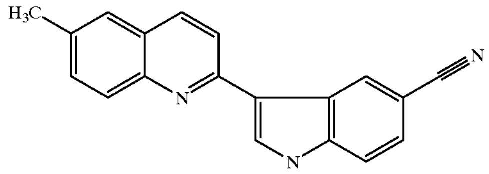 | < | 7 | > | 25 | < | & |
| 434 | 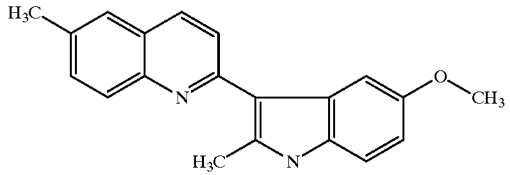 | > | 25 | > | 25 | > | 25 |

-continued
| Cmpd. # | STRUCTURE | | MRSA | | VREF | | *S. pneu* |
|---|---|---|---|---|---|---|---|
| 435 | 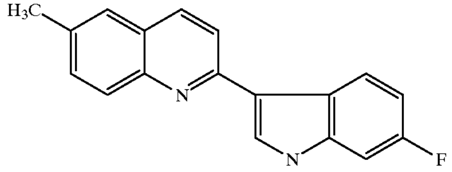 | > | 25 | > | 25 | > | 25 |
| 436 | 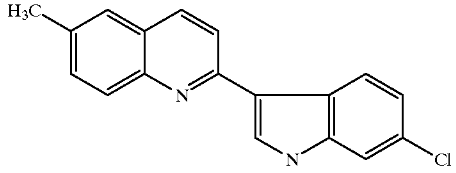 | < | 7 | > | 25 | < | 7 |
| 437 | 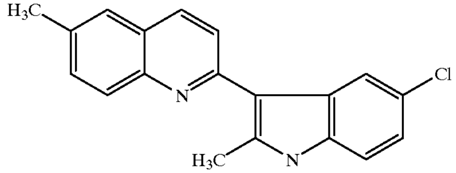 | < | 7 | > | 25 | < | 7 |
| 438 | 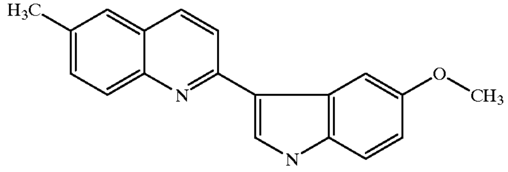 | > | 25 | > | 25 | > | 25 |
| 439 | 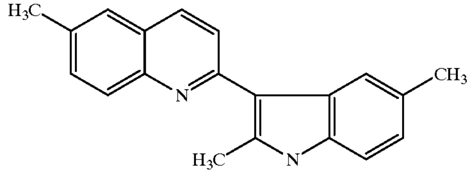 | > | 25 | > | 25 | > | 25 |

-continued
| Cmpd. # | STRUCTURE | | MRSA | | VREF | | *S. pneu* |
|---|---|---|---|---|---|---|---|
| 440 | 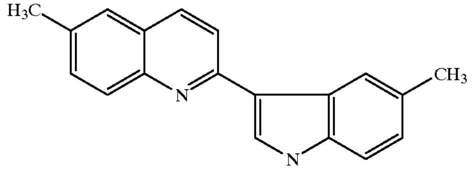 | > | 25 | > | 25 | < | 25 |
| 441 | 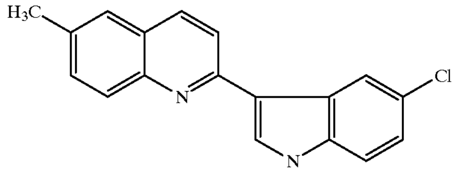 | > | 25 | > | 25 | > | 25 |
| 442 | 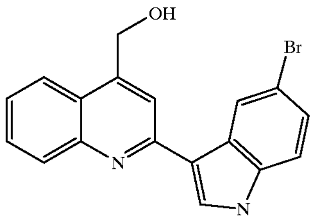 | < | 7 | < | 25 | < | 7 |
| 443 | 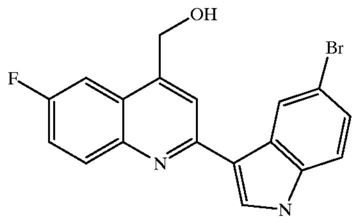 | < | 7 | < | 25 | < | 7 |

-continued
| Cmpd. # | STRUCTURE | | MRSA | | VREF | | *S. pneu* |
|---|---|---|---|---|---|---|---|
| 444 | 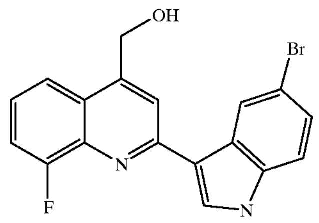 | < | 7 | < | 25 | < | 7 |
| 445 | 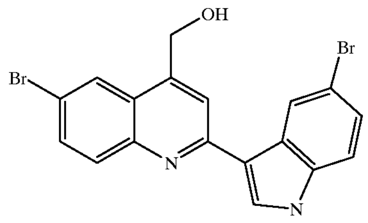 | < | 7 | < | 7 | < | 7 |
| 446 | 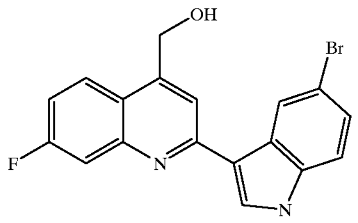 | < | 7 | < | 7 | < | 7 |
| 447 | 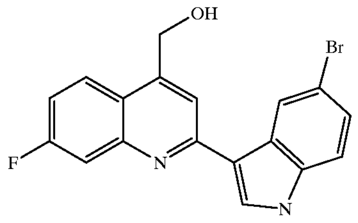 | < | 7 | < | 7 | < | 7 |

-continued
| Cmpd. # | STRUCTURE | | MRSA | | VREF | | *S. pneu* |
|---|---|---|---|---|---|---|---|
| 448 | 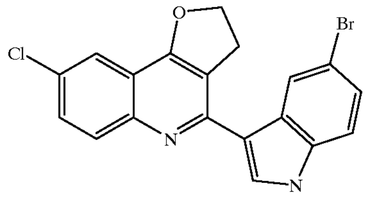 | < | 7 | > | 25 | < | 25 |
| 449 | 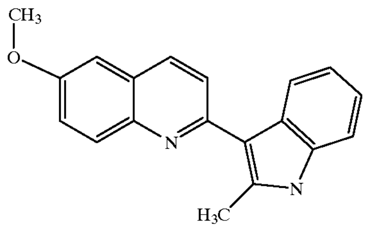 | > | 25 | > | 25 | > | 25 |
| 450 | 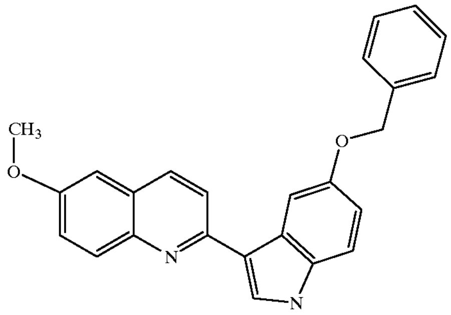 | > | 25 | > | 25 | > | 25 |
| 451 | 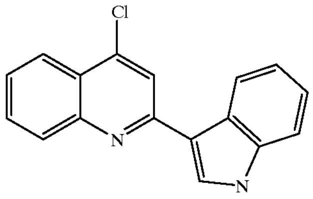 | < | 7 | > | 25 | < | 7 |

-continued
| Cmpd. # | STRUCTURE | MRSA | | VREF | | *S. pneu* | |
|---|---|---|---|---|---|---|---|
| 452 | 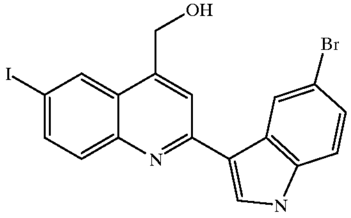 | < | 7 | > | 25 | < | 7 |
| 453 | 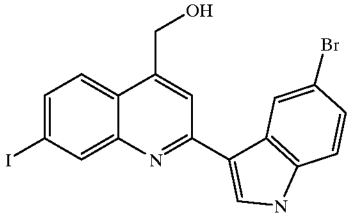 | < | 7 | < | 7 | < | 7 |
| 454 | 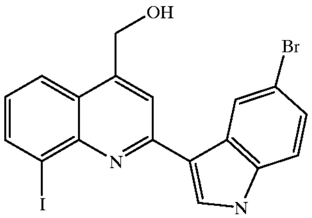 | < | 7 | < | 7 | < | 7 |
| 455 | 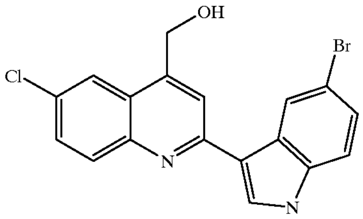 | < | 7 | < | 7 | < | 7 |

-continued
| Cmpd. # | STRUCTURE | | MRSA | | VREF | | *S. pneu* |
|---|---|---|---|---|---|---|---|
| 456 | 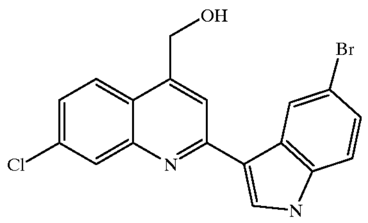 | < | 7 | < | 7 | < | 7 |
| 457 | 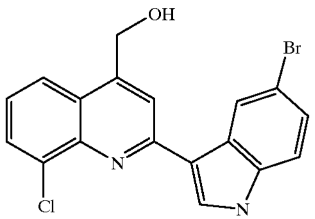 | < | 7 | < | 7 | < | 7 |
| 458 | 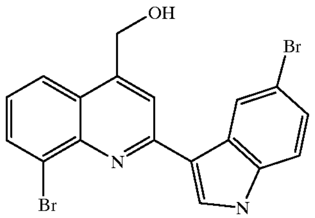 | < | 7 | < | 7 | < | 7 |
| 459 | 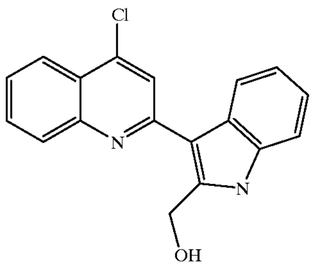 | > | 25 | > | 25 | > | 25 |

-continued
| Cmpd. # | STRUCTURE | | MRSA | | VREF | | *S. pneu* |
|---|---|---|---|---|---|---|---|
| 460 | 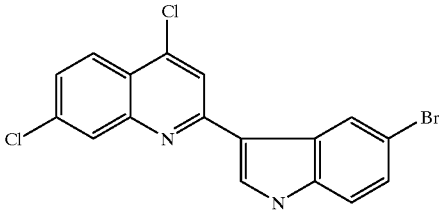 | < | 7 | < | 7 | < | 7 |
| 461 | 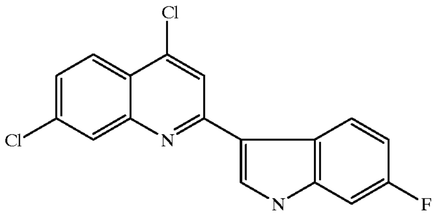 | < | 7 | < | 7 | < | 7 |
| 462 | 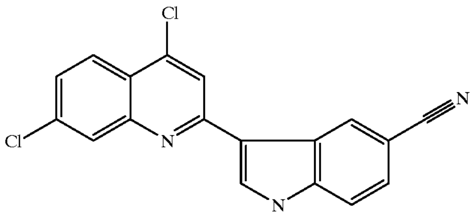 | > | 25 | > | 25 | > | 25 |
| 463 | 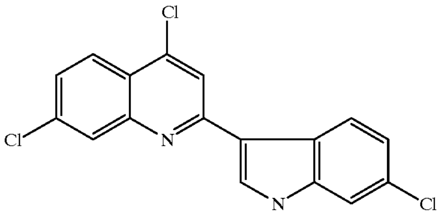 | = | 25 | > | 25 | = | 25 |

-continued
| Cmpd. # | STRUCTURE | | MRSA | | VREF | | *S. pneu* |
|---|---|---|---|---|---|---|---|
| 464 | 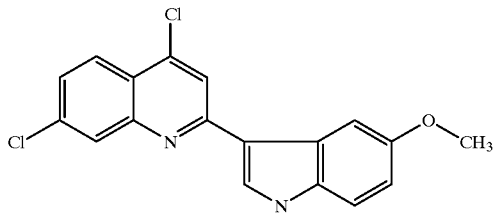 | < | 7 | > | 25 | < | 7 |
| 465 | 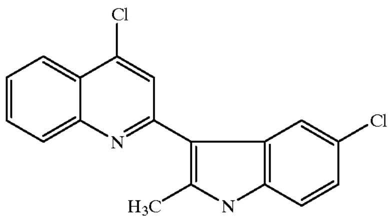 | < | 7 | < | 25 | < | 7 |
| 466 | 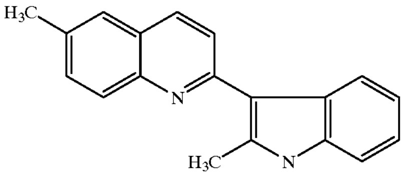 | > | 25 | > | 25 | < | 25 |
| 467 | 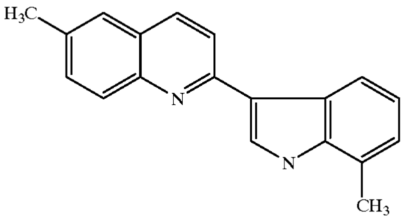 | > | 25 | > | 25 | > | 25 |

-continued
| Cmpd. # | STRUCTURE | | MRSA | | VREF | | *S. pneu* |
|---|---|---|---|---|---|---|---|
| 468 | 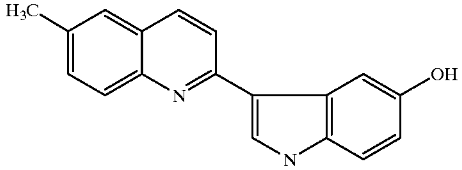 | = | 25 | > | 25 | > | 25 |
| 469 | 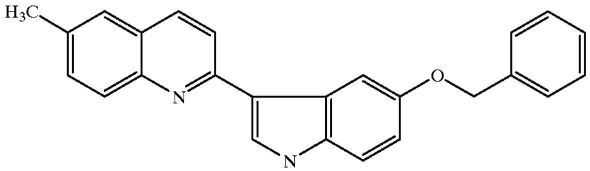 | < | 7 | > | 25 | < | 7 |
| 470 | 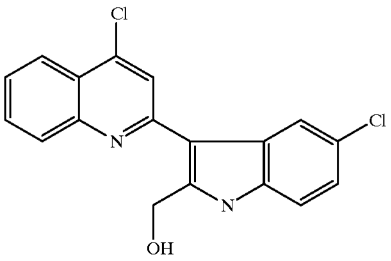 | > | 25 | > | 25 | > | 25 |
| 471 | 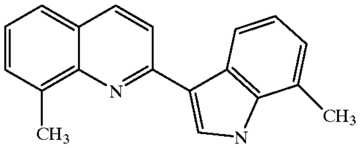 | | | > | 25 | < | 7 |
| 472 | 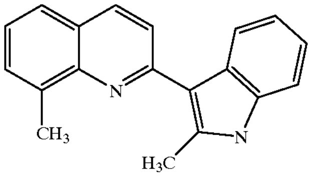 | < | 25 | > | 25 | < | 25 |

-continued
| Cmpd. # | STRUCTURE | | MRSA | | VREF | | *S. pneu* |
|---|---|---|---|---|---|---|---|
| 473 | 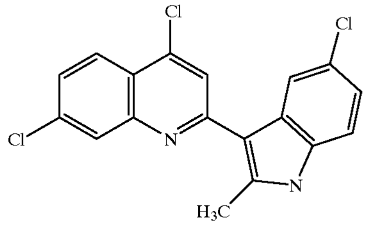 | < | 7 | < | 25 | < | 7 |
| 474 | 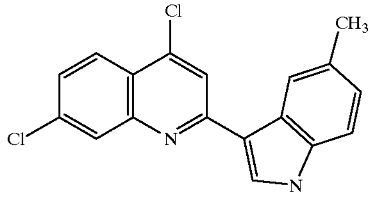 | < | 7 | < | 25 | < | 7 |
| 475 | 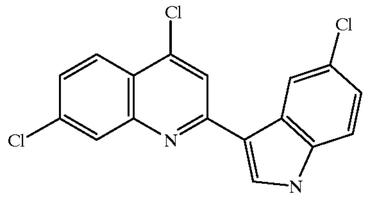 | < | 7 | < | 7 | < | 7 |
| 476 | 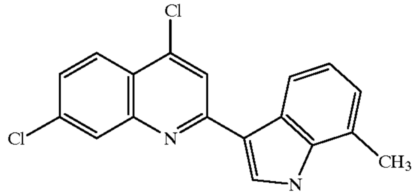 | > | 25 | > | 25 | < | 25 |

-continued
| Cmpd. # | STRUCTURE | | MRSA | | VREF | | *S. pneu* |
|---|---|---|---|---|---|---|---|
| 477 | 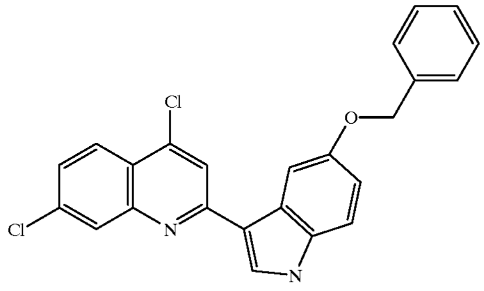 | < | 7 | > | 25 | < | 7 |
| 478 | 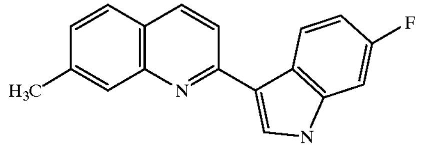 | > | 25 | > | 25 | > | 25 |
| 479 | 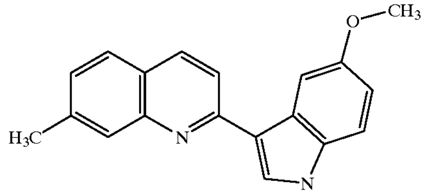 | > | 25 | > | 25 | < | 25 |
| 480 | 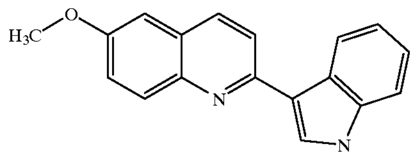 | > | 25 | > | 25 | > | 25 |
| 481 | 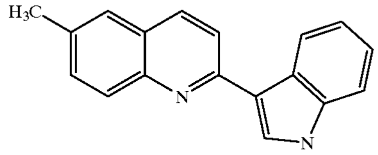 | > | 25 | > | 25 | > | 25 |

-continued
| Cmpd. # | STRUCTURE | MRSA | | VREF | | *S. pneu* | |
|---|---|---|---|---|---|---|---|
| 482 | 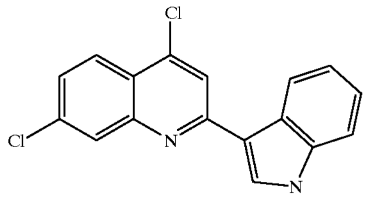 | < | 7 | < | 7 | < | 7 |
| 483 | 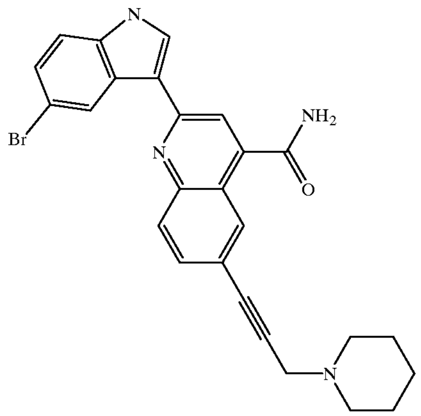 | < | 7 | < | 7 | < | 7 |
| 484 | 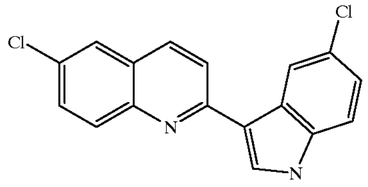 | < | 7 | > | 25 | < | 7 |

-continued
| Cmpd. # | STRUCTURE | | MRSA | | VREF | | *S. pneu* |
|---|---|---|---|---|---|---|---|
| 485 | 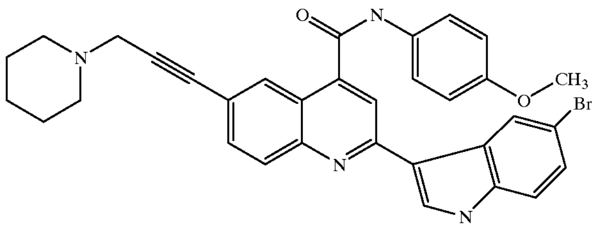 | < | 7 | > | 25 | < | 25 |
| 486 | 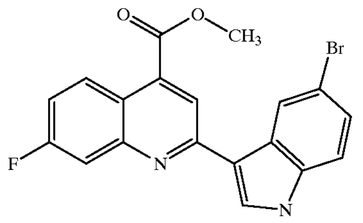 | < | 7 | < | 7 | < | 7 |
| 487 | 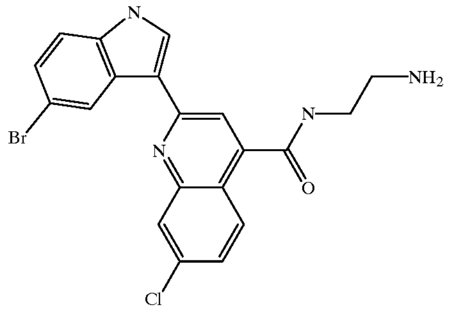 | < | 7 | < | 7 | < | 7 |
| 488 | 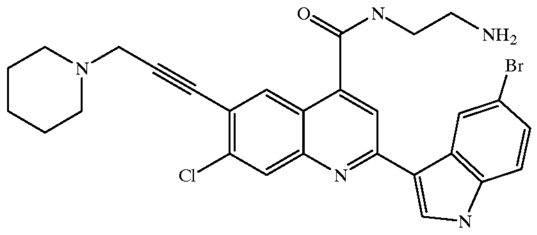 | < | 7 | | | | |

-continued
| Cmpd. # | STRUCTURE | | MRSA | | VREF | | *S. pneu* |
|---|---|---|---|---|---|---|---|
| 489 | 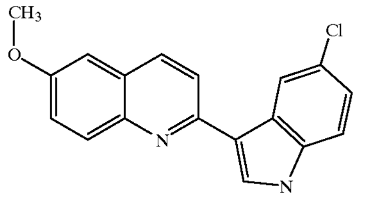 | < | 7 | > | 25 | < | 7 |
| 490 | 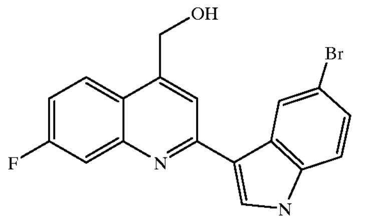 | < | 7 | > | 25 | < | 7 |
| 491 | 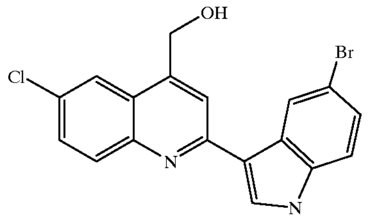 | < | 7 | > | 25 | < | 7 |
| 492 | 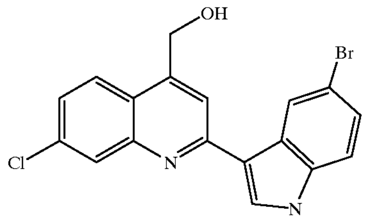 | < | 7 | < | 25 | < | 7 |

-continued
| Cmpd. # | STRUCTURE | | MRSA | | VREF | | *S. pneu* |
|---|---|---|---|---|---|---|---|
| 493 | 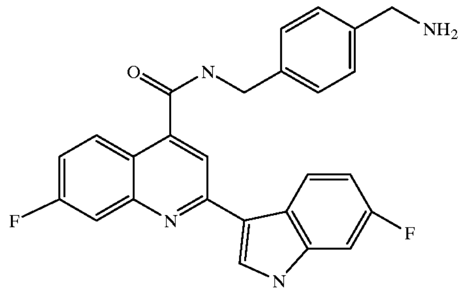 | < | 25 | < | 25 | < | 25 |
| 494 | 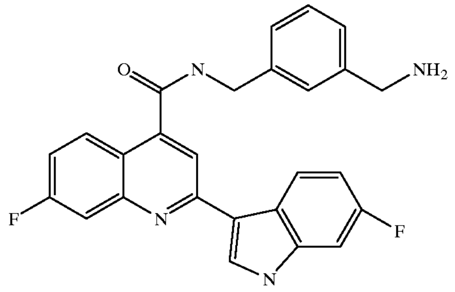 | < | 7 | < | 7 | < | 7 |
| 495 | 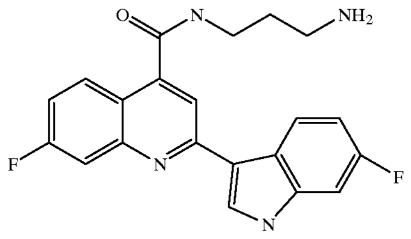 | < | 25 | > | 25 | < | 25 |

-continued
| Cmpd. # | STRUCTURE | | MRSA | | VREF | | *S. pneu* |
|---|---|---|---|---|---|---|---|
| 496 | 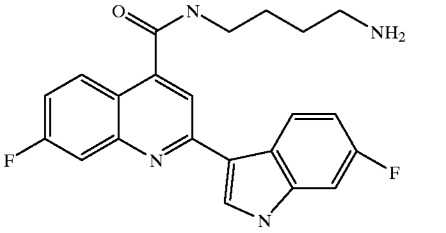 | < | 25 | > | 25 | < | 25 |
| 497 | 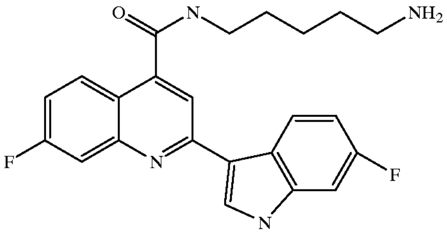 | < | 25 | < | 25 | < | 25 |
| 498 | 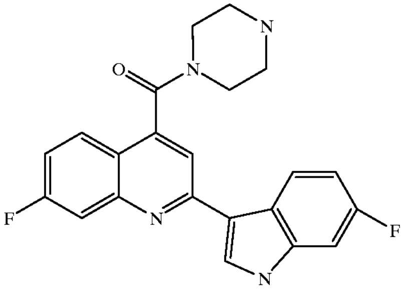 | < | 25 | > | 25 | < | 25 |

-continued
| Cmpd. # | STRUCTURE | | MRSA | | VREF | | *S. pneu* |
|---|---|---|---|---|---|---|---|
| 499 | 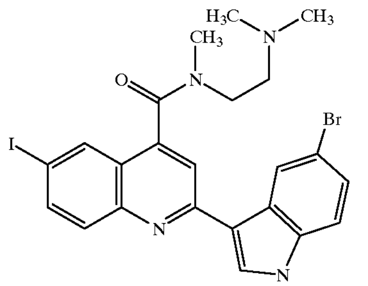 | < | 7 | < | 7 | < | 7 |
| 500 | 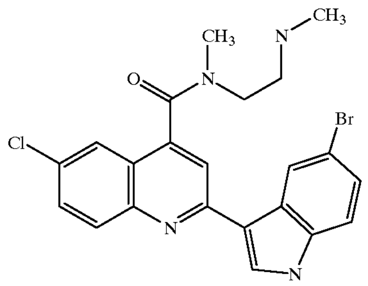 | < | 7 | < | 7 | < | 7 |
| 501 | 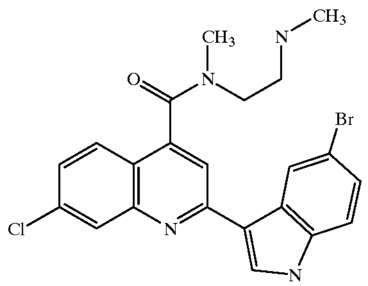 | < | 7 | < | 7 | < | 7 |

-continued
| Cmpd. # | STRUCTURE | | MRSA | | VREF | | *S. pneu* |
|---|---|---|---|---|---|---|---|
| 502 | 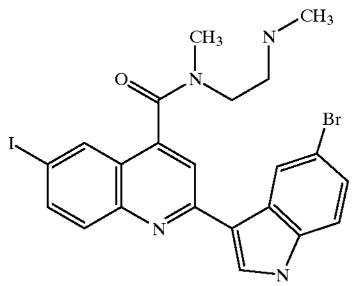 | < | 7 | < | 7 | < | 7 |
| 503 | 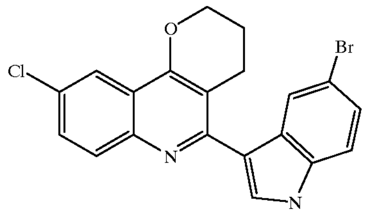 | < | 7 | > | 25 | < | 25 |
| 504 | 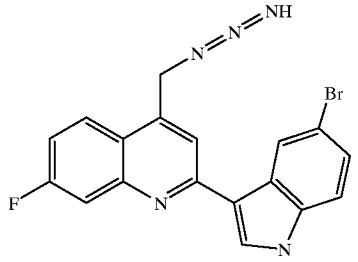 | < | 7 | < | 25 | < | 7 |

-continued
| Cmpd. # | STRUCTURE | MRSA | | VREF | | *S. pneu* | |
|---|---|---|---|---|---|---|---|
| 505 | 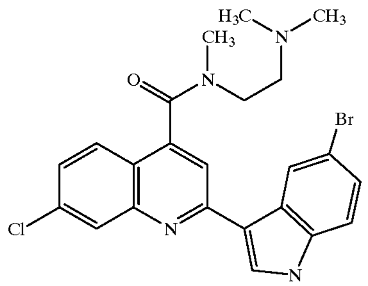 | < | 7 | < | 7 | < | 7 |
| 506 | 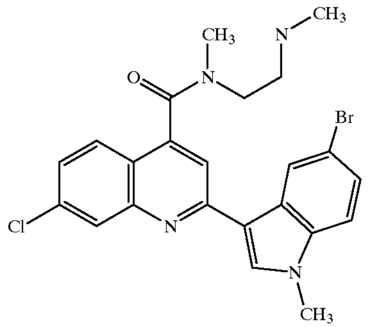 | < | 7 | < | 7 | < | 7 |
| 507 | 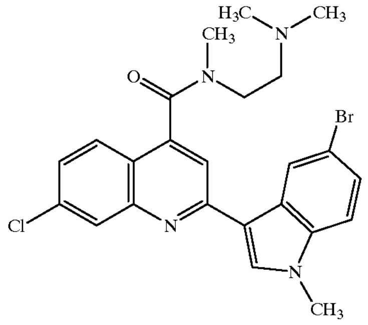 | < | 7 | < | 7 | < | 7 |

-continued
| Cmpd. # | STRUCTURE | | MRSA | | VREF | | *S. pneu* |
|---|---|---|---|---|---|---|---|
| 508 | 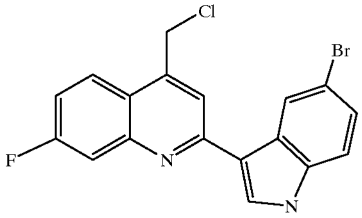 | < | 7 | < | 7 | < | 7 |
| 509 | 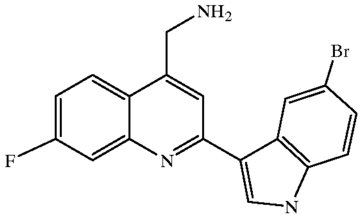 | < | 7 | < | 7 | < | 7 |
| 510 | 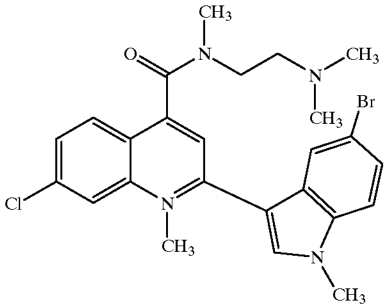 | < | 7 | < | 7 | < | 7 |
| 511 | 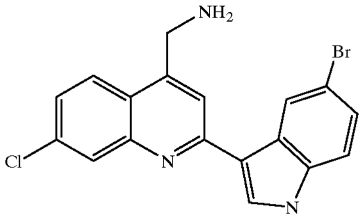 | < | 7 | < | 7 | < | 7 |

-continued
| Cmpd. # | STRUCTURE | | MRSA | | VREF | | *S. pneu* |
|---|---|---|---|---|---|---|---|
| 512 | 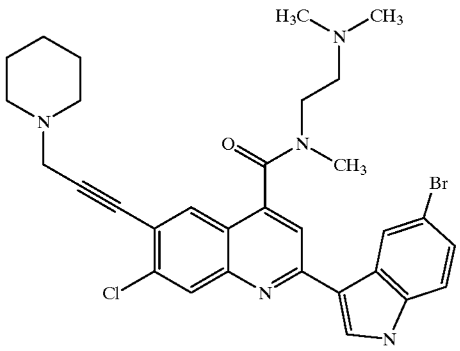 | < | 7 | < | 7 | < | 7 |
| 513 | 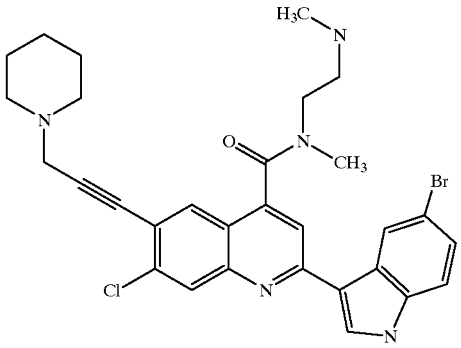 | < | 7 | < | 7 | < | 7 |

-continued
| Cmpd. # | STRUCTURE | | MRSA | | VREF | | *S. pneu* |
|---|---|---|---|---|---|---|---|
| 514 | 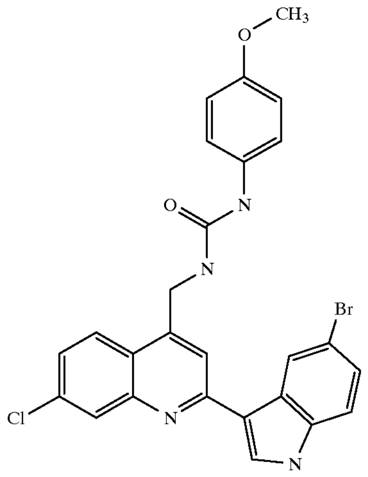 | < | 7 | > | 25 | < | 7 |
| 515 | 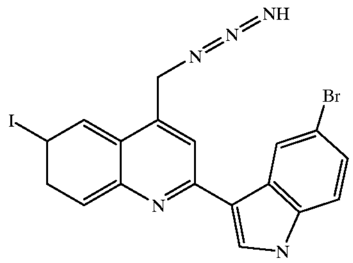 | < | 7 | > | 25 | < | 7 |
| 516 | 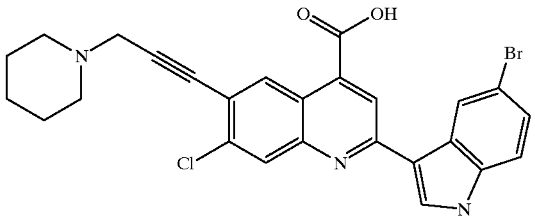 | < | 7 | < | 25 | < | 7 |

-continued
| Cmpd. # | STRUCTURE | | MRSA | | VREF | | *S. pneu* |
|---|---|---|---|---|---|---|---|
| 517 | 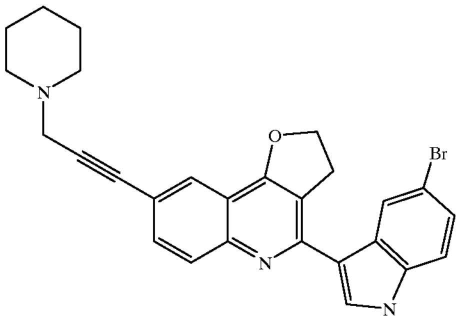 | < | 7 | > | 25 | < | 7 |
| 518 | 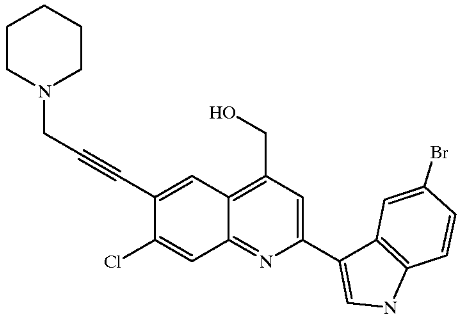 | < | 7 | < | 7 | < | 7 |
| 519 | 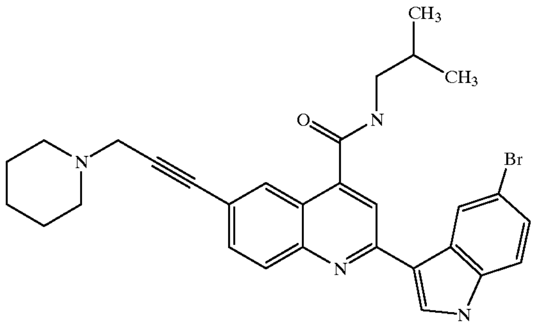 | < | 7 | > | 25 | < | 7 |

-continued
| Cmpd. # | STRUCTURE | | MRSA | | VREF | | *S. pneu* |
|---|---|---|---|---|---|---|---|
| 520 | 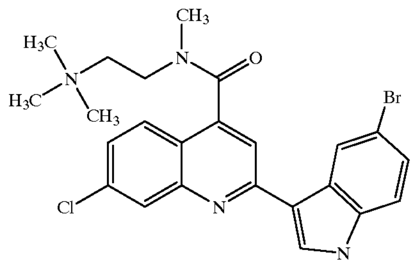 | < | 7 | < | 7 | < | 7 |
| 521 | 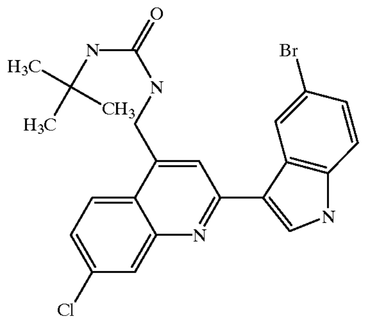 | < | 7 | > | 25 | < | 7 |
| 522 | 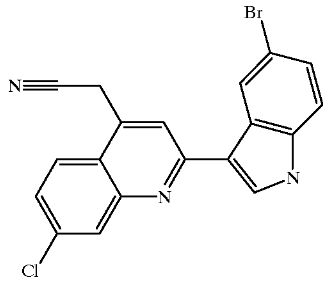 | < | 7 | < | 25 | < | 7 |

-continued
| Cmpd. # | STRUCTURE | MRSA | VREF | *S. pneu* |
|---|---|---|---|---|
| 523 | 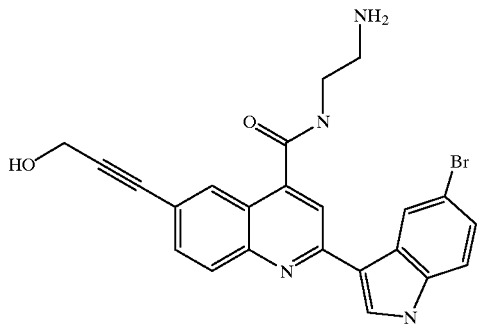 | < 7 | < 7 | < 7 |
| 524 | 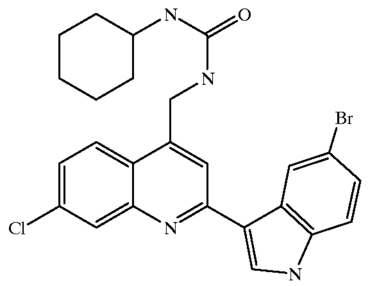 | < 7 | < 7 | < 7 |
| 525 | 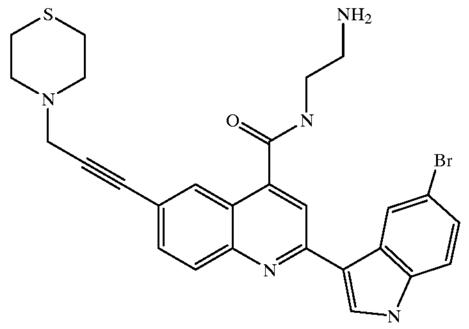 | < 7 | < 7 | < 7 |

-continued
| Cmpd. # | STRUCTURE | MRSA | | VREF | | *S. pneu* | |
|---|---|---|---|---|---|---|---|
| 526 | 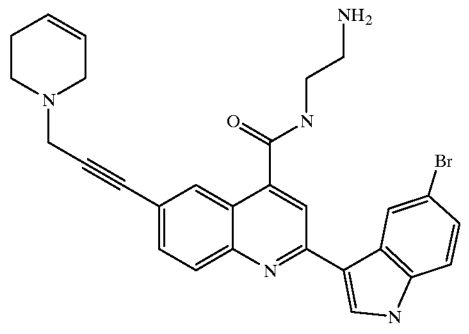 | < | 7 | < | 7 | < | 7 |
| 527 | 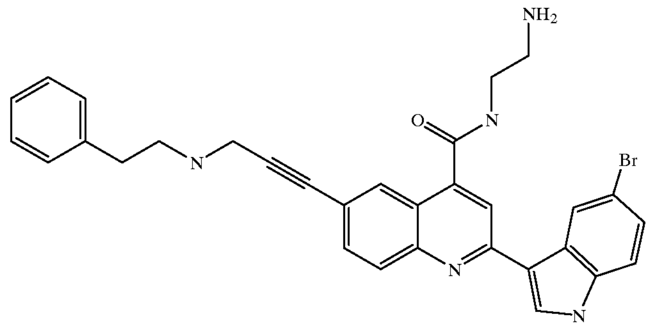 | < | 7 | < | 7 | < | 7 |
| 528 | 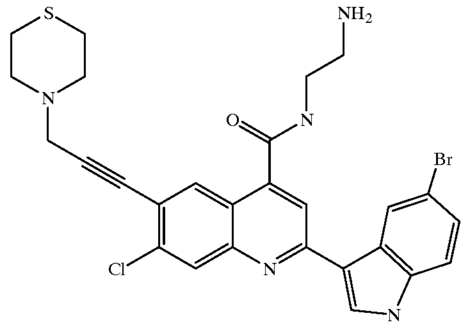 | < | 7 | < | 7 | < | 7 |

-continued
| Cmpd. # | STRUCTURE | | MRSA | | VREF | | *S. pneu* |
|---|---|---|---|---|---|---|---|
| 529 | 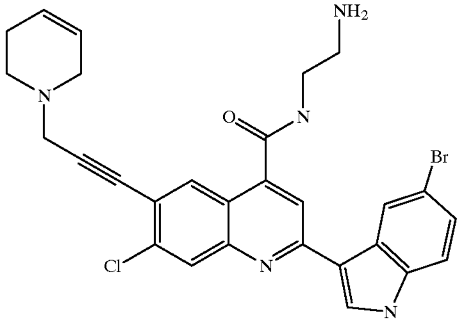 | < | 7 | < | 7 | < | 7 |
| 530 | 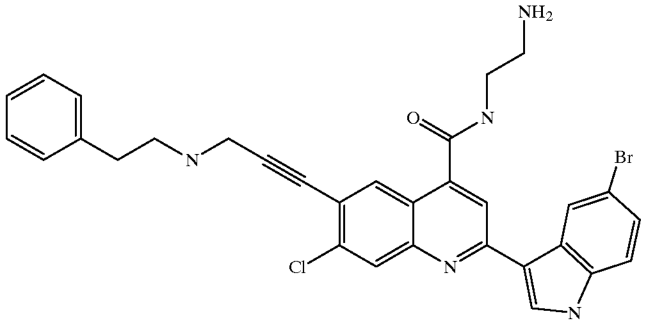 | < | 7 | < | 7 | < | 7 |
| 531 | 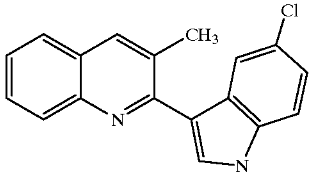 | < | 7 | < | 7 | < | 7 |

-continued
| Cmpd. # | STRUCTURE | MRSA | | VREF | | *S. pneu* | |
|---|---|---|---|---|---|---|---|
| 532 | 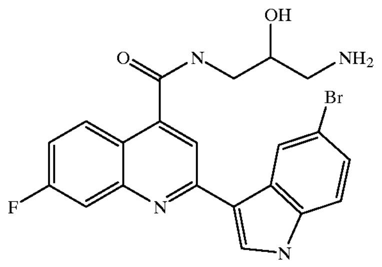 | < | 7 | < | 7 | < | 7 |
| 533 | 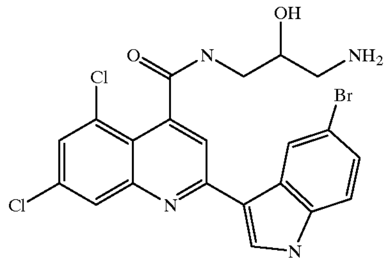 | < | 7 | < | 7 | < | 7 |
| 534 | 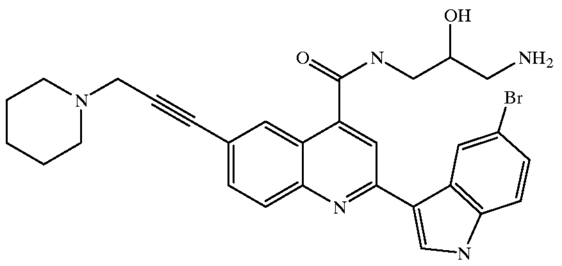 | < | 7 | < | 7 | < | 7 |

Example 33

This example demonstrates the lack of acute in vivo toxicity in mice for some antibacterial compounds of the invention. Solutions of compounds in 10% w/v hydroxypropyl-β-cyclodextrin in 0.9% w/v saline were prepared. Doses of 40 mg/kg or 120 mg/kg of each compound were administered to mice (5 mice/compound/dose) via intraperitoneal injections. The mice were observed for seven days.

| Compound # | Dose (mg/kg) | Mice Surviving on Day 7 (%) |
|---|---|---|
| 193 | 40 | 100 |
| 193 | 120 | 100 |
| 316 | 40 | 80 |
| 316 | 120 | 0 |
| 420 | 40 | 100 |
| 420 | 120 | 100 |
| 379 | 40 | 40 |
| 379 | 120 | 0 |
| 419 | 40 | 40 |
| 419 | 120 | 0 |
| 417 | 40 | 100 |
| 417 | 120 | 100 |
| 380 | 40 | 100 |
| 380 | 120 | 0 |
| 418 | 40 | 100 |
| 418 | 120 | 0 |
| 307 | 40 | 100 |
| 307 | 120 | 100 |
| 447 | 40 | 100 |
| 447 | 120 | 80 |
| 461 | 40 | 100 |
| 461 | 120 | 100 |
| 474 | 40 | 100 |
| 474 | 120 | 100 |
| 342 | 40 | 100 |
| 342 | 120 | 100 |
| 107 | 40 | 100 |
| 107 | 120 | 0 |
| 359 | 40 | 100 |
| 359 | 120 | 100 |

Example 34

The example demonstrates the in vivo efficacy of an antibacterial compound of the invention for treating a methicillin-resistant *Staphylococcus aureus* infection. An intraperitoneal (ip) mouse infection model known in the art was utilized. A group of 10 female mice (5 test animals and 5 control animals) was inoculated ip with methicillin-resistant *Staphylococcus aureus*. One hour after bacterial inoculation, five of the animals were given an interperitoneal injection of 40 mg/kg 61 as a 7 mg/mL solution in 10% w/v hydroxypropyl-β-cyclodextrin in 0.9% w/v saline. After twenty-four hours all five animals that received 61 were alive, but four of the treated animals had expired. After seven days, four of the treated animals were still alive.

Example 35

This example establishes a lack of acute in vivo toxicity in mice for an antibacterial compound of the invention when administered intravenously as a liposomal formulation. A liposomal formulation of 61 (see Example 32), with a particle size less than 700 mm, was prepared using phosphatidyl choline, cholic acid, cholesterol and α-tocopherol. The formulation was freeze-dried and then reconstituted prior to administration to the mice. A dose of 120 mg/kg was administered via tail vein injections to five female mice. The mice were then observed for seven days; they showed no visible adverse effects from the injections.

Example 36

This example establishes the efficacy of an antibacterial compound of the invention in the topical treatment of methicillin-resistant *Staphylococcus aureus* infections. Partial thickness wounds were made on properly anesthetized, specific-pathogen-free (SPF: Ken-O-Kaw Farms, Windsor, Ill.), young, female pigs weighing 25–30 kg. The wounds were inoculated with methicillin-resistant *Staphylococcus aureus* (~$10^6$ CFU/mL). Within 10 minutes of inoculation, 200 mg of 316 (Example 32) [2% w/w in polyethylene glycol (PEG)] was applied to each wound. Wounds were cultured on days 1, 2, and 3. Each site was cultured once. The culture samples were treated with a neutralizer for the antimicrobial ingredient. The samples were processed according to an art-recognized method for determining the number of colony-forming units per mL. The chart below presents the data from these experiments.

| Treatment Group | Time (h) | Log CFU/mL (mean ± SE) |
|---|---|---|
| Air exposed | 24 | 6.48 ± 0.17 |
| Air exposed | 48 | 6.79 ± 0.04 |
| Air exposed | 72 | 6.67 ± 0.22 |
| PEG ointment | 24 | 6.89 ± 0.14 |
| PEG ointment | 48 | 6.68 ± 0.17 |
| PEG ointment | 72 | 6.28 ± 0.25 |
| 2% w/w 316 (trifluoroacetate salt) | 24 | 4.90 ± 0.32 |
| 2% w/w 316 (trifluoroacetate salt) | 48 | 5.14 ± 0.15 |
| 2% w/w 316 (trifluoroacetate salt) | 72 | 5.15 ± 0.22 |

Example 37

MICs (μg/mL) of Eleven Compounds Against Four Strains of *S. aureus*

| Entry No. | STRUCTURE | *S. aureus* (ATCC 25923) | *S. aureus* (ATCC 29213) | *S. aureus* (ATCC 33591) | *S. aureus* (ATCC 33592) |
|---|---|---|---|---|---|
| 1 | 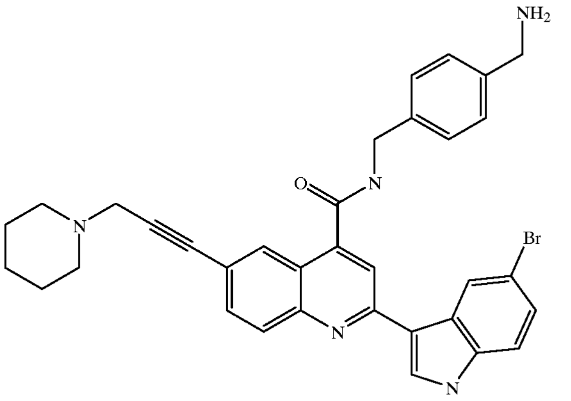 | <7 | <7 | <7 | <7 |
| 2 | 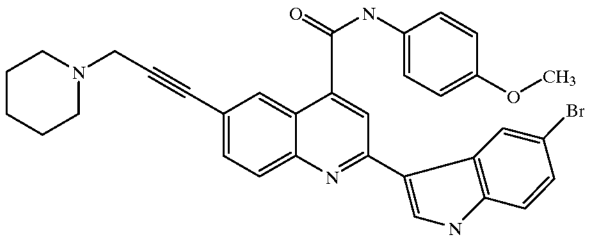 | <7 | <7 | <7 | <7 |
| 3 | 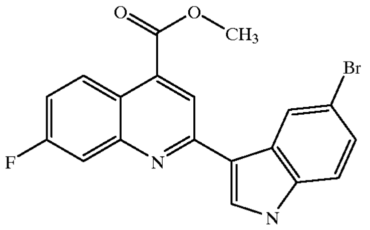 | <7 | <7 | <7 | <7 |
| 4 | 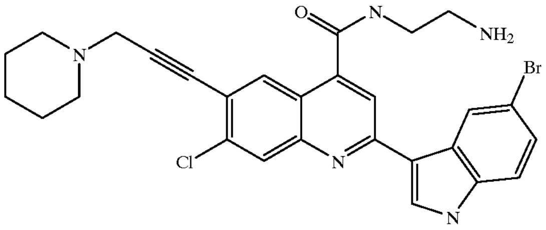 | <7 | <7 | <7 | <7 |
| 5 | 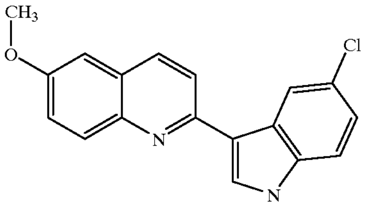 | <7 | <7 | <7 | <7 |

-continued
| Entry No. | STRUCTURE | *S. aureus* (ATCC 25923) | *S. aureus* (ATCC 29213) | *S. aureus* (ATCC 33591) | *S. aureus* (ATCC 33592) |
|---|---|---|---|---|---|
| 6 | 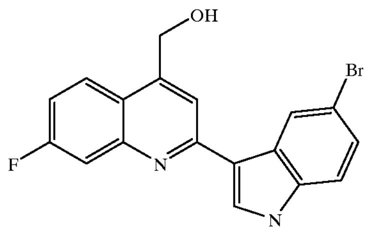 | <7 | <7 | <7 | <7 |
| 7 | 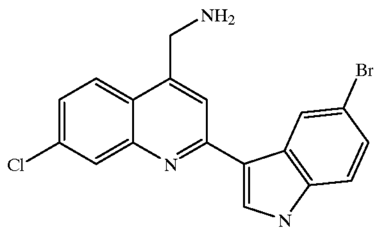 | <7 | <7 | <7 | <7 |
| 8 | 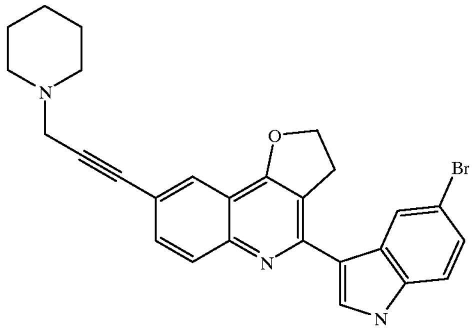 | <7 | <7 | <7 | <7 |
| 9 | 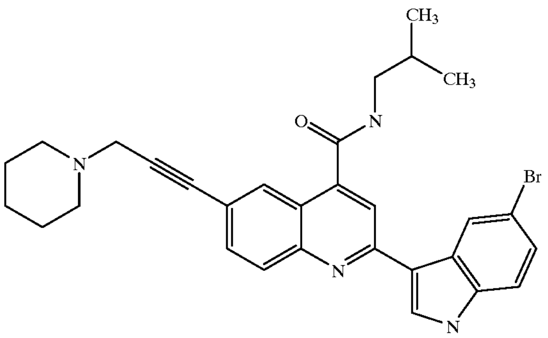 | <25 | <7 | <7 | <25 |
| 10 | 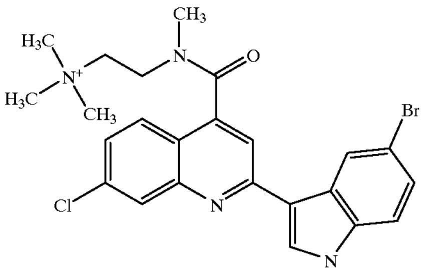 | <7 | <7 | <7 | <7 |

-continued
| Entry No. | STRUCTURE | *S. aureus* (ATCC 25923) | *S. aureus* (ATCC 29213) | *S. aureus* (ATCC 33591) | *S. aureus* (ATCC 33592) |
|---|---|---|---|---|---|
| 11 | 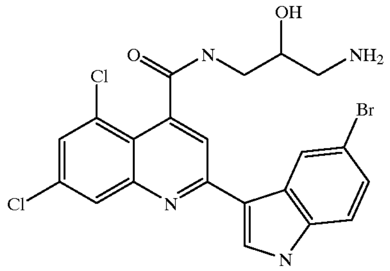 | <7 | <7 | <7 | <7 |
Example 38
MICs ($\mu$g/mL) of Ten Compounds Against MRSA, VISA-5827, and VISA-5836
| Entry No. | STRUCTURE | MRSA | VISA-5827 | VISA-5836 |
|---|---|---|---|---|
| 1 | 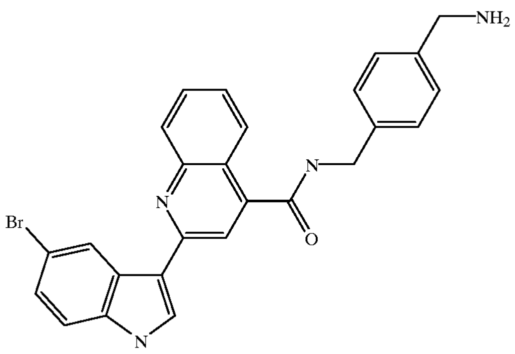 | <7 | <7 | <7 |
| 2 | 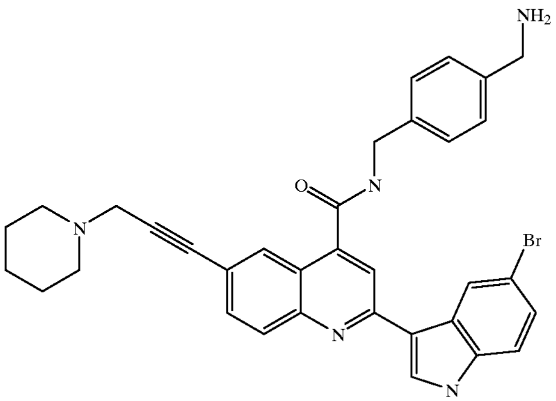 | <7 | <7 | <7 |
| 3 | 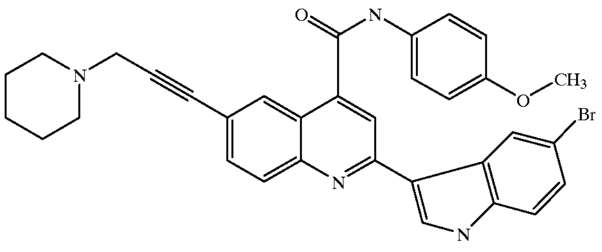 | <7 | <7 | <7 |

-continued
| Entry No. | STRUCTURE | MRSA | VISA-5827 | VISA-5836 |
|---|---|---|---|---|
| 4 | 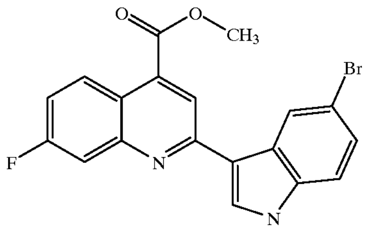 | <7 | <7 | <7 |
| 5 | 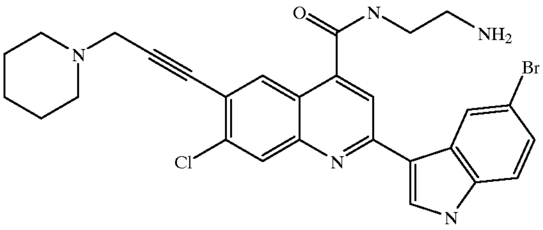 | <7 | <7 | <7 |
| 6 | 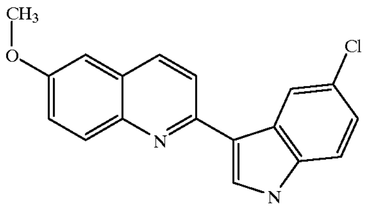 | <7 | <7 | <7 |
| 7 | 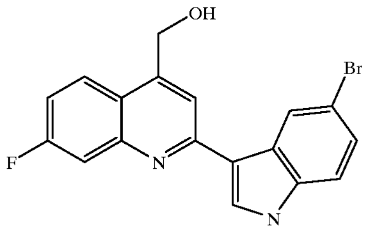 | <7 | <7 | <7 |
| 8 | 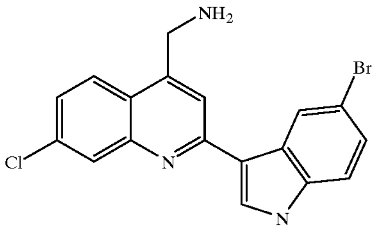 | <7 | <7 | <7 |
| 9 | 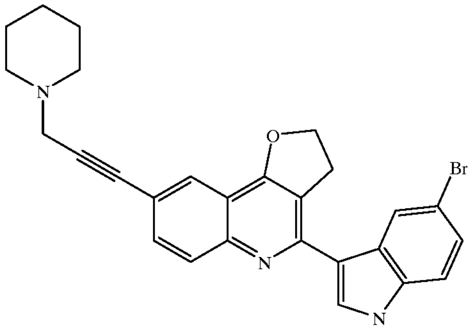 | <7 | <7 | <7 |

-continued

| Entry No. | STRUCTURE | MRSA | VISA-5827 | VISA-5836 |
|---|---|---|---|---|
| 10 | 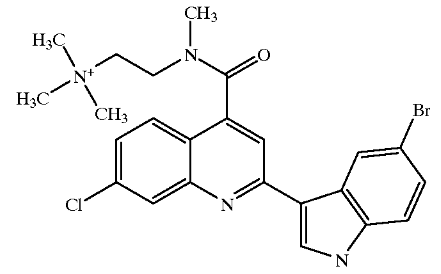 | <7 | <7 | <7 |

Example 39

Synthesis of Methyl-2-(3-indolyl)-4-quinolinecarboxylate

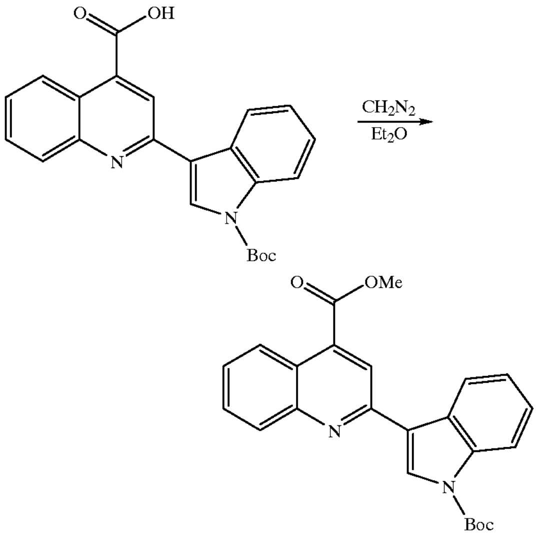

To a solution of the acid (0.21 mmol) in 2 ml of acetonitrile was added a solution of diazomethane (0.42 mmol) in 1 mL of ether. The reaction was allowed to stir for 4 h and then the reaction was quenched with acetic acid (100 uL). The mixture was diluted with dichloromethane and washed with saturated $NaHCO_3$, dried ($MgSO_4$), filtered, and concentrated in vacuo to give the methyl ester as a solid (100% yield).

Example 40

Synthesis of 4-Hydroxymethyl-2-(N-Boc-3-indolyl)quinoline

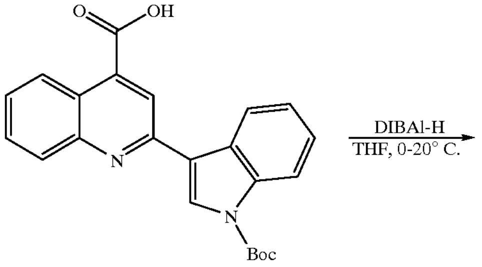

-continued

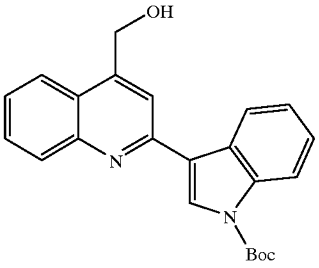

To a solution of the acid (25 mmol) in 100 mL of THF at 0° C. was added 83 mL of a 1.5 M solution of diisobutylaluminum hydride in toluene. The reaction was warmed to 20° C. and allowed to stir for 1.5 h. The reaction was diluted with EtOAc (100 mL) and 10 g of solid $Na_2SO_4$ was added. To this was added 10 mL of water and the mixture stirred until it became a thick slurry. The slurry was filtered through silica gel and the organic concentrated in vacuo. The crude material was purified by flash chromatography (silica gel, DCM/MeOH 20:1) to give pure alcohol (55% yield).

Example 41

Synthesis of 4-Hydroxymethyl-2-(3-indolyl)quinoline

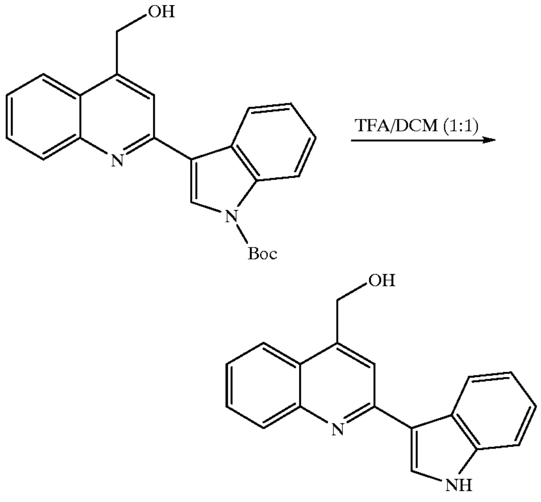

The alcohol (1 mmol) was dissolved in 5 mL of a 1:1 mixture of trifluoroacetic acid and dichloromethane. The reaction mixture was stirred for 1 h and then concentrated in vacuo. The crude material was purified by reverse phase liquid chromatography (C-18 column, acetonitrile/water 1:1) to give pure deprotected alcohol (90–100% yield).

Example 42

Synthesis of 4-Methanesulfonoxymethyl-2-(N-Boc-3-indoyl)quinoline

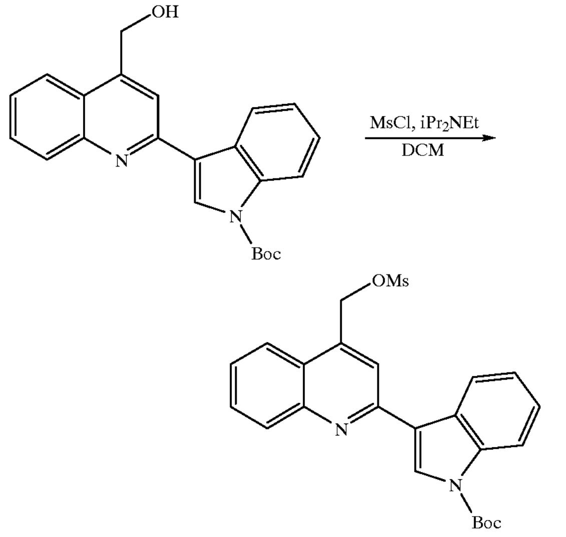

To a suspension of the alcohol (2 mmol) in 25 mL of dichloromethane was added 536 uL (3.08 mmol) of diisopropylethylamine followed by 237 uL (3.08 mmol) of methanesulfonyl chloride. The reaction was allowed to stir for 2 h and then diluted with dichloromethane (25 mL). The organic was washed with water (50 mL), dried ($MgSO_4$), filtered, and concentrated in vacuo. The crude solid was purified by flash chromatography (silica gel, DCM) to give pure mesylate as a white solid (54% yield).

Example 43

Synthesis of 4-Azidomethyl-2-(N-Boc-3-indolyl)quinoline

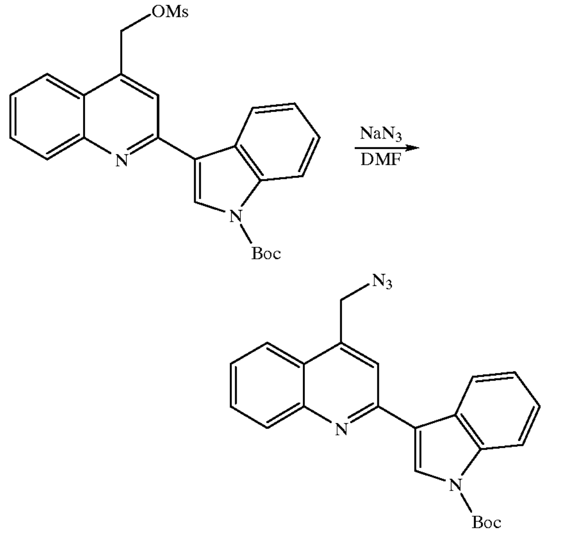

To a solution of the mesylate (6 mmol) in 50 mL of DMF was added 1.2 g of sodium azide (18 mmol). The reaction was allowed to stir for 5 h and then diluted with DCM (50 mL). The mixture was washed with saturated $NH_4Cl$ (100 mL), dried ($MgSO_4$), filtered, and concentrated in vacuo. The crude material was purified by flash chromatography (silica gel, Hex/DCM 1:1/0:1) to give pure azide (80–90% yield).

Example 44

Synthesis of 4-Azidomethyl-2-(3-indolyl)quinoline

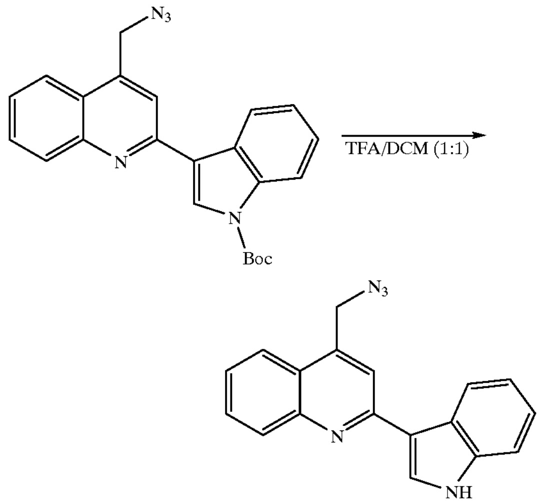

The azide (1 mmol) was dissolved in 5 ml of a 1:1 mixture of trifluoroacetic acid and dichloromethane. The reaction mixture was stirred for 1 h and then concentrated in vacuo. The crude material was purified by reverse phase liquid chromatography (C-18 column, acetonitrile/water 1:1) to give pure deprotected azide (90–100% yield).

Example 45

Synthesis of 4-Aminomethyl-2-(3-indolyl)quinoline

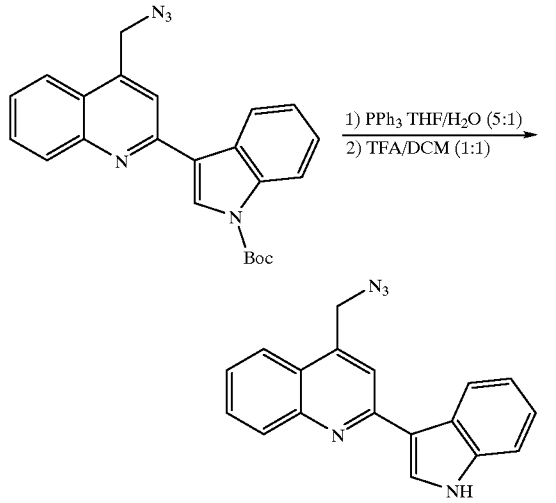

To a solution of the azide (0.2 mmol) in 2 ml of THF was added 200 uL of water followed by 61 mg of triphenylphosphine (0.24 mmol). The reaction mixture was diluted with DCM (5 mL), dried ($MgSO_4$), filtered, and concentrated in vacuo. The crude material was dissolved in 5 mL of a 1:1 mixture of trifluoroacetic acid and dichloromethane. The reaction mixture was stirred for 1 h and then concentrated in vacuo. The crude material was purified by reverse phase liquid chromatography (C-18 column, acetonitrile/water 1:1) to give pure amine (60–70% yield).

Example 46

Synthesis of 4-N-Carbamoylaminomethyl-2-(3-indolyl) quinoline

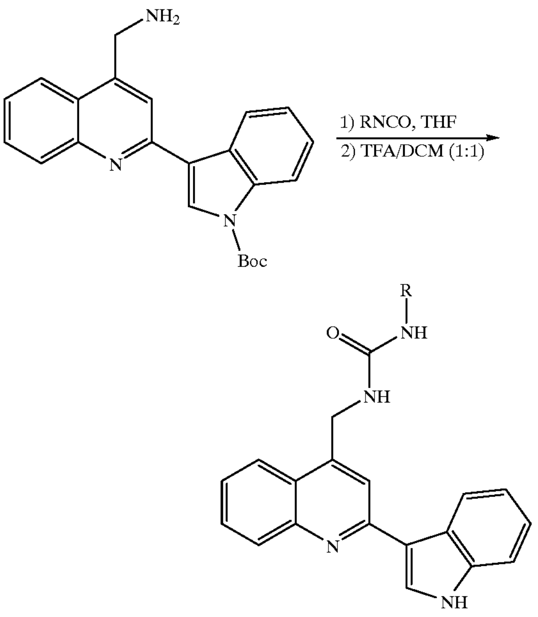

To a solution of the amine (0.2 mmol) in 2 ml of THF was added isocyanate (0.22 mmol). The reaction mixture was allowed to stir for 6 h. The reaction was quenched with water (5 mL) and extracted with EtOAc (25 mL). The organic layer was dried ($MgSO_4$), filtered, and concentrated in vacuo. The crude material was dissolved in 5 mL of a 1:1 mixture of trifluoroacetic acid and dichloromethane. The reaction mixture was stirred for 1 h and then concentrated in vacuo. The crude material was purified by reverse phase liquid chromatography (C-18 column, acetonitrile/water 1:1) to give pure urea (45–55% yield).

Example 47

Synthesis of 4-Chloromethyl-2-(3-indolyl)quinoline

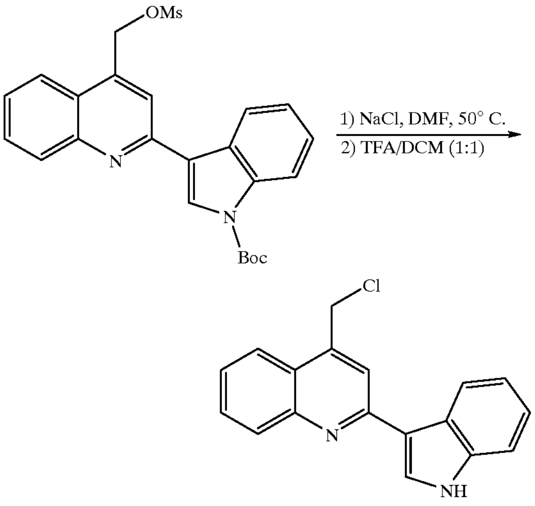

To a solution of the mesylate (6 mmol) in 50 mL of DMF was added 1.2 g of sodium chloride (18 mmol). The reaction was warmed to 50° C. and allowed to stir for 5 h. The reaction mixture was cooled to 20° C. and then diluted with DCM (50 mL). The mixture was washed with water (100 mL), dried ($MgSO_4$), filtered, and concentrated in vacuo. The crude material was dissolved in 5 mL of a 1:1 mixture of trifluoroacetic acid and dichloromethane. The reaction mixture was stirred for 1 h and then concentrated in vacuo. The crude material was purified by reverse phase liquid chromatography (C-18 column, acetonitrile/water 1:1) to give pure chloride (90–100% yield).

Example 48

Synthesis of 4-Cyanomethyl-2-(3-indolyl)quinoline

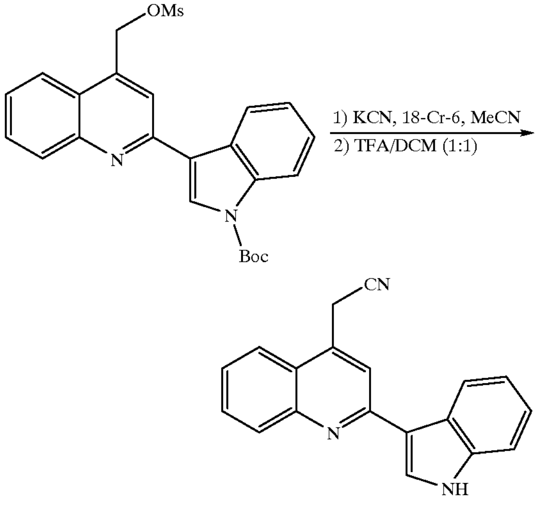

To a solution of the mesylate (1.8 mmol) in 15 mL of MeCN and 15 mL of dichloromethane was added 573 mg of potassium cyanide (8.8 mmol) and 466 mg of 18-crown-6 (1.76 mmol). The reaction was warmed to allowed to stir for 5 h and then diluted with DCM (50 mL). The mixture was washed with water (50 mL), dried ($MgSO_4$), filtered, and concentrated in vacuo. The crude material was dissolved in 5 mL of a 1:1 mixture of trifluoroacetic acid and dichloromethane. The reaction mixture was stirred for 1 h and then concentrated in vacuo. The crude material was purified by reverse phase liquid chromatography (C-18 column, acetonitrile/water 1:1) to give pure nitrile (50–60% yield).

Example 49

Synthesis of Compound 517

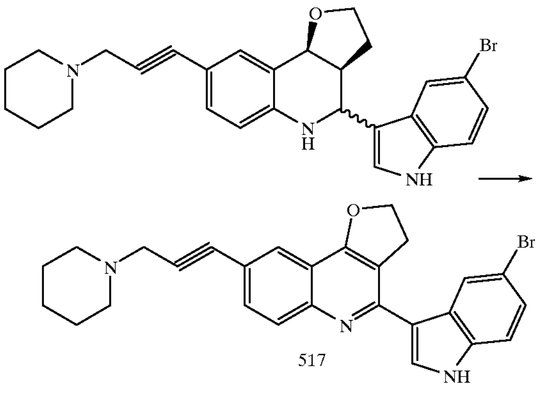

517

The indolyl-tetrahydroquinoline was made according to the established lanthanide triflate catalyzed Kobayashi chemistry (for a leading reference, see Kobayashi, S.; Ishitani, H.; Nagayama, S. Synthesis, 1995, 1195–1202). The tetrahydroquinoline (50.0 mg, 0.102 mmol) was dissolved in 10 mL anhydrous dichloromethane and the solution was cooled to 0° C. under nitrogen atmosphere. 2,3-Dichloro-5,6-dicyano-1,4-benzoquinone (47.6 mg, 0.210 mmol) in 2 mL dichloromethane was then added in a drop-wise fashion. The reaction mixture was stirred at 0° C. for additional 30 minutes. The reaction crude was filtered through celite and the solvent was evaporated in vacuo to supply a yellow solid. Further purification by flash column chromatography (alumina basic, $CH_2Cl_2$/MeOH=20:1) yielded 27.5 mg of indolyl-quinoline 517.

Y: 55% MS: 486.83 (M+H)

All of the references cited in this document are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. The compound represented by the following general structure:

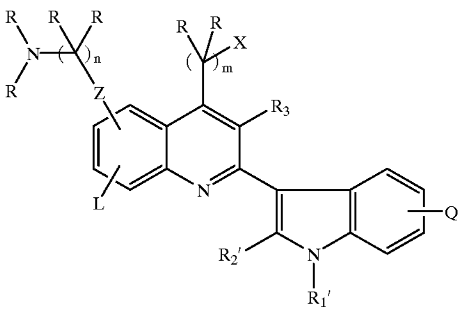

wherein

Q represents a hydrophobic group at any one of positions 4, 5, 6, or 7 of the B-ring of the indole moiety, or is absent;

X represents heterocyclyl, amidinyl, formamidonyl, guanidinyl, —CN, —C(S)$NR_2$, —N(R)C(S)R, —OR, —SR, —$NR_2$, or —$PR_2$;

Z represents —C≡C—, —(E)—CH=CH—, —(Z)—CH=CH—, or —$CH_2CH_2$—, and is bonded to any one of positions 5, 6, 7, or 8 of the B-ring of the quinoline moiety;

L represents a hydrophobic group at any one of positions 5, 6, 7, or 8 of the B-ring of the quinoline moiety that is not bonded to Z, or is absent;

R represents, independently for each occurrence, H, lower alkyl, lower heteroalkyl, aryl, heteroaryl, acyl, sulfonyl, or —$(CH_2)_mR_8$;

the two instances of R taken together in an instance of —$NR_2$ may form a ring comprising that nitrogen;

$R_1$' represents H, alkyl, aryl, p-toluenesulfonyl, —$(CH_2)_d$ N(Phth), or —$(CH_2)_dN(R)_2$ wherein d is an integer in the range 1 to 6 inclusive;

$R_2$' and $R_3$ independently for each occurrence represent H, lower alkyl, or aryl;

$R_8$ represents, independently for each occurrence, aryl, heteroaryl, cycloalkyl, cycloalkenyl, heterocyclyl, or polycyclyl;

m is, independently for each occurrence, an integer selected from the range 1–8 inclusive; and n is an integer selected from the range 1–4 inclusive.

2. The compound of claim 1, wherein X is a heteroaryl moiety.

3. The compound of claim 1, wherein X is —$NR_2$.

4. The compound of claim 1, wherein Z is bonded to the 6-position of the quinoline nucleus.

5. The compound of claim 1, wherein Q is bonded to the 5-position of the indole nucleus.

6. The compound of claim 1, wherein Q is selected from the group consisting of F, Cl, Br, I, R, —OR, —$NO_2$, and —CN.

7. The compound of claim 1, wherein Q is bonded to the 5-position of the indole nucleus; and Q is selected from the group consisting of F, Cl, Br, I, R, —OR, —$NO_2$, and —CN.

8. The compound of claim 1, wherein L is selected from the group consisting of F, Cl, Br, I, R, —OR, —$CF_3$, —$OCF_3$, —$CR_2OR$, —$CO_2R$, —$NO_2$, and —CN.

9. The compound of claim 1, wherein X represents a heteroaryl; and Q is selected from the group consisting of F, Cl, Br, I, R, —OR, —$NO_2$, and —CN.

10. The compound of claim 1, wherein X represents —$NR_2$; and Q is selected from the group consisting of F, Cl, Br, I, R, —OR, —$NO_2$, and —CN.

11. The compound of claim 1, wherein X represents a heteroaryl; Q is selected from the group consisting of F, Cl, Br, I, R, —OR, —$NO_2$, and —CN; Z is bonded to the 6-position of the quinoline nucleus; and Q is bonded to the 5-position of the indole nucleus.

12. The compound of claim 1, wherein X represents —$NR_2$; Q is selected from the group consisting of F, Cl, Br, I, R, —OR, —$NO_2$, and —CN; Z is bonded to the 6-position of the quinoline nucleus; and Q is bonded to the 5-position of the indole nucleus.

13. The compound of claim 1, 2, 3, 4, 5, 6, 7, 8, 9, 10, 11, or 12, wherein said compound has a minimum inhibitory concentration (MIC) less than 10 μg/mL against at least one Gram-positive bacterium.

14. The compound of claim 13, wherein said compound has a minimum inhibitory concentration (MIC) less than 1 μg/mL against at least one Gram-positive bacterium.

15. The compound of claim 14, wherein said compound has a minimum inhibitory concentration (MIC) less than 0.1 μg/mL against at least one Gram-positive bacterium.

16. The compound of claim 1, 2, 3, 4, 5, 6, 7, 8, 9, 10, 11, or 12, wherein said compound has a therapeutic index in primates of at least 10 for the inhibition of infection by at least one Gram-positive bacterium.

17. The compound represented by the following general structure:

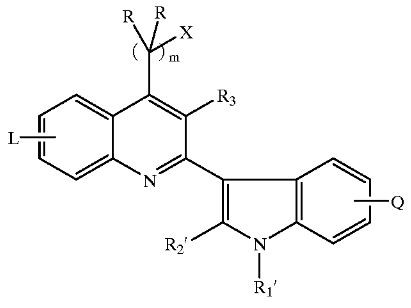

wherein

Q represents a hydrophobic group at any one of positions 4, 5, 6, or 7 of the B-ring of the indole moiety, or is absent;

X represents heterocyclyl, amidinyl, formamidonyl, guanidinyl, —CN, —C(S)$NR_2$, —N(R)C(S)R, —OR, —SR, —$NR_2$, or —$PR_2$;

L represents a hydrophobic group, or groups, at any of positions 5, 6, 7, or 8 of the B-ring of the quinoline moiety, or is absent;

R represents, independently for each occurrence, H, lower alkyl, lower heteroalkyl, aryl, heteroaryl, acyl, sulfonyl, or —$(CH_2)_mR_8$;

the two instances of R taken together in an instance of —$NR_2$ may form a ring comprising that nitrogen;

$R_1$' represents H, alkyl, aryl, p-toluenesulfonyl, —$(CH_2)_d$N(Phth), or —$(CH_2)_dN(R)_2$ wherein d is an integer in the range 1 to 6 inclusive;

$R_2$' and $R_3$ independently for each occurrence represent H, lower alkyl, or aryl;

$R_8$ represents, independently for each occurrence, aryl, heteroaryl, cycloalkyl, cycloalkenyl, heterocyclyl, or polycyclyl;

m is, independently for each occurrence, an integer selected from the range 1–8 inclusive; and n is an integer selected from the range 1–4 inclusive.

18. The compound of claim 17, wherein X is a heteroaryl moiety.

19. The compound of claim 17, wherein X is —$NR_2$.

20. The compound of claim 17, wherein Q is bonded to the 5-position of the indole nucleus.

21. The compound of claim 17, wherein Q is selected from the group consisting of F, Cl, Br, I, R, —OR, —$NO_2$, and —CN.

22. The compound of claim 17, wherein Q is selected from the group consisting of F, Cl, Br, I, R, —OR, —$NO_2$, and —CN; and Q is bonded to the 5-position of the indole nucleus.

23. The compound of claim 17, wherein L is selected from the group consisting of F, Cl, Br, I, R, —OR, —$CF_3$, —$OCF_3$, —$CR_2$OR, —$CO_2$R, —$NO_2$, and —CN.

24. The compound of claim 17, wherein X represents a heteroaryl; and Q is selected from the group consisting of F, Cl, Br, I, R, —OR, —$NO_2$, and —CN.

25. The compound of claim 17, wherein X represents —$NR_2$; and Q is selected from the group consisting of F, Cl, Br, I, R, —OR, —$NO_2$, and —CN.

26. The compound of claim 17, wherein X represents a heteroaryl; Q is selected from the group consisting of F, Cl, Br, I, R, —OR, —$NO_2$, and —CN; and Q is bonded to the 5-position of the indole nucleus.

27. The compound of claim 17, wherein X represents —$NR_2$; Q is selected from the group consisting of F, Cl, Br, I, R, —OR, —$NO_2$, and —CN; and Q is bonded to the 5-position of the indole nucleus.

28. The compound of claim 17, 18, 19, 20, 21, 22, 23, 24, 25, 26, or 27, wherein said compound has a minimum inhibitory concentration (MIC) less than 10 $\mu$g/mL against at least one Gram-positive bacterium.

29. The compound of claim 28, wherein said compound has a minimum inhibitory concentration (MIC) less than 1 $\mu$g/mL against at least one Gram-positive bacterium.

30. The compound of claim 29, wherein said compound has a minimum inhibitory concentration (MIC) less than 0.1 $\mu$g/mL against at least one Gram-positive bacterium.

31. The compound of claim 17, 18, 19, 20, 21, 22, 23, 24, 25, 26, or 27, wherein said compound has a therapeutic index in primates of at least 10 for the inhibition of infection by at least one Gram-positive bacterium.

* * * * *